United States Patent
Mao et al.

(10) Patent No.: US 11,498,922 B2
(45) Date of Patent: *Nov. 15, 2022

(54) PHARMACEUTICAL COMPOSITION COMPRISING N-(3-((2-((3-FLUORO-4-(4-METHYLPIPERAZIN-1-YL PHENYL) AMINO)-7H-PYRROLO[2,3-D]PYRIMIDIN-4-YL)OXY)PHENYLACRYLAMIDE

(71) Applicants: ACEA Therapeutics, Inc., San Diego, CA (US); Hangzhou ACEA Pharmaceutical Research Co., Ltd., Hangzhou (CN); Zhejiang ACEA Pharmaceuticals Co., Ltd, Quzhou (CN)

(72) Inventors: Long Mao, San Diego, CA (US); Jia Liu, San Diego, CA (US); Yile Chen, Hangzhou (CN); Yuning Hua, Hangzhou (CN); Kongen Dai, Hangzhou (CN); Yimei Bao, Hangzhou (CN); Bojie Weng, Hangzhou (CN); Xi-aopeng Mo, Hangzhou (CN); Jian Wu, Hangzhou (CN); Xiao Xu, San Diego, CA (US); Wanhong Xu, Hangzhou (CN); Xiaobo Wang, San Diego, CA (US)

(73) Assignees: ACEA Therapeutics, Inc., San Diego, CA (US); Hangzhou ACEA Pharmaceutical Research Co., Ltd., Hangzhou (CN); Zhejiang ACEA Pharmaceuticals Co., Ltd., Quzhou (CN)

(*) Notice: Subject to any disclaimer, the term of this patent is extended or adjusted under 35 U.S.C. 154(b) by 242 days.

This patent is subject to a terminal disclaimer.

(21) Appl. No.: 16/500,384

(22) PCT Filed: Apr. 7, 2017

(86) PCT No.: PCT/CN2017/079724
§ 371 (c)(1),
(2) Date: Oct. 2, 2019

(87) PCT Pub. No.: WO2018/184206
PCT Pub. Date: Oct. 11, 2018

(65) Prior Publication Data
US 2021/0300931 A1 Sep. 30, 2021

(51) Int. Cl.
*A61K 31/519* (2006.01)
*C07D 487/04* (2006.01)
*A61K 9/00* (2006.01)
*A61K 9/20* (2006.01)

(52) U.S. Cl.
CPC .......... *C07D 487/04* (2013.01); *A61K 9/0053* (2013.01); *A61K 9/2013* (2013.01); *A61K 9/2054* (2013.01); *A61K 9/2095* (2013.01); *C07B 2200/13* (2013.01)

(58) Field of Classification Search
CPC .......................... A61K 31/519; C07D 487/04
(Continued)

(56) References Cited

U.S. PATENT DOCUMENTS 3,974,277 A  8/1976  Horn et al.
7,192,752 B2 3/2007  Xu et al.
(Continued)

FOREIGN PATENT DOCUMENTS

AU  2013300106 B2  2/2014
CN  102083800 A  6/2011
(Continued)

OTHER PUBLICATIONS

International Preliminary Report on Patentability for international patent application PCT/CN2016/087857, dated Jan. 23, 2018, 7 pages.

(Continued)

*Primary Examiner* — Douglas M Willis
(74) *Attorney, Agent, or Firm* — McNeill Baur PLLC

(57) ABSTRACT

The present invention relates to methods of making certain pyrrolopyrimidine derivatives, which are useful in the treatment of proliferation disorders and other diseases related to the dysregulation of kinase (such as, but not limited to, EGFR (including HER), Alk, PDGFR, BLK, BMX/ETK, BTK, FLT3(D835Y), ITK, JAK1, JAK2, JAK3, TEC and TXK) and/or the respective pathways, salts, polymorphs, and amorphous forms of said compounds, synthetic intermediates for preparing said compounds, and pharmaceutical compositions comprising said compounds and methods for making such compositions.

16 Claims, 54 Drawing Sheets

(58) Field of Classification Search
USPC .................................... 514/265.1; 544/280
See application file for complete search history.

(56) References Cited

U.S. PATENT DOCUMENTS

| | | |
|---|---|---|
| 7,459,303 B2 | 12/2008 | Wang et al. |
| 7,468,255 B2 | 12/2008 | Xu et al. |
| 7,470,533 B2 | 12/2008 | Xu et al. |
| 7,560,269 B2 | 7/2009 | Wang et al. |
| 7,732,127 B2 | 6/2010 | Wang et al. |
| 8,685,988 B2 | 4/2014 | Xu et al. |
| 8,975,249 B2 | 3/2015 | Lee et al. |
| 9,010,746 B2 | 4/2015 | Zhao et al. |
| 9,034,885 B2 | 5/2015 | Xu et al. |
| 9,464,089 B2 | 10/2016 | Xu et al. |
| 9,586,965 B2 | 3/2017 | Xu et al. |
| 9,763,949 B2 | 9/2017 | Xu et al. |
| 9,908,884 B2 | 3/2018 | Gray et al. |
| 9,920,074 B2 | 3/2018 | Xu et al. |
| 9,925,188 B2 | 3/2018 | Charifson |
| 10,449,196 B2 | 10/2019 | Xu et al. |
| 10,533,011 B2 | 1/2020 | Mao et al. |
| 10,596,172 B2 | 3/2020 | Singh et al. |
| 10,596,174 B2 | 3/2020 | Xu et al. |
| 10,828,300 B2 | 11/2020 | Singh et al. |
| 11,007,197 B2 | 5/2021 | Xu et al. |
| 2004/0116422 A1 | 6/2004 | Kitano et al. |
| 2008/0318950 A1 | 12/2008 | Ahn et al. |
| 2009/0076037 A1 | 3/2009 | Connolly et al. |
| 2010/0016296 A1 | 1/2010 | Singh et al. |
| 2010/0029610 A1 | 2/2010 | Singh et al. |
| 2010/0239631 A1 | 9/2010 | Bourke et al. |
| 2010/0249092 A1 | 9/2010 | Singh et al. |
| 2011/0207736 A1 | 8/2011 | Gray et al. |
| 2012/0094999 A1 | 4/2012 | Gray et al. |
| 2013/0190320 A1 | 7/2013 | Xu et al. |
| 2014/0038940 A1 | 2/2014 | Xu et al. |
| 2014/0038981 A1 | 2/2014 | Xu et al. |
| 2015/0133457 A1 | 5/2015 | Xu et al. |
| 2015/0210702 A1 | 7/2015 | Xu et al. |
| 2017/0224689 A1 | 8/2017 | Xu et al. |
| 2018/0008607 A1 | 1/2018 | Xu |
| 2018/0251475 A1 | 9/2018 | Xu et al. |
| 2018/0312510 A1 | 11/2018 | Mao et al. |

FOREIGN PATENT DOCUMENTS

| | | |
|---|---|---|
| CN | 102482277 A | 5/2012 |
| CN | 103748096 A | 4/2014 |
| CN | 104306348 A | 1/2015 |
| CN | 107949388 A | 4/2018 |
| EP | 3019496 A2 | 5/2016 |
| EP | 2880035 B1 | 7/2016 |
| EP | 3170825 B1 | 4/2019 |
| JP | 2011-526299 A | 10/2011 |
| JP | 2012-526113 A | 10/2012 |
| JP | 2013-515786 A | 5/2013 |
| JP | 2015503625 A | 2/2015 |
| JP | 6215938 B2 | 10/2017 |
| JP | 6353788 B2 | 7/2018 |
| RU | 2645672 C2 | 2/2018 |
| WO | 01/32632 A2 | 5/2001 |
| WO | 02/083653 A1 | 10/2002 |
| WO | 03/026664 A1 | 4/2003 |
| WO | 2004/021979 A2 | 3/2004 |
| WO | 2004045624 A1 | 6/2004 |
| WO | 2005/062795 A2 | 7/2005 |
| WO | 2005/066156 A1 | 7/2005 |
| WO | 2005/084401 A2 | 9/2005 |
| WO | 2006/009755 A2 | 1/2006 |
| WO | 2006/014325 A2 | 2/2006 |
| WO | 2007/039404 A1 | 4/2007 |
| WO | 2007/042298 A1 | 4/2007 |
| WO | 2007/055514 A1 | 5/2007 |
| WO | 2007/071393 A2 | 6/2007 |
| WO | 2007/103233 A2 | 9/2007 |
| WO | 2007/126841 A2 | 11/2007 |
| WO | 2008/073687 A2 | 6/2008 |
| WO | 2008/094737 A2 | 8/2008 |
| WO | 2008/150118 A2 | 12/2008 |
| WO | 2009/017838 A2 | 2/2009 |
| WO | 2009/020990 A1 | 2/2009 |
| WO | 2009/032694 A1 | 3/2009 |
| WO | 2009/032703 A1 | 3/2009 |
| WO | 2009/051822 A1 | 4/2009 |
| WO | 2009/131687 A2 | 10/2009 |
| WO | 2009/143389 A1 | 11/2009 |
| WO | 2009/158571 A1 | 12/2009 |
| WO | 2010/045451 A1 | 4/2010 |
| WO | 2010/090764 A1 | 8/2010 |
| WO | 2011/079231 A1 | 6/2011 |
| WO | 2011/090760 A1 | 7/2011 |
| WO | 2011090760 A1 | 7/2011 |
| WO | 2011/140338 A1 | 11/2011 |
| WO | 2011/162515 A2 | 12/2011 |
| WO | 2012/061299 A1 | 5/2012 |
| WO | 2012/061303 A1 | 5/2012 |
| WO | 2012/064706 A1 | 5/2012 |
| WO | 2012094999 A1 | 7/2012 |
| WO | 2012/120048 A1 | 9/2012 |
| WO | 2012/135801 A1 | 10/2012 |
| WO | 2012/151561 A1 | 11/2012 |
| WO | 2012/156437 A1 | 11/2012 |
| WO | 2013/106792 A1 | 7/2013 |
| WO | 2013106792 A1 | 7/2013 |
| WO | 2014025486 A1 | 2/2014 |
| WO | 2015006754 A2 | 1/2015 |
| WO | WO-2016130920 A2 * | 8/2016 ............. A61P 25/28 |
| WO | 2017059702 A1 | 4/2017 |
| WO | 2018/184206 A1 | 10/2018 |
| WO | 2010129053 A2 | 11/2020 |

OTHER PUBLICATIONS

Chapter II Demand with Response to Written Opinion and Article 34 Amendments for international patent application PCT/CN2016/087857, dated Jan. 23, 2018, 4 pages.

International Search Report for international patent application PCT/CN2016/087857, dated Jan. 23, 2018, 2 pages.

Xu et al., "AC0010, an Irreversible EGFR Inhibitor Selectively Targeting Mutated EGFR and Overcoming T790M-Induced Resistance in Animal Models and Lung Cancer Patients," Molecular Cancer Therapeutics, 15(11); 1-12. (c) 2016 AACR. DOI: 10.1158/1535-7163.MCT-16-0281.

International Search Report for international patent application PCT/CN2017/079724, dated Jan. 5, 2018, 6 pages.

Written Opinion of the International Searching Authority for international patent application PCT/CN2017/079724, dated Jan. 5, 2018, 7 pages.

International Preliminary Report on Patentability for international patent application PCT/CN2017/079724, dated Oct. 8, 2019, 8 pages.

Berge et al., "Pharmaceutical Salts," Journal of Pharmaceutical Sciences, Jan. 1977, vol. 66, No. 1, Review Article, 19 pages.

Abbot et al., "Synthesis of heteroaryl-fused pyrazoles as P38 kinase inhibitors," Heterocycles (2009) 78) 11):2811-2826.

Andries et al., "TMC125, a novel next-generation nonnucleoside reverse transcriptase inhibitor active against nonnucleoside reverse transcriptase inhibitor-resistant human immunodeficiency virus type 1," Antimicrobial Agents and Chemotherapy (2004) 48(12):4680-4686.

Avizienyte et al., "Comparison of the EGFR resistance mutation profiles generated by EGFR-targeted tyrosine kinase inhibitors and the impact of drug combinations," Biochem. J. (2008) 415:197-206.

Bagshawe, "Antibody-directed enzyme prodrug therapy: A review," Drug Dev. Res. (1995) 34(2):220-230.

Baselga et al., "Critical Update and Emerging Trends in Epidermal Growth Factor Receptor Targeting in Cancer," Journal of Clinical Oncology (2005) 23(11):2445-2459.

(56) References Cited

OTHER PUBLICATIONS

Bean et al., "Acquired Resistance to Epidermal Growth Factor Receptor Kinase Inhibitors Associated with a Novel T854A Mutation in a Patient with EGFR-Mutant Lung Adenocarcinoma," Clin Cancer Res. (2008) 14(22):7519-7525.
International Preliminary Report on Patentability for PCT/US2013/021338, dated Jul. 15, 2014, 15 pages.
Bertolini et al., "A new rational hypothesis for the pharmacophore of the active metabolite of leflunomide, a potent immunosuppressive drug," J. Med Chem. (1997) 40(13):2011-2016.
Blair et al., "Structure-guided development of affinity probes for tyrosine kinases using chemical agents," Nature Chemical Biology (2007) 3(4):229-238.
Bodor, "Novel approaches to the design of safer drugs: soft drugs and site-specific chemical delivery systems," Adv. Drug. Res. (1984) 13:255-331.
Carter et al., "Inhibition of drug-resistant mutants of ABL, KIT, and EGF receptor kinases," Proc. Natl. Acad. Sci. 2005, 102(31), 11011-11016.
Chamberlain et al., "Discovery of 4,6-bis-anilino-1H-pyrrolo[2,3-d]pyrimidines: Potent inhibitors of the IGF-1R receptor tyrosine kinase," Bioorganic & Medicinal Chemistry Letters (2009) 19:469-473.
Chamberlain et al., "Optimization of 4,6-bis-anilino-1H-pyrrolo[2,3-d]pyrimidine IGF-1R tyrosine kinase inhibitors. Towards JNK selectivity," Bioorganic & Medicinal Chemistry Letters (2009) 19:360-364.
Chamberlain et al., "Optimization of a series of 4,6-bis-anilino-1H-pyrrolo[2,3-d]pyrimidine inhibitors of IGF-1R: Elimination of an acid-mediated decomposition pathway," Bioorganic & Medicinal Chemistry Letters (2009) 19:373-377.
Frenkel et al., "Concentration and pH Dependent Aggregation of Hydrophobic Drug Molecules and Relevance to Oral Bioavailability," J. Med. Chem. (2005) 48:1974-1983.
Fry et al., "Specific, irreversible inactivation of the epidermal growth factor receptor and erbB2, by a new class of tyrosine kinase inhibitor," PNAS USA (1998) 95:12022-12027.
Ghosh et al., "2,4-bis(aryloxy)pyrimidines as antimicrobial agents," J. Med. Chem. (1968) 11 (6):1237-1238.
Han et al., "Novel Hybrids of (Phenylsulfonyl)furoxan and Anilinopyrimidine as Potent and Selective Epidermal Growth Factor Receptor Inhibitors for Intervention of Non-Small-Cell Lung Cancer," Journal of Medicinal Chemistry (2013) 56:4738-4748.
Johnson et al., "Relationships between drug activity in NCI preclinical in vitro and in vivo models and early clinical trials," British Journal of Cancer, 2001, 84, 1424-1431.
Kato et al., "Ketene and its derivatives. XVII. Reaction of diketene with imidates," Chemical and Pharmaceutical Bulletin (1967) 15(9):1334-1338.
Kumar et al., "Structure and Clinical Relevance of the Epidermal Growth Factor Receptor in Human Cancer," J. Clin. Oncol. 2008, 26(10), 1742-1751 (Apr. 2008).
Ludovici et al., "Evolution of Anti-HIV Drug Candidates. Part 3: Diarylpyrimidine (DAPY) Analogues," Bioorganic & Medicinal Chemistry Letters (2001) 11:2235-2239.
Mellinghoff, "Why Do Cancer Cells Become "Addicted" to Oncogenic Epidermal Growth Factor Receptor?" PLoS Medicine (2007) 4(10):e321:1620-1622.
Modjtahedi et al., "Epidermal growth factor receptor inhibitors in cancer treatment: advances, challenges and opportunities," Anti-Cancer Drugs (2009) 220(10):851-855. (Abstract).
Patani et al., "Bioisosterism: A Rational Approach in Drug Design," Chem. Rev. (1996) 96:3147-3176.
Petter et al., A novel small-molecule drug platform to silence cancer targets—Application to the pan-ErbB kinases, Poster from AACR 2009, Denver, CO-Abstr. 3746 (presented on Apr. 18-22, 2009).
Profft et al., "Uber in 2- und 6-Stellung substituierte 4-Methylpyrimidine," Archiv der Pharmazie (1962) 295(9):649-662.
Raymond et al., "Epidermal growth factor receptor tyrosine kinase as a target for anticancer therapy," Drugs (2000) 60(Suppl 1):15-23.
Rotili et al., "Diarylpyrimidine-Dihydrobenzyloxopyrimidine Hybrids: New, Wide-Spectrum Anti-HIV-1 Agents Active at (Sub)-Nanomolar Level," J. Med. Chem. (2011) 54(8):3091-3096.
Shan et al., "Prodrug strategies based on intramolecular cyclization reactions," J. Pharm. Sci. (1997) 86(7):765-767.
Slichenmeyer et al., "CI-1033, a pan-erbB tyrosine kinase inhibitor," Semin. Oncol. (2001) 28(5 Suppl. 16):80-85.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem. (2000) 43:1380-1397.
International Search Report and Written Opinion for PCT/US2013/021338, dated Jun. 12, 2013, 25 pages.
Zhou et al., "Discovery of selective irreversible inhibitors for EGFR-T790M," Bioorganic & Medicinal Chemistry Letters (2011) 21:638-643.
Zhou et al., "Novel mutant-selective EGFR kinase inhibitors against EGFR T790M," Nature (2009) 462 (24/31):1070-1074.
CI-1033 (Canertinib, PD183805), Selleck Chemicals, retrieved from the Internet Aug. 15, 2013, 5 pages.
Li et al., "BIBW2992, an irreversible EGFR/HER2 inhibitor highly effective in preclinical lung cancer models," Oncogene (2008) 27(34):4702-4711.
U.S. Response to Office Action for U.S. Appl. No. 13/740,182, filed Aug. 15, 2014, 16 pages.
U.S. Office Action for U.S. Appl. No. 13/740,182, dated Dec. 12, 2014, 17 pages.
U.S. Final Office Action for U.S. Appl. No. 13/740,182, dated Jun. 30, 2015, 28 pages.
U.S. Response to Final Office Action for U.S. Appl. No. 13/740,182 dated Dec. 17, 2015, 17 pages.
U.S. Request for Continued Examination and Amendment after final action for U.S. Appl. No. 13/740,182, dated Dec. 17, 2015, 22 pages.
U.S. Supplemental response for U.S. Appl. No. 13/740,182, dated Feb. 9, 2016, 16 pages.
U.S. Non-final Rejection for U.S. Appl. No. 13/740,182, dated Sep. 1, 2016, 20 pages.
U.S. Final Rejection for U.S. Appl. No. 13/740,182, dated Mar. 23, 2017, 26 pages.
Response to Non-Final Office Action for U.S. Appl. No. 15/882,924, dated Aug. 16, 2019, 9 pages.
Notice of Allowance for U.S. Appl. No. 15/882,924, dated Sep. 19, 2019, 20 pages.
Non-Final Office Action for U.S. Appl. No. 13/740,182, dated Sep. 13, 2019, 16 pages.
Notice of Allowance for U.S. Appl. No. 15/708,024, dated Jun. 3, 2019, 15 pages.
Notice of Allowability for U.S. Appl. No. 15/708,024, dated Sep. 5, 2019, 16 pages.
Response to Non-Final Office Action for U.S. Appl. No. 15/435,722, dated Aug. 23, 2019, 10 pages.
U.S. Office Action for U.S. Appl. No. 13/843,554, dated Aug. 19, 2014, 7 pages.
U.S. Response to Non-Final Office Action for U.S. Appl. No. 13/843,554, filed Dec. 19, 2014, 19 pages.
U.S. Notice of Allowance for U.S. Appl. No. 13/843,554, dated Jan. 13, 2015, 8 pages.
U.S. Notice of Allowance for U.S. Appl. No. 13/917,514, dated Nov. 14, 2013, 10 pages.
U.S. Office Action for U.S. Appl. No. 14/712,794 dated Mar. 8, 2016, 20 pages.
U.S. Response to Office Action for U.S. Appl. No. 14/712,794, filed Jul. 8, 2016, 27 pages.
U.S. Final Office Action for U.S. Appl. No. 14/712,794, dated Jul. 22, 2016, 6 pages.
U.S. Notice of Allowance for U.S. Appl. No. 14/712,794, dated Dec. 2, 2016, 7 pages.
U.S. Notice of Allowance for U.S. Appl. No. 14/712,794, dated Apr. 24, 2017, 4 pages.

(56) References Cited

OTHER PUBLICATIONS

U.S. Office Action for U.S. Appl. No. 14/420,341, dated Jun. 3, 2016, 7 pages.
U.S. Response to Office Action for U.S. Appl. No. 14/420,341, filed Sep. 1, 2016, 12 pages.
U.S. Final Office Action for U.S. Appl. No. 14/420,341, dated Sep. 22, 2016, 8 pages.
U.S. Notice of Allowance for U.S. Appl. No. 14/420,341, dated Oct. 18, 2016, 16 pages.
International Search Report and Written Opinion for PCT Appln. No. PCT/US2013/050163, dated Sep. 4, 2013, 10 pages.
International Preliminary Report on Patentability for PCT/US2013/050163, dated Feb. 10, 2015, 5 pages.
U.S. Office Action for U.S. Appl. No. 14/329,890, dated Sep. 23, 2015, 16 pages.
U.S. Response to Office Action for U.S. Appl. No. 14/329,890, filed Dec. 21, 2015, 14 pages.
U.S. Final Office Action for U.S. Appl. No. 14/329,890 dated Mar. 3, 2016, 5 pages.
U.S. Notice of Allowance for U.S. Appl. No. 14/329,890, dated May 27, 2016, 7 pages.
U.S. Corrected Notice of Allowance for U.S. Appl. No. 14/329,890, dated Jun. 20, 2016, 4 pages.
U.S. Non-final Rejection for U.S. Appl. No. 15/271,124, dated Jan. 17, 2017, 6 pages.
U.S. Response for Non-final Rejection for U.S. Appl. No. 15/271,124, dated Apr. 17, 2017, 15 pages.
International Search Report and Written Opinion for PCT/US2014/046442, dated Jan. 5, 2015, 22 pages.
Response to Written Opinion with Chapter II Demand and Article 34 Amendments for PCT/US2014/046442, filed May 11, 2015, 62 pages.
International Preliminary Report on Patentability for PCT/US14/46442, dated Jul. 28, 2015, 5 pages.
Extended European Search Report for EP 16202341.0, dated Feb. 22, 2017, 5 pages.
Gura et al., "Systems for identifying new drugs are often faulty," Science 1997, 278, 1041-1042.
U.S. Non-final Office Action for U.S. Appl. No. 15/708,024, dated Feb. 9, 2018, 13 pages.
U.S. Response to Non-final Office Action for U.S. Appl. No. 15/708,024, dated Aug. 9, 2018, 8 pages.
U.S. Notice of Allowance for U.S. Appl. No. 15/708,024, dated Oct. 3, 2018, 7 pages.
Cortot, Alexis B.; et al., Resistance to Irreversible EGF Receptor Tyrosine Kinase Inhibitors through a Multistep Mechanism Involving the IGF1R Pathway. Cancer Research, 2013, 73(2), 834 843 (English).
Response to Non-final Rejection for U.S. Appl. No. 15/435,722, dated Oct. 26, 2017, 41 pages.
Response to Non-final Rejection for U.S. Appl. No. 13/740,182, dated Dec. 1, 2016, 17 pages.
Notice of Allowance for U.S. Appl. No. 15/271,124, dated Jul. 10, 2017, 7 pages.
Non-Final Office Action for U.S. Appl. No. 15/882,924, dated Feb. 19, 2019, 44 pages.
International Search Report and Written Opinion for PCT/CN2016/087857, dated Sep. 29, 2016, 10 pages.
Non-Final Office Action for U.S. Appl. No. 15/708,024, dated Feb. 9, 2018, 13 pages.
Non-final Rejection for U.S. Appl. No. 13/740,182, dated Oct. 18, 2017, 17 pages.
Response to Non-Final Rejection for U.S. Appl. No. 13/740,182, dated Jan. 18, 2018, 14 pages.
U.S. Final Office Action for U.S. Appl. No. 13/740,182, dated Jun. 1, 2018, 28 pages.
WO, International Preliminary Reporton Patentability for international patent application PCT/US2013/021338, dated Jul. 15, 2014, 15 pages.

U.S. Response to Non-Final Office Action for U.S. Appl. No. 13/740,182, dated Mar. 12, 2015, 21 pages.
U.S. Response to Non-Final Office Action for U.S. Appl. No. 13/740,182, dated Nov. 30, 2018, 10 pages.
WO, International search report and written opinion for international patent application PCT/US2013/021338, dated Jun. 12, 2013, 25 pages.
U.S. Response to non-final office action for U.S. Appl. No. 14/712,794, dated Jul. 8, 2016, 27 pages.
U.S. Response to final office action for U.S. Appl. No. 14/712,794, dated Oct. 6, 2016, 24 pages.
U.S. Final Office action for U.S. Appl. No. 15/435,722, dated Feb. 7, 2018, 15 pages.
U.S. Response to Final office action for U.S. Appl. No. 15/435,722, dated Jun. 7, 2018, 10 pages.
U.S. Notice of allowance for U.S. Appl. No. 15/435,722, dated Nov. 1, 2018, 7 pages.
U.S. Response to Final Office action for U.S. Appl. No. 14/420,341, dated Oct. 5, 2016, 9 pages.
EP, Extended search report for European patent application 16202341.0, dated Feb. 22, 2017, 7 pages.
WO, Notification, International Search Report and Written Opinion for international patent application PCT/US2013/050163, dated Sep. 4, 2013, 10 pages.
U.S. Response to final Office Action for U.S. Appl. No. 13/740,182, dated Dec. 17, 2015, 19 pages.
U.S. Non Office Action U.S. Appl. No. 15/271,124, dated Feb. 14, 2018, 4 pages.
WO, Written Opinion for international patent application WO2018184206, PCT/CN2017/079724, dated Jan. 5, 2018, 7 pages.
WO, Written Opinion for international patent application WO2017059702, dated Sep. 18, 2016, 6 pages.
WO, International Search Report for international patent application WO2017059702, dated Sep. 29, 2016, 4 pages.
WO, International preliminary report on patentability for international patent application WO2017059702, dated Jan. 23, 2018, 45 pages.
U.S. Non-Final Office Action for U.S. Appl. No. 15/435,722, dated Feb. 25, 2019, 27 pages.
U.S. Non-Final Office Action for U.S. Appl. No. 15/882,924, dated Feb. 19, 2019, 44 pages.
U.S. Non-Final Office Action for U.S. Appl. No. 15/766,736, dated Dec. 12, 2018, 7 pages.
EP, European Search Report for for EP patent application 16853009.5, dated May 6, 2019, 10 pages.
U.S. Response to Non-Final Office Action under 37 C.F.R. 1.111 for U.S. Appl. No. 15/435,722, dated Oct. 26, 2017, 41 pages.
EP, Partial Search Report for European patent application 168530095, dated Mar. 25, 2019, 17 pages.
EP, Search Report for European patent application 168530095, dated Mar. 21, 2019, 15 pages.
WO, Written Opinion for international patent application PCT/CN2017/079724, dated Jan. 2, 2018, 7 pages.
EP, Supplementary European Search Report for EP patent application 16853009.5, dated Apr. 26, 2019, 4 pages.
Mino R. Caira, "Crystalline Polymorphism of Organic Compounds," Topics in Current Chemistry, vol. 198 @ Springer Verlag Berlin Heidelberg 1998, p. 163-208.
Bouaziz et al., "Regulatory B cells as inhibitors of immune responses and inflammation," Immunological Reviews, 2008, vol. 224:201-214.
Honigberg. et al., "The Bruton tyrosine kinase inhibitor PCI-32765 blocks B-cell activation and is efficacious in models of autoimmune disease and B-cell malignancy," PNAS. Jul. 20, 2010, vol. 107, No. 29, p. 13075-13080.
Shripad S. Bhagwat, "Kinase inhibitors for the treatment of inflammatory and autoimmune disorders," Purinergic Signalling (2009) 5:107-115 DOI 10.1007/s11302-008-9117-z.
EP, Extended European Search Report for European patent application 168530095, dated May 8, 2019, 17 pages.
JP, RN 1348622-25-2 Registry,Database Registry [Online] Retrieved from STN, Dec. 4, 2011, Search Date: Jun. 27, 2018, 1 page.

(56) References Cited

OTHER PUBLICATIONS

U.S. Notice of Allowance for U.S. Appl. No. 15/708 024, dated Jun. 3, 2019, 15 pages.
EP, Partial European Search Report for EP patent application 16853009.5, dated Mar. 6, 2019, 3 pages.

* cited by examiner

PHARMACEUTICAL COMPOSITION COMPRISING N-(3-((2-((3-FLUORO-4-(4-METHYLPIPERAZIN-1-YL PHENYL) AMINO)-7H-PYRROLO[2,3-D]PYRIMIDIN-4-YL)OXY)PHENYLACRYLAMIDE

CROSS-REFERENCE TO RELATED APPLICATION

This application is a U.S. national phase filing of International Patent Application No. PCT/CN2017/079724, entitled "PHARMACEUTICAL SALTS, PHYSICAL FORMS, AND COMPOSITIONS OF PYRROLOPYRIMIDINE KINASE INHIBITORS, AND METHODS OF MAKING SAME," the content of which application is incorporated herein by reference in its entirety for all purposes.

BACKGROUND OF THE INVENTION

Field of the Invention

Described herein are methods for the preparation of certain pyrrolopyrimidine compounds that are useful for the treatment of proliferation disorders and other diseases related to the dysregulation of kinase (such as, but not limited to, EGFR (including HER), Alk, PDGFR, BLK, BMX/ETK, BTK, FLT3(D835Y), ITK, JAK1, JAK2, JAK3, TEC, and TXK) and/or the respective pathways. Also described herein are certain salt forms and physical forms of said pyrrolopyrimidine compounds, stabilized pharmaceutical compositions comprising said pyrrolopyrimidine compounds and processes for preparing such compositions, and intermediates useful in the preparation of the pyrrolopyrimidine compounds.

Description of Related Art

Certain pyrrolopyrimidine compounds are modulators of protein kinases and are therefore useful in protein kinase-mediated diseases, including cancer and chronic inflammation. A particular kinase of interest is epidermal growth factor receptor (EGFR; ErbB-1; HER1 in humans). This kinase is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). EGFR is reportedly deregulated in most solid tumor types, such as lung cancer, breast cancer, and brain tumors. Resistance to known therapies develops due to the presence of a mutation of T790M, which is the gatekeeper of EGFR. Certain pyrrolopyrimidine compounds show selective inhibition of the T790M-mutated EGFR inhibitor relative to the wild type EGFR. It is desirable to develop a more efficient EGFR inhibitor that will target substantially the mutated EGFR over the wild type protein. Other protein kinases that are useful targets for small molecule pharmaceuticals include B lymphoid tyrosine kinase (BLK), janus kinase 1 (JAK1), bone marrow kinase on the X chromosome (BMX/ETK), Bruton's tyrosine kinase (BTK), janus kinase 2 (JAK2), janus kinase 3 (JAK3), tyrosine kinase expressed in hepatocellular carcinoma (TEC), resting lymphocyte kinase (TXK, also known as RLK), FMS-like tyrosine kinase 3 (FLT3), and FLT3 (D835Y). Such compounds are described in PCT Publ. No. WO2014/025486.

An efficient method of making such pyrrolopyrimidine kinase inhibitors is needed to allow for clinical testing and commercial use. Such methods, and intermediates useful for the preparation of such compounds, are described herein. Certain salt forms and polymorphs of said compounds are also described.

Certain pyrrolopyrimidine compounds, including N-(3-((2-((3-fluoro-4-(4-methylpiperazin-1-yl)phenyl)amino)-7H-pyrrolo[2,3-d]pyrimidin-4-yl)oxy)phenyl)acrylamide and pharmaceutically acceptable salts thereof, are useful in treating tumors and related diseases related to the dysregulation of kinases such as those described herein (including, but not limited to, EGFR (including HER), Alk, and PDGFR pathways). See, e.g., U.S. Pat. No. 8,685,998 B2.

In general, drug stability is an important consideration in the design, manufacture, and storage of pharmaceutical compositions. Drug products that lack stability can form degradation products that can cause undesirable side effects or, in some cases, can cause a decrease in the efficacy and bioavailability of the drug substance itself, making it difficult for physicians to prescribe consistent and effective doses. Therefore, pharmaceutical compositions containing active therapeutic agents, such as those described herein, including N-(3-((2-((3-fluoro-4-(4-methylpiperazin-1-yl) phenyl)amino)-7H-pyrrolo[2,3-d]pyrimidin-4-yl)oxy)phenyl)acrylamide and pharmaceutically acceptable salts thereof, that have quick release characteristics, excellent stability, extensive adaptability, and medicinal significance are needed. Described herein are such pharmaceutical compositions.

BRIEF SUMMARY OF THE INVENTION

The present invention is directed to methods of preparing certain pyrrolopyrimidine derivatives and intermediates useful in their preparation. Also described herein are certain salt forms, polymorphs, and amorphous forms of said compounds. Additionally, pharmaceutical compositions comprising these pyrrolopyrimidine derivatives and their process of preparation are described.

The present disclosure provides a method of making a compound of Formula (I):

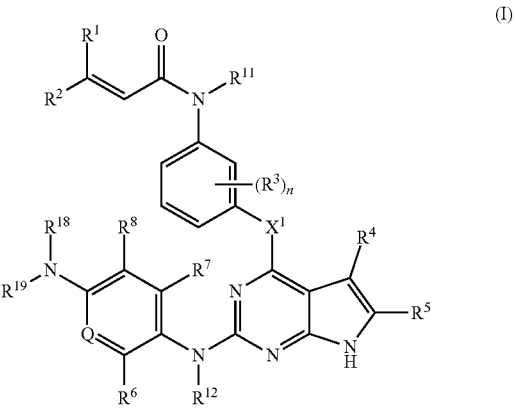

wherein
X$^1$ is O, NH, or S;
R$^1$ and R$^2$ are each independently hydrogen, halo, C$_{1-6}$alkyl, or C$_{1-6}$haloalkyl;
R$^3$ is halo, hydroxyl, C$_{1-6}$alkyl, C$_{1-6}$alkoxy, cyano, or nitro;
n is 0, 1, 2, 3, or 4;

$R^4$ is hydrogen, $C_{1-6}$alkyl, $C_{3-7}$cycloalkyl, or $-NR^{22}R^{23}$;
  wherein the alkyl and cycloalkyl are unsubstituted or substituted with hydroxyl or amino; and
  $R^{22}$ and $R^{23}$ are each independently hydrogen or $C_{1-6}$alkyl; or $R^{22}$ and $R^{23}$ taken together with the nitrogen to which they are attached form a 3- to 10-membered heterocycloalkyl ring;

$R^5$ is hydrogen or $C_{1-6}$alkyl;

$R^6$ and $R^7$ are each independently hydrogen, halo, $C_{1-6}$alkyl, $C_{1-6}$haloalkyl, $C_{2-6}$alkoxy, $C_{1-6}$haloalkoxy, hydroxyl, cyano, or nitro;

$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

$R^{11}$ and $R^{12}$ are each independently hydrogen or $C_{1-6}$alkyl;

Q is $CR^9$ or N;
  where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

$-NR^{18}R^{19}$ is:

(a)

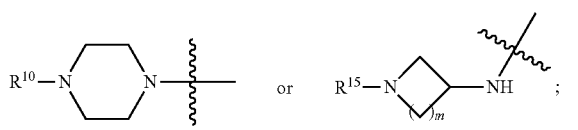

where $R^{10}$ is selected from hydrogen and $C_{1-6}$ alkyl;
  $R^{15}$ is unsubstituted methyl, or is $C_{2-4}$alkyl unsubstituted or substituted with hydroxy, methoxy, or halo; and
  m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring;

or a pharmaceutically acceptable salt thereof.

The present disclosure is directed to a method of making a compound of Formula (I) or a pharmaceutically acceptable salt thereof, comprising one or more of the following steps:

(a) reacting a compound of Formula (X):

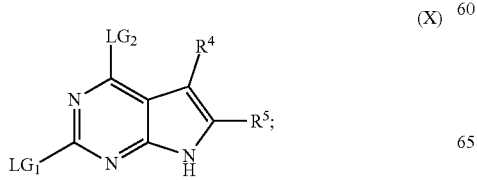

(X)

wherein $LG_1$ and $LG_2$ are each a leaving group; and $R^4$ and $R^5$ are each as defined for Formula (I);

with chloromethyl pivalate to form a compound of Formula (XI);

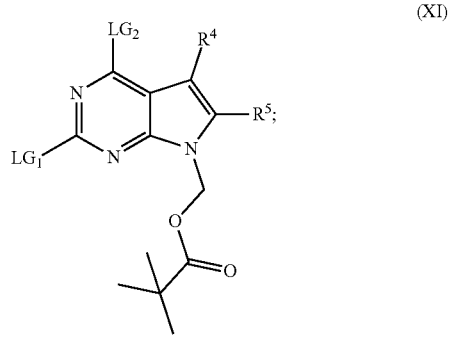

(XI)

(b) reacting a compound of Formula (XI) with a compound of Formula (XII):

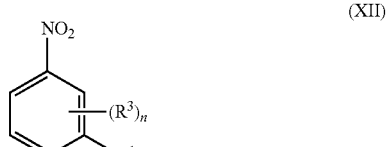

(XII)

wherein $X^1$, n, and $R^3$ are each as defined for Formula (I);

to form a compound of Formula (XIII):

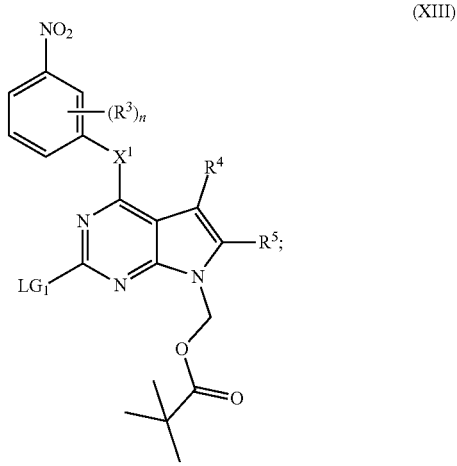

(XIII)

(c) coupling a compound of Formula (XIII) with a compound of Formula (XIV):

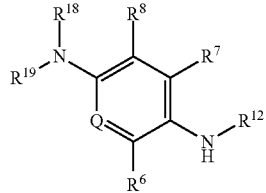
(XIV)

where $R^6$, $R^7$, $R^8$, $R^{12}$, $R^{18}$, $R^{19}$, and Q are each as defined for Formula (I);

to form a compound of Formula (XV):

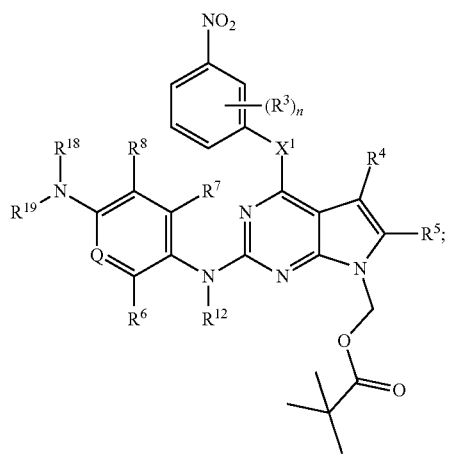
(XV)

(d) deprotecting the compound of Formula (XV) to form a compound of Formula (XVI):

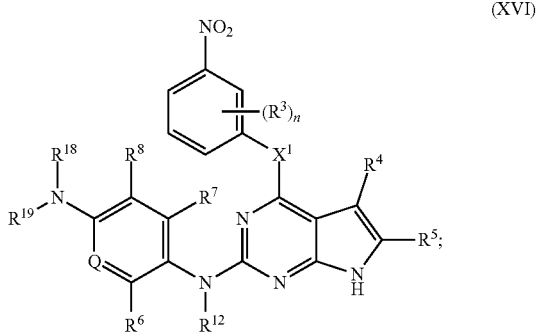
(XVI)

(e) reducing the compound of Formula (XVI) to form a compound of Formula (XVII):

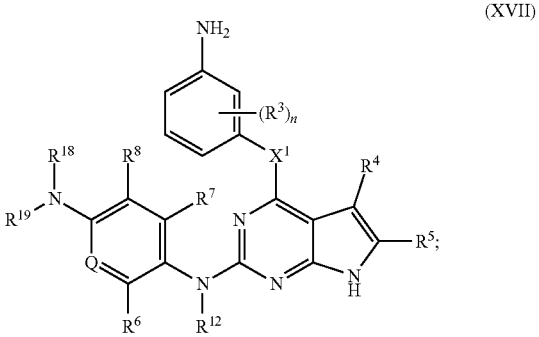
(XVII)

and (f) reacting the compound of Formula (XVII) with acryloyl chloride to form the compound of Formula (I).

In some embodiments, compounds of Formula (I) are synthesized as shown in Scheme A. In some embodiments, the compounds of Formula (I) are synthesized as a maleate salt thereof.

Scheme A

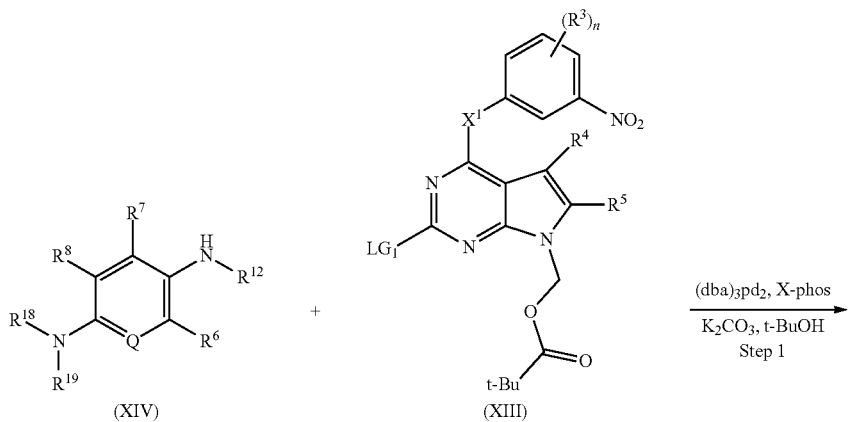

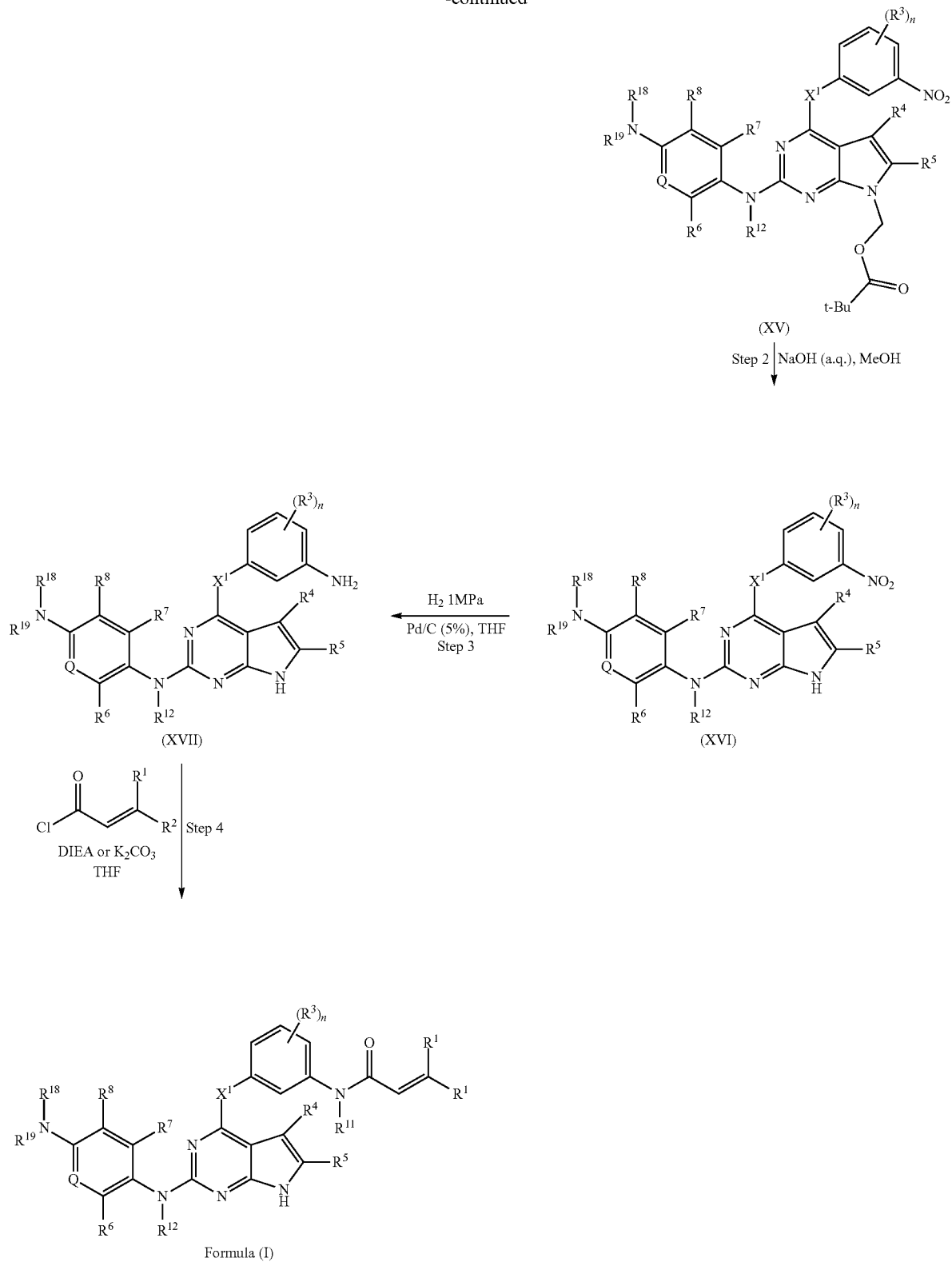
In some embodiments, the method of making a compound of Formula (I), or a pharmaceutically acceptable salt thereof, comprises:
(1) coupling a compound of Formula (XIII) with a compound of Formula (XIV) to form a compound of Formula (XV):

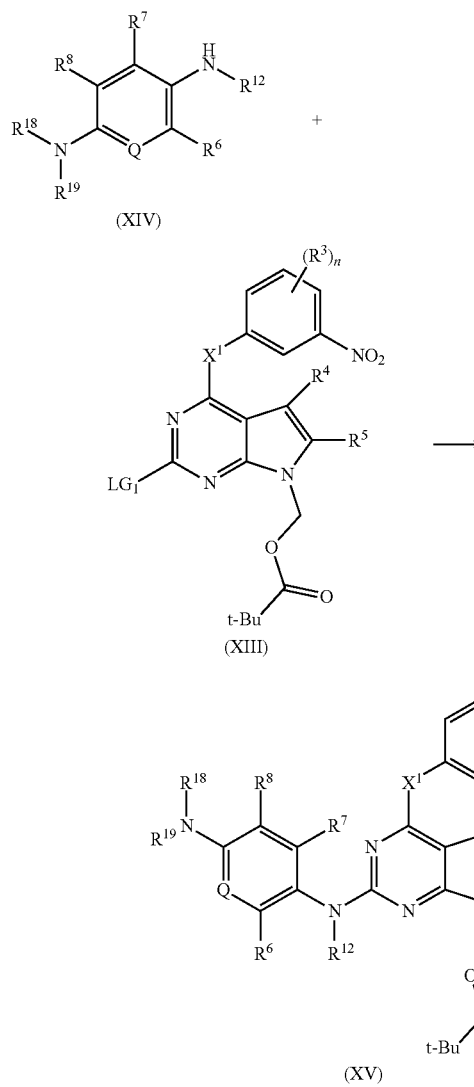

(XIV)

+

(XIII)

(XV)

wherein $X^1$ is O, NH, or S;

$R^3$ is halo, hydroxyl, $C_{1-6}$alkyl, $C_{1-6}$alkoxy, cyano, or nitro;

n is 0, 1, 2, 3, or 4;

$LG_1$ is a leaving group;

$R^4$ is hydrogen, $C_{1-6}$alkyl, $C_{3-7}$cycloalkyl, or $-NR^{22}R^{23}$;
 wherein the alkyl and cycloalkyl are unsubstituted or substituted with hydroxyl or amino; and
 $R^{22}$ and $R^{23}$ are each independently hydrogen or $C_{1-6}$alkyl; or $R^{22}$ and $R^{23}$ taken together with the nitrogen to which they are attached form a 3- to 10-membered heterocycloalkyl ring;

$R^5$ is hydrogen or $C_{1-6}$alkyl, $R^6$ and $R^7$ are each independently hydrogen, halo, $C_{1-6}$alkyl, $C_{1-6}$haloalkyl, $C_{2-6}$alkoxy, $C_{1-6}$haloalkoxy, hydroxyl, cyano, or nitro;

$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

$R^{12}$ is hydrogen or $C_{1-6}$alkyl;

Q is $CR^9$ or N;
 where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro; and $-NR^{18}R^{19}$ is:

(a)

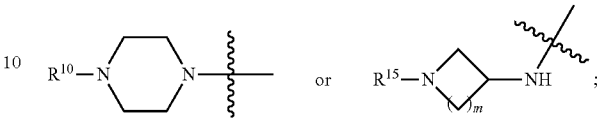

where $R^{10}$ is selected from hydrogen and $C_{1-6}$ alkyl;
$R^{15}$ is unsubstituted methyl, or is $C_{2-4}$alkyl unsubstituted or substituted with hydroxy, methoxy, or halo; and
m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring, (2) deprotecting the compound of Formula (XV) to form a compound of Formula (XVI):

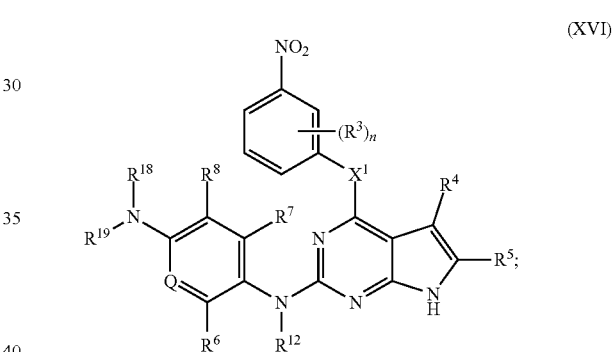

(XVI)

(3) reducing the compound of Formula (XVI) to form a compound of Formula (XVII):

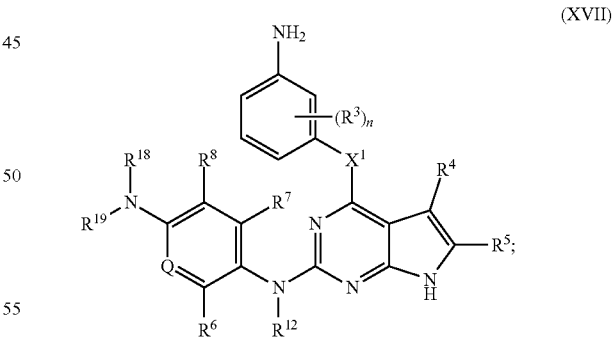

(XVII)

and (4) reacting the compound of Formula (XVII) with

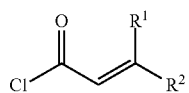

wherein $R^1$ and $R^2$ are each independently hydrogen, halo, $C_{1-6}$alkyl, or $C_{1-6}$haloalkyl, to form the compound of Formula (I)

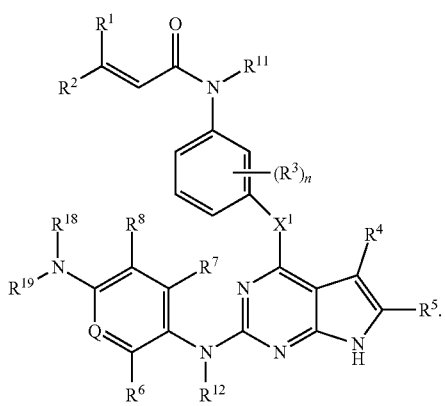

(I)

In some embodiments, step (1) is performed in the presence of a palladium catalyst. In some embodiments, step (1) is performed in the presence of tris(dibenzylideneacetone) dipalladium (Pd$_2$(dba)$_3$) and dicyclohexyl (2',4',6'-triisopropylbiphenyl-2-yl)phosphine (XPhos). In some embodiments, step (2) is performed in the presence of a base. In some embodiments, step (2) is performed in the presence of NaOH. In some embodiments, step (3) is performed in the presence of molecular hydrogen and a metal catalyst. In some embodiments, step (3) is performed in the presence of H$_2$ and Pd/C. In some embodiments, the compound of formula (XVII) from step (3) is used directly in step (4) without isolation. In some embodiments, step (4) is performed in the presence of a base. In some embodiments, step (4) is performed in the presence of DIEA. In some embodiments, step (4) is performed in the presence of K$_2$CO$_3$.

The methods described herein may further comprise the step of reacting a compound of Formula (I) with a pharmaceutically acceptable acid to form a pharmaceutically acceptable salt of a compound of Formula (I).

In some embodiments, the pharmaceutically acceptable salt of a compound of Formula (I) is selected from the group consisting of a maleate salt, a hydrochloride salt, a fumarate salt, a malate salt, a sulfate salt, a mesylate salt, a tosylate salt, and a hydrobromide salt.

In some embodiments, the compound of Formula (I) is reacted with maleic acid to form a maleic acid salt of a compound of Formula (I).

In some embodiments, the compound of Formula (I) or a pharmaceutically acceptable salt thereof is Compound 1, (Compound 1)

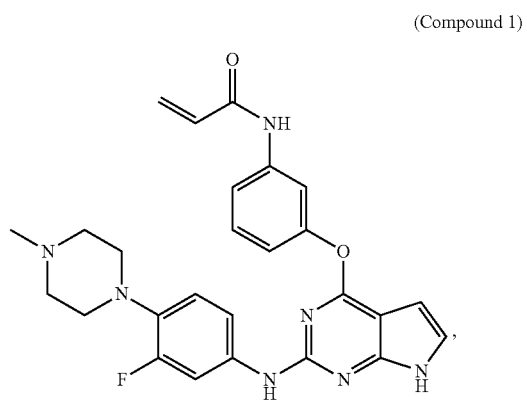 [SMILES: C=CC(=O)Nc1cccc(Oc2nc(Nc3ccc(N4CCN(C)CC4)c(F)c3)nc3[nH]ccc23)c1]

or a pharmaceutically acceptable salt thereof.

In some embodiments, the pharmaceutically acceptable salt of Compound 1 is selected from the group consisting of a maleate salt, a hydrochloride salt, a fumarate salt, a malate salt, a sulfate salt, a mesylate salt, a tosylate salt, and a hydrobromide salt. In some embodiments, the pharmaceutically acceptable salt of Compound 1 is a maleate salt.

Also contemplated are compounds of Formulae (X), (XI), (XII), (XIII), (XIV), (XV), (XVI), and (XVII), or salts thereof, which are useful as synthetic intermediates in the described methods.

Also contemplated are pharmaceutically acceptable salt forms of compounds described herein, such as compounds of Formula (I), and polymorphs or amorphous forms of such salts.

Also contemplated are pharmaceutical compositions comprising Compound 1:

(1)

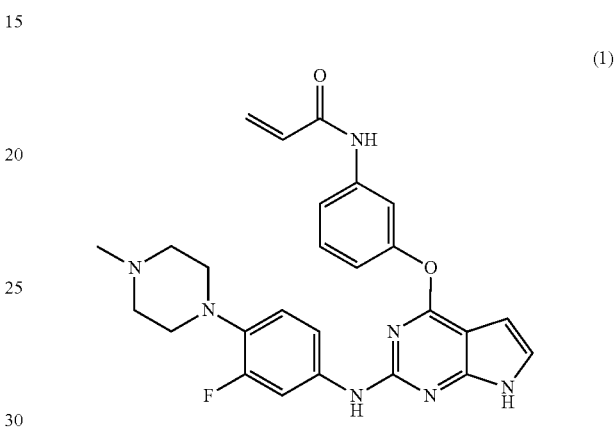

(chemical name: N-(3-((2-((3-fluoro-4-(4-methylpiperazin-1-yl)phenyl)amino)-7H-pyrrolo[2,3-d]pyrimidin-4-yl)oxy) phenyl)acrylamide) or a pharmaceutically acceptable salt thereof.

In another aspect are described methods of making and methods of manufacturing such pharmaceutical compositions into a dosage form, e.g., a solid oral formulation.

Provided herein are pharmaceutical compositions that comprise a compound of any of the formula described herein. In some embodiments, the pharmaceutical composition comprises a compound of Formula (I), or a pharmaceutically acceptable salt thereof, as described herein. In some embodiments, the pharmaceutical composition comprises Compound 1, or a pharmaceutically acceptable salt thereof. In some embodiments, the pharmaceutical composition comprises an adsorbing agent that reduces or eliminates formation of a dimer of the compound of Formula (I), or a pharmaceutically acceptable salt thereof. In some embodiments of the pharmaceutical composition, the components of the pharmaceutical composition are expressed as a percentage w/w of the total formulation. In some embodiments, the pharmaceutical composition comprises (1) at least two different types of adsorbing agents, wherein the pharmaceutical composition comprises from about 7% (w/w) to about 27% (w/w) of a first adsorbing agent and from about 45% (w/w) to about 65% (w/w) of a second adsorbing agent; (2) a disintegrating agent, wherein the pharmaceutical composition comprises from about 0.01% (w/w) to about 8.0% (w/w) of the disintegrating agent; and (3) a lubricant, wherein the pharmaceutical composition comprises from about 0.01% (w/w) to about 2.5% (w/w) of the lubricant. In some embodiments of the pharmaceutical composition, the percentage w/w of the components in the pharmaceutical composition is variable. In some embodiments of the pharmaceutical composition, the percentage w/w of the compound of Formula (I), or a pharmaceutically acceptable salt thereof (e.g., Compound 1, or a pharmaceutically acceptable salt thereof) is variable by up to ±20% w/w of the entire weight of the pharmaceutical composition. In some embodiments, each of the components of the pharmaceutical composition is variable by up to ±10% w/w of the entire weight of the pharmaceutical composition. In some embodiments, each of the adsorbing agents is variable by up to ±10% w/w of the entire weight of the pharmaceutical composition. In some embodiments, the disintegrating agent is variable by up to ±6% w/w of the entire weight of the pharmaceutical composition. In some embodiments, the lubricant is variable by up to ±2% w/w of the entire weight of the pharmaceutical composition. In some embodiments, the sum of the percent variation in each of the non-active components of the pharmaceutical composition is no more than 10% of the entire weight of the pharmaceutical composition. In some embodiments, the non-active components comprise at least two different types of adsorbing agents, a disintegrating agent, and a lubricant. In some embodiments, each of the components of the pharmaceutical composition is variable by up to ±10% w/w of the weight of each component. In some embodiments, each of the adsorbing agents is variable by up to ±10% w/w of the adsorbing agent. In some embodiments, the disintegrating agent is variable by up to ±6% w/w of the disintegrating agent. In some embodiments, the lubricant is variable by up to ±2% w/w of the lubricant.

In some embodiments, the pharmaceutical composition comprises (1) at least two different types of adsorbing agents, wherein the pharmaceutical composition comprises from about 15% (w/w) to about 20% (w/w) of a first adsorbing agent and from about 45% (w/w) to about 65% (w/w) of a second adsorbing agent; (2) a disintegrating agent, wherein the pharmaceutical composition comprises from about 1.5% (w/w) to about 2.5% (w/w) of the disintegrating agent; and (3) a lubricant, wherein the pharmaceutical composition comprises from about 0.1% (w/w) to about 1.0% (w/w) of the lubricant.

In some embodiments, the pharmaceutical composition comprises Compound 1. In some embodiments, the pharmaceutical composition comprises a pharmaceutically acceptable salt of Compound 1. In some embodiments, the pharmaceutically acceptable salt of Compound 1 is selected from the group consisting of a maleate salt, a hydrochloride salt, a fumarate salt, a malate salt, a sulfate salt, a mesylate salt, a tosylate salt, and a hydrobromide salt.

In some embodiments, the pharmaceutical composition comprises the maleate salt of Compound 1, wherein the maleate salt has polymorph Form I. In some embodiments, the maleate salt polymorph Form I is formed by crystallization from an aqueous solution comprising from about 1% (v/v) to about 90% (v/v) of ethanol, or about 100% (v/v) of ethyl acetate. In some embodiments, the maleate salt polymorph Form I is formed by crystallization from an aqueous solution comprising about 50% (v/v) of ethanol. In some embodiments, the pharmaceutical composition comprises the maleate salt of Compound 1, wherein the maleate salt has polymorph Form II. In some embodiments, the maleate salt polymorph Form II is formed by crystallization from about 100% (v/v) of methanol or ethanol. In some embodiments, the pharmaceutical composition comprises the maleate salt of Compound 1, wherein the maleate salt has polymorph Form III. In some embodiments, the maleate salt polymorph Form III is formed by crystallization from about 100% (v/v) of tetrahydrofuran. In some embodiments, the maleate salt of Compound 1 has an amorphous form. In some embodiments, the maleate salt amorphous form of Compound 1 is formed by drying or crystallization from about 100% (v/v) of acetone or acetonitrile.

In some embodiments, the pharmaceutical composition comprises the hydrochloride salt of Compound 1, wherein the hydrochloride salt has polymorph Form IV. In some embodiments, the hydrochloride salt polymorph Form IV is formed by crystallization from an aqueous solution comprising from about 0% (v/v) to about 60% (v/v) of ethanol.

In some embodiments, the pharmaceutical composition comprises the fumarate salt of Compound 1, wherein the fumarate salt has polymorph Form V. In some embodiments, the fumarate salt polymorph Form V is formed by crystallization from an aqueous solution comprising from about 0% (v/v) to about 60% (v/v) of ethanol.

In some embodiments, the pharmaceutical composition comprises the malate salt of Compound 1, wherein the malate salt has polymorph Form VI. In some embodiments, the malate salt polymorph Form VI is formed by crystallization from an aqueous solution comprising from about 0% (v/v) to about 60% (v/v) of ethanol.

In some embodiments, the pharmaceutical composition comprises the sulfate salt, mesylate salt, tosylate salt, or hydrobromide salt of Compound 1. In some embodiments, the sulfate salt, mesylate salt, tosylate salt, or hydrobromide salt of Compound 1 has an amorphous form.

In some embodiments, the pharmaceutical composition comprises at least two adsorbing agents, wherein the adsorbing agent reduces formation a dimer of Compound 1, or a pharmaceutically acceptable salt thereof. In some embodiments, the adsorbing agent eliminates formation of a dimer of Compound 1, or a pharmaceutically acceptable salt thereof. In some embodiments, the adsorbing agent is selected from the group consisting of acacia, alginic acid, croscarmellose, gelatin, gelatin hydrolysate, mannitol, maltose, frustose, Plasdone, povidone, sodium starch glycolate, sorbitol, sucrose, lactose, microcrystalline cellulose, silicified microcrystalline cellulose, croscarmellose sodium, dicalcium phosphate, carboxymethyl cellulose, hydroxypropyl cellulose, and polyethylene gylcol. In some embodiments, the adsorbing agent is silicified microcrystalline cellulose. In some embodiments, the pharmaceutical composition contains at least two different kinds of silicified microcrystalline cellulose. In some embodiments, the silicified microcrystalline cellulose is Prosolv® SMCC 50, Prosolv® SMCC 50 LD, Prosolv® SMCC 90, Prosolv® SMCC HD 90, or Prosolv® SMCC 90 LM. In some embodiments, the pharmaceutical composition contains from about 60% (w/w) to about 85% (w/w) of the adsorbing agents.

In some embodiments, the pharmaceutical composition contains Prosolv® SMCC 50 and Prosolv® SMCC 90. In some embodiments, the pharmaceutical composition contains from about 15% (w/w) to about 20% (w/w) of Prosolv® SMCC 50, and from about 45% (w/w) to about 65% (w/w) of Prosolv® SMCC 90.

In some embodiments, the pharmaceutical composition further contains one or more pharmaceutically acceptable additives. In some embodiments, the one or more pharmaceutically acceptable additives do not enhance formation of a dimer of the compound of Formula I or Compound 1, or a pharmaceutically acceptable salt thereof. In some embodiments, the one or more pharmaceutically acceptable additives is selected from the group consisting of a diluent, a binder, a vehicle, a carrier, an excipient, a disintegrating agent, a lubricant, a swelling agent, a solubilizing agent, a wicking agent, a cooling agent, a preservative, a stabilizer, a sweetener, a flavor, and a polymer. In some embodiments, the disintegrating agent is cross-linked sodium carboxymethylcellulose, croscarmellose sodium, crospovidone, or a mixture thereof. In some embodiments, the lubricant is magnesium stearate, stearic acid and its pharmaceutically acceptable alkali metal salt, sodium stearyl fumarate, Macrogol 6000, glyceryl behenate, colloidal silicon dioxide, calcium stearate, sodium stearate, Cab-O-Sil, Syloid, sodium lauryl sulfate, sodium chloride, magnesium lauryl sulfate, talc, or a mixture thereof.

In some embodiments, the pharmaceutical composition contains a disintegrating agent, and the disintegrating agent is cross-linked sodium carboxymethylcellulose or croscarmellose sodium. In some embodiments, the pharmaceutical composition contains from about 1.5% (w/w) to about 2.5% (w/w) of croscarmellose sodium.

In some embodiments, the pharmaceutical composition contains a lubricant, and the lubricant is sodium stearyl fumarate. In some embodiments, the pharmaceutical composition contains from about 0.1% (w/w) to about 1.0% (w/w) of sodium stearyl fumarate.

In some embodiments, the pharmaceutical composition is formulated for an oral dosage form, e.g., a solid oral dosage form. In some embodiments, the oral dosage form is an oral powder, a granule, a pellet, a tablet, a capsule, a troch, or a lozenge. In some embodiments, the tablet is a chewable tablet, a dispersible tablet, or a troch. In some embodiments, the pharmaceutical composition is formulated to contain a single dose or multiple doses.

In some embodiments, the pharmaceutical composition contains from about 0.001% (w/w) to about 1% (w/w) of a dimer of Compound 1, or a pharmaceutically acceptable salt thereof, after a stability test for about 10 days, or about 1 month, or about 2 months, or about 3 months, or about 6 months, or about 12 months, or about 18 months, or about 24 months. In some embodiments, the stability test is conducted at ambient temperature, or at a temperature of about 25° C., or at a temperature greater than about 25° C., or at a temperature of about 50° C., or about 60° C., or between about 50° C. to about 70° C., and/or under relative humidity conditions of about 50%, or about 60%, or about 70%, or greater than about 70%, and/or under exposure to light, e.g., visible light.

In some embodiments of the pharmaceutical compositions described herein, the pharmaceutical composition comprises excipients and pharmaceutically acceptable additive(s) as described herein. Exemplary adsorbing agents include, but are not limited to, acacia, bentonite, alginic acid, cellulose derivatives, croscarmellose, gelatin, gelatin hydrolysate, mannitol, maltose, fructose, plasdone, povidone, sodium starch glycolate, sorbitol, sucrose, lactose, microcrystalline cellulose, silicified microcrystalline cellulose, croscarmellose sodium, dicalcium phosphate, carboxymethyl cellulose, hydroxypropyl cellulose, and polyethylene glycol (particularly in spray dried formulations). Suitable additives include, but are not limited to, diluents, binders, vehicles, carriers, excipients, binders, disintegrating agents, lubricants, swelling agents, solubilizing agents, wicking agents, cooling agents, preservatives, stabilizers, sweeteners, flavors, and polymers. In some embodiments, the pharmaceutical composition comprises at least two different types of adsorbing agents. In some embodiments, the pharmaceutical composition comprises about 17% w/w±10% w/w of the first adsorbing agent, wherein the % w/w is based on the entire weight of the pharmaceutical composition. In some embodiments, the first adsorbing agent is Prosolv® SMCC 50. In some embodiments, the pharmaceutical composition comprises about 55% w/w±10% w/w of the second adsorbing agent, wherein the % w/w is based on the entire weight of the pharmaceutical composition. In some embodiments, the second adsorbing agent is Prosolv® SMCC 90. In some embodiments, the pharmaceutical composition comprises about 2.0% w/w±6% w/w of the disintegrating agent, wherein the % w/w is based on the entire weight of the pharmaceutical composition. In some embodiments, the disintegrating agent is croscarmellose sodium. In some embodiments, the pharmaceutical composition comprises about 0.5% w/w±2% w/w of the lubricant, wherein the % w/w is based on the entire weight of the pharmaceutical composition. In some embodiments, the lubricant is sodium stearyl fumarate. In some embodiments, the total additive effect of the changes in the percentage of all excipients in the pharmaceutical composition is no more than 10%. In some embodiments, the sum of the variation in the % w/w for the at least two different types of adsorbing agents, the disintegrating agent, and the lubricant is no more than 10% w/w of the entire weight of the pharmaceutical composition. In some embodiments, the excipients comprise at least two different types of adsorbing agents and one or more pharmaceutically acceptable additives. In some embodiments, the excipients comprise at least two different types of adsorbing agents, a disintegrating agent, and a lubricant. In some embodiments, the sum of the variation in the % w/w for the at least two different types of adsorbing agents, the disintegrating agent, and the lubricant is no more than 10%.

In some embodiments of the pharmaceutical compositions described herein, the pharmaceutical composition comprises about 20% (w/w) to about 30% (w/w) of the compound of Formula (I), or a pharmaceutically acceptable salt thereof, wherein the % w/w is based on the entire weight of the pharmaceutical composition. In some embodiments, the compound of Formula (I) is Compound 1, or a pharmaceutically acceptable salt thereof. In some embodiments, the compound of Formula (I) is Compound 1, or a pharmaceutically acceptable salt thereof, such as a maleate salt, a hydrochloride salt, a fumarate salt, a malate salt, a sulfate salt, a mesylate salt, a tosylate salt, or a hydrobromide salt. In some embodiments, the compound of Formula (I) is Compound 1, or a maleate salt of Compound 1.

In some embodiments of the pharmaceutical compositions described herein, the pharmaceutical composition comprises about 25 mg, about 50 mg, about 100 mg, about 150 mg, about 200 mg, about 250 mg, about 300 mg, about 350 mg, about 400 mg, about 450 mg, or about 500 mg of the free base equivalent of the compound of Formula (I), or a pharmaceutically acceptable salt thereof. In some embodiments, the compound of Formula (I) is Compound 1, or a pharmaceutically acceptable salt thereof. In some embodiments, the compound of Formula (I) is Compound 1, or a pharmaceutically acceptable salt thereof, such as a maleate salt, a hydrochloride salt, a fumarate salt, a malate salt, a sulfate salt, a mesylate salt, a tosylate salt, or a hydrobromide salt. In some embodiments, the compound of Formula (I) is Compound 1, or a maleate salt of Compound 1.

Provided herein are processes for preparing a pharmaceutical composition containing a compound of Formula (I) or Compound 1, or a pharmaceutically acceptable salt thereof, wherein the process includes:

1) combining Compound 1, or a pharmaceutically acceptable salt thereof, with the adsorbing agent to form a first mixture; and
2) formulating the first mixture into a dosage form.

In some embodiments of the process, Compound 1, or a pharmaceutically acceptable salt thereof, and the adsorbing agent are combined in a single step to form the first mixture. In some embodiments, Compound 1, or a pharmaceutically acceptable salt thereof, and the adsorbing agent are combined in multiple steps to form the first mixture.

In some embodiments of the process, Compound 1, or a pharmaceutically acceptable salt thereof, is combined with a single adsorbing agent to form the first mixture. In some embodiments, Compound 1, or a pharmaceutically acceptable salt thereof, is combined with multiple adsorbing agents to form the first mixture. In some embodiments, the multiple adsorbing agents comprise at least two different kinds of silicified microcrystalline cellulose. In some embodiments of the process, the at least two different kinds of silicified microcrystalline cellulose comprise Prosolv® SMCC 50 and Prosolv® SMCC 90.

In some embodiments of the process, Compound 1, or a pharmaceutically acceptable salt thereof, are combined with multiple different adsorbing agents sequentially. In some embodiments, the multiple different adsorbing agents comprise at least two different kinds of silicified microcrystalline cellulose. In some embodiments, the at least two different kinds of silicified microcrystalline cellulose comprise Prosolv® SMCC 50 and Prosolv® SMCC 90. In some embodiments, Compound 1, or a pharmaceutically acceptable salt thereof, is combined with Prosolv® SMCC 50 in a first step, and then combined with Prosolv® SMCC 90 in a second step.

In some embodiments, Compound 1, or a pharmaceutically acceptable salt thereof, and the adsorbing agent(s) are combined in one or more blending steps to form a first mixture. In some embodiments, the first mixture is formulated into a dosage form in the presence of one or more pharmaceutically acceptable additives. In some embodiments, the one or more pharmaceutically acceptable additives contains a disintegrating agent and a lubricant. In some embodiments, the disintegrating agent is cross-linked sodium carboxymethylcellulose or croscarmellose sodium, and the lubricant is sodium stearyl fumarate. In some embodiments, the first mixture is formulated into an oral dosage form, e.g., a solid oral dosage form.

In some embodiments, the process for preparing a pharmaceutical composition containing a compound of Formula (I) or Compound 1, or a pharmaceutically acceptable salt thereof, is a dry blend process, a roller compaction process, or a direct compression process. In some embodiments, the dry blend process comprises a pre-blending step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and filling the first mixture with a disintegrating agent, e.g., croscarmellose sodium and a lubricant, e.g., sodium stearyl fumarate, into a capsule. In some embodiments, the roller compaction process comprises a pre-blending roller compaction step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and filling the first mixture with a disintegrating agent, e.g., croscarmellose sodium, and a lubricant, e.g., sodium stearyl fumarate, into a capsule.

In some embodiments, the roller compaction process comprises a pre-blending roller compaction step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and mixing the first mixture with a disintegrating agent, e.g., croscarmellose sodium, and a lubricant, e.g., sodium stearyl fumarate, to form a tablet. In some embodiments, the direct compression process comprises a pre-blending step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and mixing the first mixture with a disintegrating agent, e.g., croscarmellose sodium, and a lubricant, e.g., sodium stearyl fumarate, to form a tablet.

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION OF THE INVENTION

Figure 1:
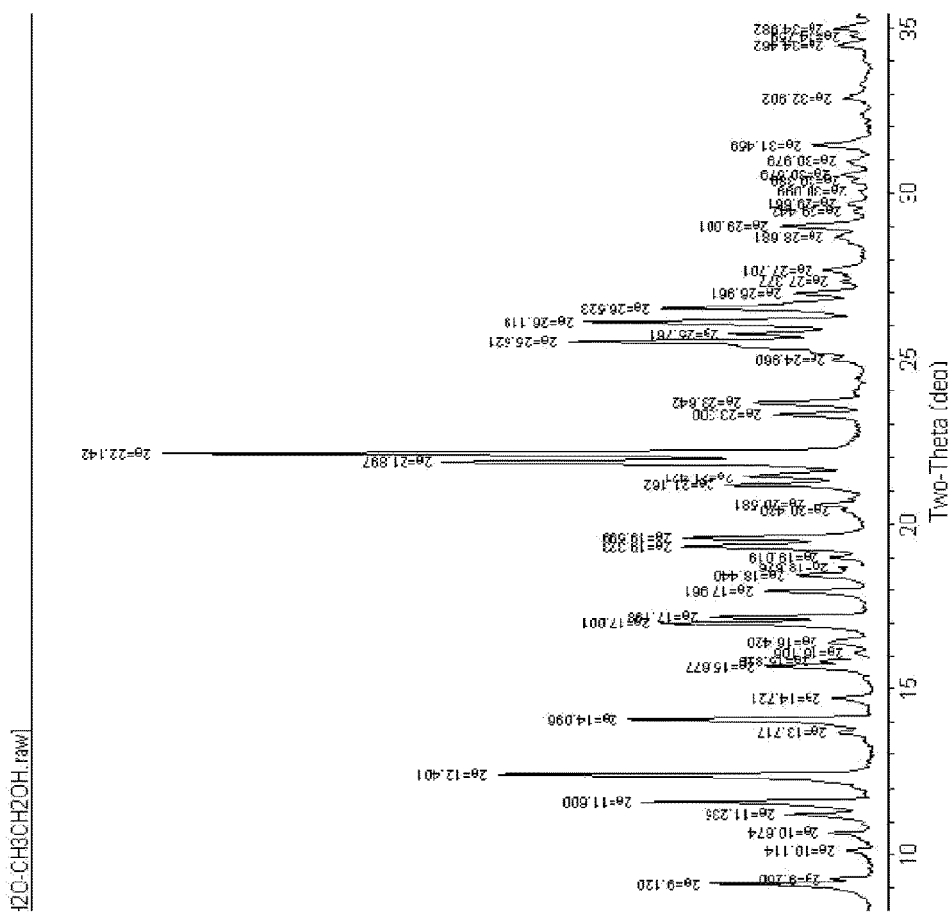
FIG. 1 is an X-ray powder diffractogram of polymorph Form I maleate salt obtained from 1:1 ethanol/$H_2O$.

The present invention is directed to methods of making certain pyrrolopyrimidine derivatives, which are useful in pharmaceutical compositions and in methods of treating proliferation disorders. The compounds as described herein exhibit anti-tumor, anticancer, anti-inflammation, anti-infectious, and anti-proliferation activity. Biological activity of these compounds is described, for example, in PCT Publ. No. WO2014/025486.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Chemical Terms

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an alkyl group as defined above, bonded to an oxygen atom. The alkoxy group is connected to the parent structure via the oxygen atom.

The term "amino" refers to an —NH$_2$ group, or a mono- or dialkylamino group.

The term "cycloalkyl" refers to a saturated or partially saturated, monocyclic, fused polycyclic, bridged polycyclic, or spiro polycyclic carbocycle having from 3 to 12 ring atoms per carbocycle. Illustrative examples of cycloalkyl groups include the following entities, in the form of properly bonded moieties:

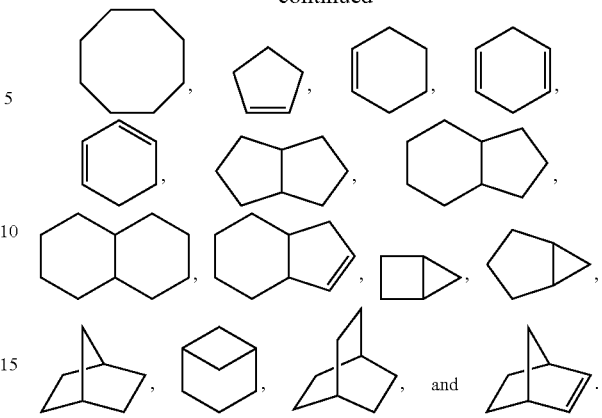

-continued

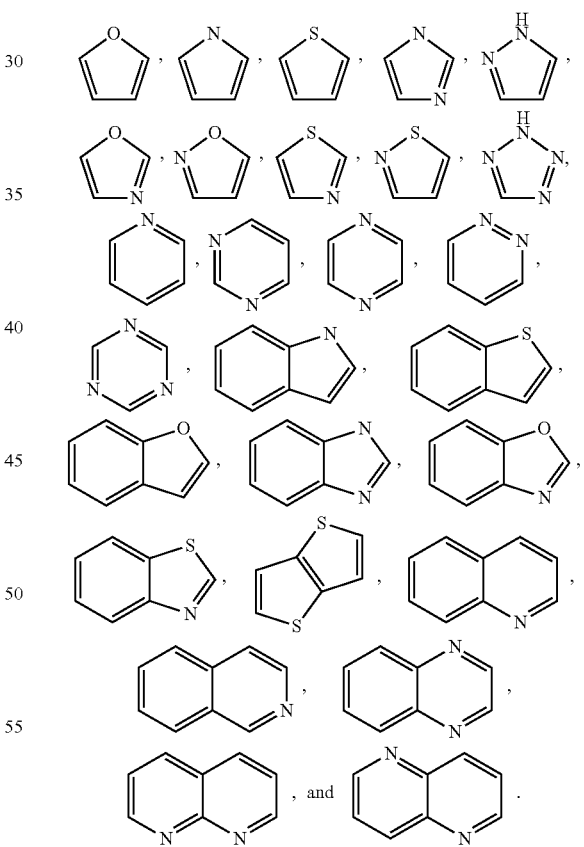

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

The term "halogen" represents chlorine, fluorine, bromine, or iodine. The term "halo" represents chloro, fluoro, bromo, or iodo. The term "haloalkyl" means an alkyl as defined above, substituted with one or more halogen atoms. The term "haloalkoxy" means an alkoxy as defined above, substituted with one or more halogen atoms.

The term "acyl" refers to a group R—C(O)— where R is from 1 to 10 carbon atoms ($C_{1-10}$) of a straight, branched, or cyclic configuration or a combination thereof, attached to the parent structure through carbonyl functionality. Such R group may be saturated or unsaturated, and aliphatic or aromatic.

The term "cyano" refers to the group —CN.
The term "nitro" refers to the group —$NO_2$.
The term "hydroxyl" refers to the group —OH.

Those skilled in the art will recognize that the species listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically-labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically-labeled compounds of the embodiments and prodrugs thereof can generally be prepared by carrying out the procedures disclosed in the schemes or in the examples and preparations described below by substituting a readily available isotopically-labeled reagent for a non-isotopically-labeled reagent.

The nomenclature "$C_{i-j}$" with j>i, when applied herein to a class of substituents, is meant to refer to embodiments for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, 7-hydroxybutyrates, glycolates, tartrates, and mandelates.

For a compound described herein that contains a basic nitrogen, a pharmaceutically acceptable salt may be prepared by any suitable method available in the art, for example treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology. In certain embodiments, the pharmaceutically acceptable salt is the HCl salt, maleic acid salt, HBr salt, hydroxybutanedioic acid salt, fumaric acid salt, lactic acid salt, tartaric acid salt, or methanesulfonic acid salt.

Representative Embodiments
Formula (I)

In some embodiments of Formula (I), $X^1$ is O, NH, or S. In other embodiments, $X^1$ is O. In other embodiments, $X^1$ is NH. In other embodiments, $X^1$ is S.

In some embodiments, $R^1$ and $R^2$ are each independently hydrogen, halo, $C_{1-6}$alkyl, or $C_{1-6}$haloalkyl. In certain instances, $R^1$ is hydrogen. In certain instances, $R^1$ is $C_{1-6}$alkyl. In certain instances, $R^1$ is methyl or ethyl. In certain instances, $R^2$ is hydrogen. In certain instances, $R^2$ is $C_{1-6}$alkyl. In certain instances, $R^2$ is methyl or ethyl. In certain instances, $R^1$ and $R^2$ are each hydrogen.

In Formula (I), n is 0, 1, 2, 3, or 4. In certain instances, n is zero. In certain instances, n is 1. In certain instances, n is 2. In certain instances, n is 3. In certain instances, n is 4.

In Formula (I), $R^3$ is halo, hydroxyl, $C_{1-6}$alkyl, $C_{1-6}$alkoxy, cyano, or nitro. In certain instances, $R^3$ is halo. In certain instances, $R^3$ is hydroxyl. In certain instances, $R^3$ is $C_{1-6}$alkyl. In certain instances, $R^3$ is $C_{1-6}$alkoxy. In certain instances, $R^3$ is cyano. In certain instances, $R^3$ is nitro.

In Formula (I), $R^4$ is hydrogen, $C_{1-6}$alkyl, $C_{3-7}$cycloalkyl, or $-NR^{22}R^{23}$; wherein the alkyl and cycloalkyl are unsubstituted or substituted with hydroxyl or amino; and wherein $R^{22}$ and $R^{23}$ are each independently hydrogen or $C_{1-6}$ alkyl; or $R^{22}$ and $R^{23}$ taken together with the nitrogen to which they are attached form a 3- to 10-membered heterocycloalkyl ring. In certain instances, $R^4$ is hydrogen. In certain instances, $R^4$ is $C_{1-6}$alkyl. In certain instances, $R^4$ is $C_{3-7}$cycloalkyl. In certain instances, $R^4$ is $-NR^{22}R^{23}$.

In certain instances, $R^4$ is unsubstituted $C_{1-6}$alkyl. In certain instances, $R^4$ is $C_{1-6}$alkyl that is substituted with hydroxyl. In certain instances, $R^4$ is $C_{1-3}$alkyl that is substituted with hydroxyl. In certain instances, $R^4$ is $C_{1-6}$alkyl that is substituted with amino. In certain instances, $R^4$ is $C_{1-6}$alkyl that is substituted with $-NH_2$. In certain instances, $R^4$ is $C_{1-6}$alkyl that is substituted with $-N(CH_3)_2$. In certain instances, $R^4$ is $C_{1-3}$alkyl that is substituted with $-NH_2$. In certain instances, $R^4$ is $C_{1-3}$alkyl that is substituted with $-N(CH_3)_2$.

In certain instances, $R^4$ is unsubstituted $C_{3-7}$cycloalkyl. In certain instances, $R^4$ is unsubstituted $C_3$cycloalkyl. In certain instances, $R^4$ is unsubstituted $C_4$cycloalkyl. In certain instances, $R^4$ is unsubstituted $C_{5-6}$cycloalkyl. In certain instances, $R^4$ is unsubstituted $C_7$cycloalkyl.

In certain instances, $R^4$ is $-NR^{22}R^{23}$, wherein $R^{22}$ and $R^{23}$ are each independently hydrogen or $C_{1-6}$ alkyl; or $R^{22}$ and $R^{23}$ taken together with the nitrogen to which they are attached form a 3- to 10-membered heterocycloalkyl ring. In certain instances, $R^{22}$ and $R^{23}$ are each hydrogen. In certain instances, $R^{22}$ and $R^{23}$ are each $C_{1-6}$alkyl. In certain instances, $R^{22}$ and $R^{23}$ are each $C_{1-3}$alkyl. In certain instances, $R^{22}$ and $R^{23}$ are each methyl.

In certain instances, $R^{22}$ and $R^{23}$ are taken together with the nitrogen to which they are attached to form a 3- to 10-membered heterocycloalkyl ring, such that $R^4$ is

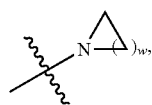

where w is a number from 1 to 8. In certain instances, $R^{22}$ and $R^{23}$ are taken together with the nitrogen to which they are attached to form a 3-, 4-, 5-, or 6-membered ring.

In Formula (I), $R^5$ is hydrogen or $C_{1-6}$alkyl. In certain instances, $R^5$ is hydrogen. In certain instances, $R^5$ is $C_{1-6}$alkyl. In certain instances, $R^5$ is methyl. In certain instances, $R^5$ is ethyl. In certain instances, $R^5$ is $C_{1-3}$alkyl. In certain instances, $R^5$ is $C_{4-6}$alkyl.

In Formula (I), $R^6$ and $R^7$ are each independently hydrogen, halo, $C_{1-6}$ alkyl, $C_{1-6}$ haloalkyl, $C_{2-6}$ alkoxy, $C_{1-6}$ haloalkoxy, hydroxyl, cyano, or nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$alkyl. In certain instances, $R^6$ is $C_{1-6}$haloalkyl. In certain instances, $R^6$ is $C_{2-6}$alkoxy. In certain instances, $R^6$ is $C_{1-6}$haloalkoxy. In certain instances, $R^6$ is hydroxyl. In certain instances, $R^6$ is cyano. In certain instances, $R^6$ is nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$alkyl. In certain instances, $R^7$ is $C_{1-6}$haloalkyl. In certain instances, $R^7$ is $C_{2-6}$alkoxy. In certain instances, $R^7$ is $C_{1-6}$haloalkoxy. In certain instances, $R^7$ is hydroxyl. In certain instances, $R^7$ is cyano. In certain instances, $R^7$ is nitro.

In Formula (I), $R^8$ is hydrogen, halo, $C_{1-6}$ alkyl, $C_{1-6}$ haloalkyl, $C_{1-6}$ alkoxy, $C_{1-6}$ haloalkoxy, hydroxyl, cyano, or nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$alkyl. In certain instances, $R^8$ is $C_{1-6}$haloalkyl. In certain instances, $R^8$ is $C_{1-6}$alkoxy. In certain instances, $R^8$ is $C_{1-6}$haloalkoxy. In certain instances, $R^8$ is hydroxyl. In certain instances, $R^8$ is cyano. In certain instances, $R^8$ is nitro.

In Formula (I), $R^{11}$ is selected from hydrogen and $C_{1-6}$ alkyl. In certain instances, $R^{11}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (I), $R^{12}$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (I), Q is $CR^9$ or N. In certain instances, Q is $CR^9$. In certain instances, Q is N.

In Formula (I), $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$alkyl. In certain instances, $R^9$ is $C_{1-6}$haloalkyl. In certain instances, $R^9$ is $C_{1-6}$alkoxy. In certain instances, $R^9$ is $C_{1-6}$haloalkoxy. In certain instances, $R^9$ is hydroxyl. In certain instances, $R^9$ is cyano. In certain instances, $R^9$ is nitro. In certain instances, $R^9$ is hydrogen or fluoro.

In Formula (I), $-NR^{18}R^{19}$ is:

(a)

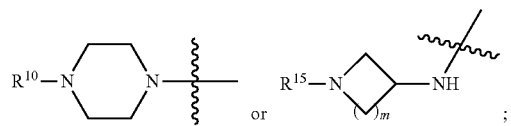

wherein $R^{10}$ is selected from hydrogen and $C_{1-6}$ alkyl;
$R^{15}$ is unsubstituted methyl, or is $C_{2-4}$alkyl unsubstituted or substituted with hydroxy, methoxy, or halo; and m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring.

In certain instances $-NR^{18}R^{19}$ is:

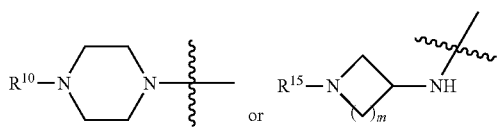

In certain instances, $-NR^{18}R^{19}$ is

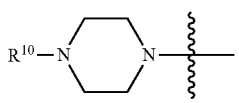

In certain instances, $-NR^{18}R^{19}$ is

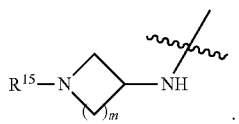

In Formula (I), $R^{10}$ is hydrogen or $C_{1-6}$alkyl. In certain instances, $R^{10}$ is hydrogen. In certain instances, $R^{10}$ is $C_{1-6}$alkyl. In certain instances, $R^{10}$ is methyl. In certain instances, $R^{10}$ is ethyl. In certain instances, $R^{10}$ is $C_{1-3}$alkyl. In certain instances, $R^{10}$ is $C_{4-6}$ alkyl.

In certain instances, $R^{15}$ is methyl, hydroxyethyl, methoxyethyl, or fluoroethyl. In other embodiments, $R^{15}$ is fluoroethyl. In some embodiments, m is 1. In other embodiments, m is 2.

In Formula (I), $-NR^{18}R^{19}$ is defined as follows: $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl, or the alkyl is substituted with amino; and $R^{18}$ is hydrogen or $C_{1-6}$alkyl, where the alkyl is unsubstituted or substituted with amino, or $R^{18}$ is absent to satisfy valency of the heteroaryl ring. In some embodiments, the heteroaryl ring is substituted with dimethylaminomethyl or piperidinylmethyl. In other embodiments, $R^9$ and $R^{19}$ taken together form optionally substituted pyrrole or pyridine. In some instances, $R^{18}$ is dimethylaminoethyl.

In certain instances, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro.

In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl.

In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen.

In certain instances, $R^6$, $R^7$, $R^8$, and $R^9$ are hydrogen and $R^{13}$ is $-CH_2OH$. In certain instances, $R^6$, $R^7$, and $R^8$ are hydrogen; $R^9$ is halo; and $R^{13}$ is $-CH_2OH$. In certain instances, $R^6$, $R^7$, and $R^8$ are hydrogen; $R^9$ is fluoro; and $R^{13}$ is $-CH_2OH$.

In certain instances, $R^6$, $R^7$, $R^8$, and $R^9$ are hydrogen and $R^{13}$ is $-(CH_2)_mF$, wherein m is a number from one to 3. In certain instances, $R^6$, $R^7$, and $R^8$ are hydrogen; $R^9$ is halo; and $R^{13}$ is $-(CH_2)_mF$, wherein m is a number from one to 3. In certain instances, $R^6$, $R^7$, and $R^8$ are hydrogen; $R^9$ is fluoro; and $R^{13}$ is $-(CH_2)_mF$, wherein m is a number from one to 3.

Formula (II)

The present disclosure is directed to methods of making a compound of Formula (II):

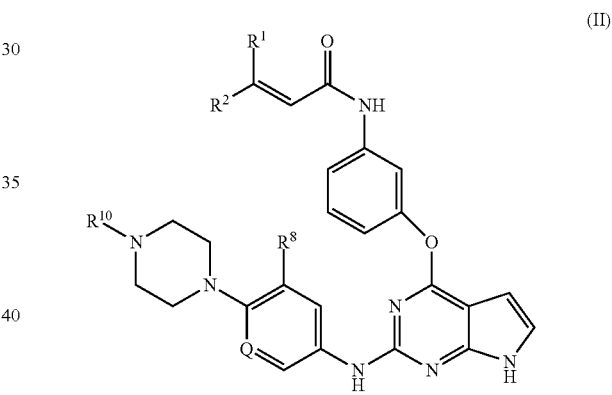

wherein $R^1$ and $R^2$ are each independently hydrogen, halo, $C_{1-6}$alkyl, or $C_{1-6}$haloalkyl;

$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

Q is $CR^9$ or N;

where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro; and $R^{10}$ is hydrogen or $C_{1-6}$alkyl;

or a pharmaceutically acceptable salt thereof.

In some embodiments of Formula (II), $R^1$ and $R^2$ are each hydrogen. In other embodiments, $R^8$ is halo, methyl, methoxy, or cyano. In still other embodiments, $R^8$ is halo. In still other embodiments, $R^8$ is fluoro. In some embodiments, $R^{10}$ is methyl, ethyl, or isopropyl. In other embodiments, $R^{10}$ is methyl.

Formula (III)

The present disclosure provides methods of making a compound of Formula (III):

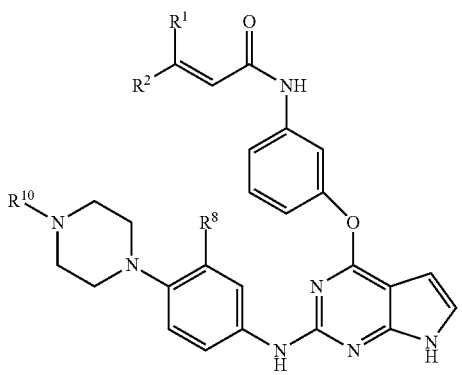

(III)

wherein
R¹ and R² are each independently hydrogen, halo, $C_{1-6}$alkyl, or $C_{1-6}$haloalkyl;
R⁸ is halo, $C_{1-6}$alkyl, $C_{1-6}$haloalkyl, $C_{1-6}$alkoxy, $C_{1-6}$haloalkoxy, hydroxyl, cyano, or nitro; and
R¹⁰ is $C_{1-6}$alkyl;
or a pharmaceutically acceptable salt thereof.

In some embodiments of Formula (III), R¹ and R² are each hydrogen. In other embodiments, R⁸ is halo, methyl, methoxy, or cyano. In still other embodiments, R⁸ is halo. In still other embodiments, R⁸ is fluoro. In some embodiments, R¹⁰ is methyl, ethyl, or isopropyl. In other embodiments, R¹⁰ is methyl.

In some embodiments of compounds of Formula (I), R⁶ and R⁷ may also be methoxy. In other embodiments, R⁶ and R⁷ may also be methoxy, provided that neither R⁶ nor R⁷ is methoxy when R¹⁰ is methyl. In some embodiments, R⁶ is methoxy. In other embodiments, R⁷ is methoxy. In certain instances, R⁷ is hydrogen or methoxy.

In other embodiments of Formula (II) or (III), the

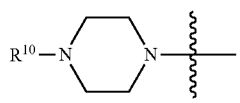

group is replaced with

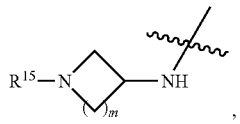

where m and R¹⁵ are as defined herein.

In certain embodiments, the present disclosure is directed to methods of making a compound selected from the compounds in Table 1, and pharmaceutically acceptable salts thereof.

TABLE 1

| Compound | Structure | Chemical Name |
|---|---|---|
| 1 | ![structure] | N-(3-((2-((3-fluoro-4-(4-methylpiperazin-1-yl)phenyl)amino)-7H-pyrrolo[2,3-d]pyrimidin-4-yl)oxy)phenyl)acrylamide |
| 2 | ![structure] | N-(3-((2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
|---|---|---|
| 3 | 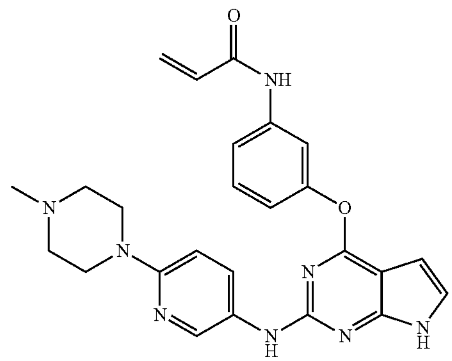 [SMILES: C=CC(=O)Nc1cccc(Oc2nc(Nc3ccc(N4CCN(C)CC4)nc3)nc3[nH]ccc23)c1] | N-(3-((2-((6-(4-methylpiperazin-1-yl)pyridin-3-yl)amino)-7H-pyrrolo[2,3-d]pyrimidin-4-yl)oxy)phenyl)acrylamide |
| 4 | 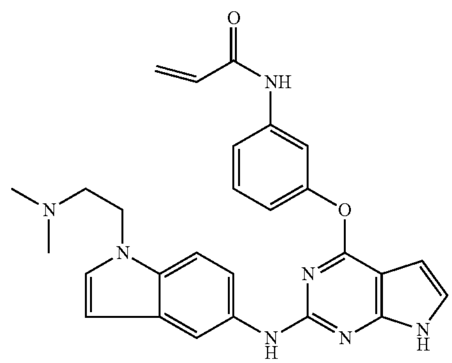 [SMILES: C=CC(=O)Nc1cccc(Oc2nc(Nc3ccc4c(ccn4CCN(C)C)c3)nc3[nH]ccc23)c1] | N-(3-((2-((1-(2-(dimethylamino)ethyl)-1H-indol-5-yl)amino)-7H-pyrrolo[2,3-d]pyrimidin-4-yl)oxy)phenyl)acrylamide |
| 5 | 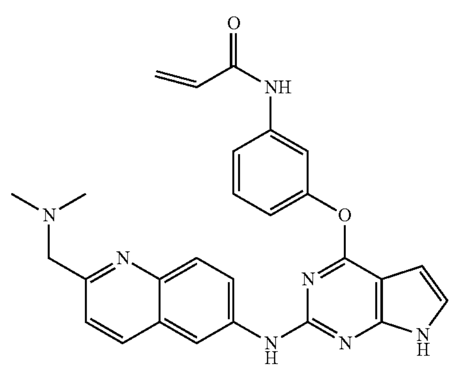 [SMILES: C=CC(=O)Nc1cccc(Oc2nc(Nc3ccc4nc(CN(C)C)ccc4c3)nc3[nH]ccc23)c1] | N-(3-((2-((2-((dimethylamino)methyl)quinolin-6-yl)amino)-7H-pyrrolo[2,3-d]pyrimidin-4-yl)oxy)phenyl)acrylamide |
| 6 | 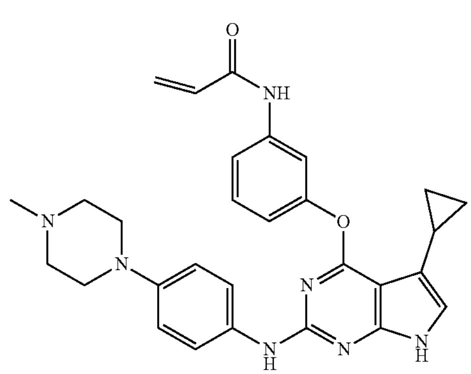 [SMILES: C=CC(=O)Nc1cccc(Oc2nc(Nc3ccc(N4CCN(C)CC4)cc3)nc3[nH]cc(C4CC4)c23)c1] | N-(3-((5-cyclopropyl-2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
|---|---|---|
| 7 | 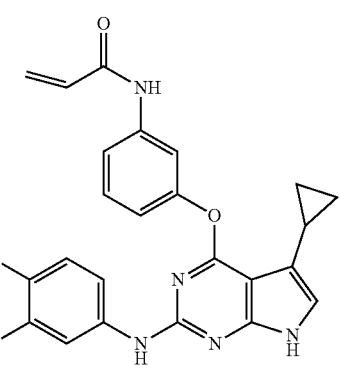 | N-(3-((5-cyclopropyl-2-((3-fluoro-4-(4-methylpiperazin-1-yl)phenyl)amino)-7H-pyrrolo[2,3-d]pyrimidin-4-yl)oxy)phenyl)acrylamide |
| 8 | 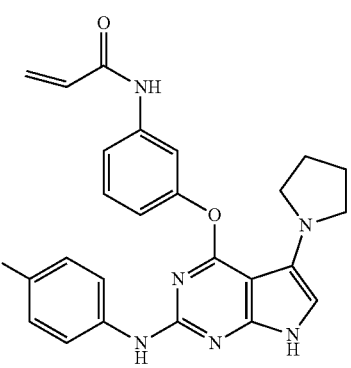 | N-(3-((2-((4-(4-methylpiperazin-1-yl)phenyl)amino)-5-(pyrrolidin-1-yl)-7H-pyrrolo[2,3-d]pyrimidin-4-yl)oxy)phenyl)acrylamide |
| 9 | 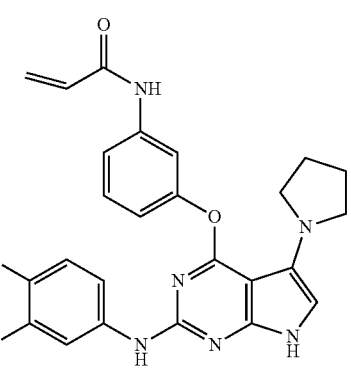 | N-(3-((2-((3-fluoro-4-(4-methylpiperazin-1-yl)phenyl)amino)-5-(pyrrolidin-1-yl)-7H-pyrrolo[2,3-d]pyrimidin-4-yl)oxy)phenyl)acrylamide |
| 10 | 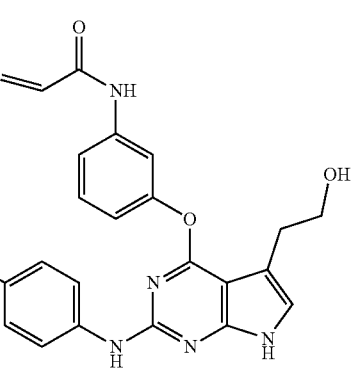 | N-(3-((5-(2-hydroxyethyl)-2-((4-(4-methylpiperazin-1-yl)phenyl)amino)-7H-pyrrolo[2,3-d]pyrimidin-4-yl)oxy)phenyl)acrylamide |

| Compound | Structure | Chemical Name |
|---|---|---|
| 11 | 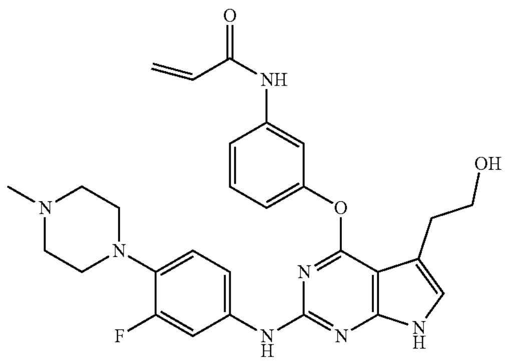 [SMILES: C=CC(=O)Nc1cccc(Oc2nc(Nc3ccc(N4CCN(C)CC4)c(F)c3)nc3[nH]cc(CCO)c23)c1] | N-(3-((2-((3-fluoro-4-(4-methylpiperazin-1-yl)phenyl)amino)-5-(2-hydroxyethyl)-7H-pyrrolo[2,3-d]pyrimidin-4-yl)oxy)phenyl)acrylamide |
| 12 | 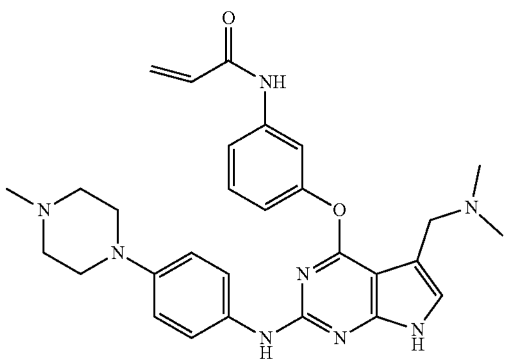 | N-(3-((5-((dimethylamino)methyl)-2-((4-(4-methylpiperazin-1-yl)phenyl)amino)-7H-pyrrolo[2,3-d]pyrimidin-4-yl)oxy)phenyl)acrylamide |
| 13 | 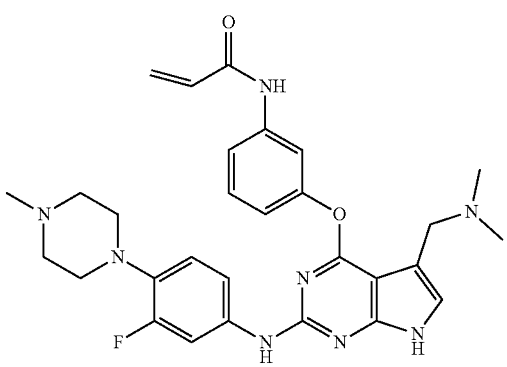 | N-(3-((5-((dimethylamino)methyl)-2-((3-fluoro-4-(4-methylpiperazin-1-yl)phenyl)amino)-7H-pyrrolo[2,3-d]pyrimidin-4-yl)oxy)phenyl)acrylamide |
| 14 | 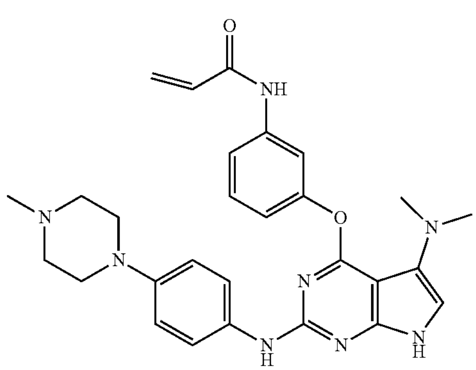 | N-(3-((5-(dimethylamino)-2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
|---|---|---|
| 15 | 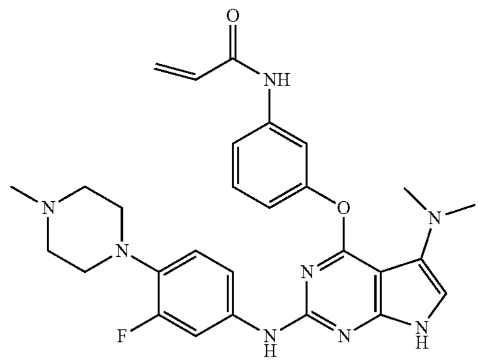 | N-(3-((5-(dimethylamino)-2-((3-fluoro-4-(4-methylpiperazin-1-yl)phenyl)amino)-7H-pyrrolo[2,3-d]pyrimidin-4-yl)oxy)phenyl)acrylamide |
| 16 | 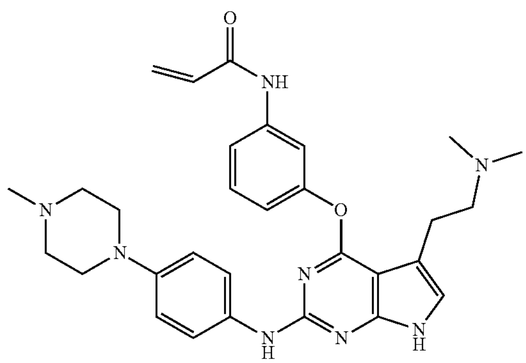 | N-(3-((5-(2-(dimethylamino)ethyl)-2-((4-(4-methylpiperazin-1-yl)phenyl)amino)-7H-pyrrolo[2,3-d]pyrimidin-4-yl)oxy)phenyl)acrylamide |
| 17 | 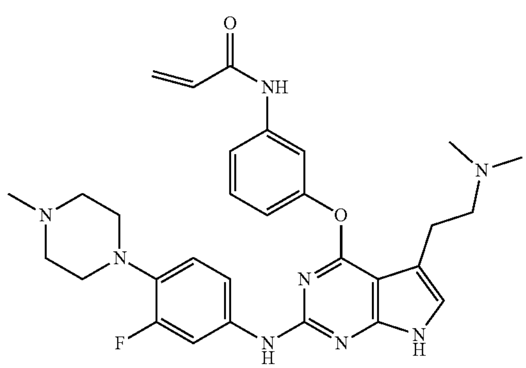 | N-(3-((5-(2-(dimethylamino)ethyl)-2-((3-fluoro-4-(4-methylpiperazin-1-yl)phenyl)amino)-7H-pyrrolo[2,3-d]pyrimidin-4-yl)oxy)phenyl)acrylamide |
| 18 | 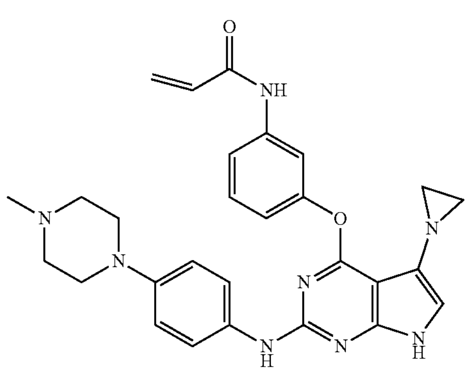 [SMILES: C=CC(=O)Nc1cccc(Oc2nc(Nc3ccc(N4CCN(C)CC4)cc3)nc3[nH]cc(N4CC4)c23)c1] | N-(3-((5-(aziridin-1-yl)-2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
|---|---|---|
| 19 | 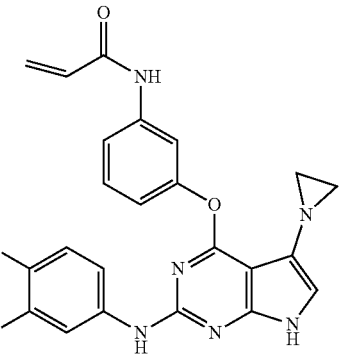 | N-(3-((5-(aziridin-1-yl)-2-((3-fluoro-4-(4-methylpiperazin-1-yl)phenyl)amino)-7H-pyrrolo[2,3-d]pyrimidin-4-yl)oxy)phenyl)acrylamide |
| 20 | 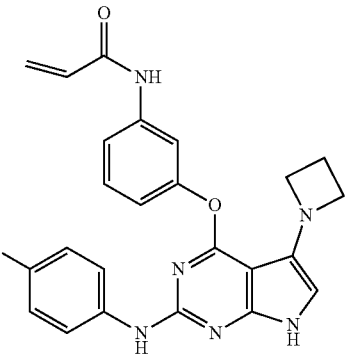 | N-(3-((5-(aziridin-1-yl)-2-((4-(4-methylpiperazin-1-yl)phenyl)amino)-7H-pyrrolo[2,3-d]pyrimidin-4-yl)oxy)phenyl)acrylamide |
| 21 | 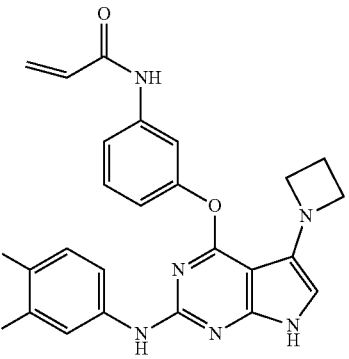 | N-(3-((5-(aziridin-1-yl)-2-((3-fluoro-4-(4-methylpiperazin-1-yl)phenyl)amino)-7H-pyrrolo[2,3-d]pyrimidin-4-yl)oxy)phenyl)acrylamide |
| 22 | 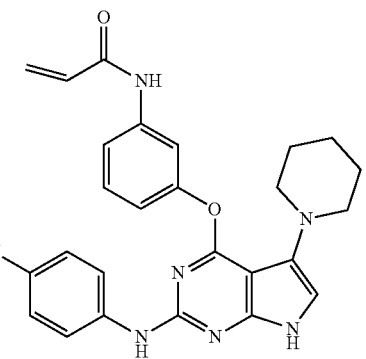 | N-(3-((2-((4-(4-methylpiperazin-1-yl)phenyl)amino)-5-(piperidin-1-yl)-7H-pyrrolo[2,3-d]pyrimidin-4-yl)oxy)phenyl)acrylamide |

TABLE 1-continued

| Compound | Structure | Chemical Name |
|---|---|---|
| 23 | 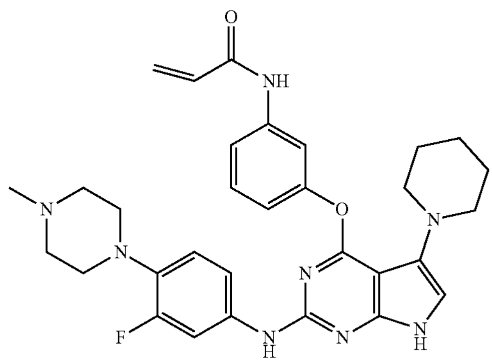 [SMILES: C=CC(=O)Nc1cccc(Oc2nc(Nc3ccc(N4CCN(C)CC4)c(F)c3)nc3[nH]cc(N4CCCCC4)c23)c1] | N-(3-((2-((3-fluoro-4-(4-methylpiperazin-1-yl)phenyl)amino)-5-(piperidin-1-yl)-7H-pyrrolo[2,3-d]pyrimidin-4-yl)oxy)phenyl)acrylamide |
| 24 | 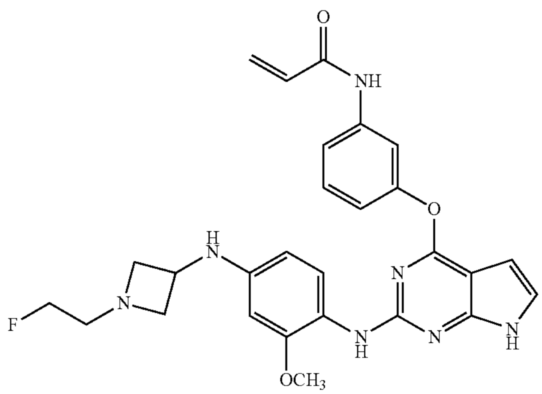 [SMILES: C=CC(=O)Nc1cccc(Oc2nc(Nc3ccc(NC4CN(CCF)C4)cc3OC)nc3[nH]ccc23)c1] | N-(3-(2-(4-(1-(2-fluoroethyl)azetidin-3-ylamino)-2-methoxyphenylamino)-7H-pyrrolo[2,3-d]pyrimidin-4-yloxy)phenyl)acrylamide |
| 25 | 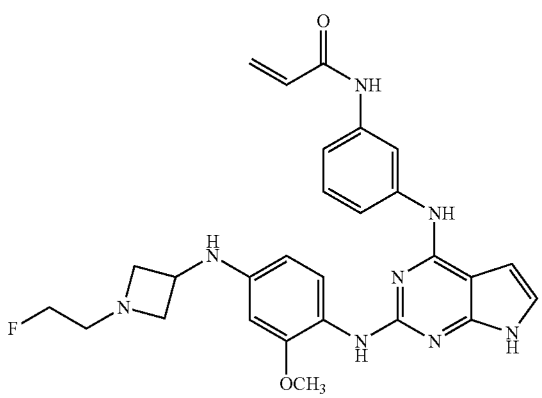 [SMILES: C=CC(=O)Nc1cccc(Nc2nc(Nc3ccc(NC4CN(CCF)C4)cc3OC)nc3[nH]ccc23)c1] | N-(3-(2-(4-(1-(2-fluoroethyl)azetidin-3-ylamino)-2-methoxyphenylamino)-7H-pyrrolo[2,3-d]pyrimidin-4-ylamino)phenyl)acrylamide and |
| 26 | | N-(3-((2-((2-(piperidin-1-ylmethyl)quinolin-6-yl)amino)-7H-pyrrolo[2,3-d]pyrimidin-4-yl)oxy)phenyl)acrylamide | and pharmaceutically acceptable salts thereof.

Chemical Embodiments

In some embodiments of step (a), $LG_1$ and $LG_2$ are each a leaving group. In some embodiments, $LG_1$ and $LG_2$ are each independently halo or trifluorosulfonate (triflate). In some embodiments, $LG_1$ and $LG_2$ are the same leaving group; in other embodiments, they are different leaving groups. In some embodiments, $LG_1$ and $LG_2$ are each halo, or are each Cl, Br, or I, or are each Cl.

In some embodiments, $R^4$ and $R^5$ are each as defined in any of the various permutations described herein.

In some embodiments of step (a), the reacting is performed in the presence of chloromethyl pivalate and an ionic base such as $K_2CO_3$, $Na_2CO_3$, $Cs_2CO_3$, NaOH, or KOH, or an amine base such as a trialkylamine, for example, $Et_3N$ or $iPr_2NEt$. In some embodiments, the reacting is performed in the presence of an ionic base. In some embodiments, the ionic base is $K_2CO_3$. In some embodiments, the solvent for step (a) is a polar solvent such as THF, DMF, or water, or a mixture thereof. In some embodiments, the solvent is a mixture of THF and water.

In some embodiments of step (b), $X^1$, n, and $R^3$ are each as defined in any of the various permutations described herein. In some embodiments of step (b), the reacting is performed in the presence of an ionic base such as $K_2CO_3$, $Na_2CO_3$, $Cs_2CO_3$, NaOH, or KOH, or an amine base such as a trialkylamine, for example, $Et_3N$ or $iPr_2NEt$. In some embodiments, the reacting is performed in the presence of an ionic base. In some embodiments, the ionic base is $K_2CO_3$. In some embodiments, the solvent for step (b) is a polar solvent such as THF, DMF, or water, or a mixture thereof. In some embodiments, the solvent is DMF.

In some embodiments of step (c), $R^6$, $R^7$, $R^8$, $R^{12}$, $R^{18}$, $R^{19}$, and Q are each as defined in any one of the various permutations described herein. In some embodiments, the coupling is a Buchwald-Hartwig cross-coupling reaction or a nucleophilic aromatic substitution. In other embodiments, the coupling is performed in the presence of a palladium catalyst and optionally in the presence of a separate phosphine ligand reagent. In some embodiments, the palladium catalyst is a palladium (0) catalyst. In other embodiments, the palladium catalyst is a palladium (II) catalyst. In other embodiments, the palladium catalyst is $Pd_2(dba)_3$, $Pd(OAc)_2$, $Pd(PPh_3)_4$, $PdCl_2(P(o-tolyl)_3)_2$, or $PdCl_2(PPh_3)_2$. In some embodiments, the phosphine ligand is $PPh_3$, a trialkyl phosphine, dppf, $P(o-tolyl)_3$, $P(t-Bu)_3$, BINAP, a dialkylbiarylphosphine, XPhos, XantPhos, or SpanPhos, or the like. In some embodiments, the palladium catalyst is $Pd_2(dba)_3$. In some embodiments, the coupling is done in the presence of a base such as a hydroxide, carbonate, alkoxide, silylamide, or phosphate base. In some embodiments, the base is $K_2CO_3$, $Cs_2CO_3$, NaOtBu, or KOH. In other embodiments, the base is $K_2CO_3$. In some embodiments of step (c), the coupling is done in a polar solvent, such as t-BuOH, THF, DMF, or water, or a mixture thereof. In other embodiments, the solvent is t-BuOH.

In some embodiments of step (d), the deprotecting is done in the presence of a aqueous hydroxide base in an alcohol solvent. In some embodiments, the hydroxide base is aqueous NaOH or aqueous KOH. In some embodiments, the base is aqueous NaOH, and the solvent is methanol.

In some embodiments of step (e), the reducing step is a catalytic hydrogenation with hydrogen gas (at atmospheric pressure or above atmospheric pressure) and a palladium, platinum, iron, or nickel catalyst. In some embodiments, the metal catalyst is Pd/C. In some embodiments, the hydrogen gas pressure is about 1 MPa.

In some embodiments, steps (d) and (e) are combined into a single step (d/e), whereby the compound of Formula (XV) is deprotected and reduced in one step to form the compound of Formula (XVII). In this instance, the reaction is performed in the presence of hydrazine hydrate and methanol.

In some embodiments of step (f), the reaction is done in the presence of an amine or ionic base. In some embodiments, the base is an amine base. In other embodiments, the base is $iPr_2NEt$.

In some embodiments, the compound of Formula (I) is converted to a pharmaceutically acceptable salt by reaction with a pharmaceutically acceptable acid. In some embodiments, the compound of Formula (I) is treated with maleic acid. In other embodiments, the acid is maleic acid, HCl, or HBr.

In some embodiments, the methods described herein are used to make a compound of Formula (II) or a pharmaceutically acceptable salt thereof, or to make a compound of Formula (III) or a pharmaceutically acceptable salt thereof.

In some embodiments, the method of making comprises step (f). In other embodiments, the method comprises steps (e) and (f). In other embodiments, the method comprises steps (d), (e), and (f). In other embodiments, the method comprises steps (c), (d), (e), and (f). In other embodiments, the method comprises steps (b), (c), (d), (e), and (f). In other embodiments, the method comprises steps (a)-(f). In other embodiments, the method comprises step (d/e) in place of steps (d) and (e).

In some embodiments of the compounds of Formula (X) and (XI):

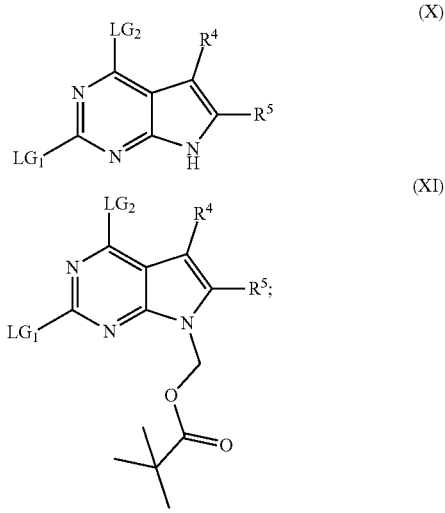

$LG_1$ and $LG_2$ are each a leaving group; and $R^4$ and $R^5$ are each as defined for Formula (I). In some embodiments, $LG_1$ and $LG_2$ are each independently halo or trifluorosulfonate (triflate). In some embodiments, $LG_1$ and $LG_2$ are the same leaving group; in other embodiments, they are different leaving groups. In some embodiments, $LG_1$ and $LG_2$ are each halo, or are each Cl, Br, or I, or are each Cl.

In some embodiments of Formulae (X), (XIII), (XV), (XVI), and (XVII):

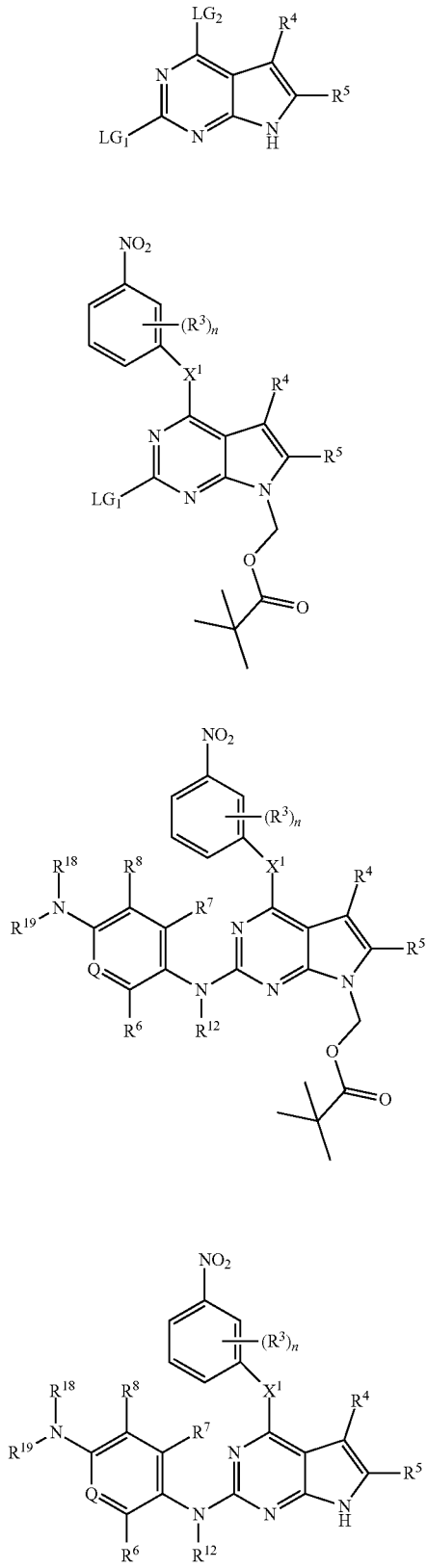

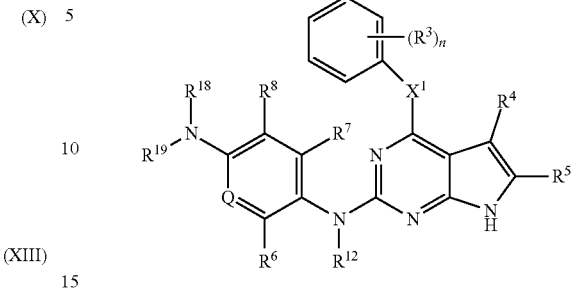

R[4] is hydrogen, $C_{1-6}$alkyl, $C_{3-7}$cycloalkyl, or —NR[22]R[23]; wherein the alkyl and cycloalkyl are unsubstituted or substituted with hydroxyl or amino; and wherein R[22] and R[23] are each independently hydrogen or $C_{1-6}$ alkyl; or R[22] and R[23] taken together with the nitrogen to which they are attached form a 3- to 10-membered heterocycloalkyl ring. In certain instances, R[4] is hydrogen. In certain instances, R[4] is $C_{1-6}$alkyl. In certain instances, R[4] is $C_{3-7}$cycloalkyl. In certain instances, R[4] is —NR[22]R[23]. In certain instances, R[4] is unsubstituted $C_{1-6}$alkyl. In certain instances, R[4] is $C_{1-6}$alkyl that is substituted with hydroxyl. In certain instances, R[4] is $C_{1-3}$alkyl that is substituted with hydroxyl. In certain instances, R[4] is $C_{1-6}$alkyl that is substituted with amino. In certain instances, R[4] is $C_{1-6}$alkyl that is substituted with —NH$_2$. In certain instances, R[4] is $C_{1-6}$alkyl that is substituted with —N(CH$_3$)$_2$. In certain instances, R[4] is $C_{1-3}$alkyl that is substituted with —NH$_2$. In certain instances, R[4] is $C_{1-3}$alkyl that is substituted with —N(CH$_3$)$_2$. In certain instances, R[4] is unsubstituted $C_{3-7}$cycloalkyl. In certain instances, R[4] is unsubstituted $C_3$cycloalkyl. In certain instances, R[4] is unsubstituted $C_4$cycloalkyl. In certain instances, R[4] is unsubstituted $C_{5-6}$cycloalkyl. In certain instances, R[4] is unsubstituted $C_7$cycloalkyl. In certain instances, R[4] is —NR[22]R[23], wherein R[22] and R[23] are each independently hydrogen or $C_{1-6}$ alkyl; or R[22] and R[23] taken together with the nitrogen to which they are attached form a 3- to 10-membered heterocycloalkyl ring. In certain instances, R[22] and R[23] are each hydrogen. In certain instances, R[22] and R[23] are each $C_{1-6}$alkyl. In certain instances, R[22] and R[23] are each $C_{1-3}$alkyl. In certain instances, R[22] and R[23] are each methyl. In certain instances, R[22] and R[23] are taken together with the nitrogen to which they are attached to form a 3- to 10-membered heterocycloalkyl ring, such that R[4] is

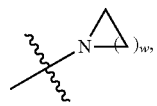

where w is a number from 1 to 8. In certain instances, R[22] and R[23] are taken together with the nitrogen to which they are attached to form a 3-, 4-, 5-, or 6-membered ring.

In some embodiments of Formulae (X), (XIII), (XV), (XVI), and (XVII), R[5] is hydrogen or $C_{1-6}$alkyl. In certain instances, R[5] is hydrogen. In certain instances, R[5] is $C_{1-6}$alkyl. In certain instances, R[5] is methyl. In certain instances, R[5] is ethyl. In certain instances, R[5] is $C_{1-3}$alkyl. In certain instances, R[5] is $C_{4-6}$alkyl.

In some embodiments of Formulae (XII), (XIII), (XV), (XVI), and (XVII):

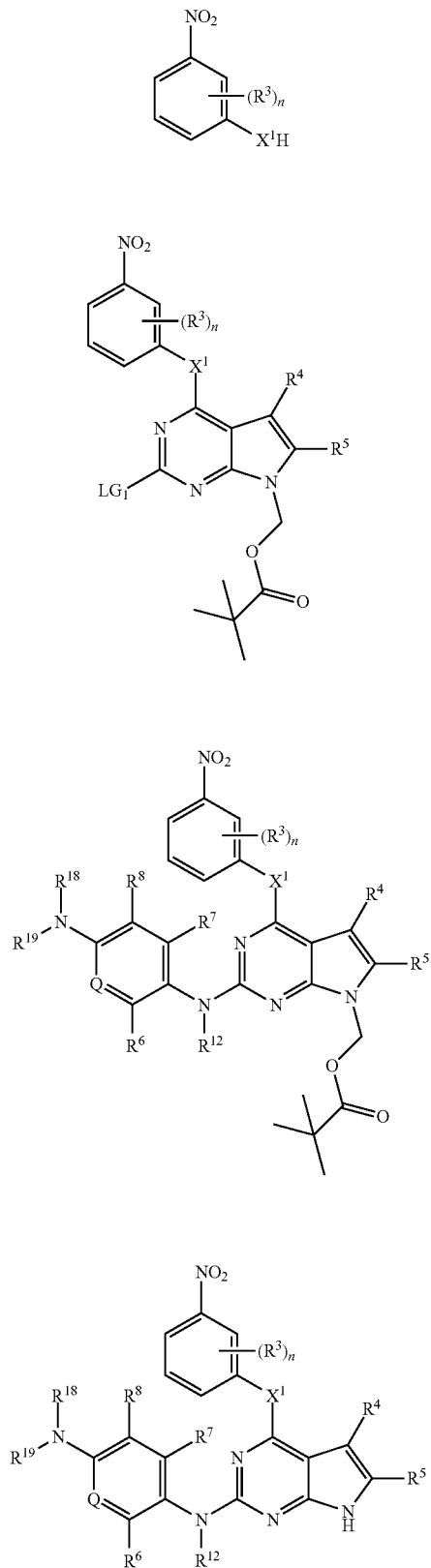

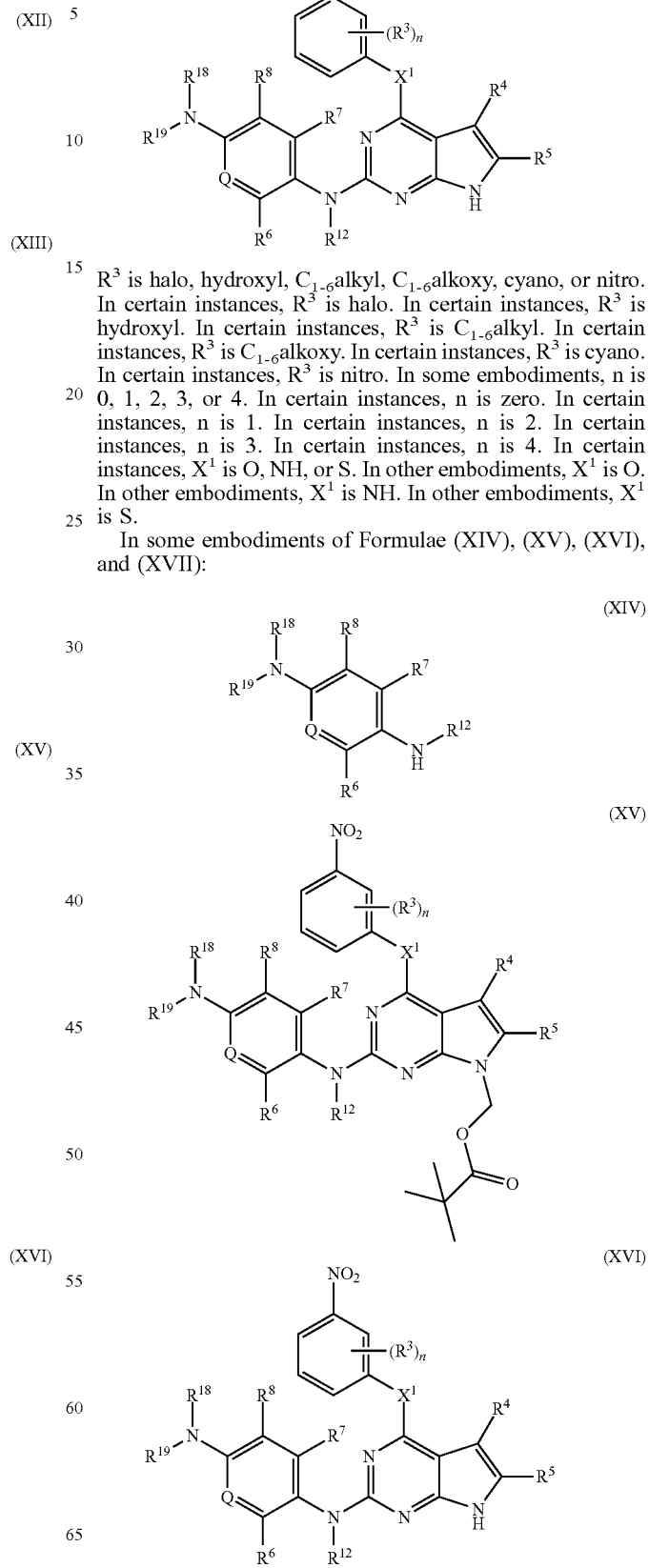

$R^3$ is halo, hydroxyl, $C_{1-6}$alkyl, $C_{1-6}$alkoxy, cyano, or nitro. In certain instances, $R^3$ is halo. In certain instances, $R^3$ is hydroxyl. In certain instances, $R^3$ is $C_{1-6}$alkyl. In certain instances, $R^3$ is $C_{1-6}$alkoxy. In certain instances, $R^3$ is cyano. In certain instances, $R^3$ is nitro. In some embodiments, n is 0, 1, 2, 3, or 4. In certain instances, n is zero. In certain instances, n is 1. In certain instances, n is 2. In certain instances, n is 3. In certain instances, n is 4. In certain instances, $X^1$ is O, NH, or S. In other embodiments, $X^1$ is O. In other embodiments, $X^1$ is NH. In other embodiments, $X^1$ is S.

In some embodiments of Formulae (XIV), (XV), (XVI), and (XVII):

-continued (XVII)

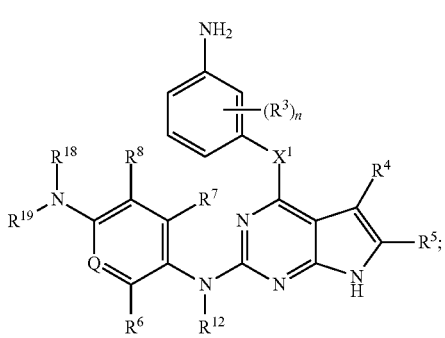

$R^6$, $R^7$, $R^8$, $R^{12}$, $R^{18}$, $R^{19}$, and Q are each as defined for Formula (I);

In certain instances of compounds of Formulae (XIV), (XV), (XVI), and (XVII), $R^6$ and $R^7$ are each independently hydrogen, halo, $C_{1-6}$ alkyl, $C_{1-6}$ haloalkyl, $C_{2-6}$ alkoxy, $C_{1-6}$ haloalkoxy, hydroxyl, cyano, or nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$alkyl. In certain instances, $R^6$ is $C_{1-6}$haloalkyl. In certain instances, $R^6$ is $C_{2-6}$alkoxy. In certain instances, $R^6$ is $C_{1-6}$haloalkoxy. In certain instances, $R^6$ is hydroxyl. In certain instances, $R^6$ is cyano. In certain instances, $R^6$ is nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$alkyl. In certain instances, $R^7$ is $C_{1-6}$haloalkyl. In certain instances, $R^7$ is $C_{2-6}$alkoxy. In certain instances, $R^7$ is $C_{1-6}$haloalkoxy. In certain instances, $R^7$ is hydroxyl. In certain instances, $R^7$ is cyano. In certain instances, $R^7$ is nitro.

In certain instances of compounds of Formulae (XIV), (XV), (XVI), and (XVII), $R^8$ is hydrogen, halo, $C_{1-6}$ alkyl, $C_{1-6}$ haloalkyl, $C_{1-6}$ alkoxy, $C_{1-6}$ haloalkoxy, hydroxyl, cyano, or nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$alkyl. In certain instances, $R^8$ is $C_{1-6}$ haloalkyl. In certain instances, $R^8$ is $C_{1-6}$alkoxy. In certain instances, $R^8$ is $C_{1-6}$haloalkoxy. In certain instances, $R^8$ is hydroxyl. In certain instances, $R^8$ is cyano. In certain instances, $R^8$ is nitro.

In certain instances of compounds of Formulae (XIV), (XV), (XVI), and (XVII), $R^{12}$ is hydrogen or $C_{1-6}$alkyl. In certain instances, $R^{12}$ is hydrogen. In certain instances, $R^{12}$ is $C_{1-6}$alkyl. In certain instances, $R^{12}$ is methyl. In certain instances, $R^{12}$ is ethyl. In certain instances, $R^{12}$ is $C_{1-3}$alkyl. In certain instances, $R^{12}$ is $C_{4-6}$alkyl.

In certain instances of compounds of Formulae (XIV), (XV), (XVI), and (XVII), Q is $CR^9$ or N. In certain instances, Q is $CR^9$. In certain instances, Q is N.

In certain instances of compounds of Formulae (XIV), (XV), (XVI), and (XVII), $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$alkyl. In certain instances, $R^9$ is $C_{1-6}$haloalkyl. In certain instances, $R^9$ is $C_{1-6}$alkoxy. In certain instances, $R^9$ is $C_{1-6}$haloalkoxy. In certain instances, $R^9$ is hydroxyl. In certain instances, $R^9$ is cyano. In certain instances, $R^9$ is nitro. In certain instances, $R^9$ is hydrogen or fluoro.

In certain instances of compounds of Formulae (XIV), (XV), (XVI), and (XVII), —$NR^{18}R^{19}$ is:

(a)

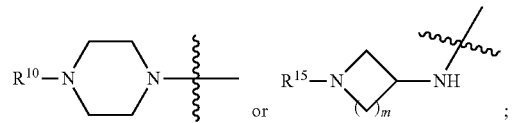

wherein $R^{10}$ is selected from hydrogen and $C_{1-6}$alkyl; $R^{15}$ is unsubstituted methyl, or is $C_{2-4}$alkyl unsubstituted or substituted with hydroxy, methoxy, or halo; and m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring.

In certain instances of compounds of Formulae (XIV), (XV), (XVI), and (XVII), —$NR^{18}R^{19}$ is:

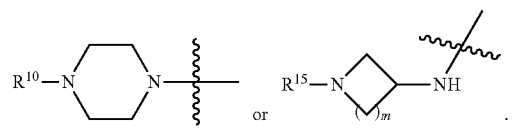

In certain instances, —$NR^{18}R^{19}$ is

In certain instances, —$NR^{18}R^{19}$ is

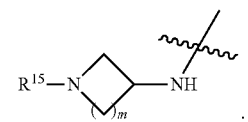

In certain instances of compounds of Formulae (XIV), (XV), (XVI), and (XVII), $R^{10}$ is hydrogen or $C_{1-6}$alkyl. In certain instances, $R^{10}$ is hydrogen. In certain instances, $R^{10}$ is $C_{1-6}$alkyl. In certain instances, $R^{10}$ is methyl. In certain instances, $R^{10}$ is ethyl. In certain instances, $R^{10}$ is $C_{1-3}$alkyl. In certain instances, $R^{10}$ is $C_{4-6}$ alkyl.

In certain instances of compounds of Formulae (XIV), (XV), (XVI), and (XVII), $R^{15}$ is methyl, hydroxyethyl, methoxyethyl, or fluoroethyl. In other embodiments, $R^{15}$ is fluoroethyl. In some embodiments, m is 1. In other embodiments, m is 2.

In certain instances of compounds of Formulae (XIV), (XV), (XVI), and (XVII), —$NR^{18}R^{19}$ is defined as follows:

$R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl, or the alkyl is substituted with amino; and $R^{18}$ is hydrogen or $C_{1-6}$alkyl, where the alkyl is unsubstituted or substituted with amino, or $R^{18}$ is absent to satisfy valency of the heteroaryl ring. In some embodiments, the heteroaryl ring is substituted with dimethylaminomethyl or piperidinylmethyl. In other embodiments, $R^9$ and $R^{19}$ taken together form optionally substituted pyrrole or pyridine. In some instances, $R^{18}$ is dimethylaminoethyl.

In certain instances of the intermediates described herein, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro. In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl. In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen. In certain instances, $R^6$, $R^7$, $R^8$, and $R^9$ are hydrogen and $R^{13}$ is —$CH_2OH$. In certain instances, $R^6$, $R^7$, and $R^8$ are hydrogen; $R^9$ is halo; and $R^{13}$ is —$CH_2OH$. In certain instances, $R^6$, $R^7$, and $R^8$ are hydrogen; $R^9$ is fluoro; and $R^{13}$ is —$CH_2OH$. In certain instances, $R^6$, $R^7$, $R^8$, and $R^9$ are hydrogen and $R^{13}$ is —$(CH_2)_mF$, wherein m is a number from one to 3. In certain instances, $R^6$, $R^7$, and $R^8$ are hydrogen; $R^9$ is halo; and $R^{13}$ is —$(CH_2)_mF$, wherein m is a number from one to 3. In certain instances, $R^6$, $R^7$, and $R^8$ are hydrogen; $R^9$ is fluoro; and $R^{13}$ is —$(CH_2)_mF$, wherein m is a number from one to 3.

The present disclosure is directed to methods of making a compound of Formula (II):

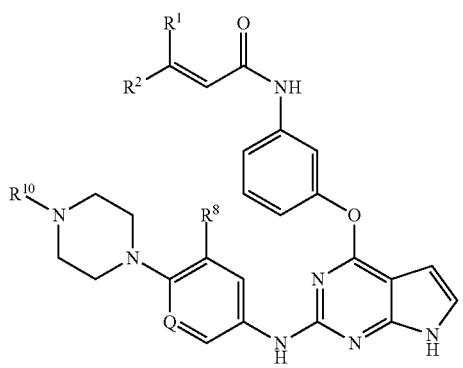

(II)

wherein
$R^1$ and $R^2$ are each independently hydrogen, halo, $C_{1-6}$alkyl, or $C_{1-6}$haloalkyl;
$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;
Q is $CR^9$ or N;
where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro; and
$R^{10}$ is hydrogen or $C_{1-6}$alkyl;
or a pharmaceutically acceptable salt thereof.

The methods of making compounds of Formula (II) comprise one or more of steps (a)-(f), where $R^1$, $R^2$, $R^8$, Q, and $R^{10}$ are each defined consistently with Formula (II) or the embodiments of Formula (II) described herein. Said methods further optionally comprise converting a compound of Formula (II) into a pharmaceutically acceptable salt thereof as described herein.

Formula (III)

The present disclosure provides methods of making a compound of Formula (III):

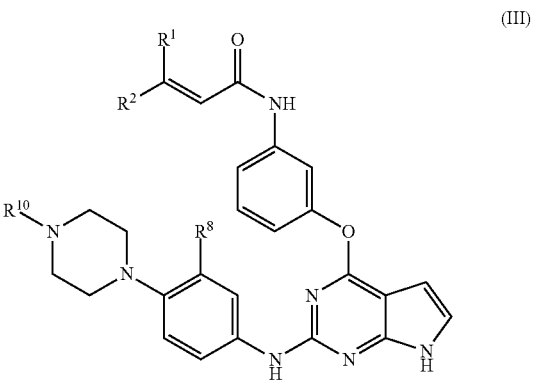

(III)

wherein
$R^1$ and $R^2$ are each independently hydrogen, halo, $C_{1-6}$alkyl, or $C_{1-6}$haloalkyl;
$R^8$ is halo, $C_{1-6}$alkyl, $C_{1-6}$haloalkyl, $C_{1-6}$alkoxy, $C_{1-6}$haloalkoxy, hydroxyl, cyano, or nitro; and
$R^{10}$ is $C_{1-6}$alkyl;
or a pharmaceutically acceptable salt thereof.

The methods of making compounds of Formula (III) comprise one or more of steps (a)-(f), where $R^1$, $R^2$, $R^8$, Q, and $R^{10}$ are each defined consistently with Formula (III) or the embodiments of Formula (III) described herein. Said methods further optionally comprise converting a compound of Formula (III) into a pharmaceutically acceptable salt thereof as described herein.

In some embodiments are methods of making a compound shown in Table 1, or a pharmaceutically acceptable salt thereof.

In some embodiments are methods of making a compound of the following structure:

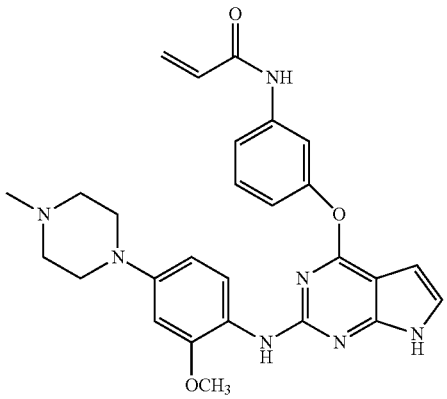 [SMILES: C=CC(=O)Nc1cccc(Oc2nc(Nc3ccc(N4CCN(C)CC4)cc3OC)nc3[nH]ccc23)c1]

or a pharmaceutically acceptable salt thereof, using one or more of steps (a)-(f) as described herein.

In certain embodiments, the present disclosure is directed to methods of making N-(3-((2-((3-fluoro-4-(4-methylpiperazin-1-yl)phenyl)amino)-7H-pyrrolo[2,3-d]pyrimidin-4-yl)oxy)phenyl)acrylamide:

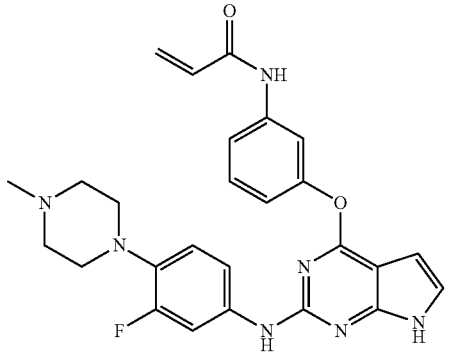

(I-1)

or a pharmaceutically acceptable salt thereof. In certain embodiments are methods of making the maleate salt of N-(3-((2-((3-fluoro-4-(4-methylpiperazin-1-yl)phenyl)amino)-7H-pyrrolo[2,3-d]pyrimidin-4-yl)oxy)phenyl)acrylamide. In certain embodiments are methods of making the hydrochloride salt of N-(3-((2-((3-fluoro-4-(4-methylpiperazin-1-yl)phenyl)amino)-7H-pyrrolo[2,3-d]pyrimidin-4-yl)oxy)phenyl)acrylamide. Said methods comprise one or more of the following steps:

(a) reacting a compound of Formula (X-1):

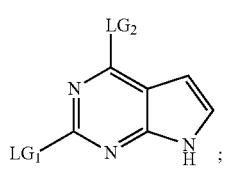

(X-1)

wherein $L_{G1}$ and $LG_2$ are each a leaving group as defined herein; or $LG_1$ and $LG_2$ are each chloro;

with chloromethyl pivalate to form a compound of Formula (XI-1);

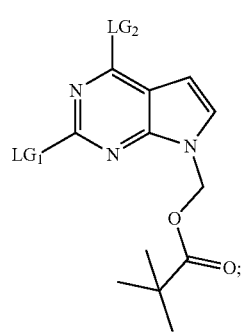

(XI-1)

(b) reacting a compound of Formula (XI-1) with a compound of Formula (XII-1):

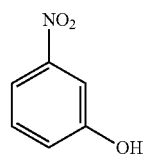

(XII-1)

to form a compound of Formula (XIII-1):

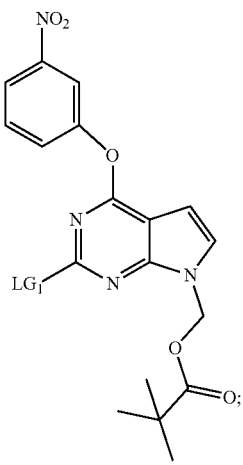

(XIII-1)

(c) coupling a compound of Formula (XIII-1) with a compound of Formula (XIV-1):

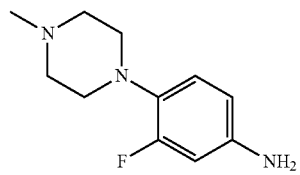

(XIV-1)

to form a compound of Formula (XV-1):

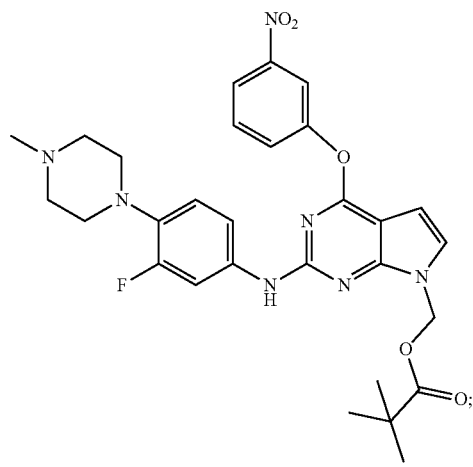

(XV-1)

(d) deprotecting the compound of Formula (XV-1) to form a compound of Formula (XVI-1):

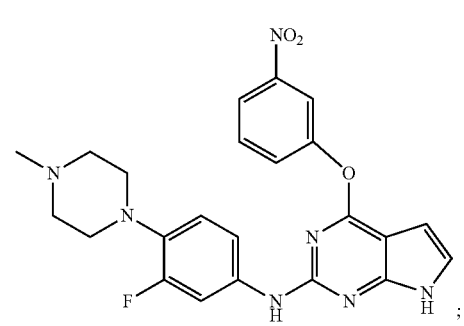

(XVI-1)

(e) reducing the compound of Formula (XVI-1) to form a compound of Formula (XVII-1):

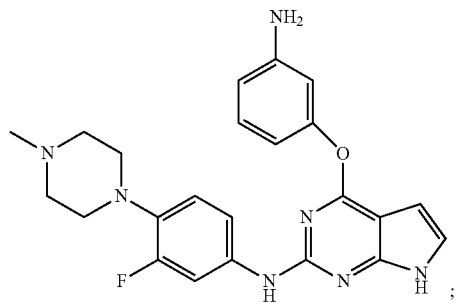

and (f) reacting the compound of Formula (XVII-1) with acryloyl chloride to form N-(3-((2-((3-fluoro-4-(4-methylpiperazin-1-yl)phenyl)amino)-7H-pyrrolo[2,3-d]pyrimidin-4-yl)oxy)phenyl)acrylamide. In some embodiments, reactions are run at a temperature from about −10° C. to about 100° C.

In other embodiments, the method of making comprises treating N-(3-((2-((3-fluoro-4-(4-methylpiperazin-1-yl)phenyl)amino)-7H-pyrrolo[2,3-d]pyrimidin-4-yl)oxy)phenyl)acrylamide with a pharmaceutically acceptable acid to form a pharmaceutically acceptable salt. In some embodiments, the acid is maleic acid, HCl, or HBr. In other embodiments, the acid is maleic acid. In other embodiments, the acid is HCl. In some embodiments, the salt thereof is the maleate, HCl, or HBr salt. In other embodiments, the salt thereof is a tosylate, mesylate, fumarate, or malate salt.

The present disclosure also contemplates certain polymorphs or amorphous forms of compounds of Formulae (I), (II), or (III), or pharmaceutically acceptable salts thereof, or of Compound 1, or a pharmaceutically acceptable salt thereof. In some embodiments are polymorphs or amorphous forms of a pharmaceutically acceptable salt of Compound 1. In some embodiments, the salt is a maleate salt, an HCl salt, an HBr salt, a sulfate salt, a malate salt, a fumarate salt, a mesylate salt, or a tosylate salt. In some embodiments, the pharmaceutically acceptable salts are optionally solvates. In some embodiments is a crystalline polymorph of a pharmaceutically acceptable salt of Compound 1. In some embodiments, the polymorph is Form I (maleate salt), or is Form II (maleate salt), or is Form III (maleate salt), or is Form IV (HCl salt), or is Form V (fumarate salt), or is Form VI (malate salt), or is Form VII (HBr salt), each having the characteristics discussed herein. In some embodiments, the compound is in amorphous form. In some embodiments, the amorphous form is a maleate, sulfate, mesylate, tosylate, or HBr salt of Compound 1.

In some embodiments, the maleate salt of Compound 1 is Form I. In some embodiments, Form I is characterized by an XRPD spectrum comprising one or more peaks at 2Θ values (within the error range of the experiment) selected from the group consisting of: 22.14, 21.90, 12.40, 25.52, 26.12, 14.10, 11.60, 26.52, and 17.00. In some embodiments, Form I is characterized by one, two, three, four, five, six, seven, eight, nine, or 10, or more peaks within the error range of those shown in the XRPD spectrum in FIG. 1, or in FIG. 4, or in FIG. 5, or in FIG. 21. The error range may be ±0.2 2Θ, ±0.1 2Θ, ±0.05 2Θ, or another suitable range. In some embodiments, Form I of the maleate salt of Compound 1 is crystallized from ethyl acetate or from an ethanol/water mixture. In some embodiments, Form I is crystallized from ethanol/water. In some embodiments, Form I is crystallized from ethanol/water at a ratio of 1:1 to 1:19 (v/v). In some embodiments, the ethanol/water ratio is 1:1, or is 3:7, or is 1:19.

In some embodiments, the maleate salt of Compound 1 is in crystalline polymorph Form II. In some embodiments Form II is characterized by an XRPD spectrum comprising one or more peaks at 2Θ values (within the error range of the experiment) at the positions shown in the XRPD spectrum in FIG. 8 or in FIG. 9. The error range may be ±0.2 2Θ, ±0.1 2Θ, ±0.05 2Θ, or another suitable range. In some embodiments, Form II of the maleate salt of Compound 1 is crystallized from methanol or ethanol.

In some embodiments, the maleate salt of Compound 1 is in crystalline polymorph Form III. In some embodiments Form III is characterized by an XRPD spectrum comprising one or more peaks at 2Θ values (within the error range of the experiment) at the positions shown in the XRPD spectrum in FIG. 12. The error range may be ±0.2 2Θ, ±0.1 2Θ, ±0.05 2Θ, or another suitable range. In some embodiments, Form III of the maleate salt of Compound 1 is crystallized from tetrahydrofuran.

In some embodiments, the maleate salt of Compound 1 is in amorphous form. In some embodiments, the amorphous form is prepared by crystallization from acetone or acetonitrile.

In some embodiments, the hydrochloride salt of Compound 1 is crystalline Form IV. In some embodiments, Form IV is characterized by an XRPD spectrum comprising one or more peaks at 2Θ values (within the error range of the experiment) at the positions shown in the XRPD spectrum in FIG. 22, or in FIG. 25, or in FIG. 28, or in FIG. 31, or in FIG. 34, or in FIG. 37. The error range may be ±0.2 2Θ, ±0.1 2Θ, ±0.05 2Θ, or another suitable range. In some embodiments, Form IV of the hydrochloride salt of Compound 1 is crystallized from water or from an ethanol/water mixture. In some embodiments, Form IV is crystallized from an ethanol/water mixture in a ration of from 3:1 to 5:7 (v/v). In other embodiments, the ethanol/water ratio is 3:1, 1:1, 5:7, 3:2, or 7:3.

In some embodiments, the fumarate salt of Compound 1 is crystalline Form V. In some embodiments, Form V is characterized by an XRPD spectrum comprising one or more peaks at 2Θ values (within the error range of the experiment) at the positions shown in the XRPD spectrum in FIG. 40. The error range may be ±0.2 2Θ, ±0.1 2Θ, ±0.05 2Θ, or another suitable range. In some embodiments, Form V is crystallized from an ethanol/water mixture, optionally 5% aqueous ethanol.

In some embodiments, the malate salt of Compound 1 is crystalline Form VI. In some embodiments, Form VI is characterized by an XRPD spectrum comprising one or more peaks at 2Θ values (within the error range of the experiment) at the positions shown in the XRPD spectrum in FIG. 43. The error range may be ±0.2 2Θ, ±0.1 2Θ, ±0.05

2Θ, or another suitable range. In some embodiments, Form VI is crystallized from an ethanol/water mixture, optionally 10% aqueous ethanol.

In some embodiments, the hydrobromide salt of Compound 1 is crystalline Form VII. In some embodiments, Form VII is characterized by an XRPD spectrum comprising one or more peaks at 2Θ values (within the error range of the experiment) at the positions shown in the XRPD spectrum in FIG. 54. The error range may be ±0.2 2Θ, ±0.1 2Θ, ±0.05 2Θ, or another suitable range. In some embodiments, Form VII is crystallized from an ethanol/water mixture.

In some embodiments, the pharmaceutically acceptable salt of Compound 1 is in an amorphous form. In some embodiments, the amorphous form is a sulfate salt, optionally prepared by crystallization from water, a mesylate salt, optionally prepared by crystallization from ethanol, a tosylate salt, optionally prepared by crystallization from an ethanol/water mixture, or a hydrobromide salt, optionally prepared by crystallization from water.

Pharmaceutical Compositions

Aside from the pharmacological activity of an active pharmaceutical ingredient (API), there are a variety of physical or physicochemical characteristics of the active substance that are relevant for the preparation of solid oral dosage forms (including oral powders, granules, pellets, tablets, capsules, chewable tablets, dispersible tables, troches or lozenges). To achieve adequate formulation characteristics, such as correct assay, content, and mass uniformity, chemical and physical stability of the drug product, and a proper dissolution rate, the characteristics of the drug product intermediates also have to support a robust manufacturing process.

Therefore, in some aspects, how to achieve suitable adequate formulation characteristics depends on making and manufacturing process for stabilized pharmaceutical compositions containing a compound of Formula (I), or a pharmaceutically acceptable salt thereof, or Compound 1, or a pharmaceutically acceptable salt thereof.

While not wishing to be bound by any particular theory, in some instances, the degradation of a compound of Formula (I) or Compound 1 is considered to occur through a pathway involving dimerization of the compound. For example, two molecules of a compound of Formula I could condense under acidic conditions (e.g., during or after salt formation with an acid) to form a dimer. In some embodiments, an amino group on one molecule reacts with the acrylamide group of a second molecule. In some embodiments, the —NR$^{10}$ or N—R$^{15}$ amino group of one molecule reacts with the acrylamide group in a second molecule to form a β-amino-substituted amido group. In some embodiments, Compound 1 dimerizes. In some embodiments, a dimer of Compound 1 may have the structure Dimer 1 as shown below:

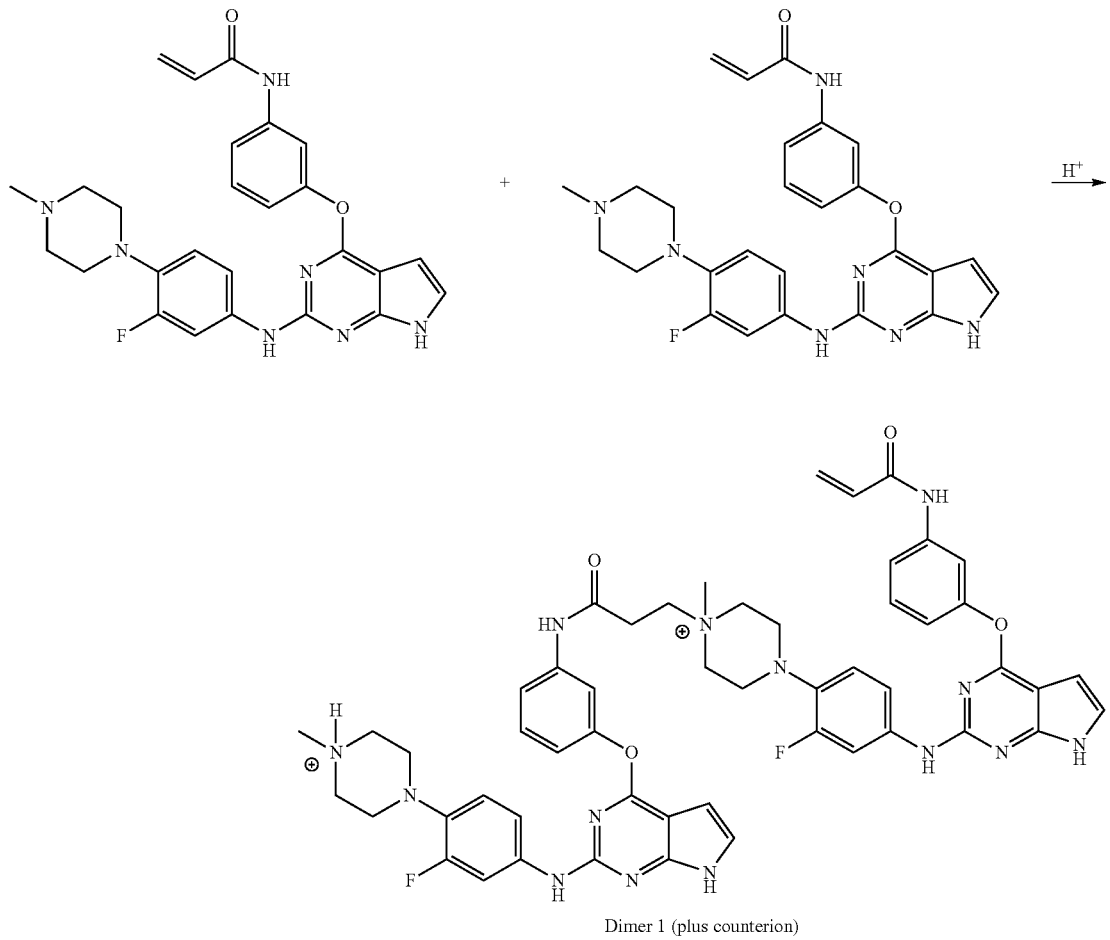

Dimer 1 (plus counterion)

In situations where the compound or salt thereof dimerizes during the formulation process, the dimer may have one or more acid counterions as appropriate for the acid used, e.g., maleate (one molecule, as the dicarboxylate), two bromide counterions, two mesylate counterions, and the like. In some embodiments, the dimer may form as shown below:

a pharmaceutically acceptable salt thereof, with a suitable adsorbing agent, prior to formulation into a dosage form, lowers dimerization rate of the compound. While not wishing to be bound by any particular theory, it is considered that the adsorbing agent(s) is able to protect the compound of Formula I or Compound 1, or a pharmaceutically acceptable

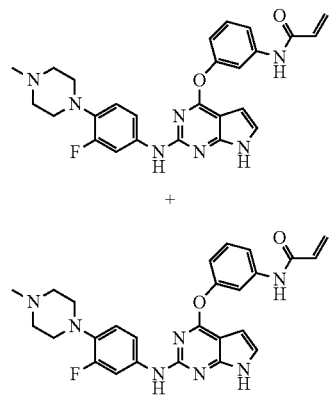

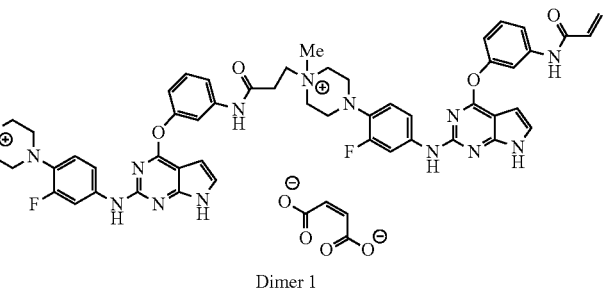

Dimer 1

Undesired dimerization may be promoted by exposure of the drug substance to heat, air, moisture, stress, compaction, or other interactions or events during the manufacturing process. This dimerization can affect particle size of the drug substance, and thus solubility, stability, and bioavailability of the resulting drug product.

Attempts to reduce dimer-based degradation in active pharmaceutical ingredients (API) have been reported in WO2004/045624 A1 (PCT/JP2003/014504) and Chinese Pat. Publ. No. CN104306348 A (Appln. No. CN20141514067). WO 2004/045624 A1 describes a physical method to control dimer formation for an API by using a coating process, which increases the cost and complexity of the manufacturing process. CN104306348 A describes reducing dimer formation through the addition of various chemical additives (butylated hydroxyanisole, BHA). However, use of such chemicals may be limited due to undesired interactions with other components of the drug product, or regulatory approval considerations.

Therefore, there is a need for stabilized pharmaceutical compositions and the manufacturing process thereof that does not require the addition of restricted chemicals or excipients. There is also a need for manufacturing process for making the stabilized pharmaceutical compositions into suitable pharmaceutical dosage forms, e.g., solid oral formulation, without resorting to a more complex manufacturing process.

In some embodiments are methods of making stabilized pharmaceutical compositions comprising a compound of Formula (I) or Compound 1, or a pharmaceutically acceptable salt thereof, comprising pre-blending a suitable adsorbing agent with the therapeutic agent, and then re-blending manufacturing excipients during manufacture of the solid oral formulation, e.g., capsules or tablets. In some embodiments, the pharmaceutical compositions comprise an effective amount of a compound of Formula (I) or Compound 1, or a pharmaceutically acceptable salt thereof.

In some embodiments, it is discovered, surprisingly, that combining a compound of Formula (I) or Compound 1, or salt thereof, from physical and environmental stress that, under unprotected conditions, lead to the formation of degradation products such as a dimers, e.g., a dimer having the structure of Dimer 1.

In some embodiments, it is demonstrated that by utilizing one or more suitable adsorbing agent(s) as a blending agent, the formation of degradation products such as a dimer of the compound of Formula I or Compound 1, or a pharmaceutically acceptable salt thereof, e.g., a dimer having the structure of Dimer 1, is significantly reduced. Indeed, it is demonstrated that a dimer of the compound of Formula (I) or Compound 1, or a pharmaceutically acceptable salt thereof, e.g., a dimer having the structure of Dimer 1, can be reduced to or maintained at a level that is less than any one of 2.0%, or less than 1.0%, or less than 0.75%, or less than 0.5%, or less than 0.25% of the total weight of the compound of Formula I or Compound 1, or a pharmaceutically acceptable salt thereof, upon completion of formulation, or upon storage for a time point that is at least 3 months, or at least 6 months, or at least 12 months, or at least 18 months, or at least 24 months, or at least 36 months from the date when the pharmaceutical compositions are first formulated. In some embodiments, the dimer or other impurity is detected by HPLC methods known to one of skill in the art.

In some embodiments, the pharmaceutical composition contains from about 0.001% (w/w) to about 1% (w/w) of a dimer of Compound 1, or a pharmaceutically acceptable salt thereof, after a stability test for about 10 days, or about 1 month, or about 2 months, or about 3 months, or about 6 months, or about 12 months, or about 18 months, or about 24 months. In some embodiments, the stability test is conducted at ambient temperature, or at a temperature greater than or equal to about 25° C., or at a temperature of about 25° C., or about 50° C., or about 60° C., or between about 50° C. to about 70° C., and/or under relative humidity conditions of about 50%, or about 60%, or about 70%, or greater than about 70%, and/or under exposure to light, e.g., visible light.

In some embodiments, the pharmaceutical compositions described herein demonstrate improved stability of the compound of Formula I or Compound 1, or a pharmaceutically acceptable salt thereof, (active agent) upon storage or under stability testing conditions relative to substantially the same formulation without the adsorbing agent. In some embodiments, the storage time and stability testing conditions are those described herein.

In some embodiments, the present invention also relates to methods of making the pharmaceutical compositions. Such methods may comprise first pre-blending or re-blending a compound of Formula I or Compound 1, or a pharmaceutically acceptable salt thereof, with a suitable adsorbing agent. The present methods may also comprise first pre-blending a compound of Formula I or Compound 1, or a pharmaceutically acceptable salt thereof, with a suitable adsorbing agent prior to formulation into a dosage form.

An "adsorbing agent" is an inactive pharmaceutical ingredient that performs a minor adsorbing function and that otherwise serves as a binder or filler.

Any suitable adsorbing agent(s) can be used. In particular embodiments, the adsorbing agent is a porous solid powder. In some embodiments, the active ingredient may be adsorbed into the pores of the adsorbing agent. Exemplary adsorbing agents include, but are not limited to, acacia, bentonite, alginic acid, cellulose derivatives, croscarmellose, gelatin, gelatin hydrolysate, mannitol, maltose, fructose, Plasdone, povidone, sodium starch glycolate, sorbitol, sucrose, lactose, microcrystalline cellulose, silicified microcrystalline cellulose, croscarmellose sodium, dicalcium phosphate, carboxymethyl cellulose, hydroxypropyl cellulose, and polyethylene glycol (particularly in spray dried formulations). In certain embodiments, adsorbing agent(s) are suitable excipients to be used in spray drying processes. In certain embodiments, adsorbing agent(s) are silicified microcrystalline celluloses. In some embodiments, the silicified microcrystalline cellulose (SMCC) is Prosolv® SMCC 50, Prosolv® SMCC 50 LD, Prosolv® SMCC 90, Prosolv® SMCC HD 90, or Prosolv® SMCC 90 LM. In other embodiments, the silicified microcrystalline cellulose is Prosolv® SMCC 50 or Prosolv® SMCC 90. In some embodiments, the SMCC is a blend of microcrystalline cellulose and colloidal silicon dioxide. In some embodiments, the SMCC has a particle size range of about 10 to 100 µm, or about 30 to 90 µm, or about 45 to 80 µm. In some embodiments, the SMCC has an average particle size by laser diffraction of about 50 µm, or about 60 µm, or about 65 µm, or about 70 µm. In some embodiments, the SMCC has average particle size by laser diffraction of 125 µm, or has a range of about 70 to about 200 µm, or about 80 to about 180 µm, or about 90 to 160 µm. In some embodiments, the SMCC has a bulk density of between about 0.20 and about 0.50 g/mL, or between about 0.20 and 0.30 g/mL, or between about 0.25 and about 0.37 g/mL, or between about 0.38 and about 0.50 g/mL, or between about 0.27 to about 0.39 g/mL.

In some embodiments, the pharmaceutical composition comprises from about 1% (w/w) to about 90% (w/w), or about 15% (w/w) to about 85% (w/w), or about 35% (w/w) to about 75% (w/w), of the adsorbing agent. In other embodiments, the pharmaceutical composition comprises at least two different kinds of adsorbing agents. In some embodiments, the pharmaceutical composition comprises at least two different kinds of silicified microcrystalline cellulose. In some embodiments, the pharmaceutical composition comprises from about 1% (w/w) to about 30% (w/w) of Prosolv® SMCC 50, and from about 30% (w/w) to about 70% (w/w) of Prosolv® SMCC 90.

In some embodiments, the present pharmaceutical compositions may also include pharmaceutically acceptable additive(s) into any suitable type of unit dosage form. Thus, in some embodiments, the pharmaceutical composition further comprises at least one pharmaceutically acceptable additive. Suitable additives include, but are not limited to, diluents, binders, vehicles, carriers, excipients, binders, disintegrating agents, lubricants, swelling agents, solubilizing agents, wicking agents, cooling agents, preservatives, stabilizers, sweeteners, flavors, and polymers. While any pharmaceutically acceptable additive is contemplated by the present disclosure, it should be understood that the additives selected for compounding with coated particles of a compound of Formula (I) or Compound 1, or a pharmaceutically acceptable salt thereof, should not defeat the stability objectives of the present disclosure. Even though some pharmaceutically acceptable additives may cause degradation of a compound of Formula (I) or Compound 1, or a pharmaceutically acceptable salt thereof, such additives may be suitable for the pharmaceutical compositions described herein as long as such additives do not increase dimer formation (relative to the formulation without the further additive) as it is combined with a blending agent, or upon storage, or in vivo.

Examples of disintegrating agents include, but are not limited to, cross-linked sodium carboxymethylcellulose, croscarmellose sodium (e.g., VIVASOL®), crospovidone, and their mixtures. In some embodiments, the pharmaceutical composition comprises from about 0.1% (w/w) to about 10% (w/w), or about 5% (w/w), of croscarmellose sodium (e.g., VIVASOL®).

Examples of lubricating agents include, but are not limited to, magnesium stearate, stearic acid or a pharmaceutically acceptable alkali metal salt thereof, sodium stearyl fumarate, polyethylene glycol (such as Macrogol 6000) (particularly in granule or flake formulations to reduce friction with the mold), glyceryl behenate, talc, colloidal or fumed silicon dioxide and silica derivatives (such as Cab-O-Sil, Syloid® products, and the like), calcium stearate, sodium stearate, sodium lauryl sulfate, sodium chloride, magnesium lauryl sulfate, talc, and their mixtures. A portion of the lubricant may be used as an internal solid lubricant which is blended and granulated with other components of the granulation. Another portion of the lubricant may be added into the final blended material just before compression or encapsulation that coats the outside of the granules in the final formulation. In some embodiments, the pharmaceutical composition further comprises a disintegrating agent and a lubricant. In some embodiments, the lubricant is sodium stearyl fumarate. In some embodiments, the pharmaceutical composition comprises from about 0.05% (w/w) to about 5% (w/w) of sodium stearyl fumarate.

Oral pharmaceutical compositions as described herein can generally be in the form of individualized or multi-unit doses, such as tablets, caplets, powders, suspension tablets, chewable tablets, rapid melt tablets, capsules, e.g., a single- or double-shell gelatin capsule, tablet-filled capsules, effervescent powders, effervescent tablets, pellets, granules, liquids, solutions, or suspensions, respectively. In some embodiments, the pharmaceutical composition is formulated as an oral dosage form, or as a solid oral dosage form. In some embodiments, the oral dosage form is an oral powder, a granule, a pellet, a tablet, a capsule, a troch or a lozenge. In some embodiments, the tablet is a chewable tablet, a dispersible tablet, or a troch. In some embodiments, the pharmaceutical composition is formulated to contain a single dose or multiple doses. In some embodiments, each pharmaceutical composition dosage form (e.g., each tablet or capsule) comprises 25 mg, or 50 mg, or 100 mg, or 150 mg, or 200 mg, or 250 mg, or 300 mg, or 350 mg, or 400 mg, or 450 mg, or 500 mg free base equivalent of the compound of Formula I or Compound 1. In some embodiments, the active ingredient (e.g., compound of Formula I or Compound 1 or a pharmaceutically acceptable salt thereof) is present in the pharmaceutical composition at a concentration of about 15 to about 40% (w/w), or about 25 to about 35% (w/w), or about 25% (w/w), or about 30% (w/w), or about 35% (w/w). For salt forms, the concentration is stated as the free base equivalent of the salt form.

Also contemplated are methods of making pharmaceutical compositions with improved stability, bioavailability, and shelf-life. The following exemplary methods of making pharmaceutical compositions in accordance with the presently described processes can be used with any suitable drug. Specifically, the methods described herein are directed to making pharmaceutical compositions comprising any suitable drug that is susceptible to degradation when exposed to the environment or exposed to physical stresses during the manufacturing process.

The pharmaceutical compositions described herein can be made by first combining a drug substance with a suitable adsorbing agent before being processed into capsules or tablets. Combining the drug substance with the adsorbing agent can be accomplished by any suitable methods, e.g., blending, mixing, milling or co-milling, compressing, granulating, dissolving, or precipitating the drug and the adsorbing agent together.

In some embodiments, the combined drug and adsorbing agent are suitable for use in preparing dosage forms by processes including, but not limited to, dry blending, direct compression formulations, and roller compaction formulations.

In some embodiments is a pharmaceutical composition comprising: (a) a compound of Formula (I), or Compound 1:

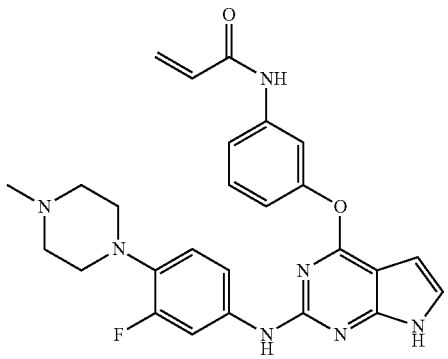

(Compound 1)

or a pharmaceutically acceptable salt thereof; and (b) an adsorbing agent that reduces or eliminates formation of a dimer of Compound 1, or a pharmaceutically acceptable salt thereof. In some embodiments, the reduction or elimination of dimer formation is upon storage or stability testing, and in other embodiments, the reduction or elimination is in vivo, e.g., after administration of the pharmaceutical composition. In some embodiments, the reduction or elimination is relative to substantially the same formulation, without the adsorbing agent, under the same conditions.

In some embodiments, the pharmaceutical composition comprises Compound 1. In other embodiments, the pharmaceutical composition comprises a pharmaceutically acceptable salt of Compound 1. In some embodiments, the pharmaceutically acceptable salt is selected from the group consisting of a maleate salt, a hydrochloride salt, a fumarate salt, a malate salt, a sulfate salt, a mesylate salt, a tosylate salt, and a hydrobromide salt.

In some embodiments, the maleate salt has polymorph Form I. In some embodiments, the maleate salt polymorph Form I is formed by crystallization from an aqueous solution comprising from about 1% (v/v) to about 90% (v/v) of ethanol, or about 100% (v/v) of ethyl acetate. In some embodiments, the maleate salt polymorph Form I is formed by crystallization from an aqueous solution comprising about 50% (v/v) of ethanol. In some embodiments, the maleate salt has polymorph Form II. In some embodiments, the maleate salt polymorph Form II is formed by crystallization from about 100% (v/v) of methanol or ethanol. In some embodiments, the maleate salt has polymorph Form III. In some embodiments, the maleate salt polymorph Form III is formed by crystallization from about 100% (v/v) tetrahydrofuran. In some embodiments, the maleate salt has an amorphous form. In some embodiments, the maleate salt amorphous form is prepared by drying or crystallizing from about 100% (v/v) of acetone or acetonitrile.

In some embodiments, the pharmaceutically acceptable salt of Compound 1 is the hydrochloride salt. In some embodiments, the hydrochloride salt has polymorph Form IV. In some embodiments, the hydrochloride salt polymorph Form IV is formed by crystallization from an aqueous solution comprising from about 0% (v/v) to about 60% (v/v) of ethanol.

In some embodiments, the pharmaceutically acceptable salt of Compound I is the fumarate salt. In some embodiments, the fumarate salt has polymorph Form V. In some embodiments, the fumarate salt polymorph Form V is formed by crystallization from an aqueous solution comprising from about 0% (v/v) to about 60% (v/v) of ethanol.

In some embodiments, the pharmaceutically acceptable salt of Compound I is the malate salt. In some embodiments, the malate salt has polymorph Form VI. In some embodiment, the malate salt polymorph Form VI is formed by crystallization from an aqueous solution comprising from about 0% (v/v) to about 60% (v/v) of ethanol.

In some embodiments, the pharmaceutically acceptable salt of Compound 1 is the sulfate salt, the mesylate salt, the tosylate salt, or the hydrobromide salt. In some embodiments, the sulfate salt, the mesylate salt, the tosylate salt, or the hydrobromide salt is in amorphous form.

In some embodiments, the adsorbing agent reduces the formation of a dimer of Compound 1, or a pharmaceutically acceptable salt thereof. In some embodiments, the dimer level in the pharmaceutical composition is below the limits of quantitation of the detection method. In other embodiments, no dimer formation is detected in the pharmaceutical composition.

Also described herein are processes for preparing a pharmaceutical composition as discussed herein, wherein said method comprises: 1) combining a compound of Formula I, or Compound 1, or a pharmaceutically acceptable salt thereof, with an adsorbing agent to form a first mixture; and 2) formulating the first mixture into a dosage form. In some embodiments, the compound or pharmaceutically acceptable salt thereof and the adsorbing agent are combined in a single step to form the first mixture. In some embodiments, the compound or salt and the adsorbing agent are combined in multiple steps to form the first mixture. In some embodiments, the adsorbing agent is a single adsorbing agent. In some embodiments, the adsorbing agent is multiple adsorbing agents. In some embodiments, the multiple adsorbing agents comprise at least two different kinds of silicified microcrystalline cellulose. In some embodiments, the at least two different kinds of silicified microcrystalline cellulose comprise Prosolv® SMCC 50 and Prosolv® SMCC 90. In some embodiments, the compound or a pharmaceutically acceptable salt thereof is combined with multiple different adsorbing agents sequentially, in some cases in one or more blending steps. In some embodiments, the compound or pharmaceutically acceptable salt thereof is combined with Prosolv® SMCC 50 in a first step, and then combined with Prosolv® SMCC 90 in a second step.

In some embodiments, the process further comprises formulating the first mixture into a dosage form in the presence of a pharmaceutically acceptable additive. In some embodiments, the additive comprises a disintegrating agent and/or a lubricant. In some embodiments, the additive comprises a disintegrating agent and a lubricant. In some embodiments, the disintegrating agent is cross-linked sodium carboxymethylcellulose or croscarmellose sodium (e.g., VIVASOL®), and the lubricant is sodium stearyl fumarate.

In some embodiments, the first mixture is formulated into an oral dosage form, e.g., a solid oral dosage form. In some embodiments, the formulating step comprises a dry blend process, a roller compaction process, or a direct compression process. In some embodiments, the dry blend process comprises a pre-blending step to combine the compound of Formula I, or Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and filling the first mixture with a disintegrating agent, e.g., croscarmellose sodium (VIVASOL®) and a lubricant, e.g., sodium stearyl fumarate, into a capsule.

In some embodiments, the roller compaction process comprises a pre-blending roller compaction step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and filling the first mixture with a disintegrating agent, e.g., croscarmellose sodium (VIVASOL®) and a lubricant, e.g., sodium stearyl fumarate, into a capsule. In some embodiments, the roller compaction process comprises a pre-blending roller compaction step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and mixing the first mixture with a disintegrating agent, e.g., croscarmellose sodium (VIVASOL®) and a lubricant, e.g., sodium stearyl fumarate, to form a tablet.

In some embodiments, the direct compression process comprises a pre-blending step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and mixing the first mixture with a disintegrating agent, e.g., croscarmellose sodium (VIVASOL®) and a lubricant, e.g., sodium stearyl fumarate, to form a tablet.

In some embodiments, the pharmaceutical composition comprising a compound of Formula I or Compound 1, or a pharmaceutically acceptable salt thereof, is supplied as a capsule or tablet for oral administration. In some embodiments, the capsule or tablet comprises from about 15% (w/w) to about 40% (w/w) of the compound of Formula I or Compound 1, or a pharmaceutically acceptable salt thereof. In some embodiments, the capsule or tablet comprises a compound of Formula I or Compound 1, or a pharmaceutically acceptable salt thereof, at least two different types of adsorbing agents, one or more disintegrants, and one or more lubricants. In some embodiments, the capsule or tablet comprises from about 35% (w/w) to about 75% (w/w) of the adsorbing agent. In some embodiments, the capsule or tablet comprises from about 60% (w/w) to about 85% (w/w) of the adsorbing agent. In some embodiments, the at least two different types of adsorbing agents comprise silicified microcrystalline cellulose (e.g., Prosolv® SMCC 50 and/or Prosolv® SMCC 90). In some embodiments, the capsule or tablet comprises from about 1% (w/w) to about 30% (w/w) of Prosolv® SMCC 50, and from about 30% (w/w) to about 70% (w/w) of Prosolv® SMCC 90. In some embodiments, the capsule or tablet comprises from about 15% (w/w) to about 20% (w/w) of Prosolv® SMCC 50, and from about 45% (w/w) to about 65% (w/w) of Prosolv® SMCC 90. In some embodiments, the capsule or tablet comprises from about 0.1% (w/w) to about 10% (w/w) of disintegrant. In some embodiments, the one or more disintegrants is selected from sodium carboxymethylcellulose, croscarmellose sodium (e.g., VIVASOL®), and crospovidone. In some embodiments, the capsule or tablet comprises from about 1.5% (w/w) to about 2.5% (w/w) of croscarmellose sodium. In some embodiments, the capsule or tablet comprises from about 0.05% (w/w) to about 5% (w/w) of the lubricant. In some embodiments, the one or more lubricant comprises sodium stearyl fumarate. In some embodiments, the capsule or tablet comprises from about 0.1% (w/w) to about 1.0% (w/w) of sodium stearyl fumarate.

In some embodiments of the pharmaceutical composition, the percentage w/w of the compound of Formula (I), or a pharmaceutically acceptable salt thereof (e.g., Compound 1, or a pharmaceutically acceptable salt thereof) is variable by up to ±20% w/w of the entire weight of the pharmaceutical composition. In some embodiments, each of the components of the pharmaceutical composition is variable by up to ±10% w/w of the entire weight of the pharmaceutical composition. In some embodiments, each of the adsorbing agents is variable by up to ±10% w/w of the entire weight of the pharmaceutical composition, the disintegrating agent is variable by up to ±6% w/w of the entire weight of the pharmaceutical composition, and the lubricant is variable by up to ±2% w/w of the entire weight of the pharmaceutical composition. In some embodiments, the capsule or tablet comprising a compound of Formula I or Compound 1 has a composition as described in Table 1A. In some embodiments, each of the adsorbing agents is variable by up to ±10% w/w of the adsorbing agent, the disintegrating agent is variable by up to ±6% w/w of the disintegrating agent, and the lubricant is variable by up to ±2% w/w of the lubricant. In some embodiments, the capsule or tablet comprising a compound of Formula I or Compound 1 has a composition as described in Table 1B.

TABLE 1A

| Component | Content (% w/w) |
| --- | --- |
| API/API maleate (e.g., Compound 1/Compound 1 maleate) | 20-30 |
| Silicified Microcrystalline Cellulose (Prosolv ®SMCC50) | 7.0-27.0 |

TABLE 1A-continued

| Component | Content (% w/w) |
| --- | --- |
| Silicified Microcrystalline Cellulose (Prosolv ®SMCC90) | 45.0-65.0 |
| Croscarmellose sodium (VIVASOL ®) | 0.01-8.0 |
| Sodium Stearyl Fumarate (PRUV ®) | 0.01-2.5 |

TABLE 1B

| Component | Content (% w/w) |
| --- | --- |
| API/API maleate (e.g., Compound 1/Compound 1 maleate) | 20-30 |
| Silicified Microcrystalline Cellulose (Prosolv ®SMCC50) | 15.3-18.7 |
| Silicified Microcrystalline Cellulose (Prosolv ®SMCC90) | 49.74-60.80 |
| Croscarmellose sodium (VIVASOL ®) | 1.88-2.12 |
| Sodium Stearyl Fumarate (PRUV ®) | 0.49-0.51 |

In some embodiments, the capsule or tablet comprising a compound of Formula I or Compound 1 is packaged inside a High-Density Polyethylene (HDPE) bottle and capped with a High-Density Polyethylene (HDPE) cap containing a silicon desiccant In certain instances, the processes for preparing pharmaceutical compositions further comprise one or more steps as described herein for preparation of a compound of Formula (I) or Compound 1, or of a pharmaceutically acceptable salt thereof. Embodiments are directed to the other processes described herein; and to the product prepared by any of the processes described herein.

EXAMPLES

Exemplary chemical entities, pharmaceutical compositions, and methods of making such compounds and compositions will now be described by reference to the specific examples that follow. Artisans will recognize that, for the chemical syntheses, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the examples below may be performed in any order that is compatible with the functionality of the particular pendant groups. Each of the reactions depicted in the general schemes is preferably run at a temperature from about 0° C. to the reflux temperature of the organic solvent used. Some of the reactions described in the examples provided below are run at a temperature from about −10° C. to about 100° C. With respect to the pharmaceutical composition examples, one of ordinary skill in the art will recognize that variations of the examples that follow may be appropriate.

The examples described herein are provided solely to illustrate representative embodiments of the invention. Accordingly, it should be understood, that the invention is not to be limited to the specific conditions or details described in these or any other example discussed herein, and that such examples are not to be construed as limiting the scope of the invention in any way. Throughout the specification, any and all references are specifically incorporated herein by reference in their entireties.

The following abbreviations have been used in the specification and examples: DCM=dichloromethane; DIEA=DIPEA=N,N-diisopropylethylamine; DMF=N,N-dimethylformamide; EtOH=ethanol; EtOAc=ethyl acetate; MeOH=methanol; t-BuOH=tert-butyl alcohol; and THF=tetrahydrofuran.

All solvents and reagents obtained from commercial sources were used without further purification. Both $^{1}$H NMR and $^{13}$C spectra were performed on a Bruker Avance III 500 MHz spectrometer. The mass spectra (MS) were obtained on a LC-MS PE SCIEX API 150EX using 0.05% HCOOH (aq.)/acetonitrile as the mobile phase.

Compounds of Examples 3-7 were also synthesized as shown in Schemes 1, 2A and 2B.

Scheme 1.

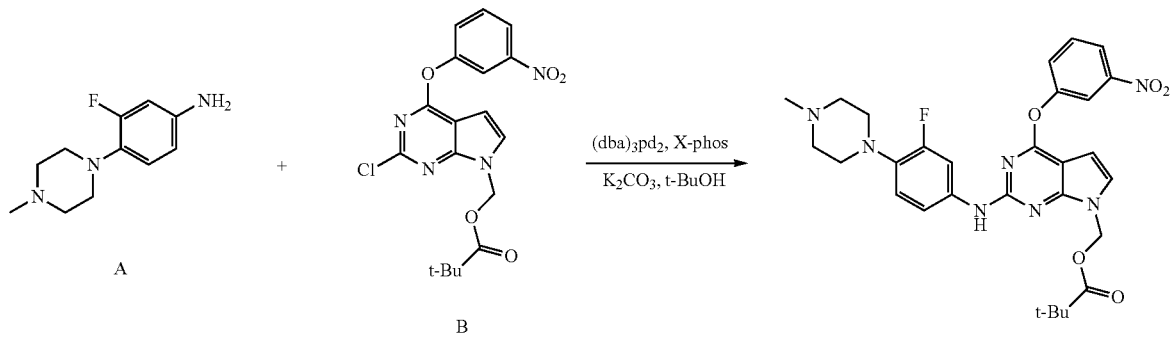

Example 3, 3A

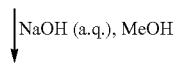

-continued
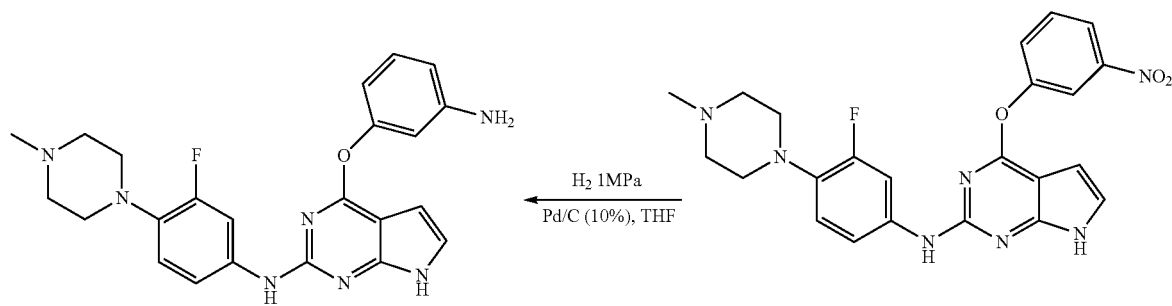
Example 5, 5A    Example 4, 4A
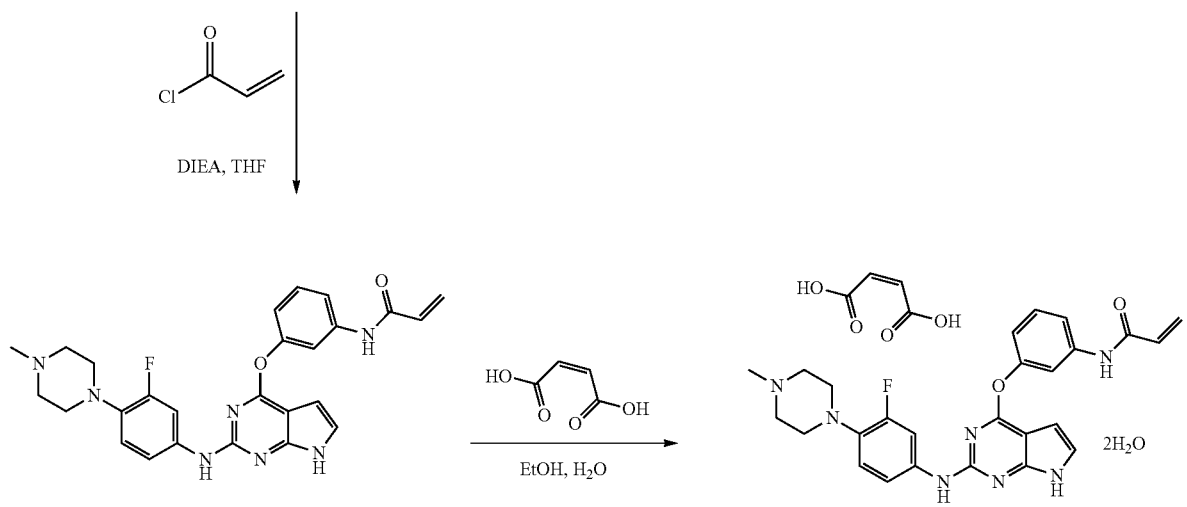
Example 6, 6A    Example 7, 7A
Scheme 2A.
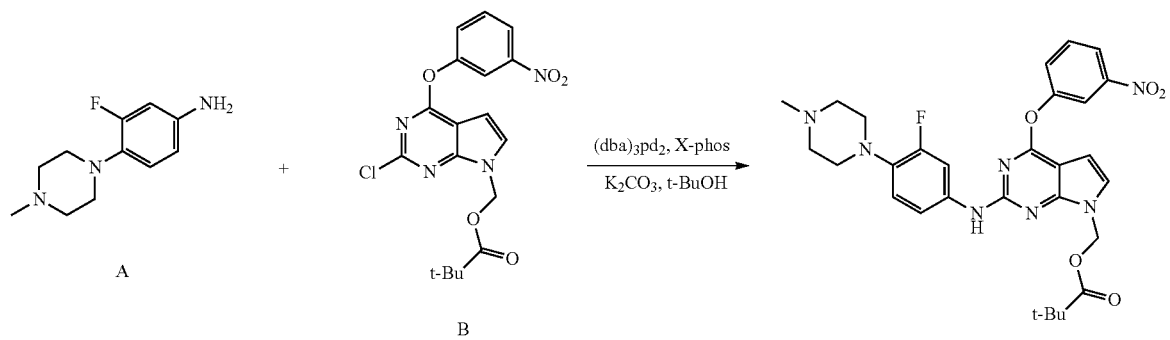
Example 3B
NaOH (a.q.), MeOH -continued
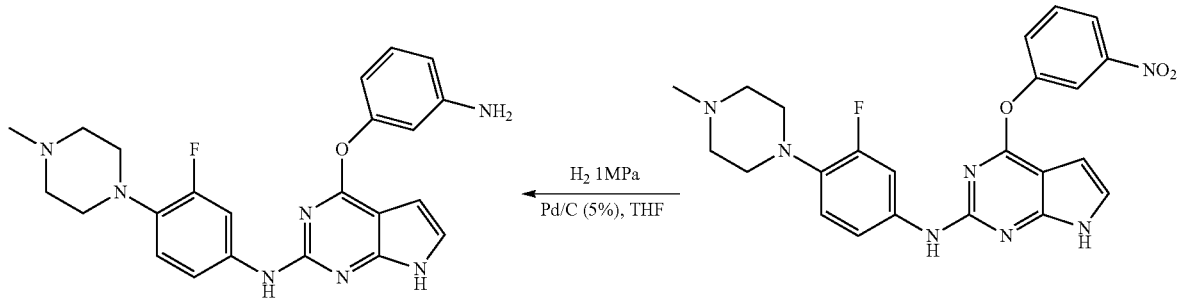
Example 5B          Example 4B
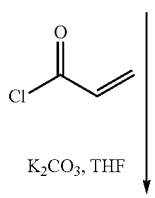
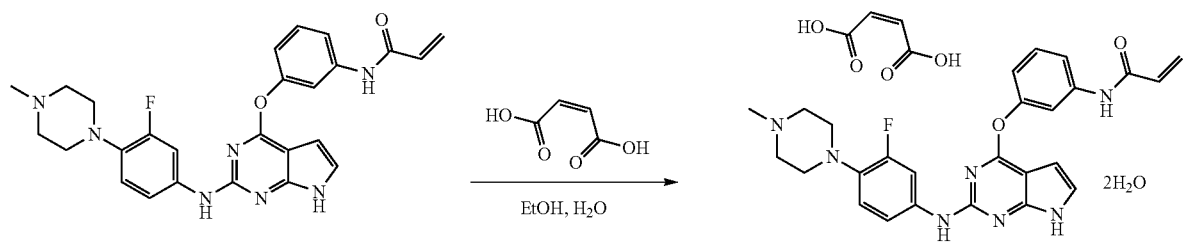
Example 6B          Example 7B
Scheme 2B.
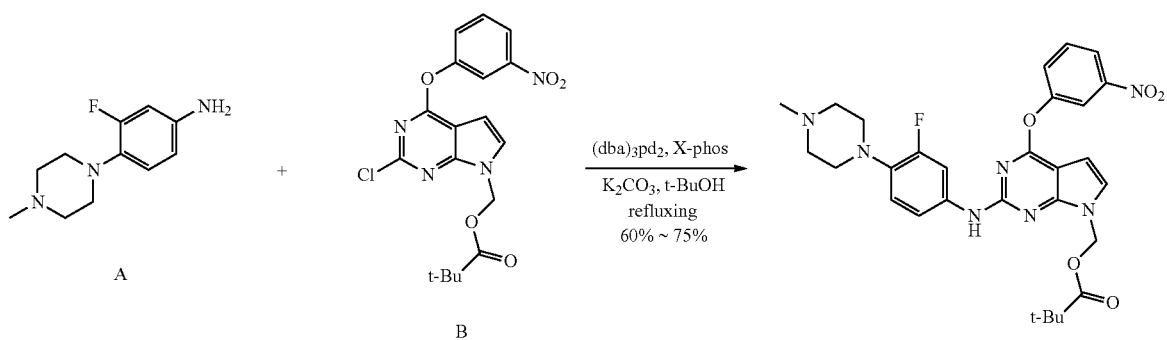
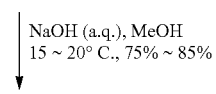

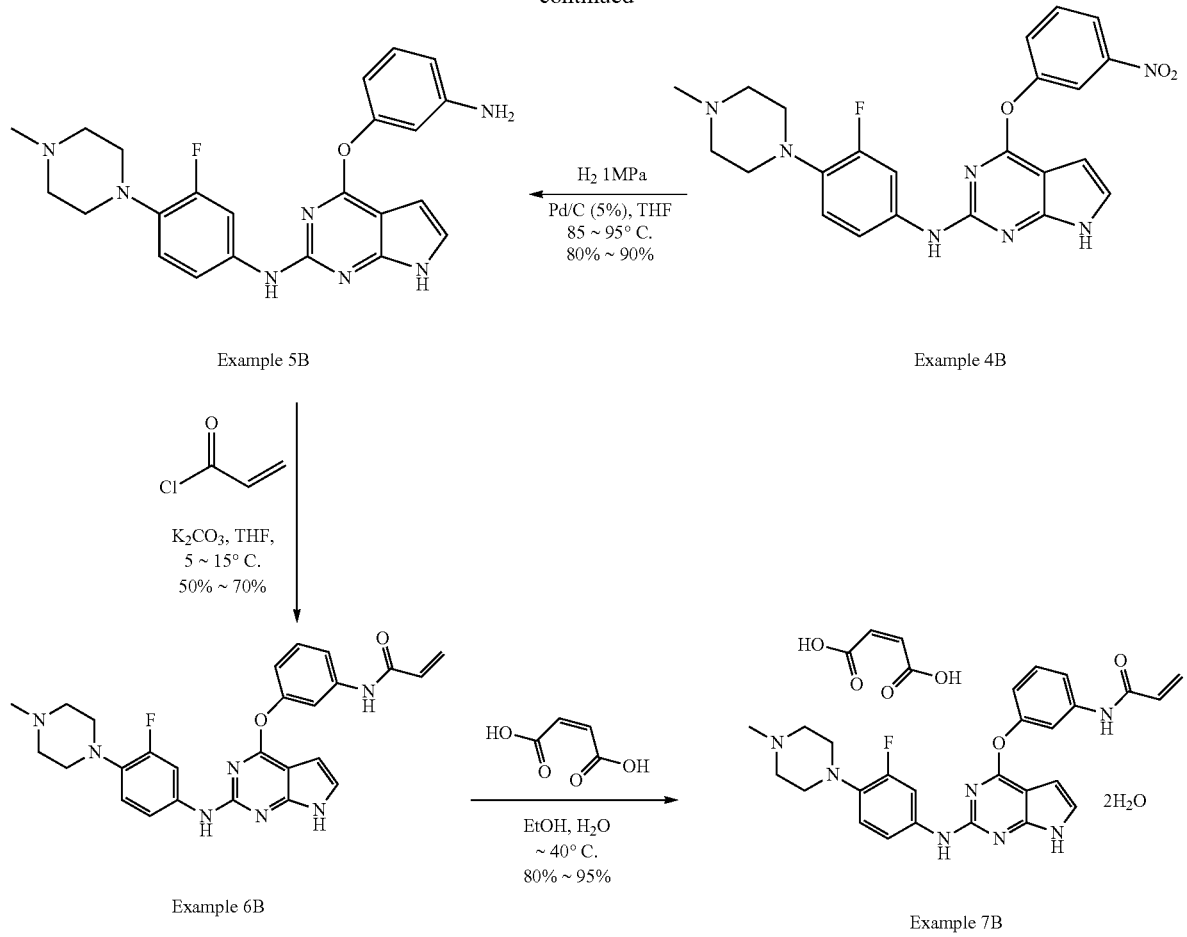

The following examples are offered to illustrate but not to limit the invention.

Example 1. Synthesis of (2,4-dichloro-7H-pyrrolo[2,3-d]pyrimidin-7-yl)methyl pivalate

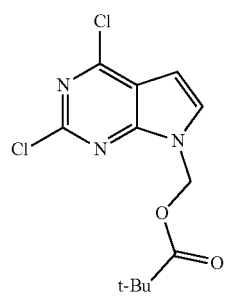 [SMILES: CC(C)(C)C(=O)OCn1ccc2c(Cl)nc(Cl)nc21]

To a 500 L reactor was sequentially added 2,4-dichloro-7H-pyrrolo[2,3-d]pyrimidine (31.5 kg), tetrahydrofuran (THF; 280 kg), chloromethyl pivalate (POMCl; 27.5 kg), K$_2$CO$_3$ (70 kg), and water (30 kg). The mixture was stirred for 12 h while the reaction temperature was kept between 35±5° C. The reaction mixture was filtered, and the residue was washed with THF until compound 2b was not detected in the filtrate (by thin layer chromatography (TLC)). The filtrate was combined and concentrated under reduced pressure. The residue was then re-dissolved in ethyl acetate (300 kg) and was washed with water until a neutral pH was reached. The organic layer was separated, dried over Na$_2$SO$_4$, and concentrated under reduced pressure to afford the title compound, which was used directly for next step without further purification. LC-MS: m/z 302.1 [M+H]$^+$.

Example 2. Synthesis of (2-chloro-4-(3-nitrophenoxy)-7H-pyrrolo[2,3-d]pyrimidin-7-yl)methyl pivalate

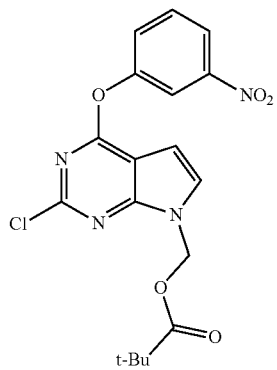 [SMILES: CC(C)(C)C(=O)OCn1ccc2c(Oc3cccc([N+](=O)[O-])c3)nc(Cl)nc21]

The product of Example 1 was combined with DMF (300 kg), 3-nitrophenol (24 kg), and K$_2$CO$_3$ (70 kg). The mixture was stirred for 48 h while the reaction temperature was kept between 35±5° C. The reaction mixture was filtered, and the collected solid was washed with ethyl acetate until no product was detected in the eluting filtrate (by TLC). Approximately one third of the filtrate was diluted with ethyl acetate (180 kg) and water (300 kg). The mixture was stirred for 2 h and the aqueous layer was separated. The upper layer was washed with water (3×300 kg), resulting in a pH neutral solution. The aqueous layers were combined and extracted with ethyl acetate until no product was detected in the aqueous layer by TLC. All the organic layers were combined, dried over Na$_2$SO$_4$, and filtered. The filtrate was concentrated under reduced pressure to a volume of ~400 L, which was de-colored with activated carbon and then filtered. The filtrate was concentrated under reduced pressure. The residue was re-dissolved in ethyl acetate (25 kg) and petroleum ether (150 kg) and stirred at reflux temperature. The resulting clear solution was allowed to cool to room temperature. The precipitate was collected and dried to afford the title compound. The same procedures were performed on the two remaining portions of the filtrate. The three portions of product were combined and suspended in petroleum ether (300 kg). The suspension was vigorously stirred at reflux for 3 h, and then was allowed to cool to room temperature. The resulting solid was collected and dried to afford the title compound (42.5 kg, 63% over two steps) as a white solid. LC-MS: m/z 405.2 [M+H]$^+$. $^1$H NMR (500 MHz, CDCl$_3$) δ 8.17-8.14 (m, 1H), 8.14-8.13 (m, 1H), 7.63-7.62 (m, 2H), 7.37 (d, J=3.7 Hz, 1H), 6.62 (d, J=3.7 Hz, 1H), 6.18 (s, 2H), 1.17 (s, 9H). $^{13}$C NMR (125 MHz, CDCl$_3$) δ 178.4, 161.6, 154.6, 152.7, 152.5, 149.1, 130.3, 128.6, 128.2, 120.8, 117.4, 104.8, 100.3, 65.9, 39.0, 27.0 (*3).

Example 3. Synthesis of (2-(3-fluoro-4-(4-methylpiperazin-1-yl)phenylamino)-4-(3-nitrophenoxy)-7H-pyrrolo[2,3-d]pyrimidin-7-yl)methyl pivalate

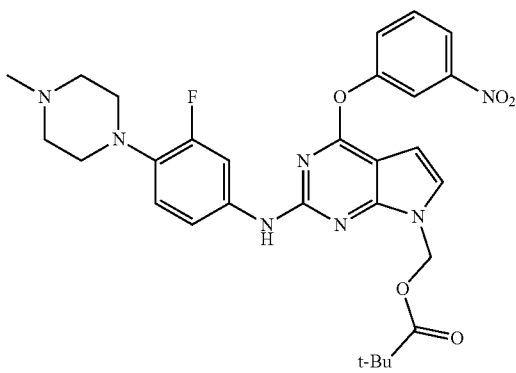 [SMILES: CN1CCN(c2ccc(Nc3nc(Oc4cccc([N+](=O)[O-])c4)c4ccn(COC(=O)C(C)(C)C)c4n3)cc2F)CC1]

A 500-L, glass-lined reactor was put under an inert atmosphere with nitrogen gas, then was charged with t-butanol (147 kg) under vacuum. Agitation was initiated, and the reactor was heated to 40±5° C. and nitrogen gas was again introduced. To the reactor was added (2-chloro-4-(3-nitrophenoxy)-7H-pyrrolo[2,3-d]pyrimidin-7-yl)methyl pivalate (19.10 kg, compound B), anhydrous K$_2$CO$_3$ (32.02 kg), tris(dibenzylideneacetone)dipalladium (Pd$_2$(dba)$_3$; 0.88 kg), dicyclohexyl (2',4',6'-triisopropylbiphenyl-2-yl)phosphine (XPhos; 0.90 kg), and 3-fluoro-4-(4-methylpiperazin-1-yl)aniline (9.70 kg, compound A). The resulting mixture was heated at 85±5° C. for 6 h. The mixture was cooled to 60±5° C. and then filtered through a pad of diatomaceous earth (4.9 kg) at 50° C. The reactor was washed with ethyl acetate (36 kg). The diatomaceous earth pad was slurried with ethyl acetate for 30 min at 50° C. (two times) and then was filtered.

The above procedure was repeated and the filtrates were all combined to afford 351 kg of ethyl acetate solution (assay amount 50.36 kg of title compound (compound of Example 3, see Scheme 1)). The ethyl acetate solution was concentrated to dryness. Ethyl acetate (281 kg) was added and the mixture was stirred for 30 min to dissolve the residue. Silica gel (37 kg) was then added and the resulting mixture was stirred for 1 h. The mixture was filtered and the resulting filtrate was charged into a 1000-L glass-lined reactor. The solution was washed with purified water (125 kg×2) and then brine (125 kg). The organic layer was concentrated to dryness at 45±5° C. at a vacuum pressure below ~0.02 MPa. Ethanol (124 kg) was added to the residue and the resulting mixture was heated at 85±5° C. for 1 h. Heptane (70 kg) was added and the resulting mixture was heated at 85±5° C. and stirred for 1 h. The mixture was cooled to 5±5° C. at a rate of 20° C./h and then was stirred for 5 h. The resulting precipitate was centrifuged. The solid was washed with heptane (20 kg) and dried at 50±5° C. at a pressure below ~0.02 MPa for 16 h to give the title compound (compound of Example 3, see Scheme 1) (46.46 kg, 86.4%, 99.21% HPLC purity) as an orange solid. LC-MS: m/z 578.5 [M+H]$^+$. $^1$H NMR (500 MHz, CD$_3$OD) δ 8.17-8.14 (m, 2H), 7.69-7.64 (m, 2H), 7.41 (d, J=15.1 Hz, 1H), 7.13 (d, J=3.7 Hz, 1H), 7.00 (d, J=8.0 Hz, 1H), 6.77 (t, J=9.2 Hz, 1H), 6.49 (d, J=3.6 Hz, 1H), 6.10 (s, 2H), 2.97 (s, 4H), 2.59 (s, 4H), 2.32 (s, 3H), 1.14 (s, 9H); $^{13}$C NMR (125 MHz, CD$_3$OD) δ 179.32, 163.26, 157.81, 156.67, 155.88, 154.79, 150.34, 138.03 (d, J=10 Hz), 134.50 (d, J=10 Hz), 131.60, 129.92, 126.31, 121.34, 120.12 (d, J=3.75 Hz), 119.02, 115.29, 107.96 (d, J=26.25 Hz), 100.72, 100.39, 67.88, 56.05 (*2), 51.69 (d, J=2.5 Hz, *2), 46.12, 39.84, 27.32 (*3).

Example 3A. Alternative synthesis of (2-(3-fluoro-4-(4-methylpiperazin-1-yl)phenylamino)-4-(3-nitrophenoxy)-7H-pyrrolo[2,3-d]pyrimidin-7-yl)methyl pivalate To a 5 L round bottom flask was added t-BuOH (2.5 L), (2-chloro-4-(3-nitrophenoxy)-7H-pyrrolo[2,3-d]pyrimidin-7-yl)methyl pivalate (300 g, 0.74 mol), and 3-fluoro-4-(4-methylpiperazin-1-yl)aniline (154 g, 0.74 mol). The reaction mixture was stirred at a speed of 360 rpm for 5-10 min. Potassium carbonate (220 g, 1.59 mol), tris(dibenzylideneacetone)dipalladium (14 g, 0.0153 mol), dicyclohexyl (2',4',6'-triisopropylbiphenyl-2-yl)phosphine (14 g, 0.0294 mol) and another portion of t-BuOH (0.5 L) were then added. The flask was placed in an oil bath (110-120° C.), and the reaction mixture was stirred at reflux under N$_2$ at the speed of 320 rpm. After stirring for 3-3.5 h, the mixture was allowed to cool to 40-50° C., filtered through diatomaceous earth, and washed with ethyl acetate (300 mL). The combined filtrate was concentrated under reduced pressure to afford the crude product.

The crude material was re-dissolved in ethyl acetate (2.5 L), and silica gel (300 g) was added (for de-colorization). After the mixture was stirred for 15-30 min, the mixture was filtered and washed with ethyl acetate (2 L). The combined filtrate was washed with water (1 L×2) and brine (1 L), and concentrated under reduced pressure to give a second crude product, which was then re-dissolved in hot EtOH (1 L, ~75°

C.) with stirring. The solution was allowed to cool to room temperature. The resulting crystals were collected and washed with n-hexane (200 mL) and dried at 45° C. for 4 h to afford the title compound as a light brown solid (compound of Example 3A, see Scheme 1) (280 g, 96.26% purity by HPLC, 65% yield). mp: 99.5-101.5° C.; [M+H]⁺: m/z 578.5; ¹H NMR and ¹³C NMR spectral data for (2-(3-fluoro-4-(4-methylpiperazin-1-yl)phenylamino)-4-(3-nitrophenoxy)-7H-pyrrolo[2,3-d]pyrimidin-7-yl)methyl pivalate are consistent with those reported in Example 3.

Example 3B. Alternative synthesis of (2-(3-fluoro-4-(4-methylpiperazin-1-yl)phenylamino)-4-(3-nitrophenoxy)-7H-pyrrolo[2,3-d]pyrimidin-7-yl)methyl pivalate A 1000-L, glass-lined reactor was put under an inert atmosphere with nitrogen gas, then was charged with t-butanol (300 kg) under vacuum. Agitation was initiated, and the reactor was heated to 40±5° C. and nitrogen gas was again introduced. To the reactor was added (2-chloro-4-(3-nitrophenoxy)-7H-pyrrolo[2,3-d]pyrimidin-7-yl)methyl pivalate (39.37 kg, compound B), anhydrous K₂CO₃ (65.94 kg), tris(dibenzylideneacetone)dipalladium (Pd2(dba)3; 1.82 kg), dicyclohexyl (2',4',6'-triisopropylbiphenyl-2-yl) phosphine (XPhos; 1.80 kg), and 3-fluoro-4-(4-methylpiperazin-1-yl)aniline (20 kg, compound A). The resulting mixture was heated at 85±5° C. for 4 h. The sample was taken for HPLC analysis, which showed the reaction was completed with only 0.1% of compound B remained; The mixture was cooled to 60±5° C. and then filtered through a pad of diatomaceous earth (10 kg) at 50° C. The reactor was washed with ethyl acetate (70 kg). The diatomaceous earth pad was slurried with this ethyl acetate for 30 min at 50° C. and then was filtered. The cake was further marinated with ethyl acetate (90 kg) for 30 min at 50° C., and then filtered. The filtrate was collected.

The above procedure was repeated and the filtrates were all combined to afford 1386 kg of ethyl acetate solution with 96% HPLC purity. The ethyl acetate solution was transferred into another reactor (3000 L), and concentrated to ~300 L residual. Ethyl acetate (1088 kg) was added and the mixture was stirred for 30 min to dissolve the residue. Silica gel (142.9 kg) was then added and the resulting mixture was stirred for 1 h. The mixture was filtered, and washed the reactor with ethyl acetate (862 Kg), and then transferred it to the filter to wash the cake. The resulting combined filtrate (2145 Kg) was charged into a 3000-L glass-lined reactor. The solution was washed with purified water (490 Kg×2) and then brine (488 kg). The organic layer (2110 Kg) was concentrated to ~300 L at 45±5° C. at a vacuum pressure below ~0.08 MPa. Ethanol (180 L) was added and then concentrated to 300 L at 45±5° C. at a vacuum pressure below ~0.08 MPa. This process was repeated one more time. Ethanol (480 kg) was then added to the residue, and the resulting mixture was heated at 85±5° C. for 1 h. Heptane (262 kg) was added into the reactor for 1 hr. The resulting mixture was heated at 85±5° C. and stirred for 1 h. The mixture was cooled to 5±5° C. at a rate of 20° C./h and then was stirred for 20 h. The resulting precipitate was centrifuged and washed with the mother liquor. The solid was further washed with heptane (20 kg) and dried at 50±5° C. at a pressure below ~0.02 MPa for 16 h to give the title compound (159.58 kg, 77.33% yield, 98.61% HPLC purity) as an orange solid (compound of Example 3B, see Schemes 2A and 2B). LC-MS: m/z 578.5 [M+H]⁺. ¹H NMR (500 MHz, DMSO-d6): δ ppm 9.46 (s, 1H), 8.30-8.20 (m, 2H), 7.88-7.82 (m, 1H), 7.80 (t, J=8.0 Hz, 1H), 7.56-7.36 (m, 1H), 7.31 (d, J=3.7 Hz, 1H), 7.15 (br s, 1H), 6.77 (t, J=9.3 Hz, 1H), 6.55 (d, J=3.7 Hz, 1H), 6.12 (s, 2H), 2.87 (br s, 4H), 2.43 (br s, 4H), 2.21 (s, 3H), 1.12 (s, 9H). ¹³C NMR (125 MHz, DMSO-d6): δ ppm 177.03 (s), 161.54 (s), 155.49 (s), 154.90 (s), 153.56 (s), 152.87 (s), 148.50 (s), 135.91 (d, J=11.1 Hz), 133.31 (d, J=9.6 Hz), 131.03 (s), 129.15 (s), 125.62 (s), 120.46 (s), 118.76 (s), 117.70 (s), 114.22 (s), 106.38 (d, J=26.6 Hz), 99.52 (s), 98.55 (s), 66.98 (s), 54.73 (s, ×2), 50.34 (s, ×2), 45.75 (s), 38.27 (s), 26.59 (s, ×3).

Example 4. Synthesis of N-(3-fluoro-4-(4-methylpiperazin-1-yl) phenyl)-4-(3-nitrophenoxy)-7H-pyrrolo[2,3-d]pyrimidin-2-amine

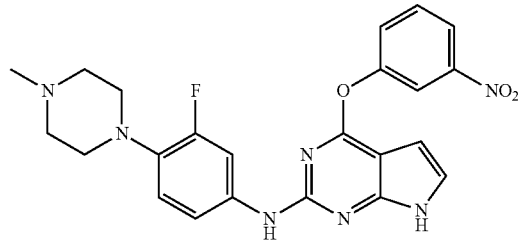 [SMILES: CN1CCN(c2ccc(Nc3nc(Oc4cccc(N)c4)c4cc[nH]c4n3)cc2F)CC1]

To a 2000-L glass-lined reactor under vacuum was added methanol (734 kg). Agitation was initiated, and the reactor was charged with (2-(3-fluoro-4-(4-methylpiperazin-1-yl) phenylamino)-4-(3-nitrophenoxy)-7H-pyrrolo[2,3-d]pyrimidin-7-yl)methyl pivalate (46.46 kg). The reaction mixture was cooled to 10±5° C. and was agitated for 1 h. Aqueous NaOH (2.5 M, 66.4 kg (6.40 kg NaOH dissolved in 60 kg purified water)) was added drop-wise to the reactor over 75 min. The resulting mixture was warmed to 15±5° C. and was stirred for 3 h. The reaction mixture was cooled to 10±5° C. and purified water (372 kg) was added over 60 min. The resulting mixture was stirred at 5±5° C. for 3 h. The resulting precipitate was centrifuged and the cake was washed with purified water (48 kg). The wet cake (88.30 kg) and purified water (372 kg) were stirred for 3 h and then filtered by press filtration, washing with purified water (47 kg). The wet cake (100.80 kg) and ethyl acetate (250 kg) were combined, heated to 75±5° C., and stirred for 1 h. The resulting mixture was allowed to stand for 30 min. The aqueous layer was separated while the top organic layer was cooled to 10±5° C. at a rate of 20° C./h, and was stirred for 10 h. The resulting precipitate was centrifuged to provide 28.6 kg of a first wet cake (98.7% purity by HPLC (1.1% of starting material)). The mother liquor was concentrated at 45±5° C. at a vacuum pressure of below 0.02 MPa to about 55-90 L, heated to 75±5° C., and stirred for 1 h. The solution was cooled to 10±5° C. at a rate of 20° C./h, and was stirred for 5 h. The resulting solid was collected by centrifugation to provide a second wet cake (4.94 kg (95.7% purity by HPLC (2.9% of starting material)). The two wet cake portions of product were combined and dried at 50±5° C. under vacuum at below 0.02 MPa for 16 h to give the title compound (compound of Example 4, see Scheme 1) (28.38 kg, 76.1%) as a yellow solid. LC-MS: m/z 464.1 [M+H]⁺. ¹H NMR (500 MHz, CDCl₃) δ 9.77 (s, 1H), 8.22-8.10 (m, 2H), 7.66-7.55 (m, 2H), 7.41 (dd, J=14.8, 2.4 Hz, 1H), 6.96 (s, 1H), 6.88-6.82 (m, 2H), 6.77 (t, J=9.1 Hz, 1H), 6.46 (dd, J=3.5, 1.9 Hz, 1H), 3.05 (s, 4H), 2.63 (s, 4H), 2.37 (s, 3H). ¹³C NMR (125 MHz, CDCl₃) δ 161.93 (s), 156.52 (s), 155.41 (s), 154.92 (s), 154.57 (s), 153.28 (s), 148.87 (s), 135.13 (d, J=11.0 Hz), 134.56 (d, J=9.7 Hz), 130.04 (s), 128.60 (s), 121.10 (s), 120.29 (s), 119.01 (d, J=4.1 Hz), 117.84 (s), 114.57 (s), 107.77 (d, J=25.9 Hz), 99.38 (d, J=4.4 Hz), 55.13 (s, *2), 50.74 (s, *2), 46.05 (s).

Example 4A. Alternative synthesis of N-(3-fluoro-4-(4-methylpiperazin-1-yl) phenyl)-4-(3-nitrophenoxy)-7H-pyrrolo[2,3-d]pyrimidin-2-amine To a 50-L jacketed reactor heated using hot water (75° C.) were charged (2-(3-fluoro-4-(4-methylpiperazin-1-yl)phenylamino)-4-(3-nitrophenoxy)-7H-pyrrolo[2,3-d]pyrimidin-7-yl)methyl pivalate (1.5 kg, 2.6 mol) and MeOH (30 L). The mixture was heated at reflux until the (2-(3-fluoro-4-(4-methylpiperazin-1-yl)phenylamino)-4-(3-nitrophenoxy)-7H-pyrrolo[2,3-d]pyrimidin-7-yl)methyl pivalate was completely dissolved and then was stirred for another 30 min at ~65° C. At this point, the hot water was removed from jacket, and replaced with cold alcohol (−10~−15° C.) to cool the reactor. When the temperature inside the reactor reached 10-18° C., a NaOH solution (2.5 M, 2.1 L) was added drop-wise into the reaction over a ~1 h period. The temperature was kept below 20° C. during the addition. After the addition was completed, the reaction mixture was stirred between 15-20° C. for another ~5 h. At this point, an in-process HPLC analysis indicated that the (2-(3-fluoro-4-(4-methylpiperazin-1-yl)phenylamino)-4-(3-nitrophenoxy)-7H-pyrrolo[2,3-d]pyrimidin-7-yl)methyl pivalate was completely consumed and that there was a partially de-protected intermediate (MW=463.5+30) (less than 10%) in the reaction mixture. The reaction mixture was cooled to 0-5° C., and water (12 L) was added drop-wise into the reactor over 60 min. The temperature was kept below 20° C. during the addition of the water. After the addition of the water, the reaction mixture was stirred for another 15 min. The resulting precipitate (crude product) was collected, washed with water (2 L), and dried under vacuum. The crude material was re-dissolved in ethyl acetate (30 L). The resulting solution was washed with water (10 L×3) and brine (10 L×1). The organic layer was passed through a pad of diatomaceous earth to remove the residual insoluble material. The filtrate was concentrated under reduced pressure at 38-42° C. until the volume of the remaining solution was around 5 L. The remaining solution was allowed to cool to 0-5° C. and was stirred overnight. The precipitate was collected and dried under vacuum to afford the title compound (compound of Example 4A, see Scheme 1) (968 g, 89.98% purity by HPLC, 80% yield) as a light yellow powder. mp: 132.5-134.5° C.; [M+H]$^+$: m/z 464.1; $^1$H NMR and $^{13}$C NMR spectral data for N-(3-fluoro-4-(4-methylpiperazin-1-yl) phenyl)-4-(3-nitrophenoxy)-7H-pyrrolo[2,3-d]pyrimidin-2-amine are consistent with those reported in Example 4.

Example 4B. Alternative synthesis of N-(3-fluoro-4-(4-methylpiperazin-1-yl) phenyl)-4-(3-nitrophenoxy)-7H-pyrrolo[2,3-d]pyrimidin-2-amine To a 5000-L glass-lined reactor under vacuum was added methanol (1870 kg). Agitation was initiated, and the reactor was charged with (2-(3-fluoro-4-(4-methylpiperazin-1-yl)phenylamino)-4-(3-nitrophenoxy)-7H-pyrrolo[2,3-d]pyrimidin-7-yl)methyl pivalate (compound of Example 3B, see Schemes 2A and 2B, 159.9 kg). The reaction mixture was cooled to 10±5° C. and was agitated for 1 h. Aqueous NaOH (2.5 M, 230.6 kg (22.6 Kg NaOH dissolved in purified water 208 Kg)) was added drop-wise to the reactor over 1 h. The resulting mixture was warmed to 15±5° C. and was stirred for 3 h, sampling for HPLC analysis, which showed 0.8% of the compound of Example 3B (see Schemes 2A and 2B) were remained. The reaction mixture was cooled to 10±5° C. and purified water (960 kg) was added over 45 min. The resulting mixture was stirred at 5±5° C. for 3 h. The resulting precipitate was centrifuged, and the resulting cake was washed with purified water (480 kg). The wet cake (325.74 kg) was transferred into a 3000 L reactor, and ethyl acetate (848 kg) was added. The mixture was then heated to 75±5° C., stirred for 1 h, and allowed to stand for 30 min. The aqueous layer was separated while the top organic layer was cooled to 10±5° C. at a rate of 20° C./h, and was stirred for 5 h. The resulting precipitate was centrifuged to provide 105.3 kg of a first wet cake (97.4% purity by HPLC). The mother liquor was transferred into a 1000 L reactor, and concentrated at 45±5° C. at a vacuum pressure of below 0.08 MPa to about 128-192 L, heated to 75±5° C., and stirred for 1 h. The solution was cooled to 10±5° C. at a rate of 20° C./h, and was stirred for 3 h. The resulting solid was collected by centrifugation to provide a second wet cake 60.9 kg (92.1 purity by HPLC). The two wet cake portions of product were combined and dried at 50±5° C. under vacuum at below 0.08 MPa for 16 h to give the title compound (compound of Example 4B, see Schemes 2A and 2B) (100.96 kg, 78.7% yield and 95.1% purity) as a yellow solid. LC-MS: m/z 464.1 [M+H]$^+$. $^1$H NMR (500 MHz, DMSO-d$_6$): δ ppm 11.68 (s, 1H), 9.19 (s, 1H), 8.24-8.17 (m, 2H), 7.85-7.81 (m, 1H), 7.79 (t, J=8.0 Hz, 1H), 7.52 (d, J=15.3 Hz, 1H), 7.16 (dd, J=3.3, 2.2 Hz, 1H), 7.13 (d, J=8.3 Hz, 1H), 6.79 (t, J=9.4 Hz, 1H), 6.43 (dd, J=3.3, 1.5 Hz, 1H), 2.87 (br s, 4H), 2.43 (br s, 4H), 2.20 (s, 3H). $^{13}$C NMR (125 MHz, DMSO-d$_6$): δ ppm 161.24 (s), 155.61 (s), 154.95 (d, J=101.4 Hz), 153.69 (s), 153.16 (s), 148.51 (s), 136.41 (d, J=11.2 Hz), 133.02 (d, J=9.5 Hz), 131.01 (s), 129.11 (s), 122.39 (s), 120.24 (s), 118.86 (d, J=4.4 Hz), 117.54 (s), 114.10 (s), 106.23 (d, J=26.2 Hz), 98.50 (s), 98.19 (s), 54.77 (s, ×2), 50.43 (s), 50.41 (s), 45.78 (s).

Example 5. Synthesis of 4-(3-aminophenoxy)-N-(3-methyl-4-(4-methylpiperazin-1-yl)phenyl)-7H-pyrrolo[2,3-d]pyrimidin-2-amine

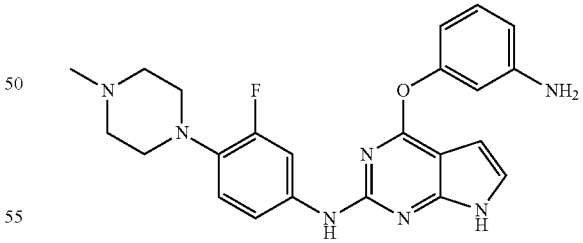

A 500-L pressure reactor was pressurized with N$_2$ to 0.9 MPa for 30 min. The atmosphere in the reactor was exchanged with 0.2 MPa of N$_2$ (5×). The reactor was charged sequentially with THF (204 kg), N-(3-fluoro-4-(4-methylpiperazin-1-yl) phenyl)-4-(3-nitrophenoxy)-7H-pyrrolo[2,3-d]pyrimidin-2-amine (28.38 kg), and Pd/C (1.42 kg). The reactor atmosphere was exchanged with 0.2 MPa of N$_2$ (5×), and then pressurized with N$_2$ to 0.9 MPa for 30 min. The reactor was put under a 0.2 MPa H$_2$ atmosphere (5×), and then was pressurized with H$_2$ to ~0.8-1.0 MPa. The reaction mixture was heated to ~90-100° C. and stirred under a pressure of ~0.8-1.0 MPa for 6 h. The reaction mixture was filtrated through a pad of diatomaceous earth (6.0 kg). The reactor and filter cake were washed with ethyl acetate (14 kg+56 kg). The filtrates were combined and concentrated under vacuum (0.02 MPa) at ~40-50° C. to a residual volume of ~30-50 L. The solution was diluted with ethyl acetate (226 kg) and was stirred for 30 min. The solution was washed with ~20% aq. NaCl (141 kg×2). The organic phase was collected and was filtered through a pad of diatomaceous earth (6.0 kg), washing with ethyl acetate (14 kg+56 kg). The filtrates were combined and concentrated under vacuum (0.02 MPa) at ~40-50° C. to a residual volume of ~30-50 L. A distill and replace operation was then performed using THF (70 kg×2) to achieve 800 ppm $H_2O$ by KF analysis (<2000 ppm) and Residual of Solvent (ROS) of 4.5% of ethyl acetate (<10.0%) in the residual THF solution with a volume of ~30-50 L. The solution was diluted with THF (112 kg) and the resulting solution (167 kg, 98.3% purity, 12.9% concentration of title compound by external standard assay, 81.13% assay yield, ~21.54 kg of title compound (compound of Example 5, see Scheme 1)) was used directly in the next step. LC-MS: m/z 434.4 $[M+H]^+$. $^1$H NMR (500 MHz, $CD_3OD$) δ 7.66 (d, J=15.3 Hz, 1H), 7.14 (t, J=8.0 Hz, 1H), 7.09 (dd, J=9 Hz, 1.5 Hz, 1H), 6.92 (d, J=3.5 Hz, 1H), 6.83 (t, J=9.2 Hz, 1H), 6.63 (d, J=8.1 Hz, 1H), 6.57 (s, 1H), 6.51 (d, J=8.0 Hz, 1H), 6.20 (d, J=3.5 Hz, 1H), 2.99 (s, 4H), 2.58 (s, 4H), 2.31 (s, 3H). $^{13}$C NMR (125 MHz, $CD_3OD$) δ 164.18, 158.03, 156.53 (d, J=18 Hz), 156.10, 155.69, 150.64, 138.59 (d, J=11.1 Hz), 134.17 (d, J=9.6 Hz), 130.94, 122.03, 120.31 (d, J=4.1 Hz), 115.12 (d, J=2.8 Hz), 113.42, 112.12, 109.82, 107.831 (d, J=26.3 Hz), 100.32, 100.00, 56.031 (*2), 51.61 (d, J=2.6 Hz, *2), 46.10.

Example 5A. Alternative synthesis of 4-(3-aminophenoxy)-N-(3-methyl-4-(4-methylpiperazin-1-yl)phenyl)-7H-pyrrolo[2,3-d]pyrimidin-2-amine Pd/C (10% on activated carbon, 22.58 g, 0.021 mol), THF (1.8 L) and N-(3-fluoro-4-(4-methylpiperazin-1-yl) phenyl)-4-(3-nitrophenoxy)-7H-pyrrolo[2,3-d]pyrimidin-2-amine (447.77 g, 0.97 mol) were charged into a high-pressure hydrogenation reactor. The air in the reactor was removed by nitrogen flow. Then hydrogen was charged into the reactor to replace the nitrogen (repeated 4 times). Hydrogen pressure was applied at 1 MPa, and temperature was set at 90-100° C. The reaction was agitated for approximately 5 h until no more hydrogen was consumed. The reaction mixture was cooled to room temperature, filtered through a pad of diatomaceous earth to remove the catalyst, and washed with ethyl acetate (0.2 L×3). The combined organic layers were concentrated under reduced pressure at a temperature below 38° C. to afford the crude product. The crude product was re-dissolved in ethyl acetate (5 L) and washed with water (2 L×2). The organic layer was passed through a pad of diatomaceous earth to remove insolubles and washed with ethyl acetate (0.5 L×2). The organic solvent was concentrated under reduced pressure (at a temperature below 38° C.) until the remaining solution was around 1.5 L. The remaining solution was allowed to cool to room temperature. The resulting precipitate was collected and dried under vacuum to afford the title compound (compound of Example 5A, see Scheme 1) (360 g, 97.9% purity by HPLC, 86% yield) as an off-white powder. mp: 213.5-215.5° C.; $[M+H]^+$: m/z 434.4; $^1$H NMR and $^{13}$C NMR spectral data for 4-(3-aminophenoxy)-N-(3-methyl-4-(4-methylpiper-azin-1-yl)phenyl)-7H-pyrrolo[2,3-d]pyrimidin-2-amine are consistent with those reported in Example 5.

Example 5B. Alternative synthesis of 4-(3-aminophenoxy)-N-(3-methyl-4-(4-methylpiperazin-1-yl) phenyl)-7H-pyrrolo[2,3-d]pyrimidin-2-amine A 3000-L pressure reactor was pressurized with $N_2$ to 0.8±0.2 MPa for 30 min. The atmosphere in the reactor was exchanged with 0.2 MPa of $N_2$ (5×). The reactor was charged sequentially with THF (482 kg), N-(3-fluoro-4-(4-methylpiperazin-1-yl) phenyl)-4-(3-nitrophenoxy)-7H-pyrrolo[2,3-d]pyrimidin-2-amine (89.4 kg, (compound of Example 4B, see Schemes 2A and 2B), and Pd/C (3.6 kg). The reactor atmosphere was exchanged with 0.2 MPa of $N_2$ (5×), and then pressurized with $N_2$ to 0.8±0.2 MPa for 30 min. The reactor was put under a 0.2 MPa $H_2$ atmosphere (5×), and then was pressurized with $H_2$ to 0.8±0.2 MPa. The reaction mixture was heated to 85±5° C. and stirred under a pressure of 0.8±0.2 MPa for 11 h. Sampling for HPLC analysis showed 0.05% the compound of Example 4B (see Schemes 2A and 2B) remained. The reaction mixture was heated to 90-95° C. and stirred under a pressure of 0.8±0.2 MPa for another 6 h. At this point, sampling for HPLC analysis showed 0.01% the compound of Example 4B (see Schemes 2A and 2B) remained. The reaction mixture was chill to 25±5 C, and exchanged the reactor under with $N_2$ to 0.2 Mpa for 5 h, and then filtrated the mixture through a pad of diatomaceous earth (18.0 kg). The reactor was washed with THF (90 kg), and filtered through the pad of diatomaceous earth. The pad of diatomaceous earth was rinsed with THF (225 kg) for 30 min. No further washing or isolation steps were performed. All the filtrates were combined to give a THF solution of the compound of Example 5B (see Schemes 2A and 2B) (822 kg) with 9.9% assay (compound of Example 5B, see Schemes 2A and 2B, 81.4 kg) in 97.3% assay yield and 97.4% HPLC purity. The compound of Example 5B (see Schemes 2A and 2B) was used directly for the next step, without isolation. LC-MS: m/z 434.4 $[M+H]^+$.

Example 6. Synthesis of N-(3-(2-(3-fluoro-4-(4-methylpiperazin-1-yl)phenylamino)-7H-pyrrolo[2,3-d]pyrimidin-4-yloxy)phenyl)acrylamide

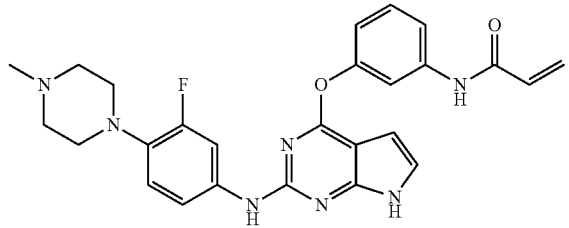 [SMILES: C=CC(=O)Nc1cccc(Oc2nc(Nc3ccc(N4CCN(C)CC4)c(F)c3)nc3[nH]ccc23)c1]

The solution of 4-(3-aminophenoxy)-N-(3-methyl-4-(4-methylpiperazin-1-yl)phenyl)-7H-pyrrolo[2,3-d]pyrimidin-2-amine in THF from Example 5 (166 kg (21.4 kg of starting material)) was agitated under vacuum, and then treated with THF (72 kg) and DIEA (10.8 kg). The reaction mixture was cooled to 5±5° C. Acryloyl chloride (6.70 kg) was diluted with THF (18 kg) and was added drop-wise to the mixture at 5±5° C. over 1.5 h. After 3 h, the reaction mixture was warmed to 10±5° C., and 1 N NaOH (150 kg) was added at 10±5° C. over 2 h. The resulting mixture was then warmed to 20±5° C. and stirred for an additional 3 h. The upper THF layer was separated, and was concentrated under vacuum at 45±5° C. to about 40-60 L. A distillation and replacement operation was then performed using ethyl acetate (55 kg) to obtain a residual ethyl acetate solution (~40-60 L). The aqueous layer was extracted with ethyl acetate (100 kg). The ethyl acetate layer was combined with the residual ethyl acetate solution, diluted further with ethyl acetate (210 kg), and stirred for 0.5 h. The solution was washed with 20% brine (110 kg×3) and concentrated under vacuum at 45±5° C. to a volume of ~40-60 L. A distillation and replacement operation was then performed twice using EtOH (44 kg×2) to obtain a residual EtOH solution (~40-60 L). The resulting solution was diluted with EtOH (88 kg) at 40±5° C., was treated with purified water (154 kg) slowly at 40±5° C. over 2 h, and then was stirred for 2 h. The mixture was cooled to 15±5° C. and was stirred for another 5 h. The resulting precipitate was centrifuged, and the wet cake was washed with 1:1 EtOH/$H_2O$ (22 kg) and then centrifuged again to afford the title compound (22.4 kg) as a pale yellow solid.

The crude material was dissolved in ethyl acetate (75 kg) and EtOH (22 kg), and the resulting solution was added to a silica gel column (88 kg, 200~300 mesh). The title compound was eluted with 4:1 ethyl acetate/EtOH (396 kg/88 kg). Fractions were collected and concentrated under vacuum at 45±5° C. to about 40-50 L. A distill and replace operation was then performed using EtOH (44 kg) to obtain ~40-60 L of a residual ethanol solution. The solution was diluted with EtOH (107 kg) and was heated to 40±5° C. Purified water (39.6 kg) was added over 1 h, and the resulting mixture was stirred for 2 h. A white solid started to precipitate and the suspension was cooled to 15±5° C. and stirred for 5 h. The mixture was centrifuged and the wet cake was washed with $H_2O$:EtOH (8.8 kg:13.2 kg). The wet cake was dried under vacuum at 50±5° C. for 16 h to afford the title compound (compound of Example 6, see Scheme 1) (12.24 kg, 99.39% purity, 50.8% assay yield) as a white solid. LC-MS: m/z 488.6 [M+H]$^+$. $^1$H NMR (500 MHz, $CD_3OD$) δ 7.69 (t, J=2.0 Hz, 1H), 7.62-7.55 (m, 2H), 7.41 (t, J=8.1 Hz, 1H), 7.06 (d, J=8.7 Hz, 1H), 7.01-6.99 (m, 2H), 6.80 (t, J=9.2 Hz, 1H), 6.44 (dd, J=17.0, 9.9 Hz, 1H), 6.39-6.32 (m, 2H), 5.77 (dd, J=9.9, 1.9 Hz, 1H), 2.99 (s, 4H), 2.59 (s, 4H), 2.32 (s, 3H). $^{13}$C NMR (125 MHz, $CD_3OD$) δ 164.74, 162.50, 156.58, 155.17 (d, J=3.9 Hz), 154.7, 153.6, 139.7, 137.15 (d, J=11.1 Hz), 132.79 (d, J=9.8 Hz), 131.00, 129.41, 126.71, 120.97, 118.79 (d, J=3.9 Hz), 117.52, 116.51, 113.77 (t, J=2.8 Hz), 106.65, 106.44, 98.97, 98.34, 54.64 (*2), 50.36 (d, J=2.5 Hz, *2), 44.72.

Example 6A. Alternative synthesis of N-(3-(2-(3-fluoro-4-(4-methylpiperazin-1-yl)phenylamino)-7H-pyrrolo[2,3-d]pyrimidin-4-yloxy)phenyl)acrylamide A reactor (30 L) was charged with 4-(3-aminophenoxy)-N-(3-methyl-4-(4-methylpiperazin-1-yl)phenyl)-7H-pyrrolo[2,3-d]pyrimidin-2-amine (1199 g, 2.77 mol), DIEA (685 g, 5.30 mol) and THF (13 L). When the temperature inside the reactor reached~–3° C., a solution of acryloyl chloride (466.5 g, 5.15 mol) in THF (1 L) was added drop-wise into the reactor over a period of 1 h. The temperature was kept between −5-0° C. during the addition. After stirring for another 30 min, a NaOH solution (1 M, 7.5 L) was added slowly to quench the reaction (the temperature kept between −5-0° C.). The final pH value of the solution was around 9-10. The resulting mixture was stirred for another 3-4 h. The upper THF layer was separated and concentrated under reduced pressure at <40° C. The residue was re-dissolved in ethyl acetate (15 L). The lower aqueous layer was extracted with ethyl acetate (5 L). The residue/ethyl acetate solution was combined with the ethyl acetate layers and all were washed with water (5 L×3) and concentrated under reduced pressure to give a crude product (~1680 g). The crude material was re-dissolved in EtOH (18 L) at 35-40° C. and water (12 L) was added with stirring. The resulting solution was allowed to cool to room temperature and was stirred overnight (16 h). The resulting precipitate was collected and dried under vacuum to afford a second crude product (1010 g). To further purify this crude product (1010 g), silica gel chromatography (4:1 ethyl acetate/EtOH as mobile phase) and two re-crystallizations from EtOH/water (4:1) were performed to yield the title compound (compound of Example 6A, see Scheme 1) (727 g, 99.2% by HPLC, 54% yield) as off-white powder. mp: 122.0-123.5° C.; [M+H]$^+$: m/z 488.6; $^1$H NMR and $^{13}$C NMR spectral data for N-(3-(2-(3-fluoro-4-(4-methylpiperazin-1-yl)phenylamino)-7H-pyrrolo[2,3-d]pyrimidin-4-yloxy)phenyl)acrylamide are consistent with those reported in Example 6.

Example 6B. Alternative synthesis of N-(3-(2-(3-fluoro-4-(4-methylpiperazin-1-yl)phenylamino)-7H-pyrrolo[2,3-d]pyrimidin-4-yloxy)phenyl)acrylamide In a 3000-L reactor purified water (407 kg) was charged, and started the agitator. $K_2CO_3$ (51.9 kg) was added into the 3000 L reactor. After stirred for 30 min, the solution of 4-(3-aminophenoxy)-N-(3-methyl-4-(4-methylpiperazin-1-yl)phenyl)-7H-pyrrolo[2,3-d]pyrimidin-2-amine in THF from Step 4 (822 kg, contained the compound of Example 5B (see Schemes 2A and 2B): 81.4 kg) was added and agitated. The reaction mixture was cooled to 10±5° C. Acryloyl chloride (36.0 kg) was charged into the reactor at 10±5° C. over 1 h. The reaction mixture was stirred for 1 h at 10±5° C., and sampling for HPLC analysis showed 0.5% of the compound of Example 5B (see Schemes 2A and 2B) remained. Aqueous NaOH (40%, 67 Kg) was added into the reactor at 10±5° C. over 1 h. The reaction mixture was then warmed to 25±5° C. and stirred for 6 h. The upper THF layer was separated, washed with brine (407 Kg×2). The organic layer was concentrated under vacuum at 45±5° C. to about 200-300 L. Ethanol (195 Kg) was added and the mixture was concentrated under vacuum at 45±5° C. to about 200-300 L. Repeated this same procedure one more time. Ethanol (455 Kg) was added at 38±5° C. and purified water (244 Kg) was added drop-wise at 38±5° C. over 1 h. The mixture was stirred at 38±5° C. for 2 h, and then cooled down to 15±5° C. at a rate of 10° C./hr. and continued to stir at 15±5° C. for 5 h. The mixture was centrifuged, wet cake was washed with the mixture of EtOH and purified water (81 Kg purified water and 17 Kg purified water). The resulting wet cake was dried in vacuum at 50±5C for 16 h to yield a crude product (after 1st crystallization product) 68.38 Kg of the compound of Example 6B (see Schemes 2A and 2B) with 98.4% purity and 100.3% assay in 74.5% yield.

The crude material was dissolved in ethyl acetate (294 kg) and EtOH (130 kg), and the resulting solution (262 kg for column #1 and 232 kg for column #2, respectively) were added to two silica gel columns (90 kg for column #1 and 80 kg for column #2, respectively, 200-300 mesh). The title compound was eluted with 4:1 ethyl acetate/EtOH (506 kg for column #1 and 450 kg for column #2, respectively) to wipe off the impurity (TLC and HPLC controlled). Qualified the fractions were collected and concentrated under vacuum at 45±5° C. to about 200 L. A distill and replace operation was then performed using EtOH (205 kg) to obtain ~200 L of a residual ethanol solution. The solution was diluted with EtOH (273 kg), transferred into a 1000-L reactor in the clean room, and then was heated to 40±5° C. Purified water (103 kg) was added over 1 h, and the resulting mixture was stirred at 40±5° C. for 2 h. A white solid started to precipitate and the suspension was cooled to 15±5° C. and stirred for 5 h. The mixture was centrifuged and the wet cake was washed with $H_2O$:EtOH (20.5 kg:50 kg). The wet cake was dried under vacuum at 50±5° C. for 16 h to afford the title compound (62.97 kg, 99.62% purity, 92.09% assay yield) as a white solid (compound of Example 6B, see Schemes 2A and 2B). The overall yield of step 4 was 68.6%. LC-MS: m/z 488.6 [M+H]$^+$. $^1$H NMR (500 MHz, DMSO-d$_6$): δ ppm 11.61 (s, 1H), 10.32 (s, 1H), 9.16 (s, 1H), 7.67 (t, J=1.8 Hz, 1H), 7.63-7.53 (m, 2H), 7.42 (t, J=8.1 Hz, 1H), 7.23 (d, J=8.1 Hz, 1H), 7.10 (dd, J=3.4, 2.3 Hz, 1H), 7.00 (dd, J=7.9, 1.9 Hz, 1H), 6.79 (t, J=9.4 Hz, 1H), 6.43 (dd, J=16.9, 10.2 Hz, 1H), 6.29 (dd, J=3.3, 1.8 Hz, 1H), 6.25 (dd, J=17.0, 1.9 Hz, 1H), 5.76 (dd, J=10.1, 1.9 Hz, 1H), 2.87 (br s, 4H), 2.43 (br s, 4H), 2.21 (s, 3H). $^{13}$C NMR (125 MHz, DMSO-d$_6$): δ ppm 163.75 (s), 162.30 (s), 156.16 (s), 155.44 (d, J=35.6 Hz), 154.24 (s), 153.62 (s), 140.77 (s), 137.10 (d, J=11.1 Hz), 133.38 (d, J=9.5 Hz), 132.17 (s), 130.31 (s), 127.66 (s), 122.42 (s), 119.36 (s), 117.30 (s), 116.50 (s), 114.44 (s), 113.23 (s), 106.70 (d, J=26.3 Hz), 99.06 (s), 98.79 (s), 55.26 (s, ×2), 50.91 (s, ×2), 46.27 (s).

Example 7. Synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate

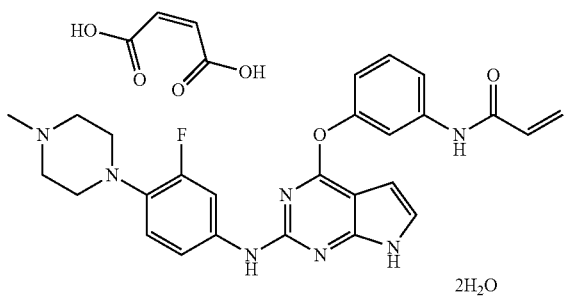

N-(3-(2-(3-Fluoro-4-(4-methylpiperazin-1-yl)phenylamino)-7H-pyrrolo[2,3-d]pyrimidin-4-yloxy)phenyl)acrylamide (12.20 kg) was added to a reactor containing purified water (180 kg) and ethanol (7.54 kg). The mixture was heated to 40±5° C. A solution of maleic acid (3.14 kg) in purified H$_2$O (53.1 kg) and EtOH (2.26 kg) was added to the reactor. The resulting mixture was agitated for 1 h at 40±5° C., then was cooled to 25±5° C. at a rate of 20° C./h and was stirred for another 5 h. The resulting precipitate was centrifuged and the cake was washed with the rest of the H$_2$O/EtOH solution. The wet cake (16.92 kg) was dried for 48 h at 30±5° C. under vacuum to afford the title compound (compound of Example 7, see Scheme 1) (14.30 kg, 89.3%). LC-MS: m/z 488.6 [M+H]$^+$. $^1$H NMR (500 MHz, DMSO-d$_6$) δ 11.39 (s, 1H), 10.44 (s, 1H), 9.02 (s, 1H), 7.62 (s, 1H), 7.53 (d, J=8.3 Hz, 1H), 7.50 (d, J=15.4 Hz, 1H), 7.42 (t, J=8.2 Hz, 1H), 7.11-7.05 (m, 2H), 6.97 (ddd, J=8.1, 2.3, 0.7 Hz, 1H), 6.82 (t, J=9.4 Hz, 1H), 6.38 (dd, J=16.9, 10.2 Hz, 1H), 6.26 (ddd, J=18.5, 10.2, 1.7 Hz, 2H), 6.14 (s, 2H), 5.76 (dd, J=10.2, 1.5 Hz, 1H), 3.30 (br, 4H), 3.11 (br, 4H), 2.80 (s, 3H). $^{13}$C NMR (125 MHz, DMSO-ds) δ 168.68 (*2), 164.50, 162.36, 156.18, 155.36, 154.97, 154.25, 153.34, 140.30, 137.90 (d, J=11.1 Hz), 136.25 (*2), 131.50, 131.42 (d, J=9.8 Hz), 130.53, 128.52, 122.80, 120.03, 117.70, 116.92, 114.43, 113.47, 106.65 (d, J=26.5 Hz), 98.93 (d, J=23.6 Hz), 53.38 (*2), 48.15 (*2), 42.88.

Example 7A. Alternative synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate In a 30-L reactor, a combination of several batches of N-(3-(2-(3-fluoro-4-(4-methylpiperazin-1-yl)phenylamino)-7H-pyrrolo[2,3-d]pyrimidin-4-yloxy)phenyl)acrylamide (1481 g, ~99.2% HPLC purity) was dissolved in EtOH (15 L) at 36° C. Water (2 L) was added drop-wise at this temperature. The mixture was allowed to cool to room temperature and was stirred overnight. The resulting crystals were collected, washed with a small amount of EtOH, and dried under vacuum at 25° C. overnight to afford the free base of N-(3-(2-(3-fluoro-4-(4-methylpiperazin-1-yl)phenylamino)-7H-pyrrolo[2,3-d]pyrimidin-4-yloxy)phenyl)acrylamide (1255 g, 99.61% HPLC purity) as an off-white powder, which was used in the salt formation step.

A reactor (50 L) was charged with 5% EtOH (20 L) at 40° C. The free base of N-(3-(2-(3-fluoro-4-(4-methylpiperazin-1-yl)phenylamino)-7H-pyrrolo[2,3-d]pyrimidin-4-yloxy)phenyl)acrylamide (1255 g, 2.57 mol, 99.61% HPLC purity) was added with stirring. The resulting suspension was stirred vigorously at 40° C. until a slurry was formed. A solution of maleic acid (325 g, 2.8 mol) in 5% EtOH (2 L) was added drop-wise over 15 min. Once the addition was complete, a clear homogeneous solution was obtained. The solution was allowed to cool to room temperature and was stirred overnight. The resulting crystals were collected, washed with 5% EtOH (0.5 L×3), and dried under vacuum at 25° C. for 48 h to afford the title compound (compound of Example 7A, see Scheme 1) as a light-yellow powder (1420 g, 99.67% HPLC purity, 86.4% yield). mp: 171.1-173.2° C.; [M+H]$^+$: m/z 488.6; $^1$H NMR and $^{13}$C NMR spectral data for N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate are consistent with those reported in Example 7.

Example 7B. Alternative synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate N-(3-(2-(3-Fluoro-4-(4-methylpiperazin-1-yl)phenylamino)-7H-pyrrolo[2,3-d]pyrimidin-4-yloxy)phenyl)acrylamide (54.3 kg, compound of Example 6B, see Schemes 2A and 2B) was added to a reactor containing purified water (784 kg) and ethanol (33.02 kg). The mixture was heated to 40±5° C. A solution of maleic acid (13.80 kg) in purified H$_2$O (233.0 kg) and EtOH (10.0 kg) was added to the reactor. The resulting mixture was agitated for 1 h at 40±5° C., then was cooled to 25±5° C. at a rate of 10° C./h and was stirred for another 5 h. The resulting precipitate was centrifuged and the cake was washed with the rest of the H$_2$O/EtOH solution. The wet cake (78.34 kg) was dried for 175 h at 30±5° C. under vacuum to afford the title compound (compound of Example 7B, see Schemes 2A and 2B) (63.51 kg, 89.2% yield, 99.617% purity). LC-MS: m/z 488.6 [M+H]$^+$. $^1$H NMR (500 MHz, DMSO-d$_6$): δ ppm 11.64 (s, 1H), 10.34 (s, 1H), 9.25 (s, 1H), 7.69 (d, J=15.0 Hz, 1H), 7.67 (t, J=2.1 Hz, 1H), 7.60 (d, J=8.2 Hz, 1H), 7.43 (t, J=8.1 Hz, 1H), 7.26 (d, J=7.7 Hz, 1H), 7.12 (dd, J=3.5, 2.3 Hz, 1H), 7.02 (ddd, J=8.1, 2.2, 0.6 Hz, 1H), 6.89 (t, J=9.4 Hz, 1H), 6.44 (dd, J=17.0, 10.2 Hz, 1H), 6.30 (dd, J=3.4, 1.9 Hz, 1H), 6.27 (dd, J=17.0, 1.9 Hz, 1H), 6.08 (s, 2H), 5.77 (dd, J=10.1, 1.9 Hz, 1H), 3.33 (br s, 4H), 3.13 (br s, 4H), 2.85 (s, 3H). $^{13}$C NMR (125 MHz, DMSO-d$_6$): δ ppm 167.32 (s, ×2), 163.34 (s), 161.86 (s), 155.82 (s), 154.90 (d, J=43.5 Hz), 153.90 (s), 153.17 (s), 140.32 (s), 137.75 (d, J=11.1 Hz), 135.84 (s, ×2), 131.72 (s), 131.01 (d, J=9.7 Hz), 129.87 (s), 127.26 (s), 122.13 (s), 119.63 (s), 116.88 (s), 116.11 (s), 113.97 (s), 112.76 (s), 106.17 (d, J=25.8 Hz), 98.75 (s), 98.36 (s), 52.87 (s, ×2), 47.90 (s, ×2), 42.41 (s).

Additional exemplary compounds not shown in these synthetic examples are prepared from appropriate starting materials using methods analogous to those described in the preceding schemes and examples.

In some embodiments, the synthesis of N-(3-(2-(3-fluoro-4-(4-methylpiperazin-1-yl)phenylamino)-7H-pyrrolo[2,3-d]

pyrimidin-4-yloxy)phenyl)acrylamide maleate di-hydrate comprises steps as described in Example 3, Example 4, Example 5, Example 6, and Example 7. In some embodiments, the synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate comprises steps as described in Example 3A, Example 4A, Example 5A, Example 6A, and Example 7A. In some embodiments, the synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate comprises steps as described in Example 3B, Example 4B, Example 5B, Example 6B, and Example 7B.

Example 8. Synthesis of N-(3-(2-(3-fluoro-4-(4-methylpiperazin-1-yl)phenylamino)-7H-pyrrolo[2,3-d]pyrimidin-4-yloxy)phenyl)acrylamide maleate salt Example 8-1 (Ethanol/Water (1:1))

Figure 2:
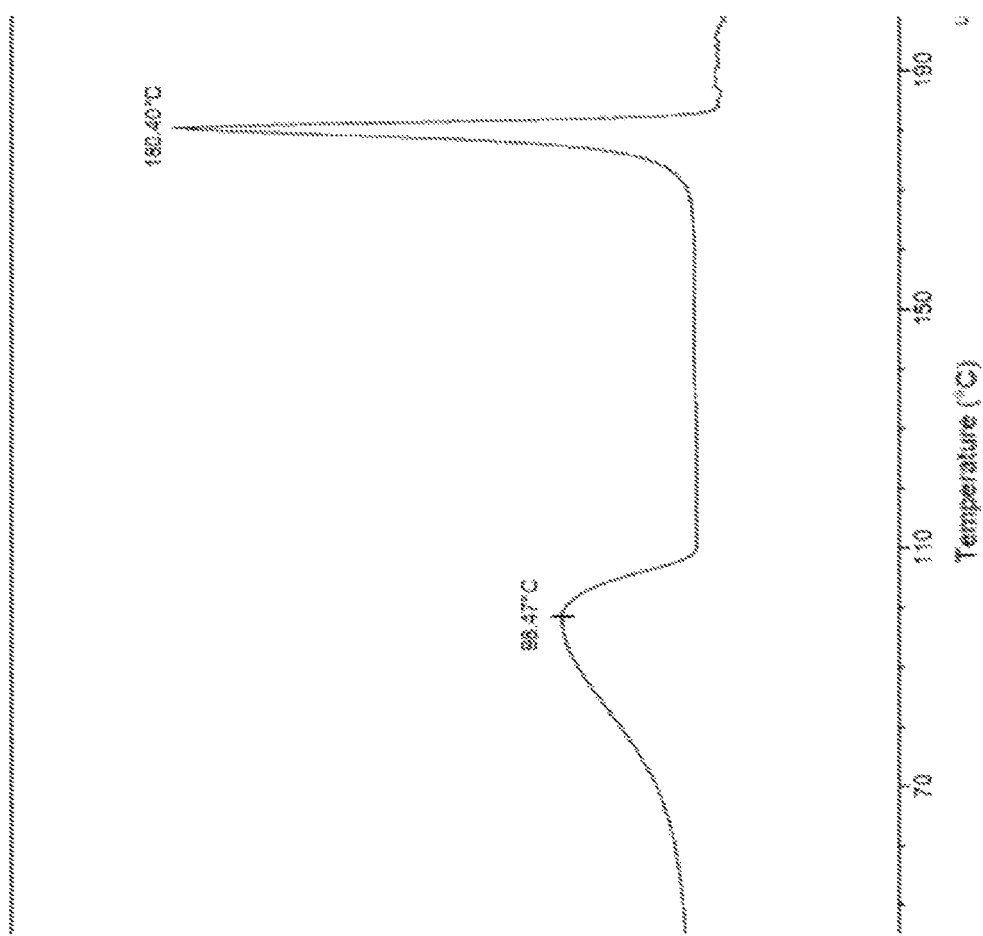
FIG. 2 is a differential scanning calorimetry curve of polymorph Form I maleate salt obtained from 1:1 ethanol/$H_2O$.
Figure 3:
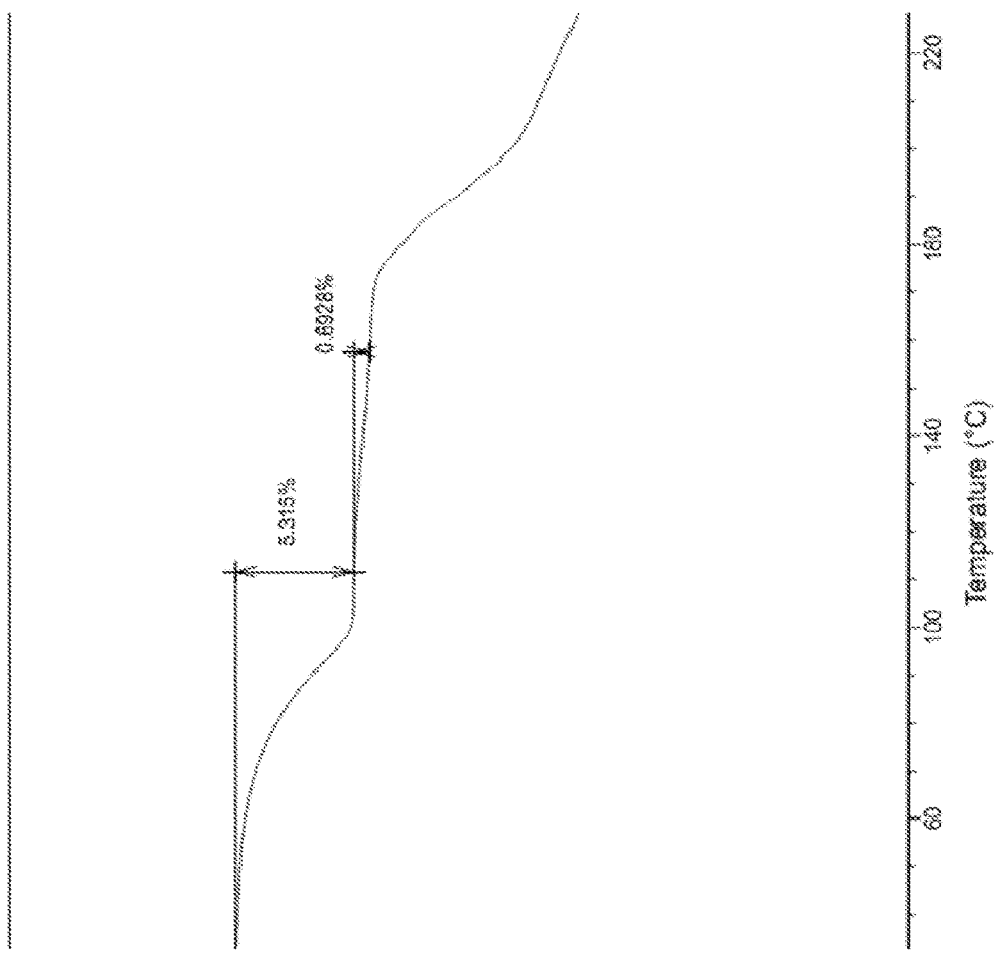
FIG. 3 shows a thermogravimetric analysis of polymorph Form I maleate salt obtained from 1:1 ethanol/$H_2O$.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in ethanol (5 mL) at 40° C. was treated with a solution of maleic acid (262 mg, 2.26 mmol) in water (5 mL). The solution was cooled to room temperature with stirring. The resulting crystals were collected and dried to yield the title compound (1 g, 76.3% yield) defined as polymorph Form I. Elemental analysis: N: 14.90%; C: 56.54%; H: 5.34%. The XRPD, DSC, and TGA traces for this material are shown in FIGS. 1, 2, and 3, respectively.

Example 8-2 (Ethanol/Water (3:7))

Figure 4:
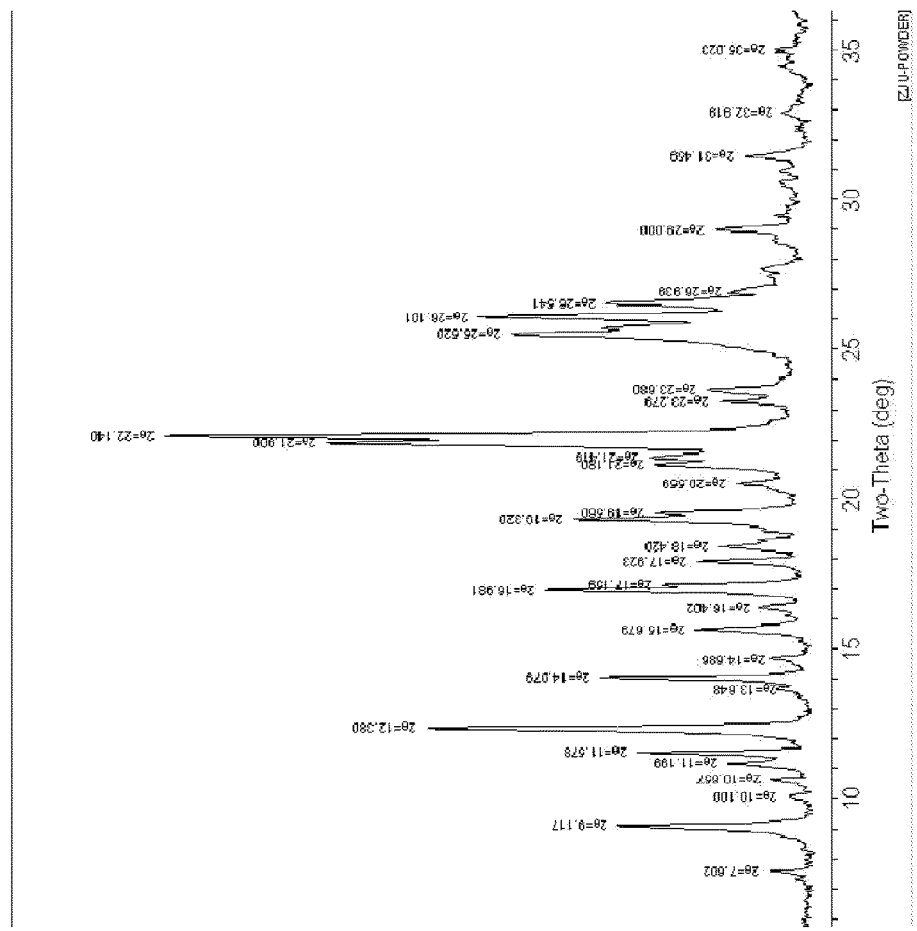
FIG. 4 is an X-ray powder diffractogram of polymorph Form I maleate salt obtained from 3:7 ethanol/$H_2O$.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in ethanol (4.5 mL) and water (8.5 mL) at 40° C. was treated with 1 M aqueous maleic acid (2 mL). The solution was cooled to room temperature with stirring. The resulting crystals were collected and dried to yield the title compound (0.9 g, 68.7% yield) defined as polymorph Form I. The XRPD trace for this material is shown in FIG. 4.

Example 8-3 (Ethanol/Water (1:19))

Figure 5:
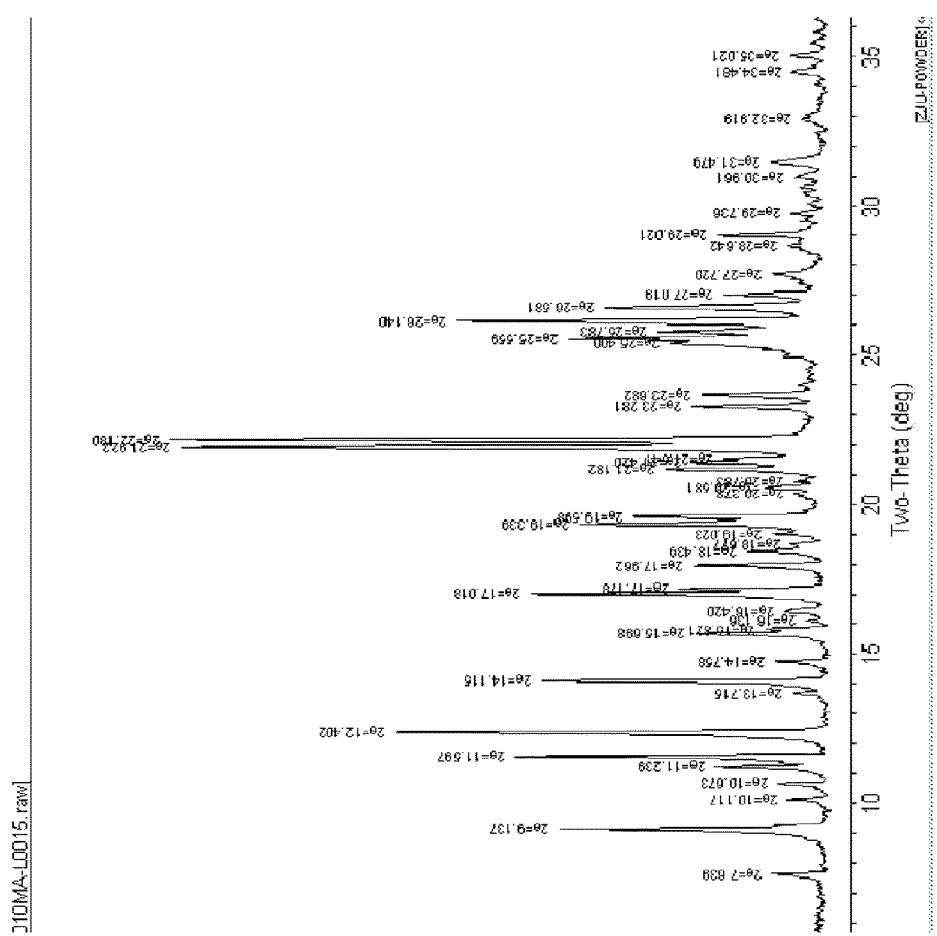
FIG. 5 is an X-ray powder diffractogram of polymorph Form I maleate salt obtained from 1:19 ethanol/$H_2O$.
Figure 6:
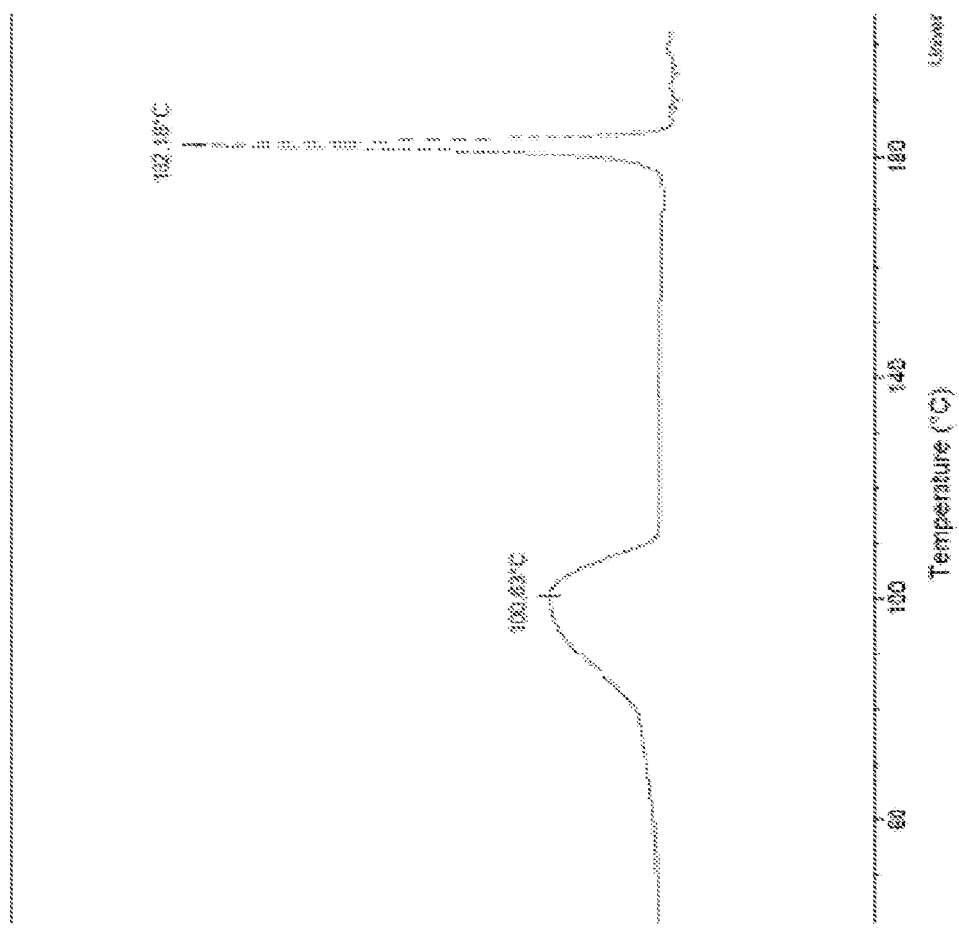
FIG. 6 is a differential scanning calorimetry curve of polymorph Form I maleate salt obtained from 1:19 ethanol/$H_2O$.
Figure 7:
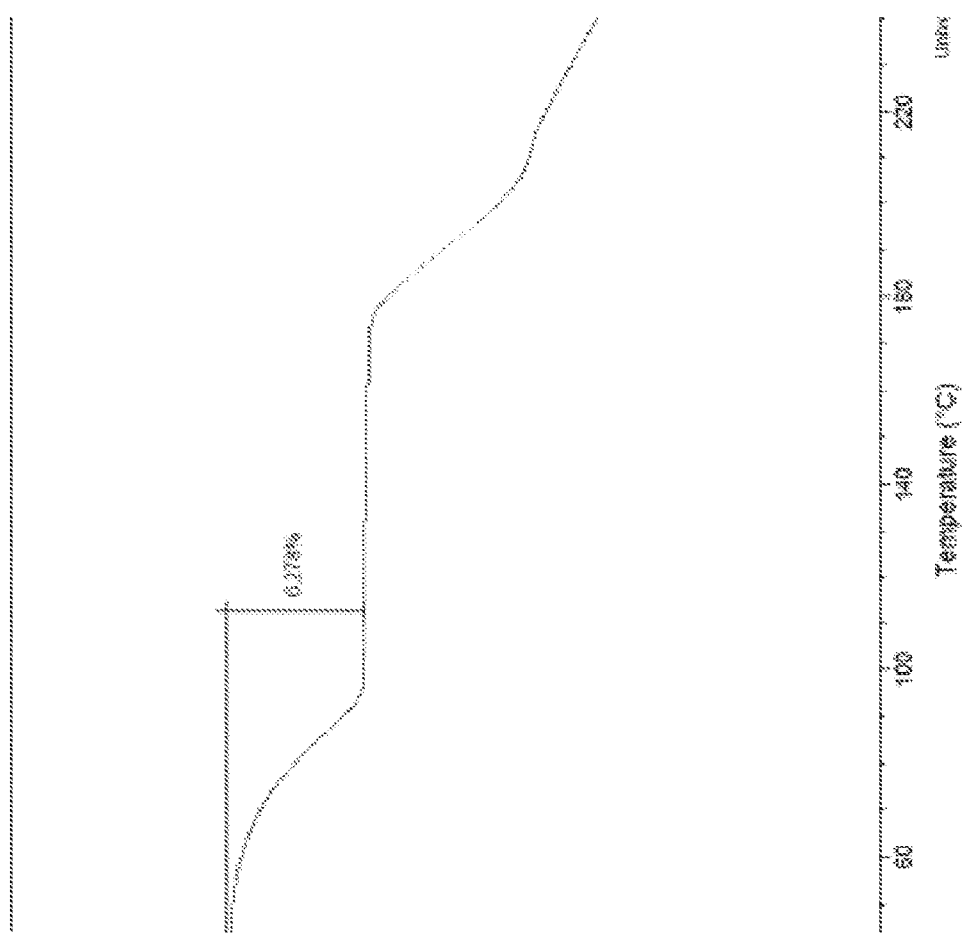
FIG. 7 shows a thermogravimetric analysis of polymorph Form I maleate salt obtained from 1:19 ethanol/$H_2O$.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1255 g, 2.57 mol) in 5% ethanol (20 L) at 40° C. was treated slowly over 15 min with a solution of maleic acid (325 g, 2.8 mol) in 5% ethanol (2 L). The solution was cooled to room temperature and was stirred overnight. The resulting crystals were collected, washed with 5% ethanol (0.5 L×3), and dried under vacuum at 25° C. for 48 h to yield the title compound (1420 g, 86.4% yield) defined as polymorph Form I. Elemental analysis: N: 14.90%; C: 56.54%; H: 5.34%. The XRPD, DSC, and TGA traces for Form I are shown in FIGS. 5, 6, and 7, respectively. Elemental analysis: N: 14.95%; C: 56.54%; H: 5.40%. The XRPD, DSC, and TGA traces for this material are shown in FIGS. 5, 6, and 7, respectively.

Example 8-4 (Ethanol)

Figure 8:
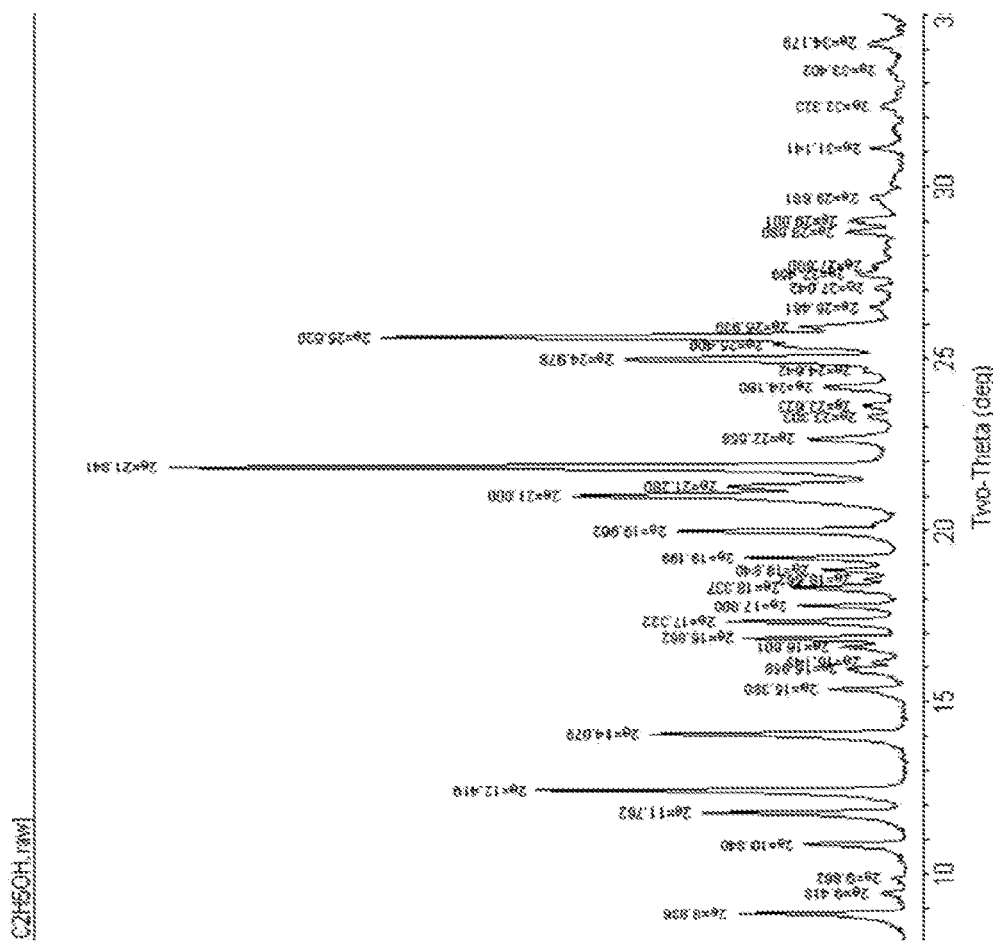
FIG. 8 is an X-ray powder diffractogram of polymorph Form II maleate salt obtained from ethanol.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in ethanol (9 mL) at 40° C. was treated with maleic acid (262 mg, 2.26 mmol). The solution was cooled to room temperature with stirring. The resulting crystals were collected and dried to yield the title compound (0.8 g, 61.0% yield) defined as polymorph Form H (possible ethanol solvate). Elemental analysis: N: 15.09%; C: 59.08%; H: 5.48%. The XRPD trace for this material is shown in FIG. 8.

Example 8-5 (Methanol)

Figure 9:
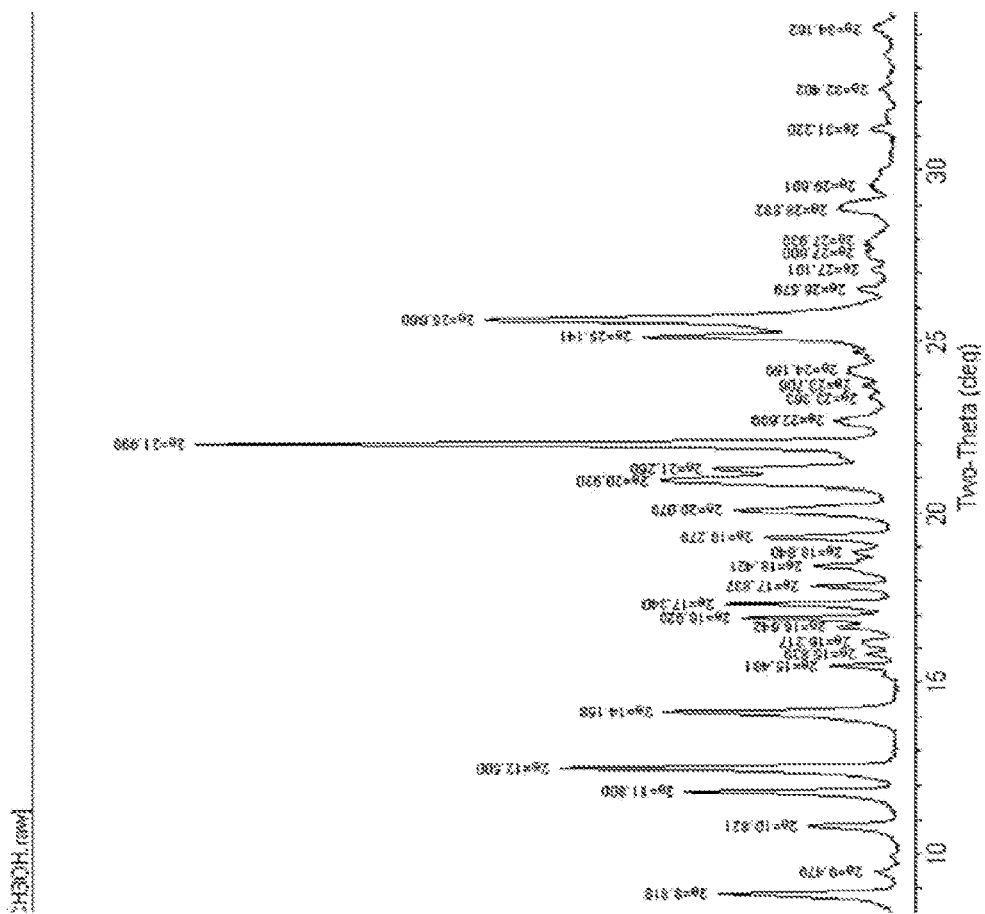
FIG. 9 is an X-ray powder diffractogram of polymorph Form II maleate salt obtained from methanol.
Figure 10:
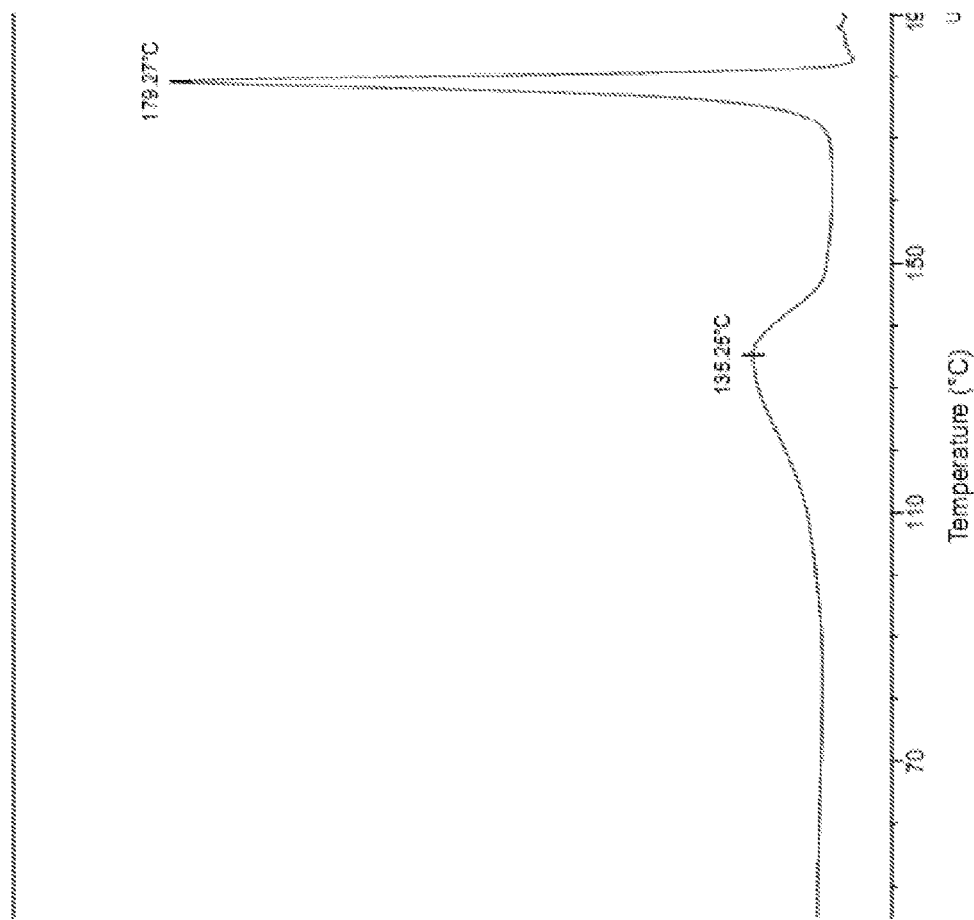
FIG. 10 is a differential scanning calorimetry curve of polymorph Form II maleate salt obtained from methanol.
Figure 11:
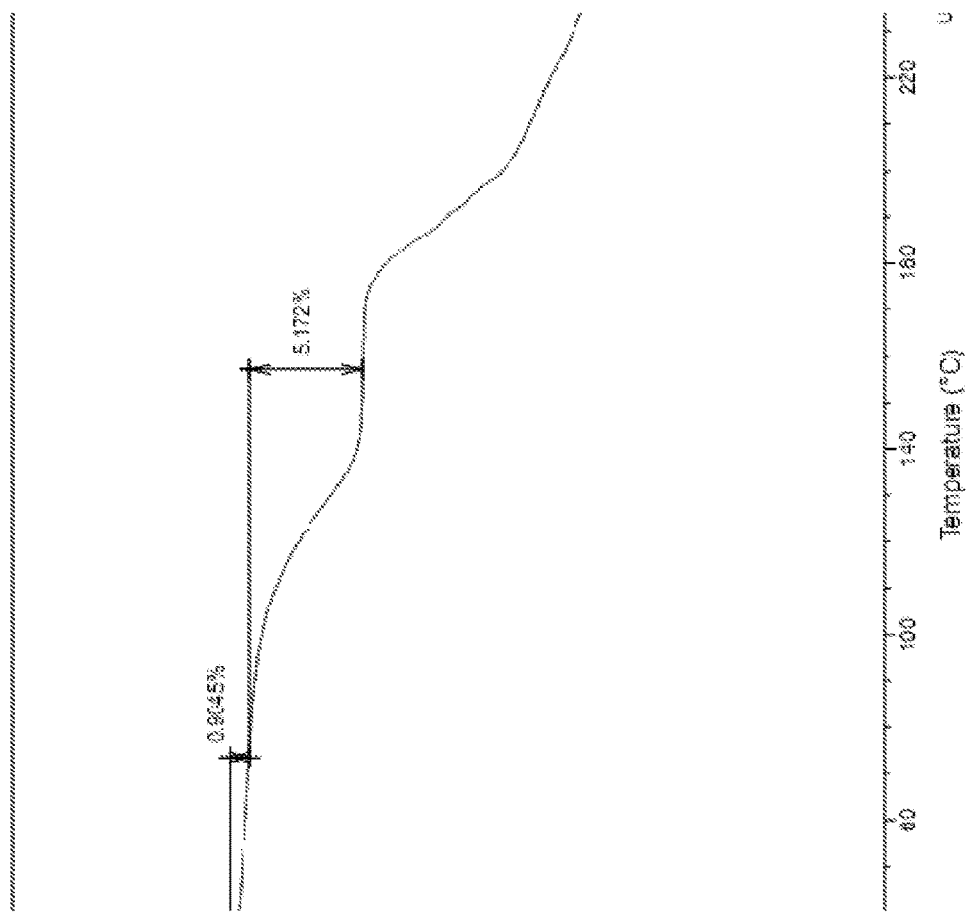
FIG. 11 shows a thermogravimetric analysis of polymorph Form II maleate salt obtained from methanol.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in methanol (9 mL) at 40° C. was treated with maleic acid (262 mg, 2.26 mmol). The solution was cooled to room temperature with stirring. The resulting crystals were collected and dried to yield the title compound (0.8 g, 61.0% yield) defined as polymorph Form H (possible methanol solvate). Elemental analysis: N: 14.90%; C: 57.76%; H: 5.37%. The XRPD, DSC, and TGA traces for this material are shown in FIGS. 9, 10, and 11, respectively.

Example 8-6 (Tetrahydrofuran)

Figure 12:
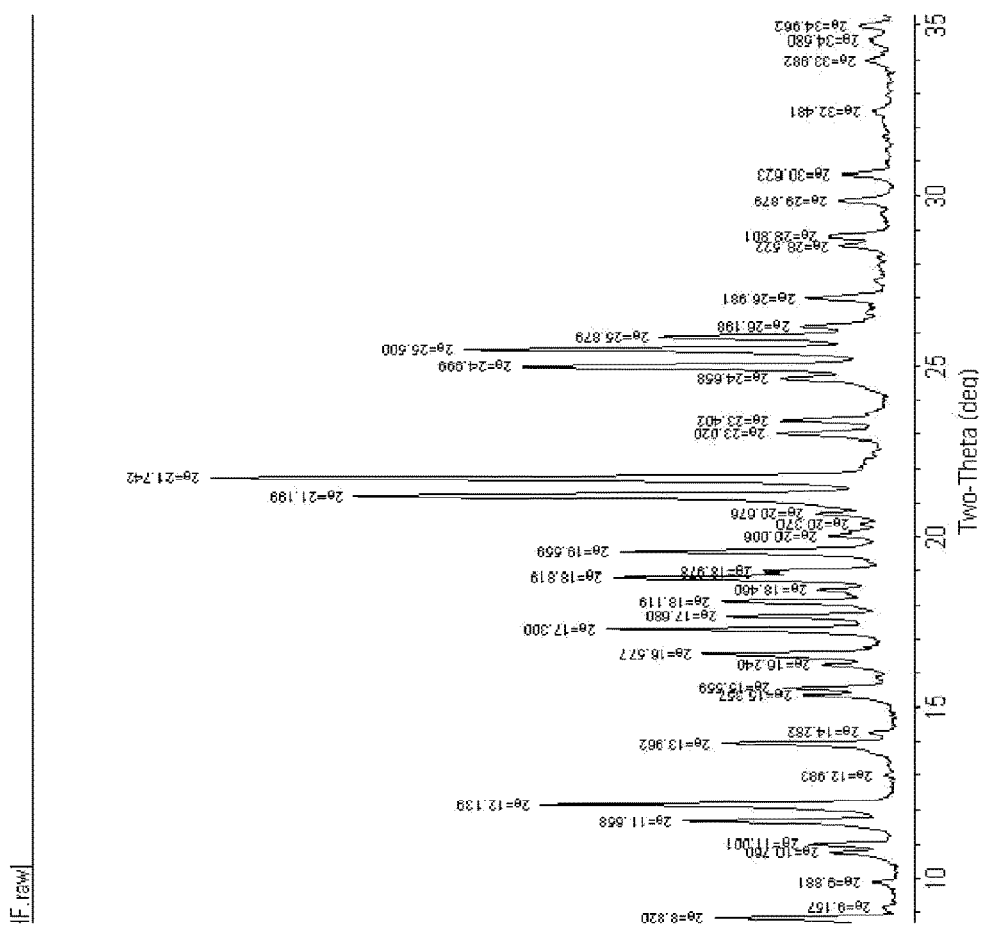
FIG. 12 is an X-ray powder diffractogram of polymorph Form III maleate salt obtained from tetrahydrofuran.
Figure 13:
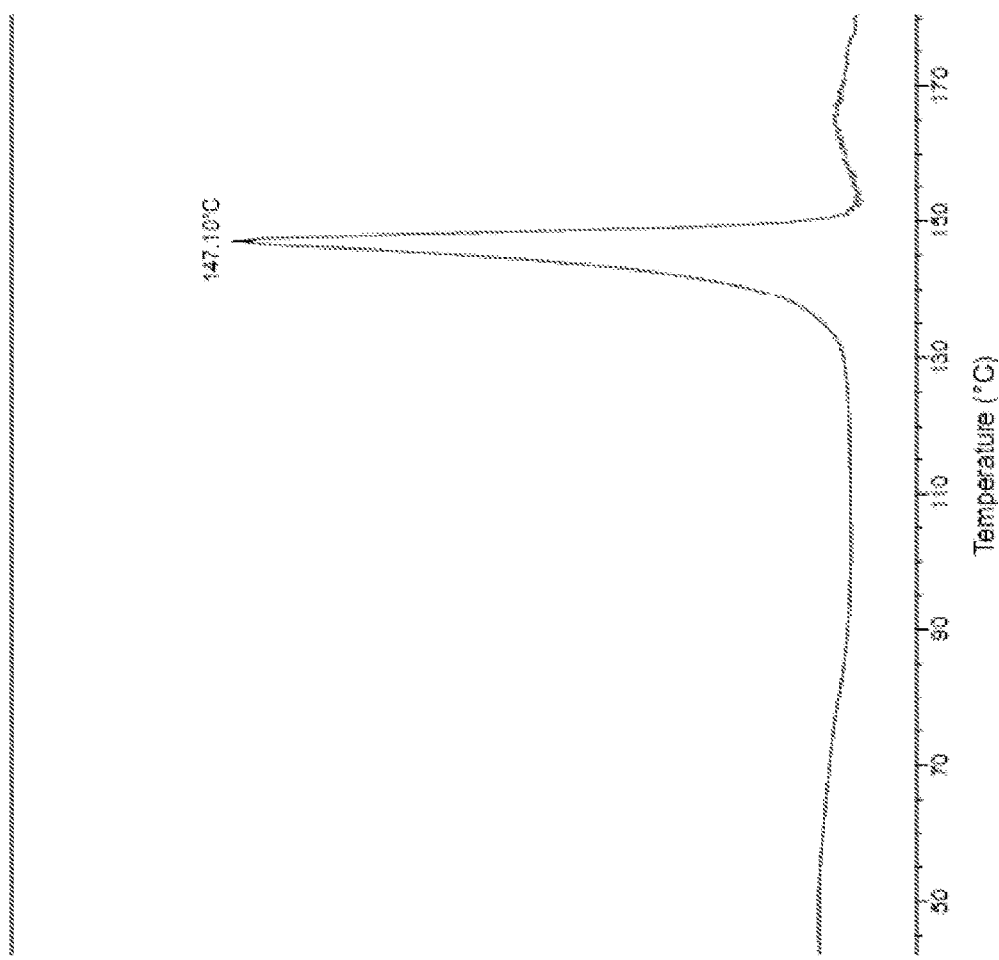
FIG. 13 is a differential scanning calorimetry curve of polymorph Form III maleate salt obtained from tetrahydrofuran.
Figure 14:
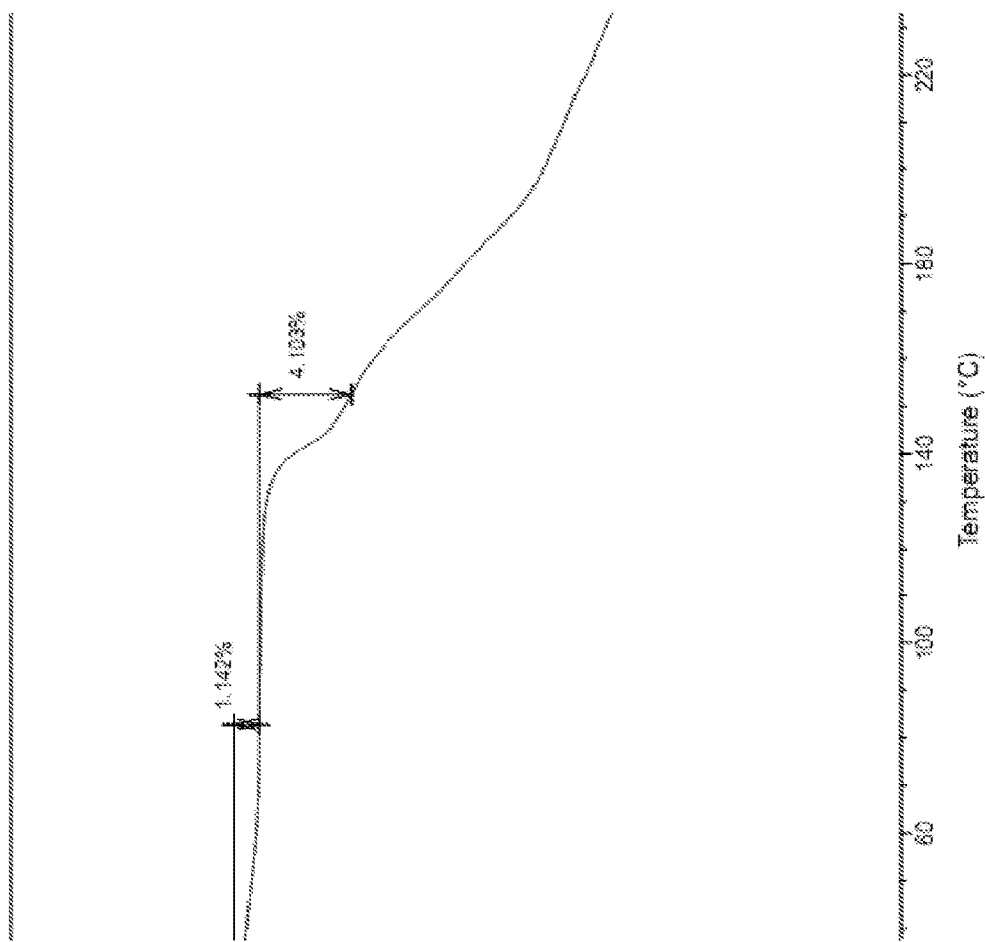
FIG. 14 shows a thermogravimetric analysis of polymorph Form III maleate salt obtained from tetrahydrofuran.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in THF (8 mL) at 40° C. was treated with maleic acid (262 mg, 2.26 mmol). The solution was cooled to room temperature and was stirred overnight. The resulting crystals were collected and dried to yield the title compound (0.7 g, 53.4% yield) defined as polymorph Form III. Elemental analysis: N: 14.64%; C: 59.02%; H: 5.29%. The XRPD, DSC, and TGA traces for this material are shown in FIGS. 12, 13, and 14, respectively.

Example 8-7 (Acetone)

Figure 15:
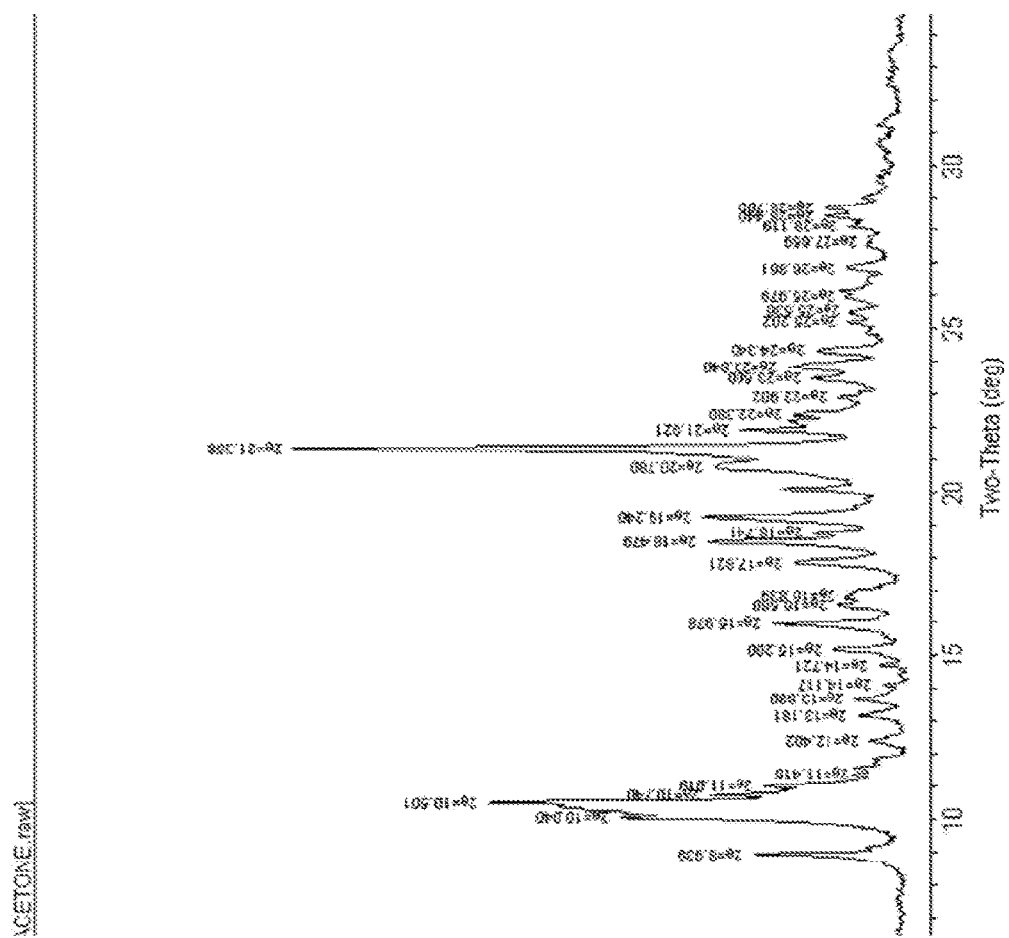
FIG. 15 is an X-ray powder diffractogram of an amorphous form of the maleate salt obtained from acetone.
Figure 16:
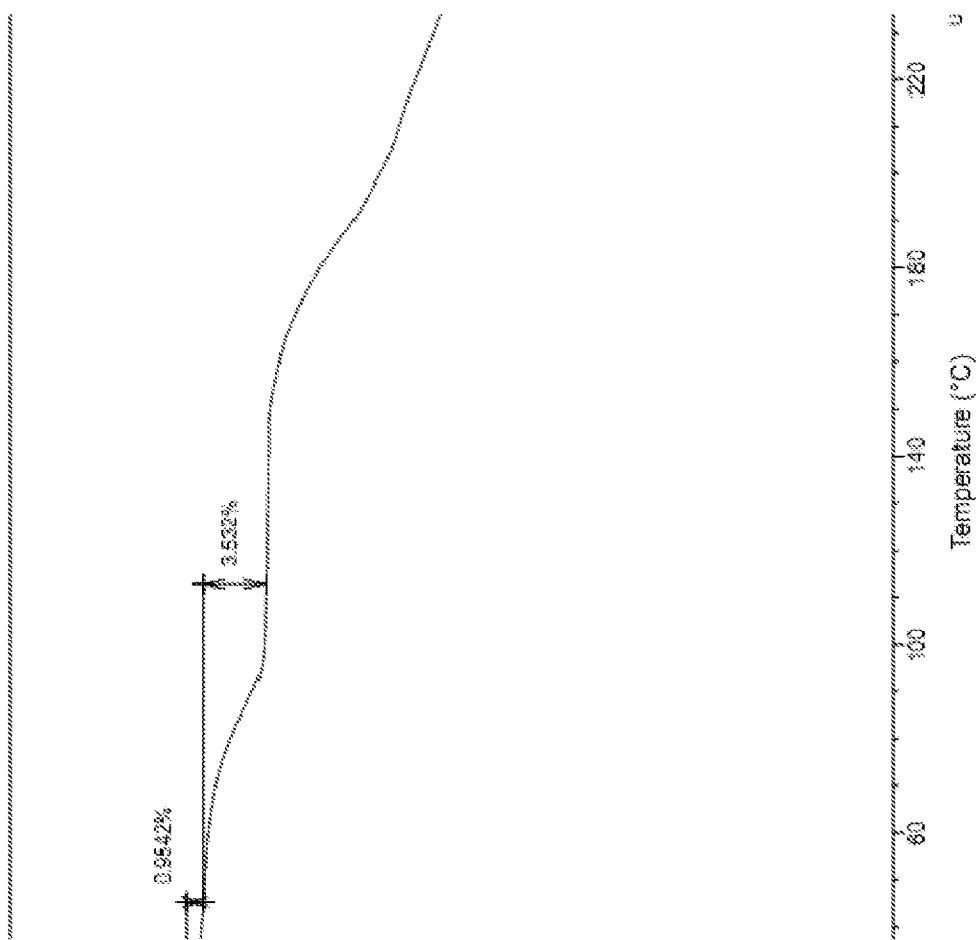
FIG. 16 is a differential scanning calorimetry curve of the amorphous form of the maleate salt obtained from acetone.
Figure 17:
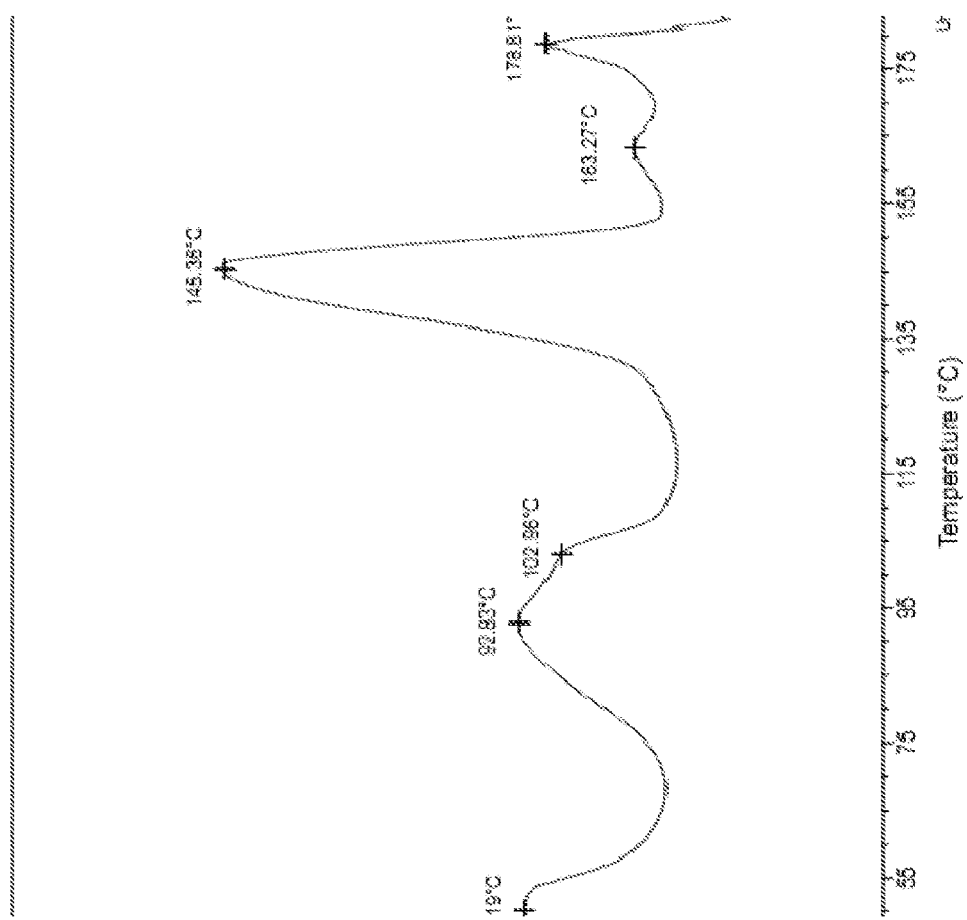
FIG. 17 shows a thermogravimetric analysis of the amorphous form of the maleate salt obtained from acetone.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in acetone (25 mL) at 40° C. was treated with a solution of maleic acid (262 mg, 2.26 mmol) in acetone (5 mL). The solution was cooled to room temperature and was stirred overnight. The mixture was then exposed to air with stirring for 6 h. The resulting crystals were collected and dried to yield the title compound (0.7 g, 53.4% yield) defined as an amorphous form. Elemental analysis: N: 14.97%; C: 58.37%; H: 5.09%. The XRPD, DSC, and TGA traces for this material are shown in FIGS. 15, 16, and 17, respectively.

Example 8-8 (Acetonitrile)

Figure 18:
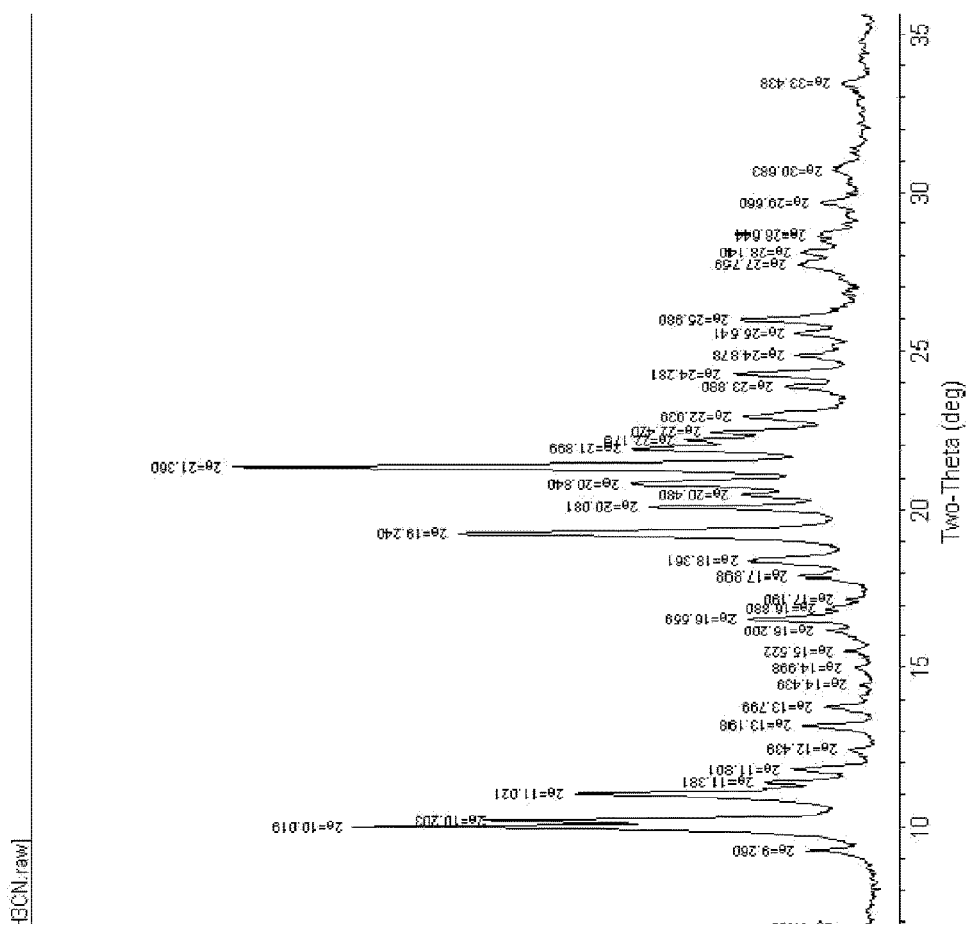
FIG. 18 is an X-ray powder diffractogram of the amorphous form of the maleate salt obtained from acetonitrile.
Figure 19:
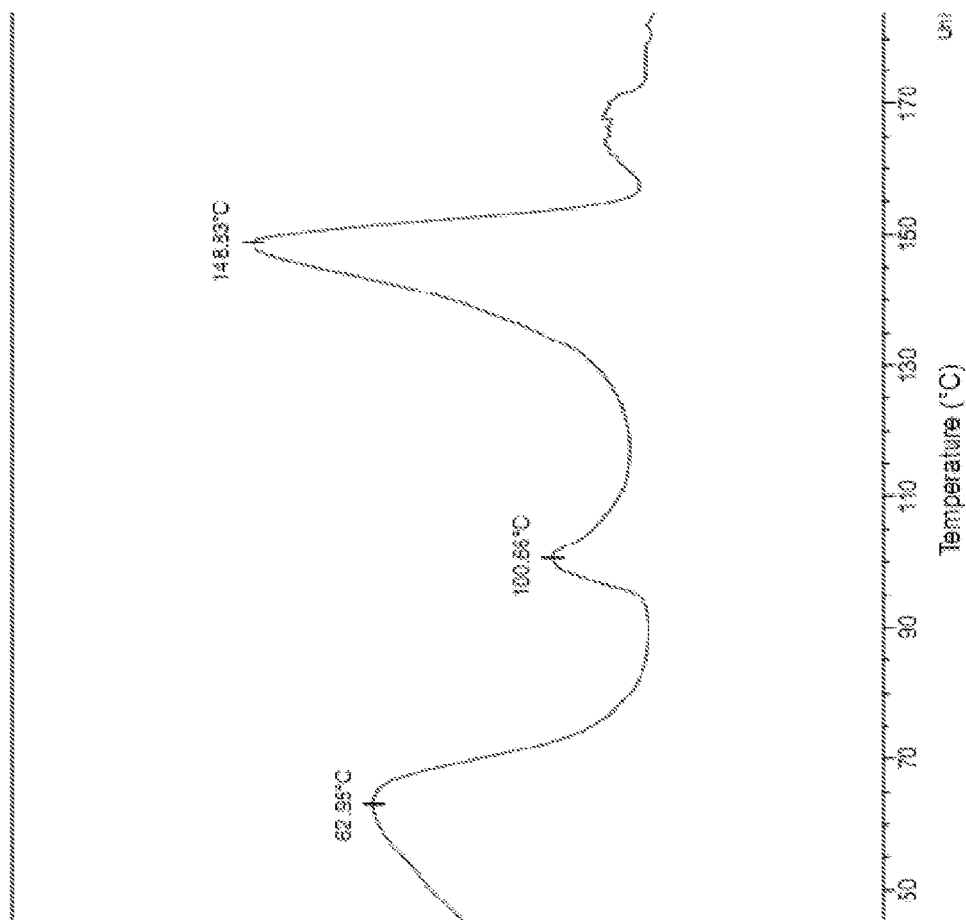
FIG. 19 is a differential scanning calorimetry curve of the amorphous form of the maleate salt obtained from acetonitrile.
Figure 20:
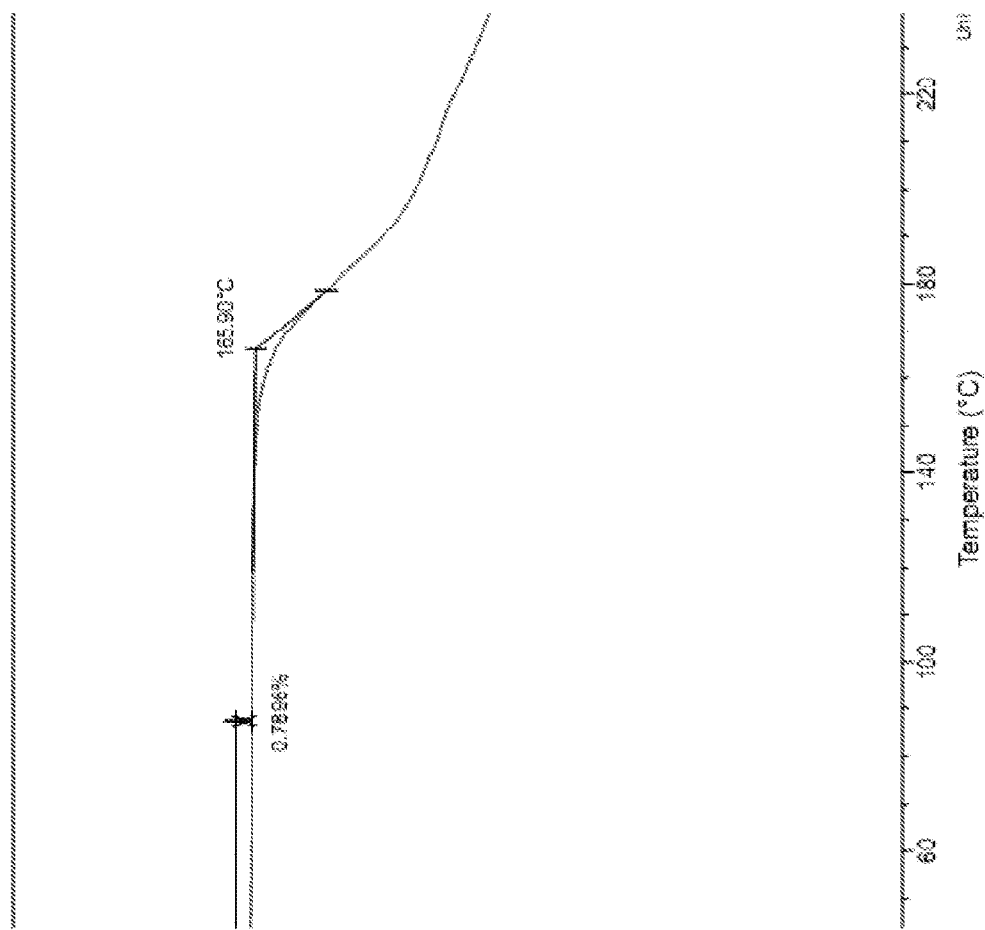
FIG. 20 shows a thermogravimetric analysis of the amorphous form of the maleate salt obtained from acetonitrile.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in acetonitrile (25 mL) at 40° C. was treated with a solution of maleic acid (262 mg, 2.26 mmol) in acetonitrile (5 mL). The solution was cooled to room temperature and was stirred overnight. The resulting crystals were collected and dried to yield the title compound (1 g, 76.3% yield) defined as an amorphous form. Elemental analysis: N: 15.71%; C: 59.03%; H: 5.06%. The XRPD, DSC, and TGA traces for this material are shown in FIGS. 18, 19, and 20, respectively.

Example 8-9 (Ethyl Acetate)

Figure 21:
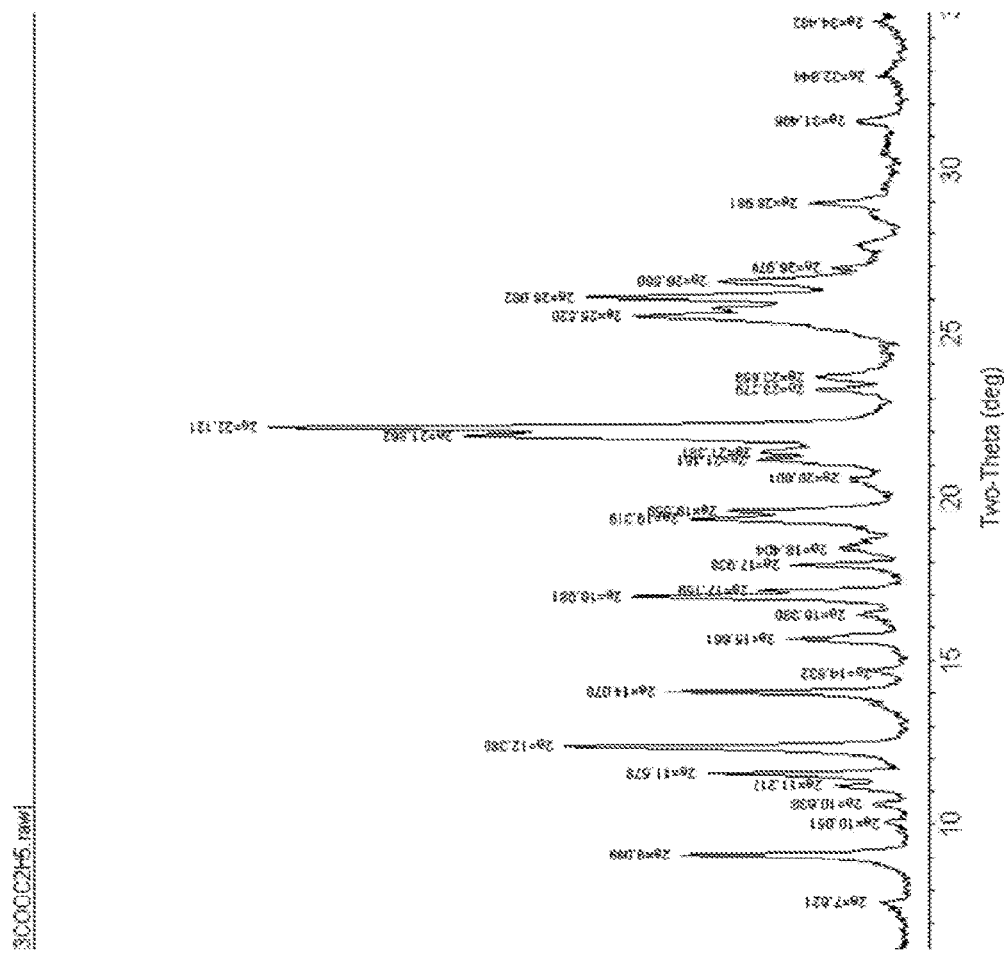
FIG. 21 is an X-ray powder diffractogram of polymorph Form I maleate salt obtained from ethyl acetate.

A sample of N-(3-(2-(3-fluoro-4-(4-methylpiperazin-1-yl)phenylamino)-7H-pyrrolo[2,3-d]pyrimidin-4-yloxy)phenyl)acrylamide maleate salt (0.5 g) was dissolved in ethyl acetate (100 mL) at 40° C. with stirring. The solution was cooled to room temperature and stood overnight without stirring. The resulting crystals were collected and dried to yield the title compound (~50 mg, 10% yield) defined as polymorph Form I. The XRPD trace for this material is shown in FIG. 21.

Example 9. Synthesis of N-(3-(2-(3-fluoro-4-(4-methylpiperazin-1-yl)phenylamino)-7H-pyrrolo[2,3-d]pyrimidin-4-yloxy)phenyl)acrylamide hydrochloride salt

Example 9-1 (Water)

Figure 22:
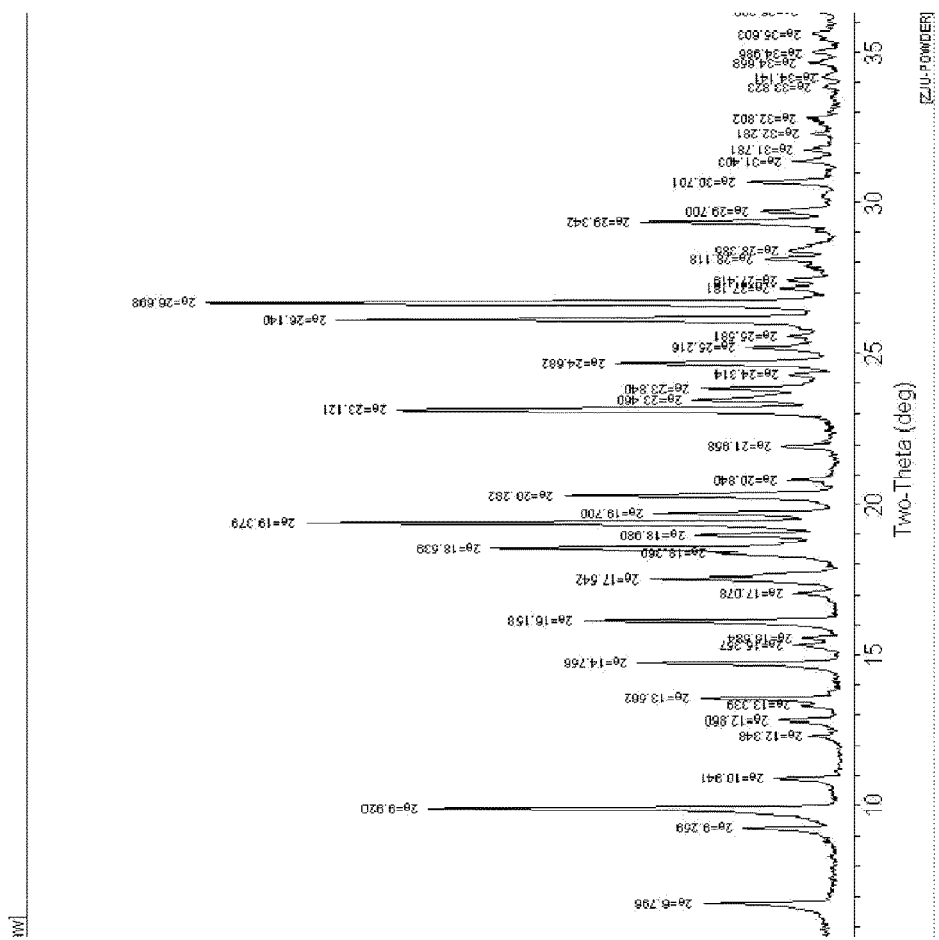
FIG. 22 is an X-ray powder diffractogram of polymorph Form IV hydrochloride salt obtained from water.
Figure 23:
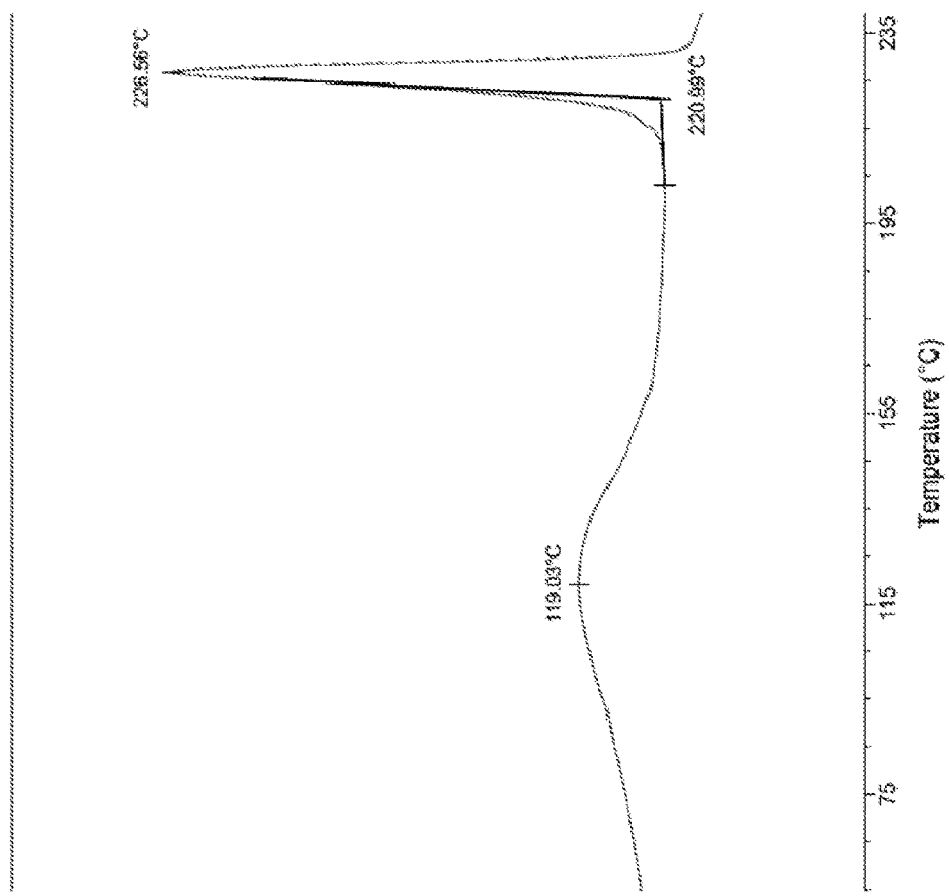
FIG. 23 is a differential scanning calorimetry curve of polymorph Form IV hydrochloride salt obtained from water.
Figure 24:
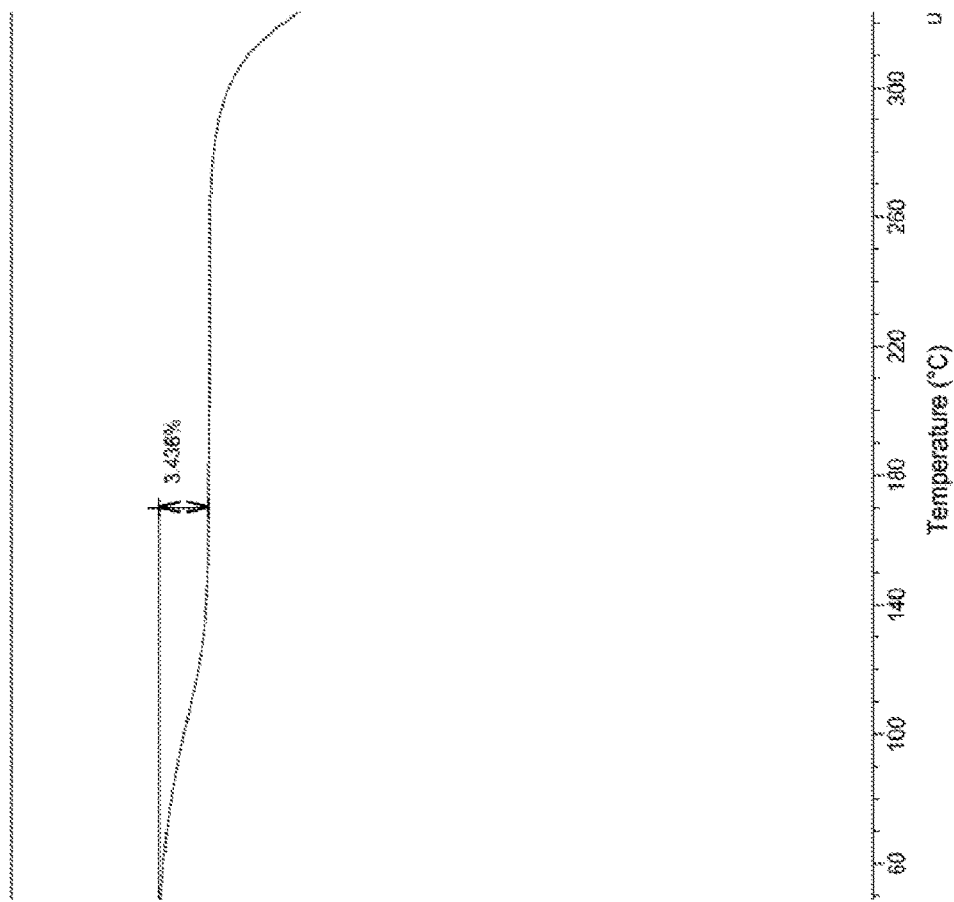
FIG. 24 shows a thermogravimetric analysis of polymorph Form IV hydrochloride salt obtained from water.

To a suspension of N-(3-(2-(3-fluoro-4-(4-methylpiperazin-1-yl)phenylamino)-7H-pyrrolo[2,3-d]pyrimidin-4-yloxy)phenyl)acrylamide (5 g, 10.3 mmol) in water (25 mL) was added aqueous HCl (1 M, 25 mL, 25 mmol). The mixture was stirred at~40-50° C. until it the starting material dissolved. The solution was cooled to room temperature with stirring. The resulting crystals were collected and dried to yield the title compound (6 g, 95.2% yield), defined as polymorph Form IV. Elemental analysis: N: 17.49%; C: 57.51%; H: 5.32%. The XRPD, DSC, and TGA traces for this material are shown in FIGS. 22, 23, and 24, respectively.

Example 9-2 (Ethanol/Water (3:1))

Figure 25:
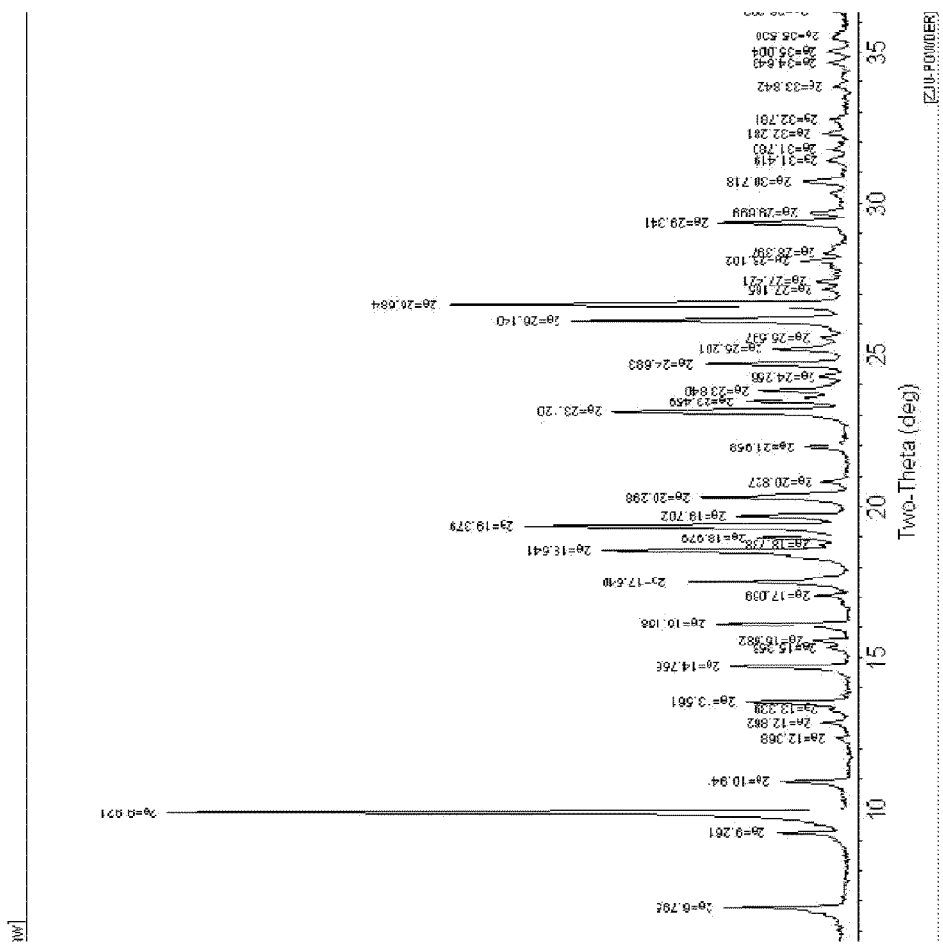
FIG. 25 is an X-ray powder diffractogram of polymorph Form IV hydrochloride salt obtained from 3:1 ethanol/water.
Figure 26:
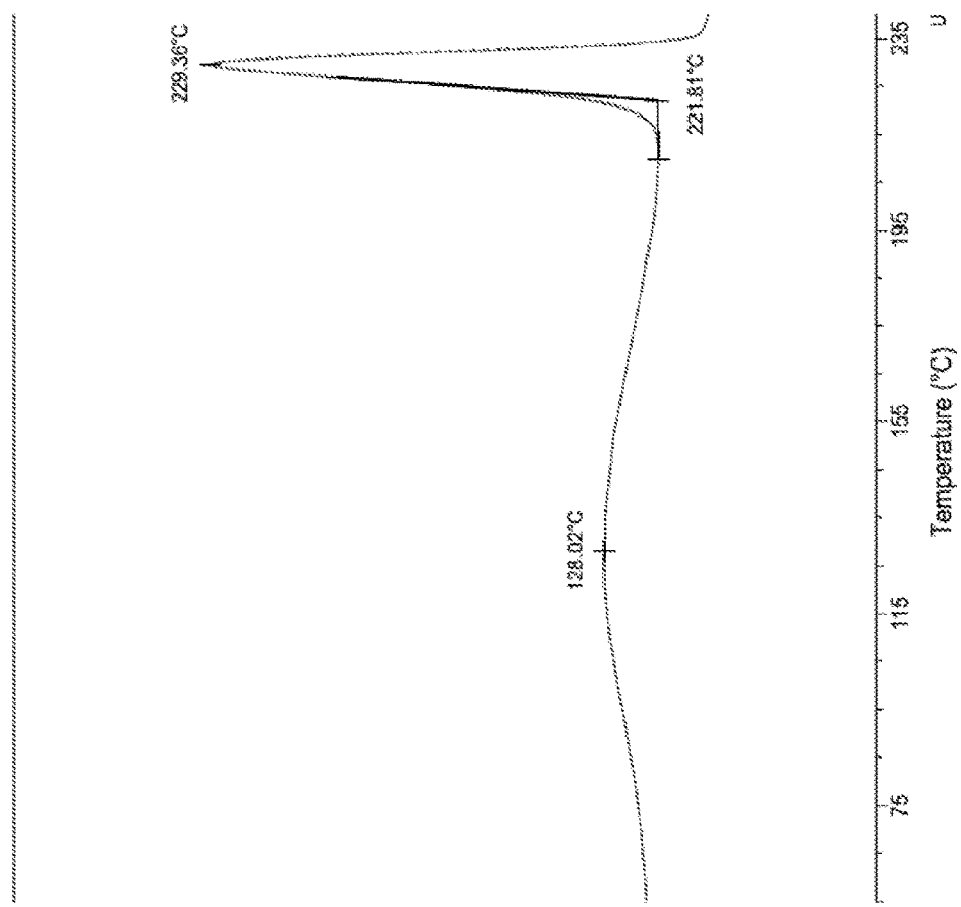
FIG. 26 is a differential scanning calorimetry curve of polymorph Form IV hydrochloride salt obtained from 3:1 ethanol/water.
Figure 27:
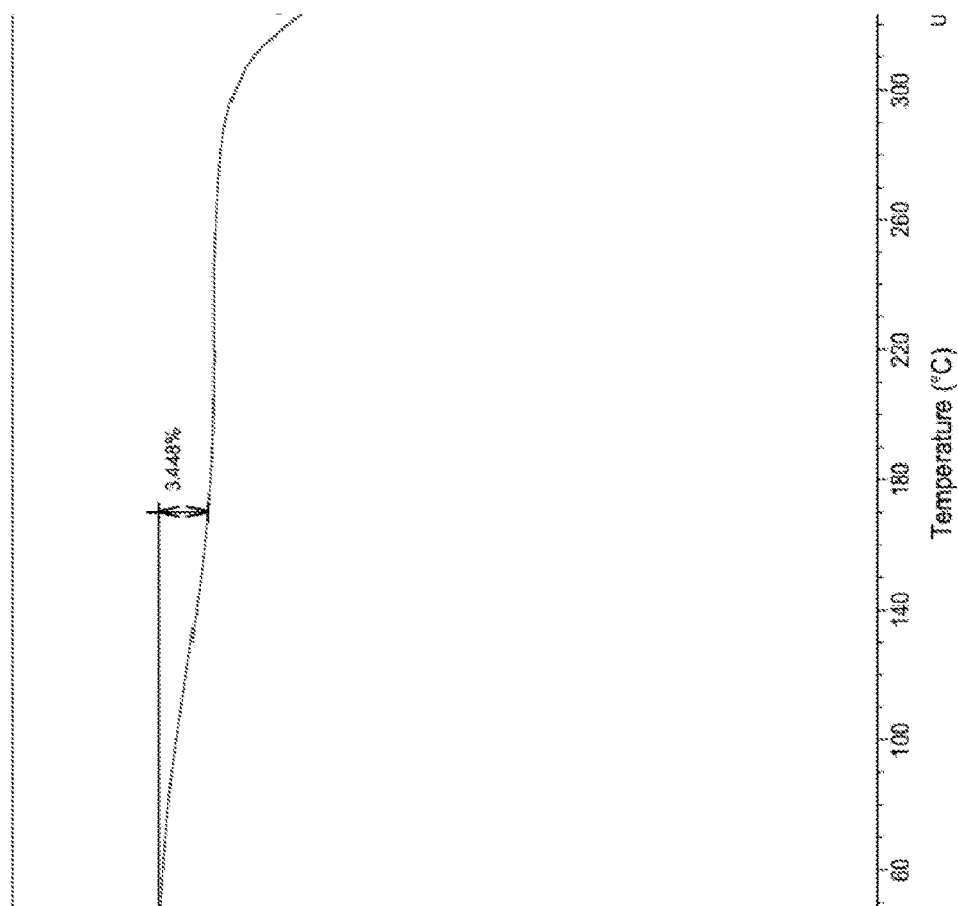
FIG. 27 shows a thermogravimetric analysis of polymorph Form IV hydrochloride salt obtained from 3:1 ethanol/water.

To the salt obtained in Example 9-1 (1.0 g) was added ethanol (15 mL) and water (5 mL). The resulting suspension was stirred at reflux temperature until it became clear and homogeneous. The solution was then allowed to cool to room temperature with stirring. The resulting crystals were collected and dried to yield the title compound (1 g, 100% yield) in a solid form defined as polymorph Form IV. Elemental analysis: N: 17.76%; C: 57.75%; H: 5.37%. The XRPD, DSC, and TGA traces for this material are shown in FIGS. 25, 26, and 27, respectively.

Example 9-3 (Ethanol/Water (1:1))

Figure 28:
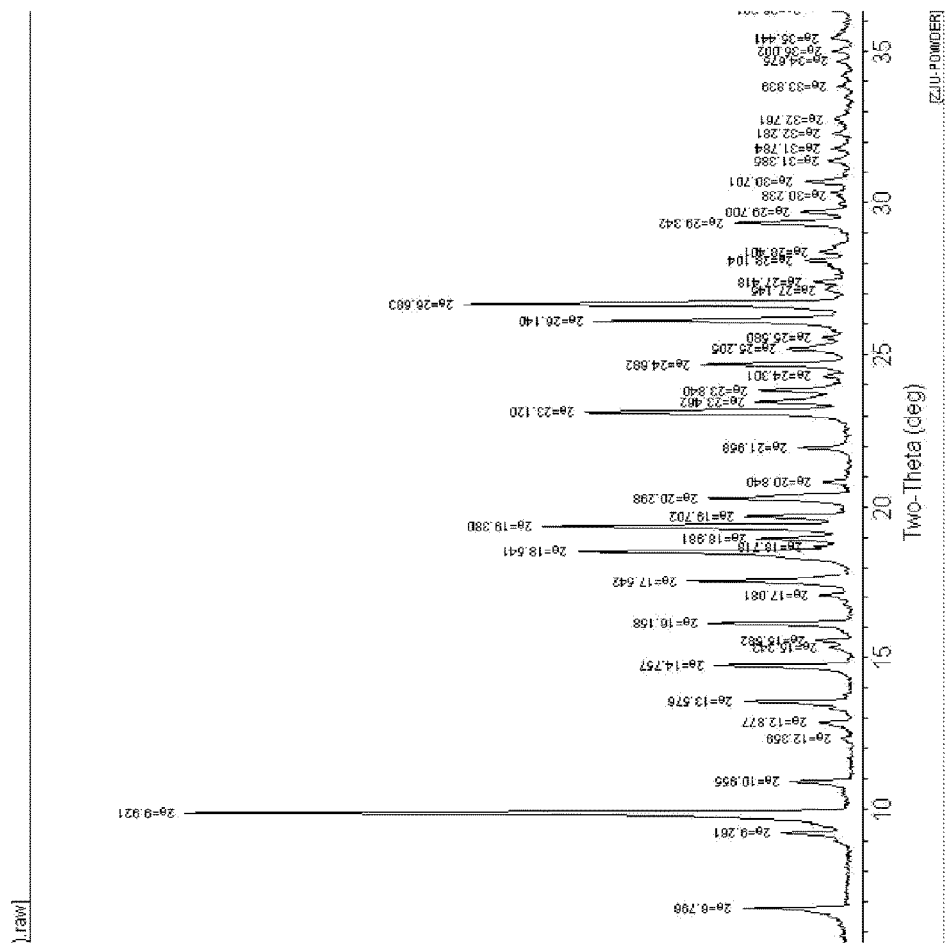
FIG. 28 is an X-ray powder diffractogram of polymorph Form IV hydrochloride salt obtained from 1:1 ethanol/water.
Figure 29:
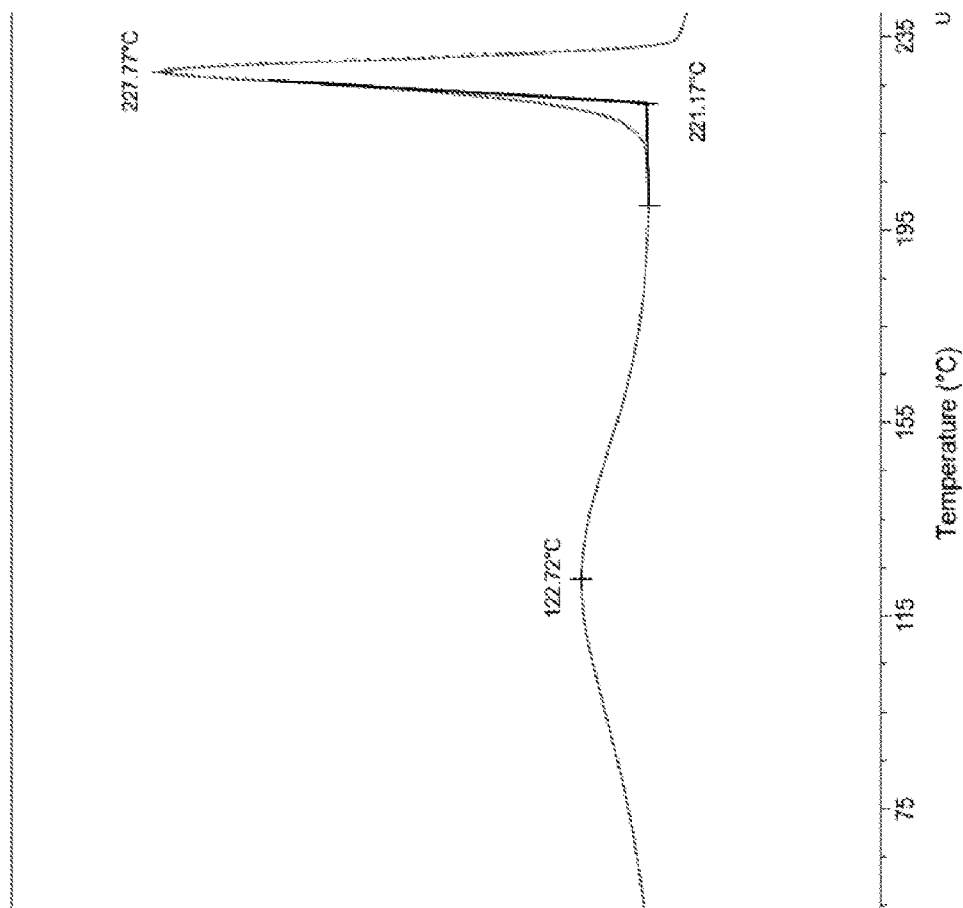
FIG. 29 is a differential scanning calorimetry curve of polymorph Form IV hydrochloride salt obtained from 1:1 ethanol/water.
Figure 30:
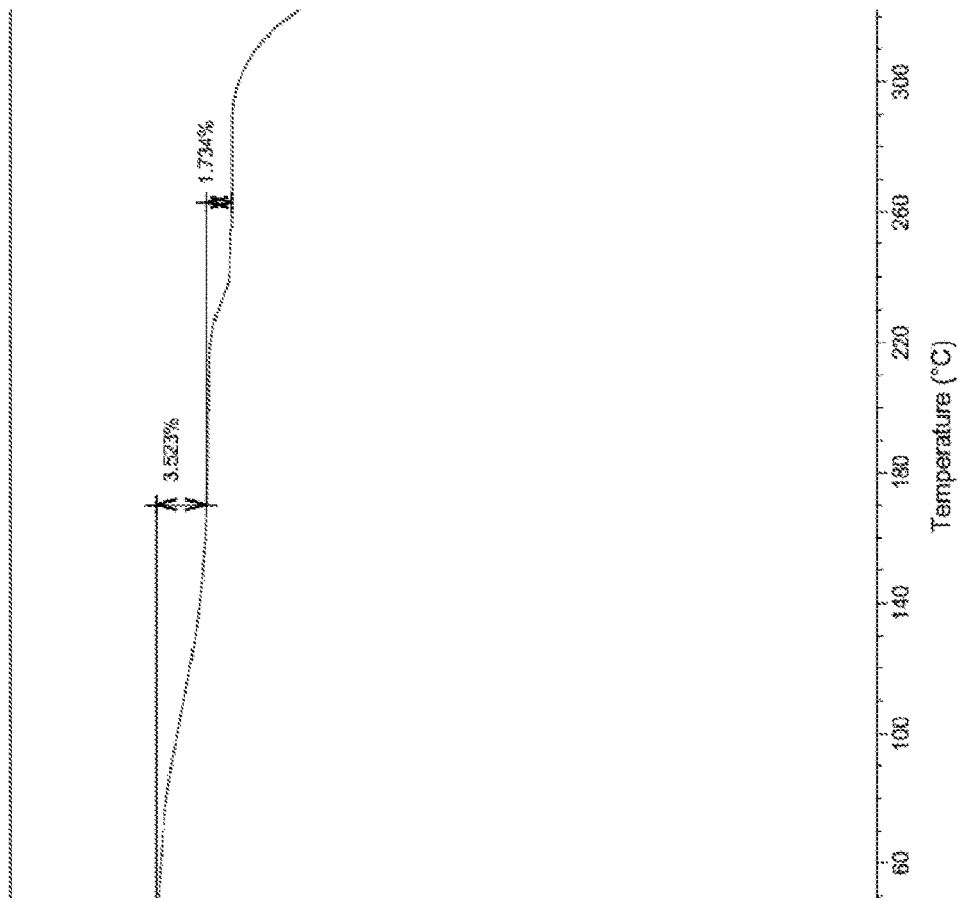
FIG. 30 shows a thermogravimetric analysis of polymorph Form IV hydrochloride salt obtained from 1:1 ethanol/water.

To the above HCl salt as polymorph Form IV (1.0 g) was added 50% aqueous ethanol (10 mL). The resulting suspension was stirred at reflux temperature until it became clear and homogeneous. The solution was then cooled to room temperature with stirring. The resulting crystals were collected and dried to yield the title compound (0.61 g, 61% yield) in a solid form defined as polymorph Form IV. Elemental analysis: N: 17.69%; C: 57.87%; H: 5.40%. The XRPD, DSC, and TGA traces for this material are shown in FIGS. 28, 29, and 30, respectively.

Example 9-4 (Ethanol/Water (5:7))

Figure 31:
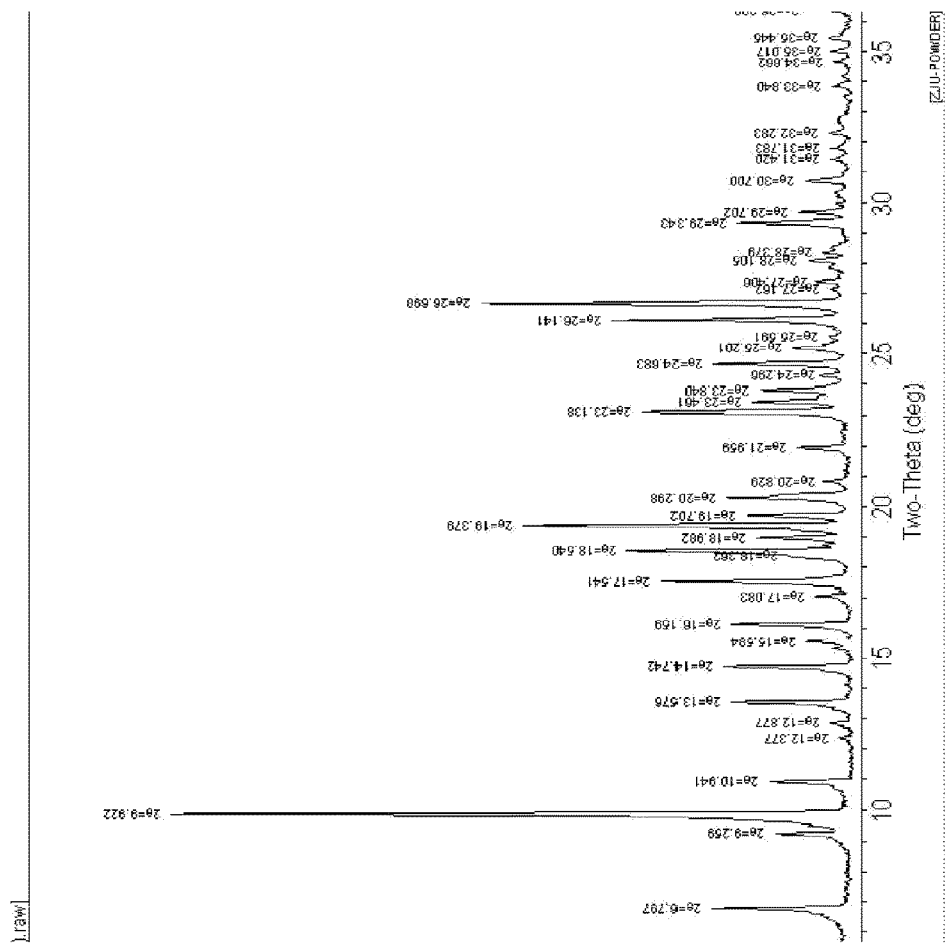
FIG. 31 is an X-ray powder diffractogram of polymorph Form IV hydrochloride salt obtained from 5:7 ethanol/water.
Figure 32:
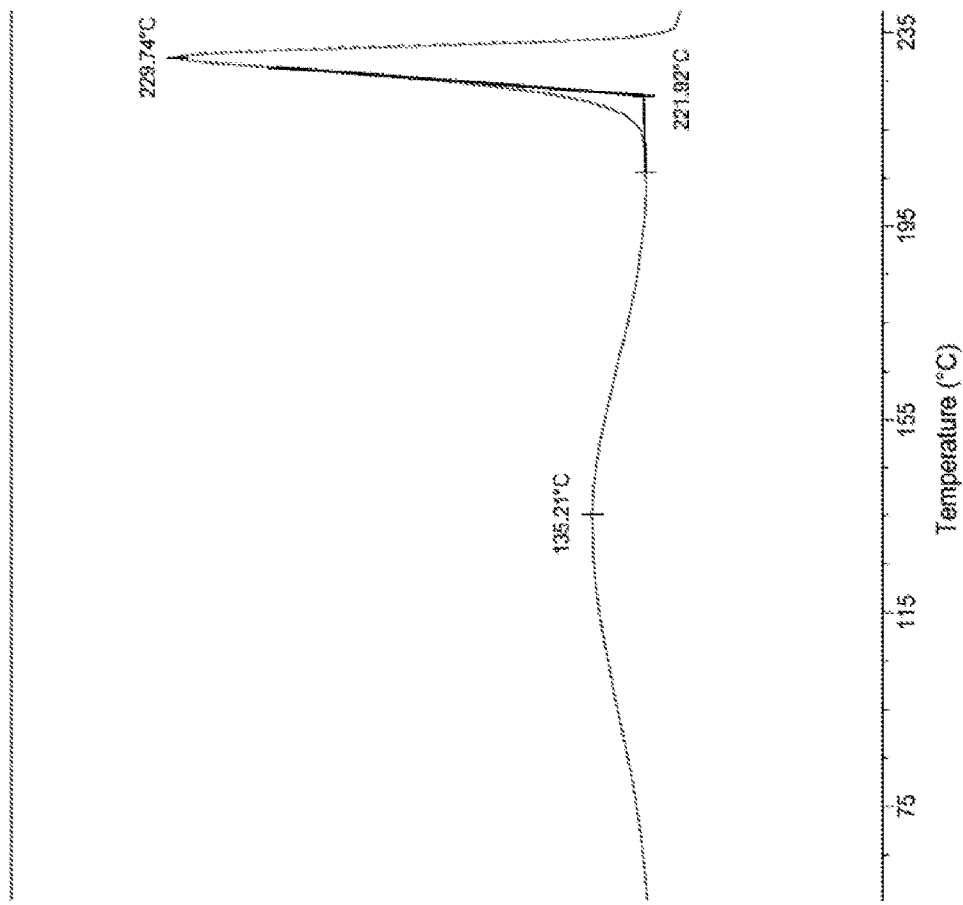
FIG. 32 is a differential scanning calorimetry curve of polymorph Form IV hydrochloride salt obtained from 5:7 ethanol/water.
Figure 33:
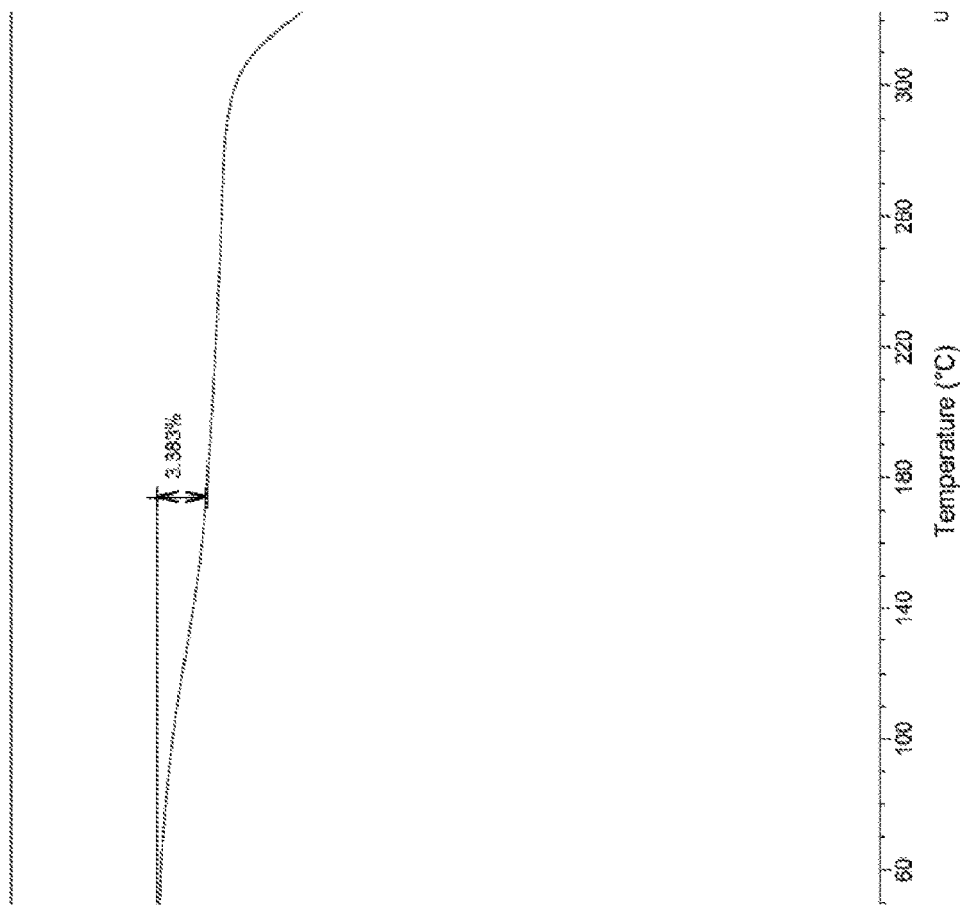
FIG. 33 shows a thermogravimetric analysis of polymorph Form IV hydrochloride salt obtained from 5:7 ethanol/water.

To the HCl salt (1.0 g) was added ethanol (7.5 mL) and water (10.5 mL). The resulting suspension was stirred at reflux temperature until it became clear and homogeneous. The solution was then cooled to room temperature with stirring. The resulting crystals were collected and dried to yield the title compound (0.6 g, 60% yield) in a solid form defined as polymorph Form IV. Elemental analysis: N: 17.79%; C: 57.92%; H: 5.40%. The XRPD, DSC, and TGA traces for this material are shown in FIGS. 31, 32, and 33, respectively.

Example 9-5 (Ethanol/Water (3:2))

Figure 34:
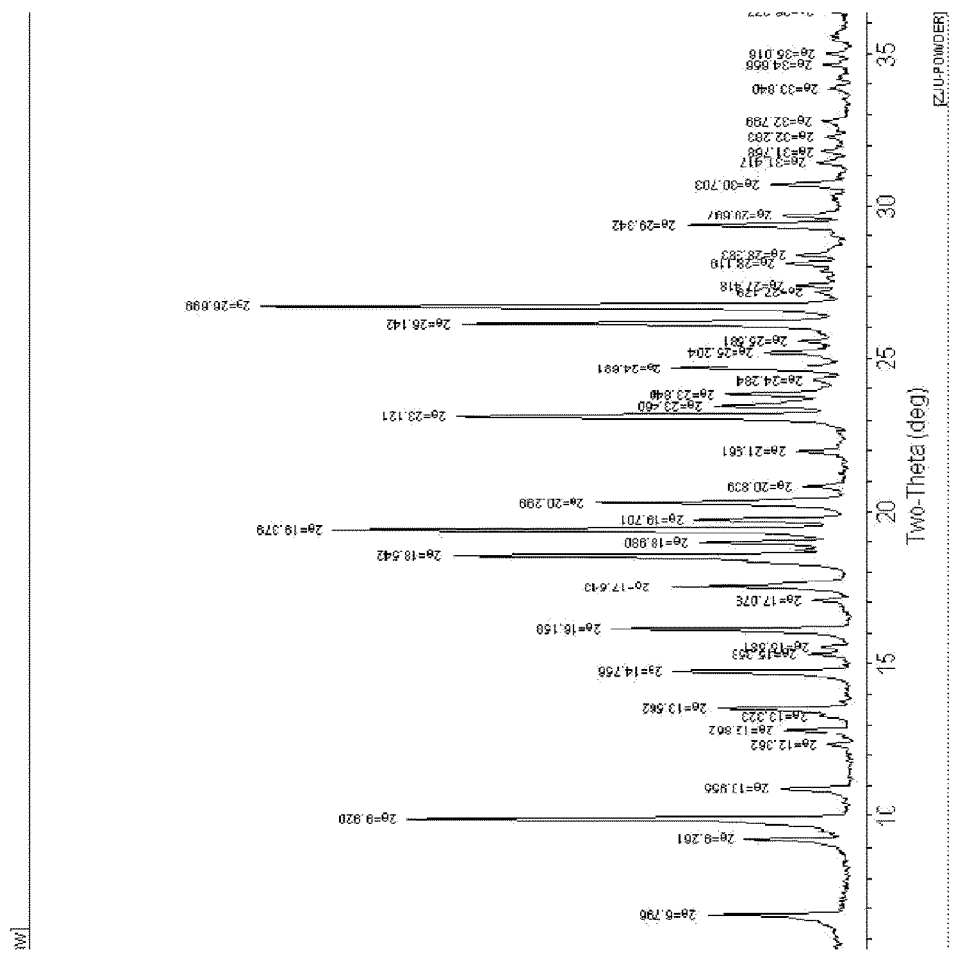
FIG. 34 is an X-ray powder diffractogram of polymorph Form IV hydrochloride salt obtained from 3:2 ethanol/water.
Figure 35:
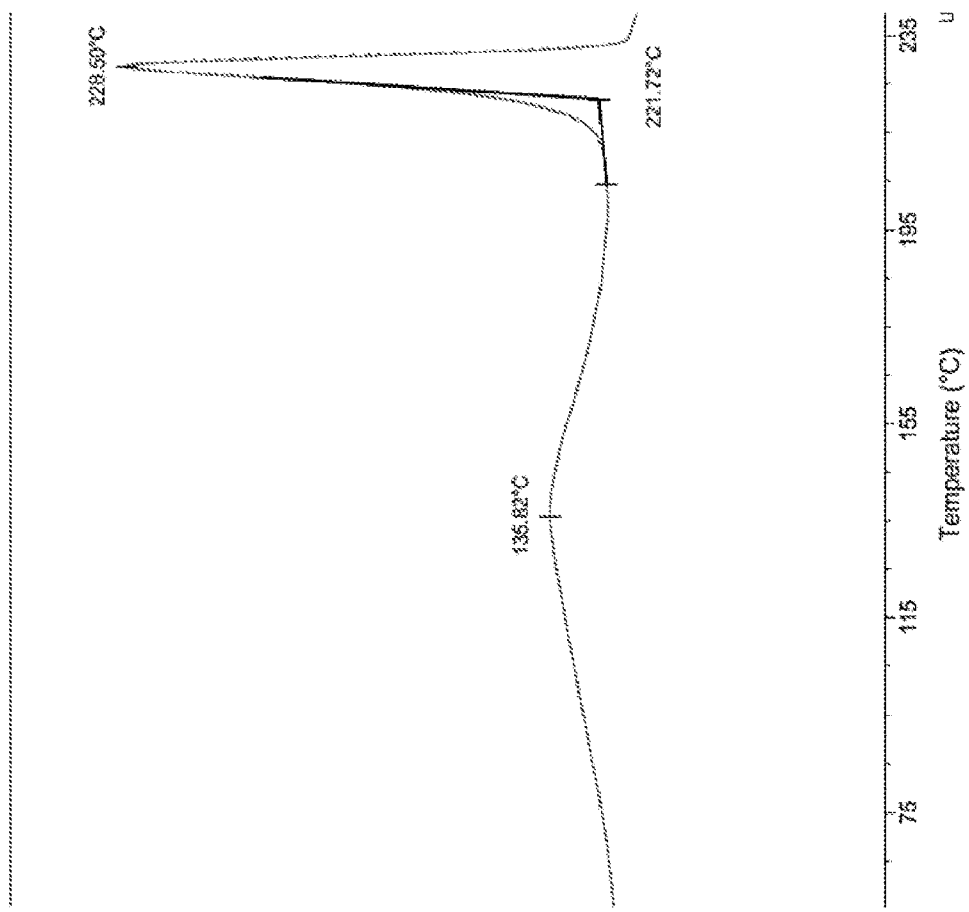
FIG. 35 is a differential scanning calorimetry curve of polymorph Form IV hydrochloride salt obtained from 3:2 ethanol/water.
Figure 36:
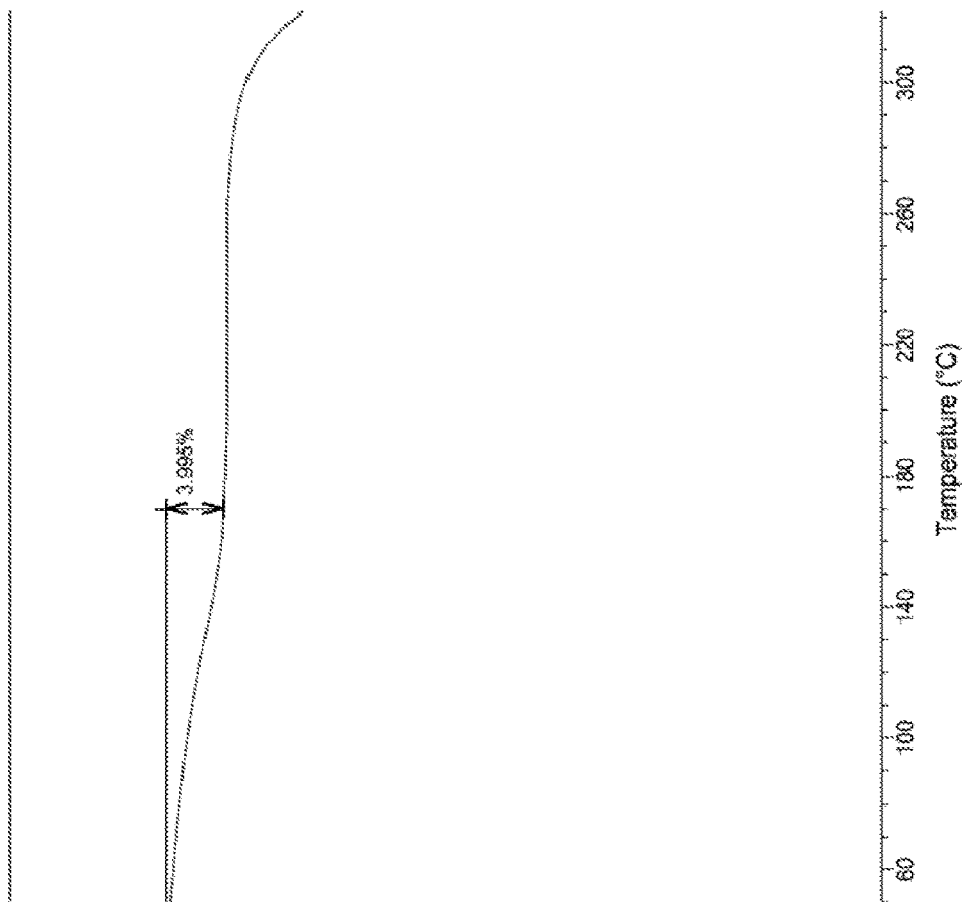
FIG. 36 shows a thermogravimetric analysis of polymorph Form IV hydrochloride salt obtained from 3:2 ethanol/water.

To the HCl salt (1.0 g) was added ethanol (6 mL) and water (4 mL). The resulting suspension was stirred at reflux temperature until it became clear and homogeneous. The solution was then cooled to room temperature with stirring. The resulting crystals were collected and dried to yield the title compound (0.64 g, 64% yield) in a solid form defined as polymorph Form IV. Elemental analysis: N: 17.66%; C: 57.77%; H: 5.42%. The XRPD, DSC, and TGA traces for this material are shown in FIGS. 34, 35, and 36, respectively.

Example 9-6 (Ethanol/Water (7:3))

Figure 37:
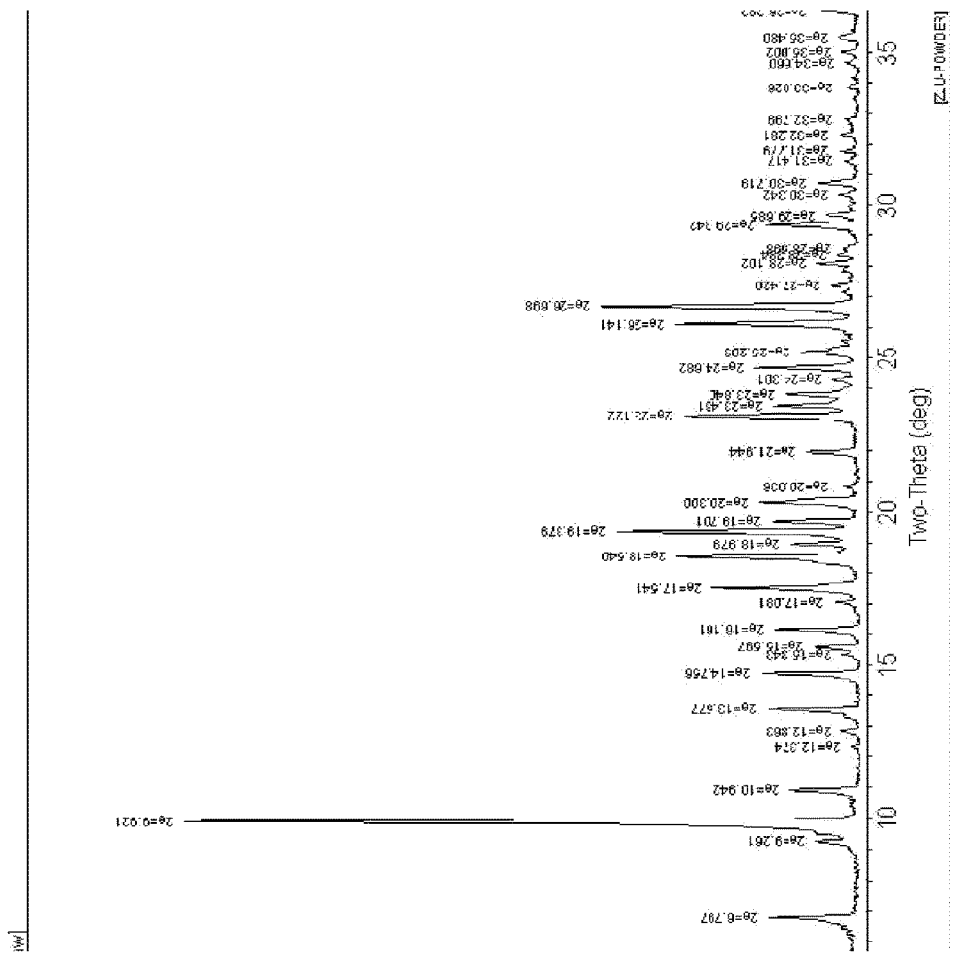
FIG. 37 is an X-ray powder diffractogram of polymorph Form IV hydrochloride salt obtained from 7:3 ethanol/water.
Figure 38:
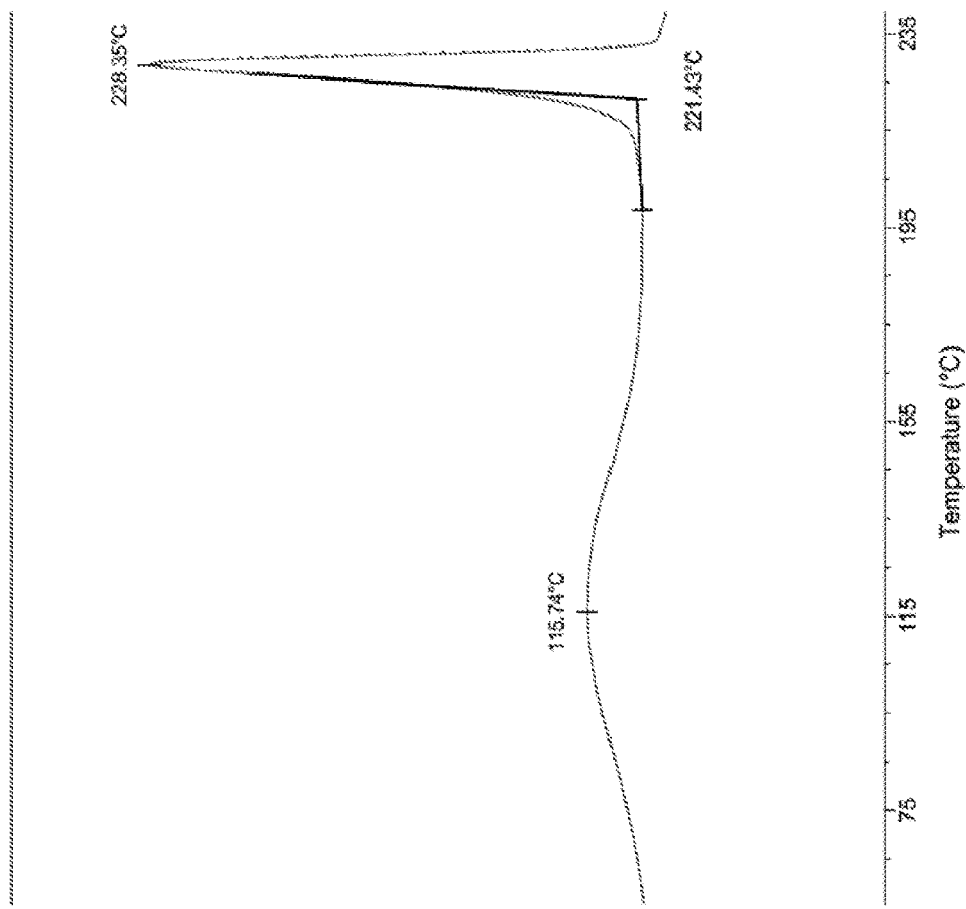
FIG. 38 is a differential scanning calorimetry curve of polymorph Form IV hydrochloride salt obtained from 7:3 ethanol/water.
Figure 39:
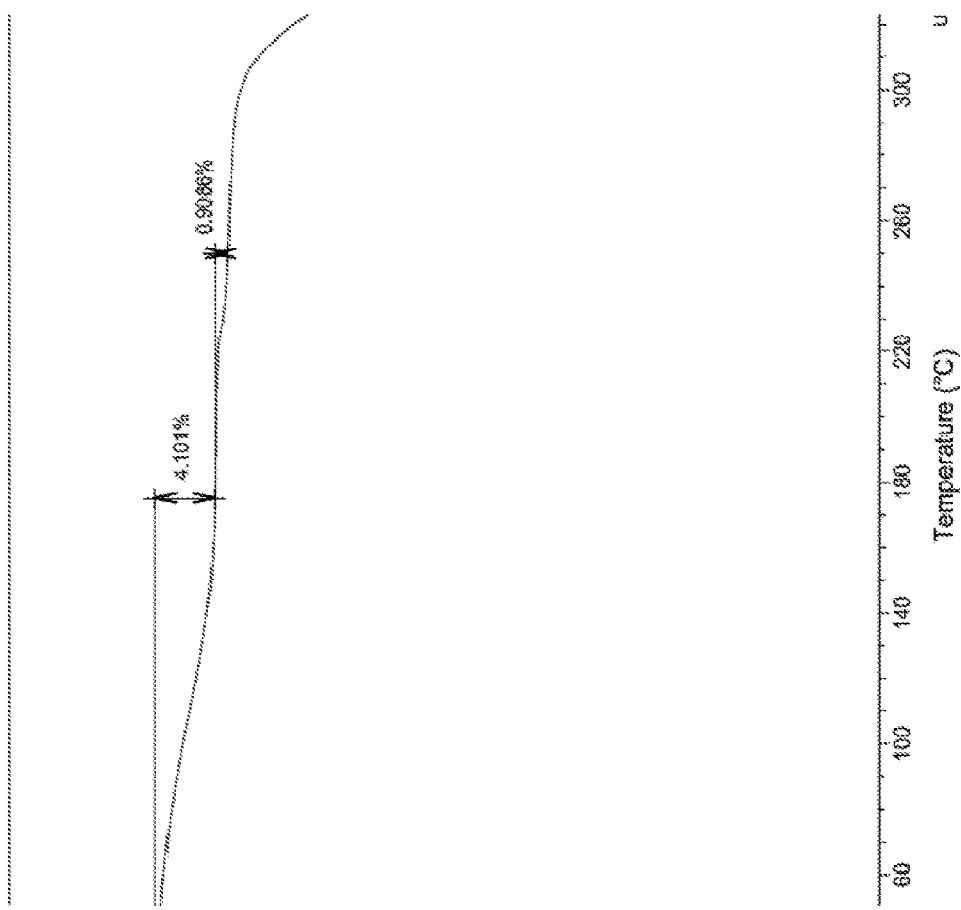
FIG. 39 shows a thermogravimetric analysis of polymorph Form IV hydrochloride salt obtained from 7:3 ethanol/water.

To the HCl salt (1.0 g) was added 70% aqueous ethanol (20 mL). The resulting suspension was stirred at reflux temperature until it became clear and homogeneous. The solution was then cooled to room temperature with stirring. The resulting crystals were collected and dried to yield the title compound (0.7 g, 70% yield) in a solid form defined as polymorph Form IV. Elemental analysis: N: 17.78%; C: 57.76%; H: 5.40%. The XRPD, DSC, and TGA traces for this material are shown in FIGS. 37, 38, and 39, respectively.

Figure 40:
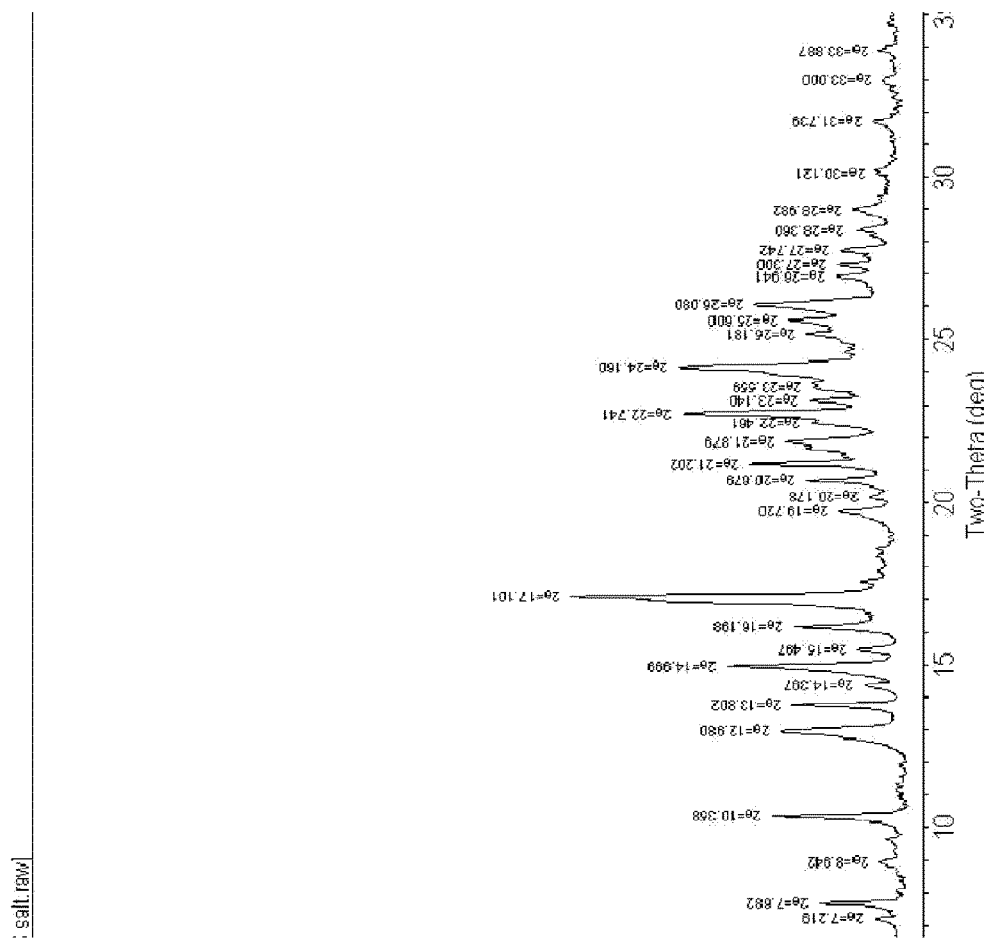
FIG. 40 is an X-ray powder diffractogram of polymorph Form V fumarate salt obtained from 1:19 ethanol/water.
Figure 41:
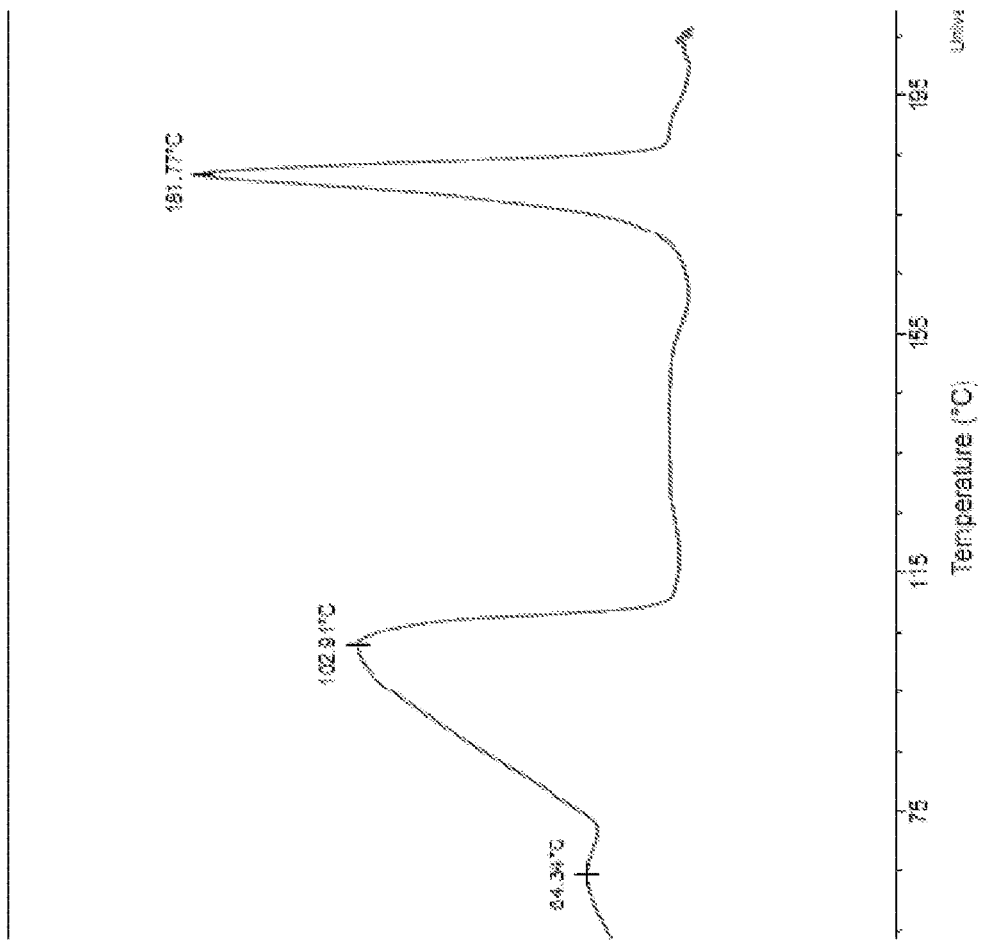
FIG. 41 is a differential scanning calorimetry curve of polymorph Form V fumarate salt obtained from 1:19 ethanol/water.
Figure 42:
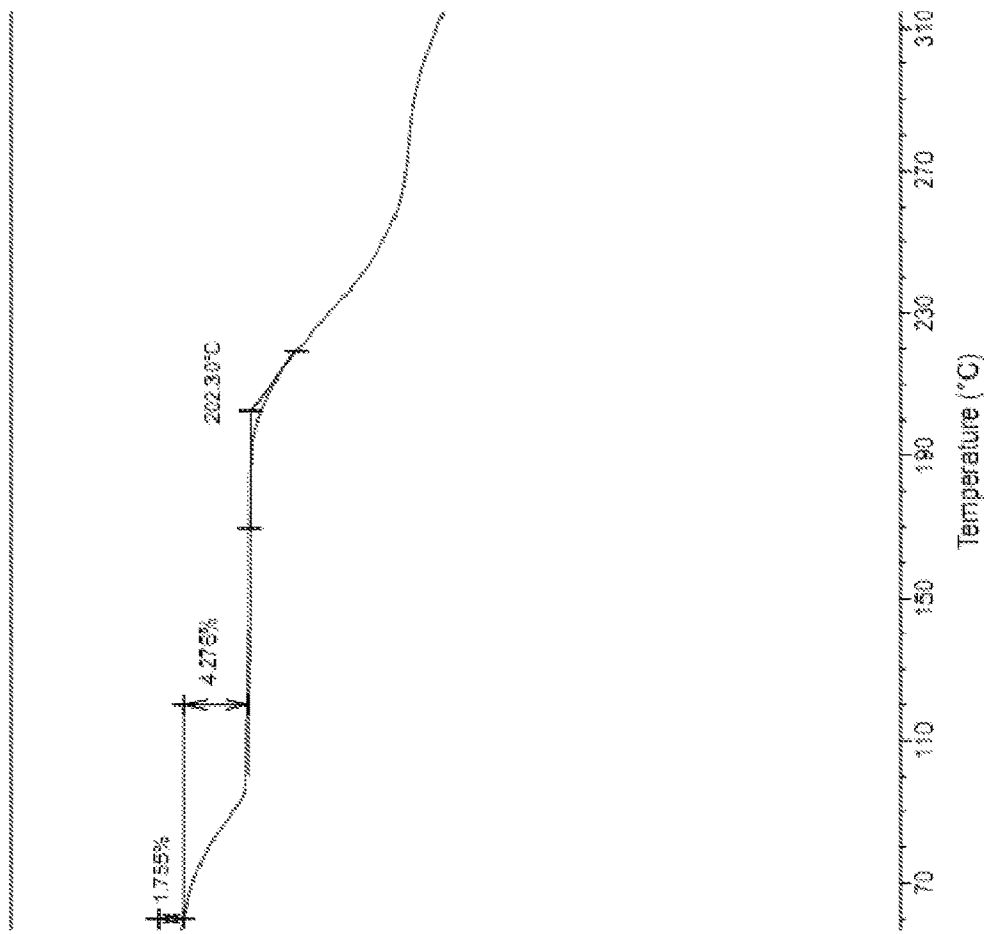
FIG. 42 shows a thermogravimetric analysis of polymorph Form V fumarate salt obtained from 1:19 ethanol/water.

Example 10. Synthesis of N-(3-(2-(3-fluoro-4-(4-methylpiperazin-1-yl)phenylamino)-7H-pyrrolo[2,3-d]pyrimidin-4-yloxy)phenyl)acrylamide fumarate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (5 g, 10.3 mmol) in 5% aq. ethanol (60 mL) at 40° C. was treated with a solution of fumaric acid (1.5 g, 12.9 mmol) in 5% aq. ethanol (15 mL). Crystals formed, which were collected and dried to yield the title compound (5.4 g, 87.2% yield) defined as polymorph Form V. Elemental analysis: N: 15.31%; C: 57.59%; H: 5.38%. The XRPD, DSC, and TGA traces for this material are shown in FIGS. 40, 41, and 42, respectively.

Figure 43:
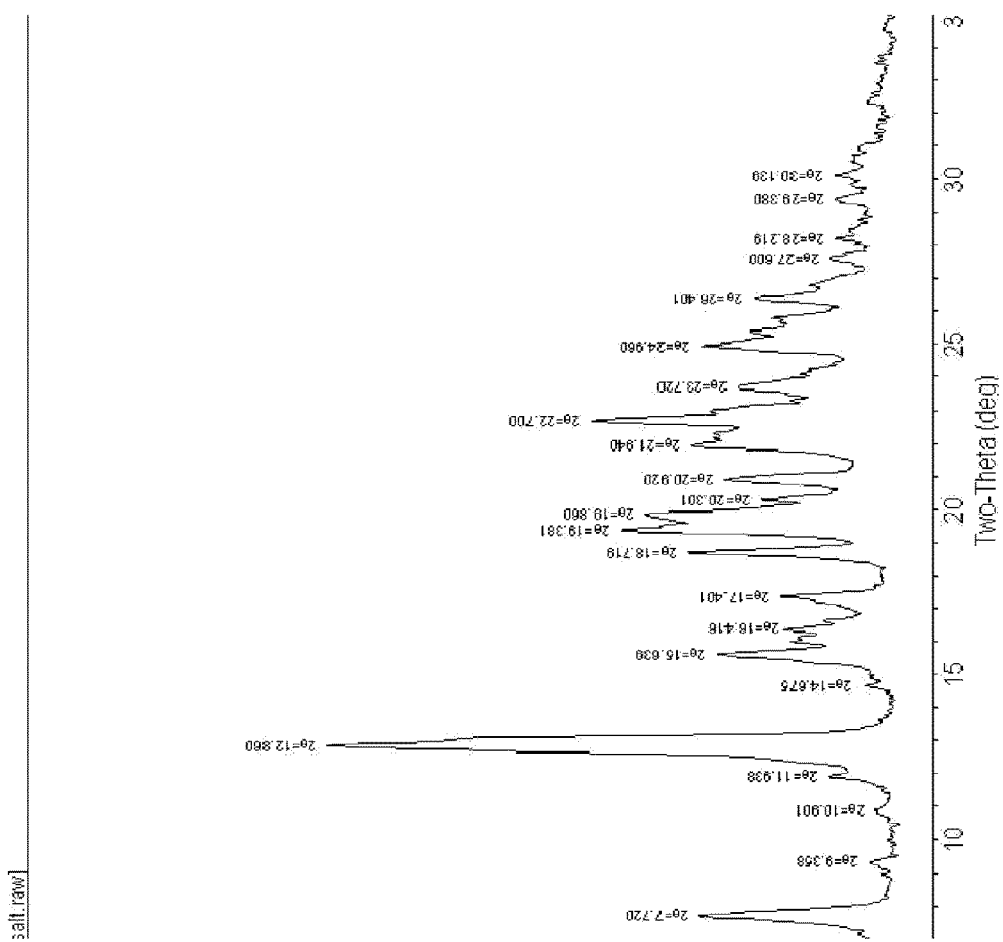
FIG. 43 is an X-ray powder diffractogram of polymorph Form VI malate salt obtained from 1:9 ethanol/water.
Figure 44:
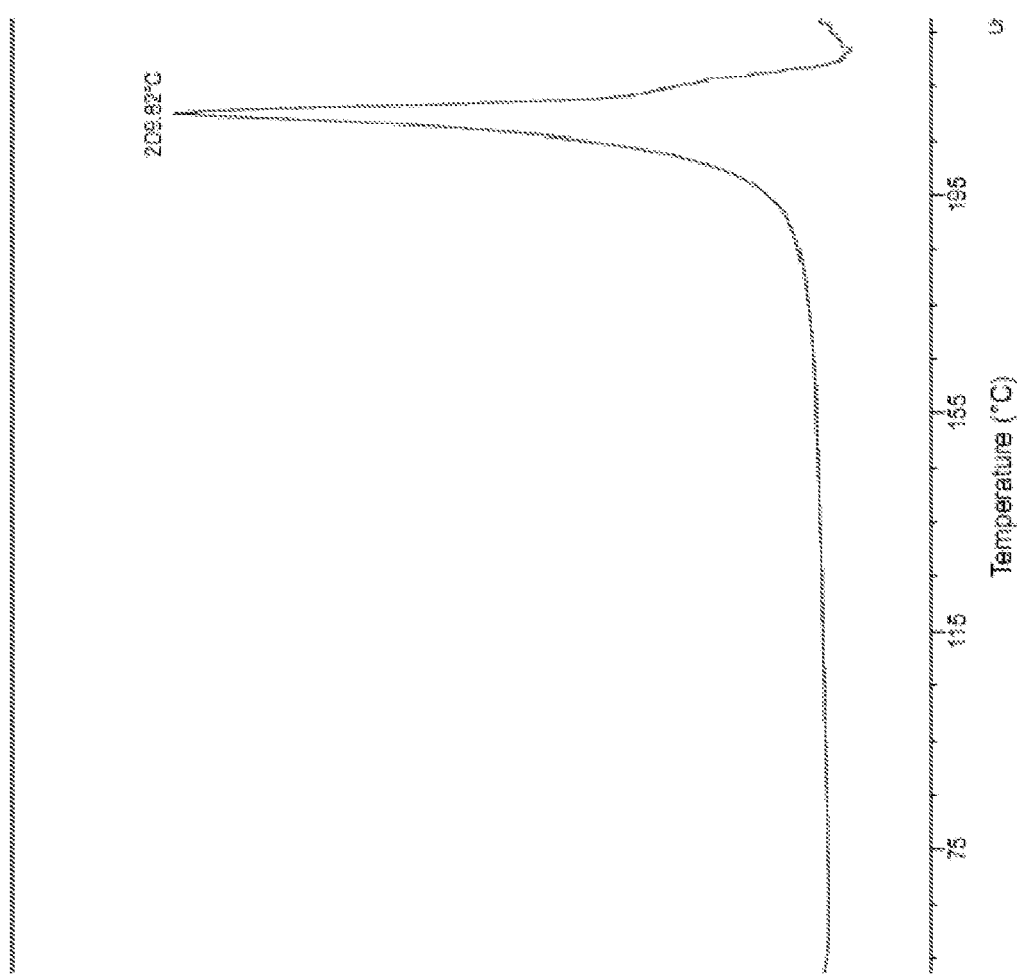
FIG. 44 is a differential scanning calorimetry curve of polymorph Form VI malate salt obtained from 1:9 ethanol/water.
Figure 45:
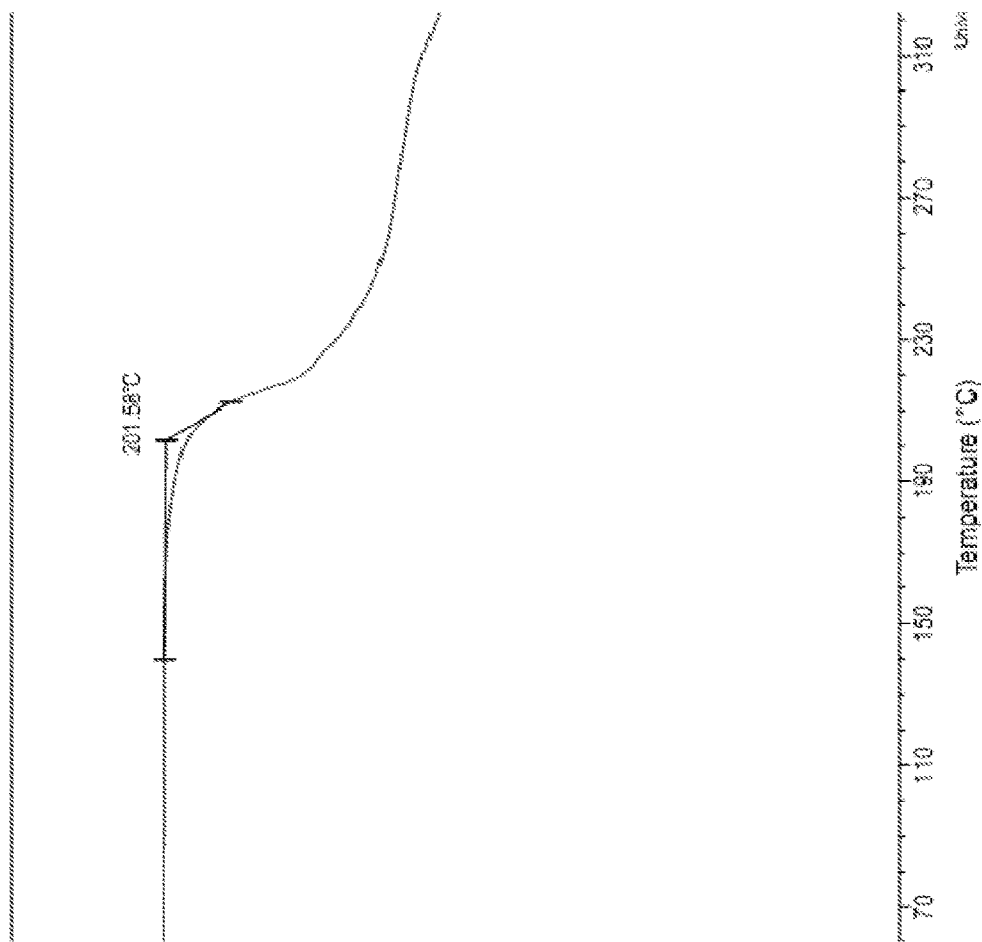
FIG. 45 shows a thermogravimetric analysis of polymorph Form VI malate salt obtained from 1:9 ethanol/water.

Example 11. Synthesis of N-(3-(2-(3-fluoro-4-(4-methylpiperazin-1-yl)phenylamino)-7H-pyrrolo[2,3-d]pyrimidin-4-yloxy)phenyl)acrylamide malate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2 g, 4.1 mmol) in 10% aq. ethanol (20 mL) at 40° C. was treated with a solution of DL-malic acid (660 mg, 4.93 mmol) in 10% aq. ethanol (5 mL). The solution was cooled to room temperature with stirring. Crystals formed, which were collected and dried to yield the title compound (1.4 g, 55% yield) defined as polymorph Form VI. Elemental analysis: N: 15.17%; C: 57.28%; H: 5.09%. The XRPD, DSC, and TGA traces for this material are shown in FIGS. 43, 44, and 45, respectively.

Figure 46:
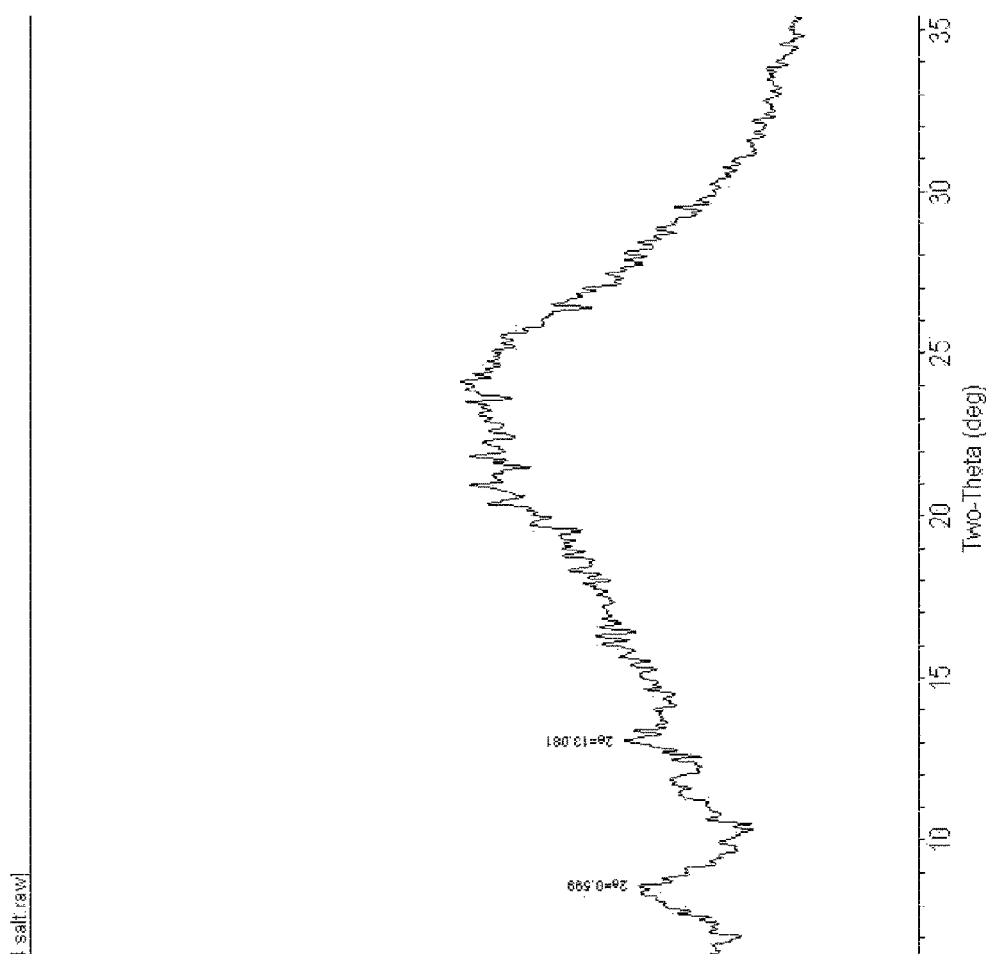
FIG. 46 is an X-ray powder diffractogram of an amorphous form of the sulfate salt obtained from water.
Figure 47:
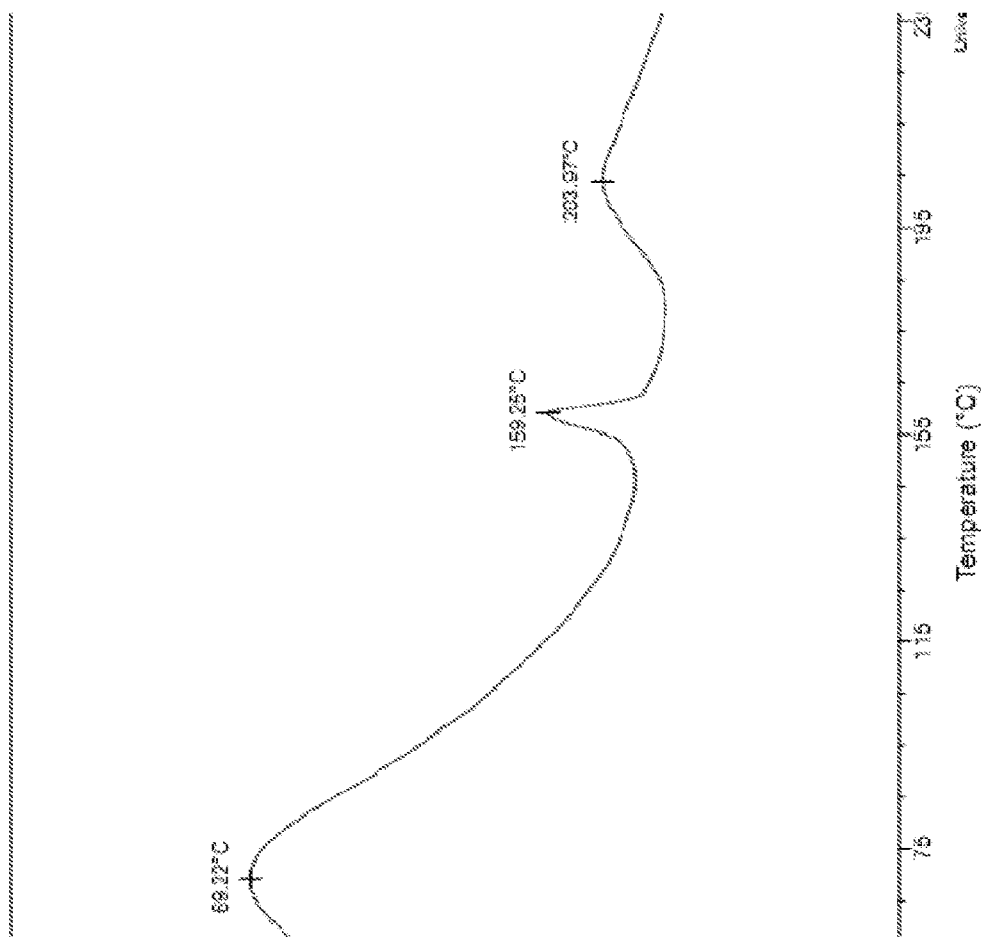
FIG. 47 is a differential scanning calorimetry curve of an amorphous form of the sulfate salt obtained from water.
Figure 48:
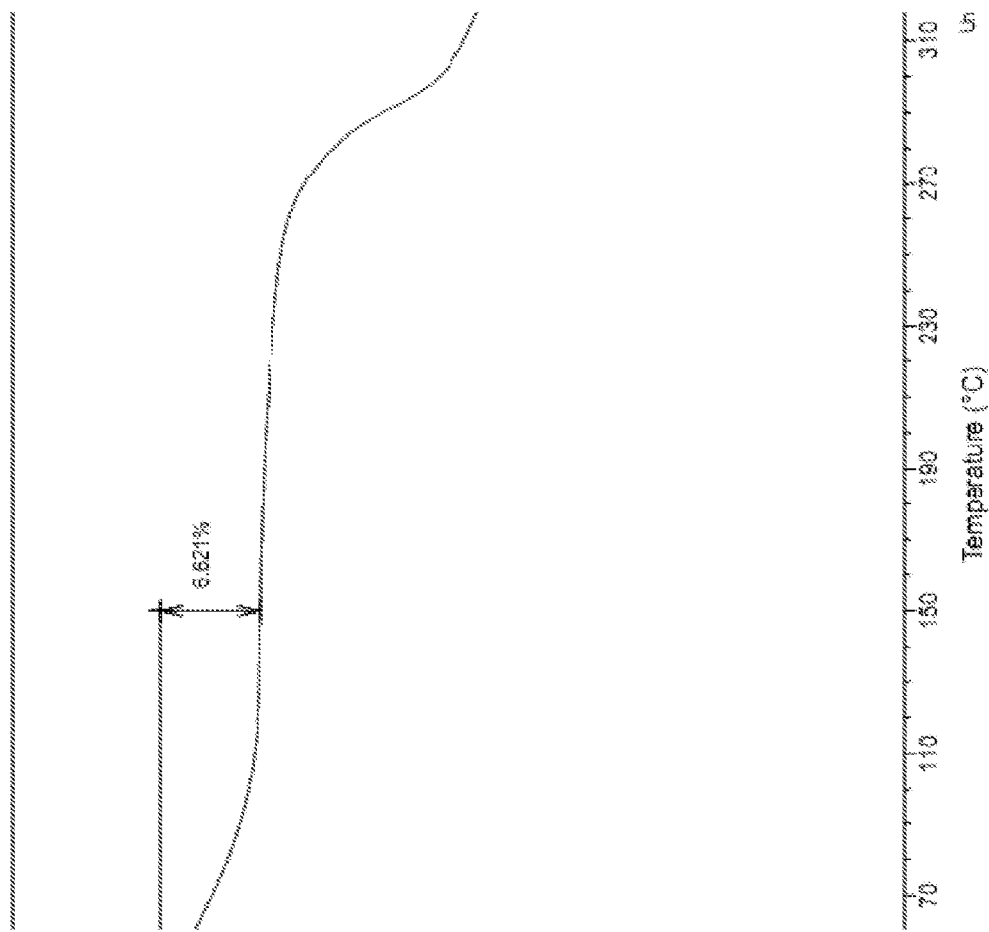
FIG. 48 shows a thermogravimetric analysis of an amorphous form of the sulfate salt obtained from water.

Example 12. Synthesis of N-(3-(2-(3-fluoro-4-(4-methylpiperazin-1-yl)phenylamino)-7H-pyrrolo[2,3-d]pyrimidin-4-yloxy)phenyl)acrylamide sulfate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2 g, 4.1 mmol) in water (10 mL) at room temperature was treated with 1 M $H_2SO_4$ (5 mL). Crystals formed, which were collected and dried to yield the title compound (1.7 g, 70.8% yield) defined as an amorphous form. Elemental analysis: N: 15.76%; C: 51.15%; H: 5.41%. The XRPD, DSC, and TGA traces for this material are shown in FIGS. 46, 47, and 48, respectively.

Figure 49:
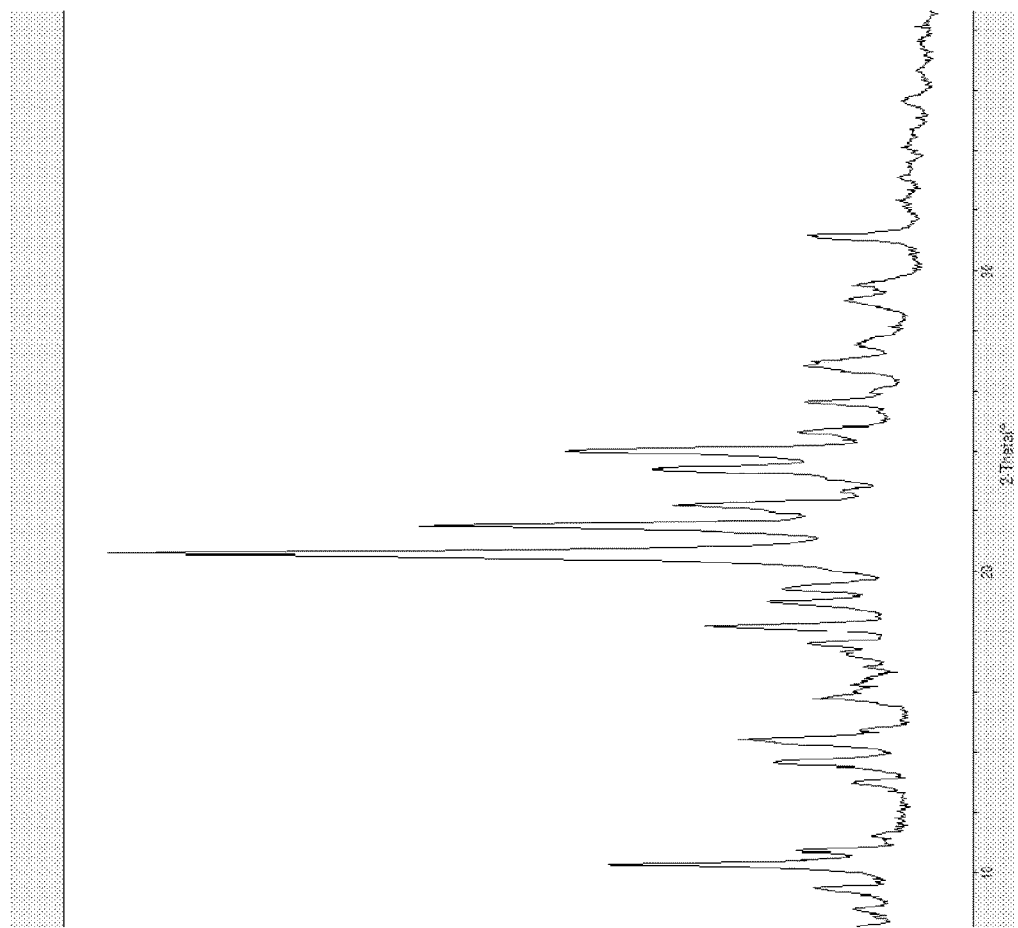
FIG. 49 is an X-ray powder diffractogram of an amorphous form of the mesylate salt obtained from ethanol/ethyl acetate/water.

Example 13. Synthesis of N-(3-(2-(3-fluoro-4-(4-methylpiperazin-1-yl)phenylamino)-7H-pyrrolo[2,3-d]pyrimidin-4-yloxy)phenyl)acrylamide mesylate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1.3 g, 2.67 mmol) in ethanol (10 mL) at 50° C. was treated with methanesulfonic acid (563 mg, 5.86 mmol). The solution was cooled to −10 C without crystal formation. The mixture was concentrated, and the residue dissolved in a mixture of ethanol (5 mL), ethyl acetate (10 mL), and water (0.5 mL), and was stirred at reflux temperature. The solution was cooled to 35° C. and crystals appeared. The resulting crystals were collected and dried to yield the title compound (1.2 g, 66.3% yield) in a solid form defined as amorphous form. The XRPD trace for this material is shown in FIG. 49.

Figure 50:
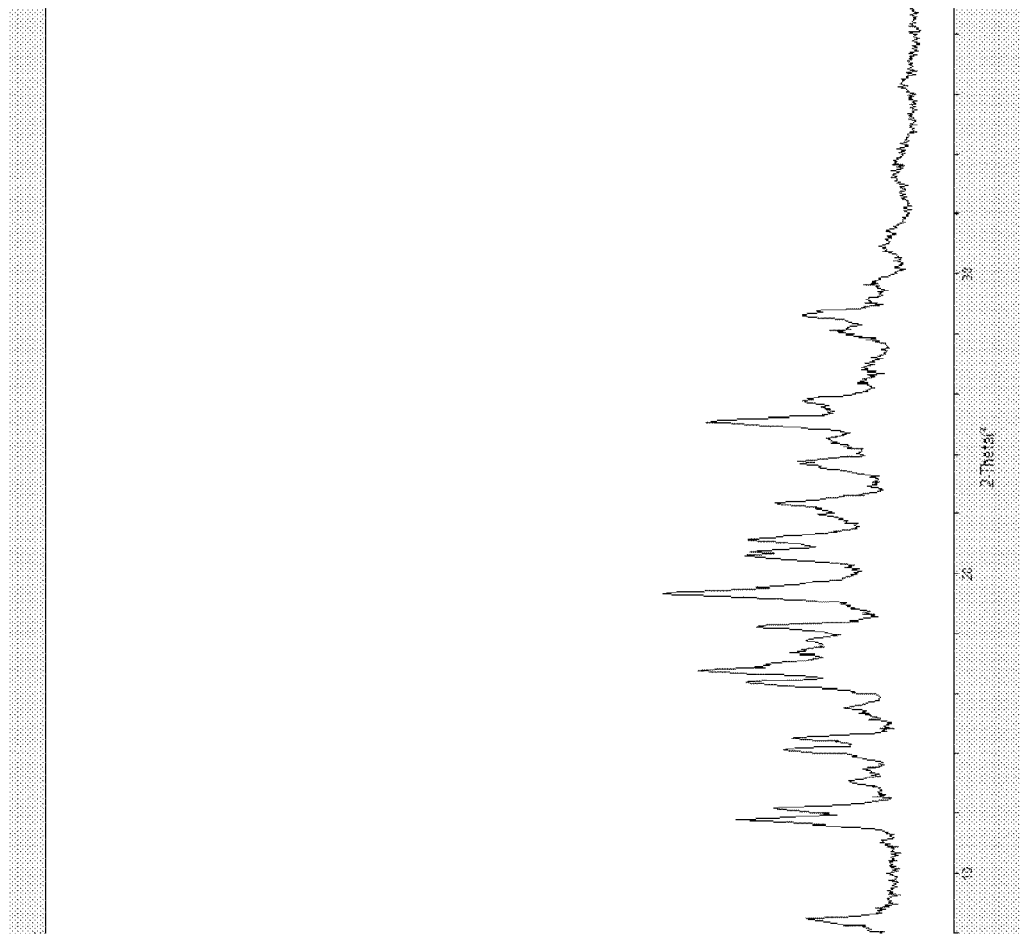
FIG. 50 is an X-ray powder diffractogram of an amorphous form of the tosylate salt obtained from water/ethyl acetate.

Example 14. Synthesis of N-(3-(2-(3-fluoro-4-(4-methylpiperazin-1-yl)phenylamino)-7H-pyrrolo[2,3-d]pyrimidin-4-yloxy)phenyl)acrylamide tosylate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2.0 g, 4.10 mmol) in ethanol (4 mL) and water (1 mL) at 60° C. was treated with p-toluenesulfonic acid (1.7 g, 9.88 mmol). Ethyl acetate (20 mL) was then added, and the resulting solution was stirred at reflux temperature. The solution was cooled to 0° C. and crystals appeared. The resulting crystals were collected and dried to yield the title compound (2.2 g, 81.5% yield) in a solid form defined as amorphous form. The XRPD trace for this material is shown in FIG. 50.

Figure 51:
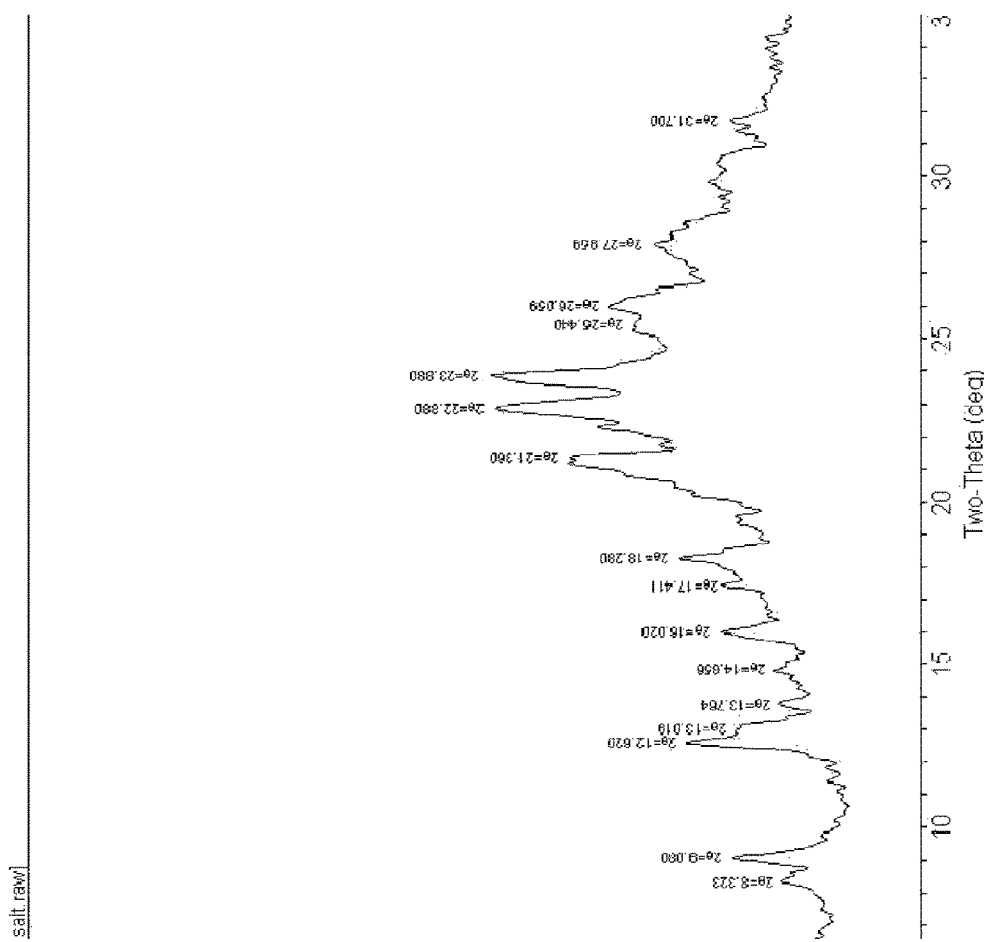
FIG. 51 is an X-ray powder diffractogram of an amorphous form of the hydrobromide salt obtained from water.
Figure 52:
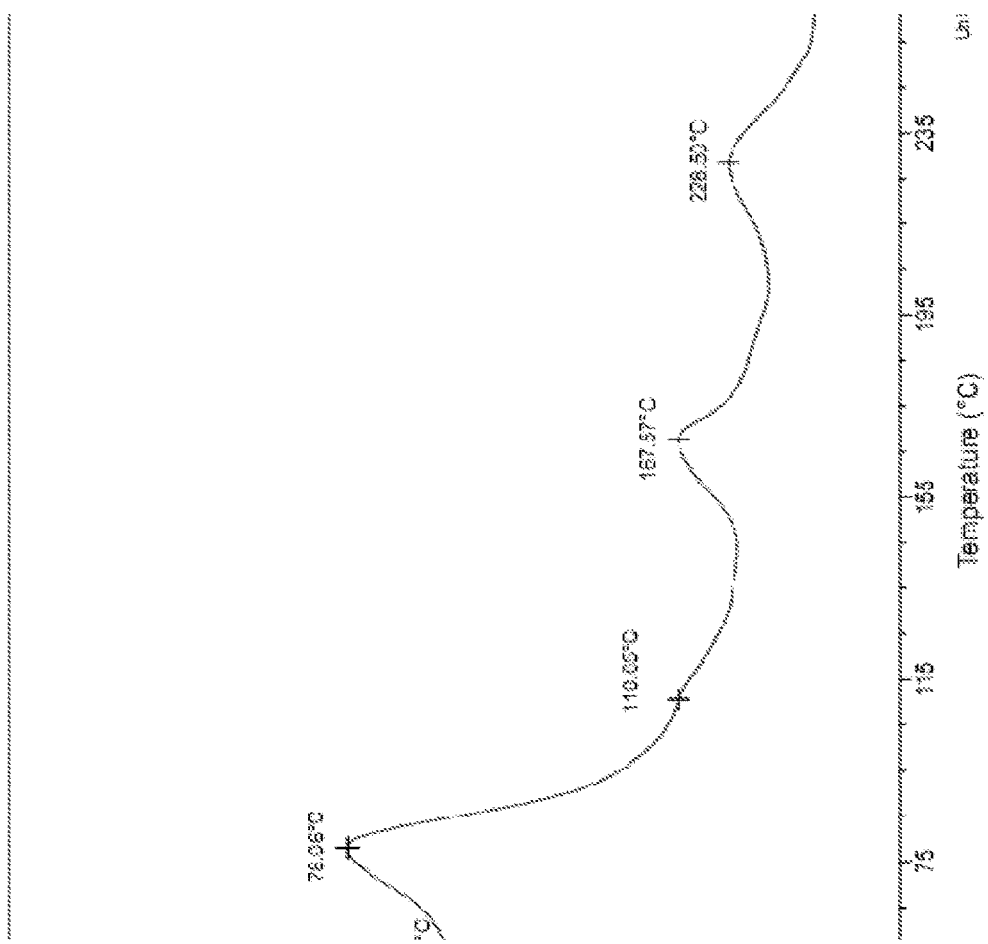
FIG. 52 is a differential scanning calorimetry curve of an amorphous form of the hydrobromide salt obtained from water.
Figure 53:
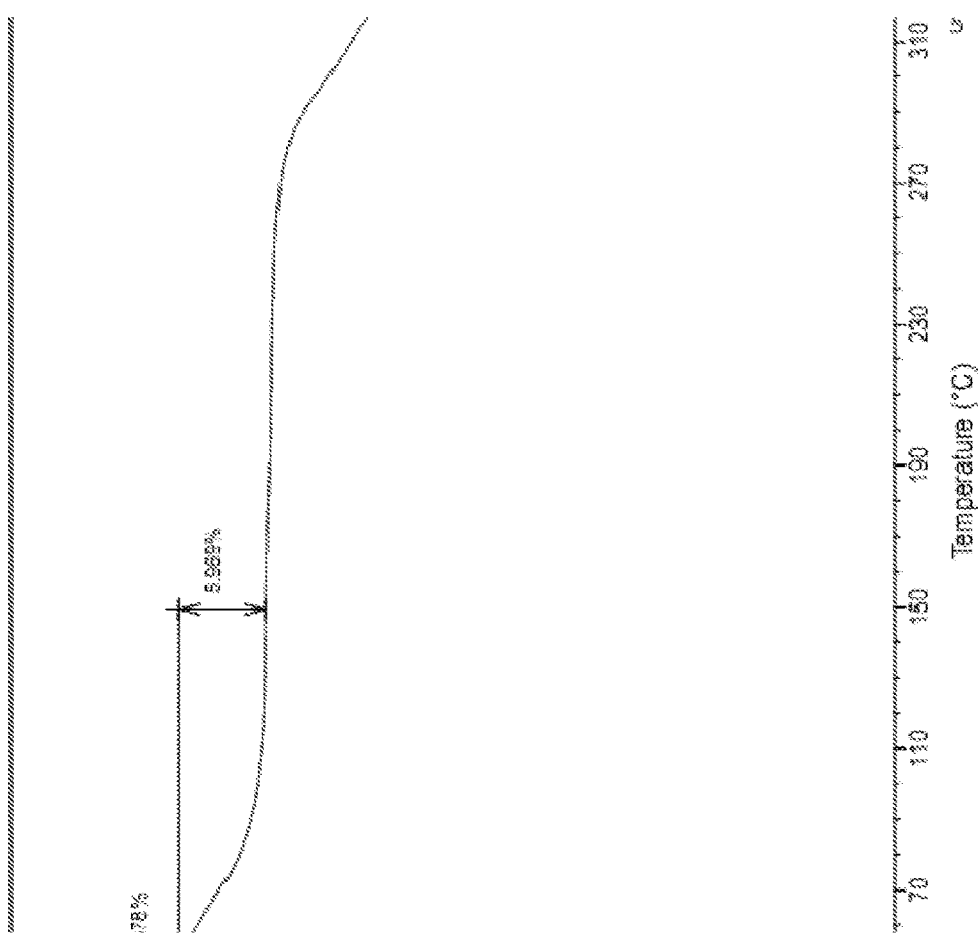
FIG. 53 shows a thermogravimetric analysis of an amorphous form of the hydrobromide salt obtained from water.

Example 15. Synthesis of N-(3-(2-(3-fluoro-4-(4-methylpiperazin-1-yl)phenylamino)-7H-pyrrolo[2,3-d]pyrimidin-4-yloxy)phenyl)acrylamide hydrobromide salt Example 15-1 (Water). A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2.0 g, 4.10 mmol) in water (10 mL) at room temperature was treated with 1 M HBr (10 mL). The resulting crystals were collected and dried to yield the title compound (1.8 g, 67.7% yield) in a solid form defined as amorphous form. Elemental analysis: N: 14.92%; C: 48.26%; H: 5.02%. The XRPD, DSC, and TGA traces for this material are shown in FIGS. 51, 52, and 53, respectively.

Example 15-2 (Ethanol/Water (1:3))

Figure 54:
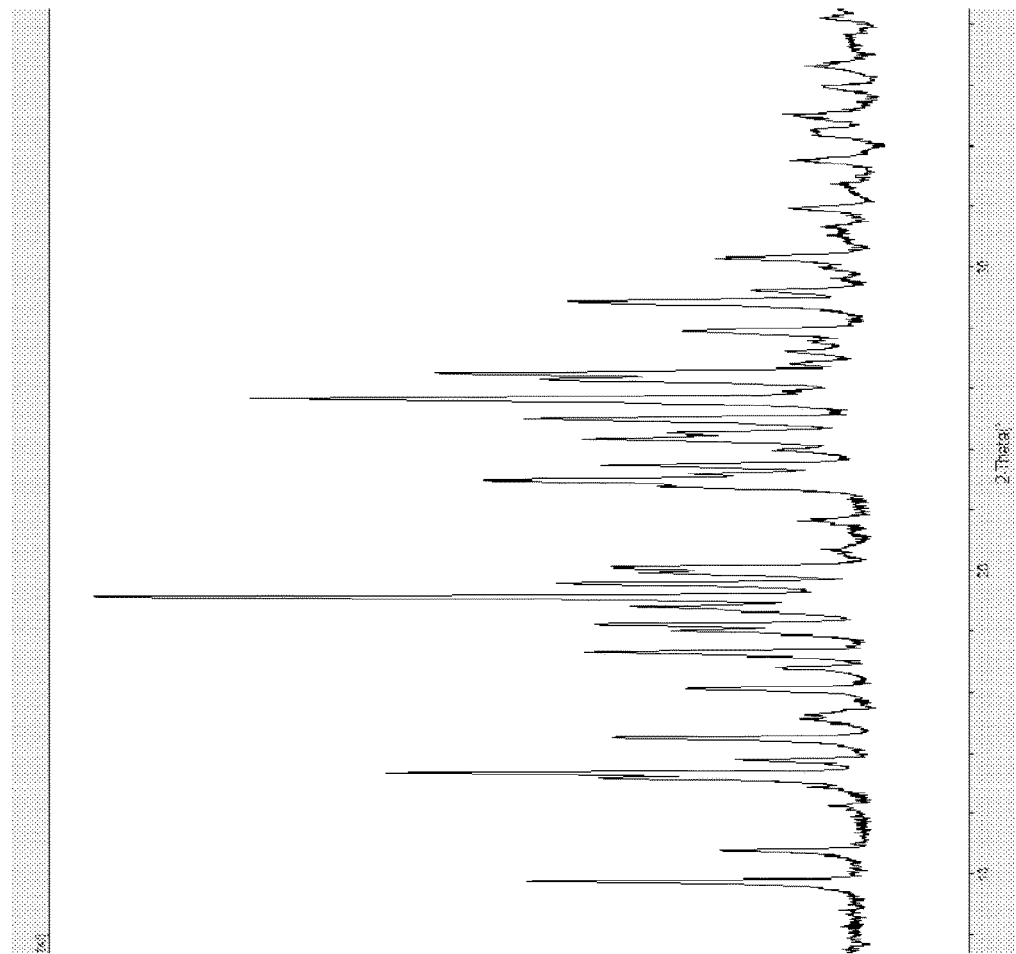
FIG. 54 is an X-ray powder diffractogram of polymorph Form VII hydrobromide salt obtained from 1:3 ethanol/water.

The above amorphous HBr salt form (1 g, 2.05 mmol) was dissolved in ethanol (2 mL) at 50° C. with stirring. Water (6 mL) was then added. The solution was cooled to room temperature with stirring overnight. The resulting crystals were collected and dried to yield the title compound (0.7 g, 70% yield) in a solid form defined as polymorph Form VII. The XRPD trace for this material is shown in FIG. 54.

Formulation Example A: Manufacture of Capsules by Dry Blend Process (Rx1)

Capsules containing Compound 1, maleate salt, were prepared by a dry blend process as described below. The final composition of the capsules is shown in Table A1. In some embodiments, each of the adsorbing agents is variable by up to ±10% w/w of the adsorbing agent, the disintegrating agent is variable by up to ±6% w/w of the disintegrating agent, and the lubricant is variable by up to 2% w/w of the lubricant.

Table A2 includes additional ranges for the composition of the capsules. In some embodiments of the capsule, the percentage w/w of the compound of Formula (I), or a pharmaceutically acceptable salt thereof (e.g., Compound 1, or a pharmaceutically acceptable salt thereof) is variable by up to ±20% w/w of the entire weight of the capsule. In some embodiments, each of the components of the capsule is variable by up to ±10% w/w of the entire weight of the capsule. In some embodiments, each of the adsorbing agents is variable by up to ±10% w/w of the entire weight of the capsule, the disintegrating agent is variable by up to ±6% w/w of the entire weight of the capsule, and the lubricant is variable by up to ±2% w/w of the entire weight of the capsule.

The flow diagram for the process is shown in Chart A and the process is described in detail below.

TABLE A1

Composition of dry blend capsules (Rx1)

| Ingredient | Rx1 Quantity (per capsule) | Quantity (400 capsules) |
|---|---|---|
| Pre-blending (dry blend) | | |
| API/API Maleate (e.g., Compound 1/ Compound 1 maleate) | 20-30 mg/26.24-39.36 mg (e.g., 25.00 mg/32.80 mg) | 10.5-15.74 g (e.g., 13.12 g) |
| Prosolv ® SMCC 50 | 19.89-24.31 mg (e.g., 22.10 mg) | 7.96-9.72 g (e.g., 8.84 g) |
| Re-blending | | |
| Prosolv ® SMCC 90 | 64.67-79.04 mg (e.g., 71.85 mg) | 25.87-31.61 g (e.g., 28.74 g) |
| Capsule Preparation | | |
| Vivasol ® sodium croscarmellose | 2.44-2.76 mg (e.g., 2.60 mg) | 0.98-1.10 g (e.g., 1.04 g) |
| sodium stearyl fumarate | 0.637-0.663 mg (e.g., 0.65 mg) | 0.255-0.265 g (e.g., 0.26 g) |
| Capsule weight | 113.88 – 146.13 (e.g., 130 mg) | — |
| Batch weight | — | 45.57-58.44 g (e.g., 52.0 g) |

TABLE A2

Composition of dry blend capsules (Rx1)

| Ingredient | Rx1 Quantity (per capsule) | Quantity (400 capsules) |
|---|---|---|
| Pre-blending (dry blend) | | |
| API/API Maleate (e.g., Compound 1/ Compound 1 maleate) | 20-30 mg/26.24-39.36 mg (e.g., 25.00 mg/32.80 mg) | 10.5-15.74 g (e.g., 13.12 g) |
| Prosolv ® SMCC 50 | 9.0-35.0 mg (e.g., 22.10 mg) | 3.6-13.8 g (e.g., 8.84 g) |
| Re-blending | | |
| Prosolv ® SMCC 90 | 59.0-85.0 mg (e.g., 71.85 mg) | 23.5-33.9 g (e.g., 28.74 g) |
| Capsule Preparation | | |
| Vivasol ® sodium croscarmellose | 0.01-10.4 mg (e.g., 2.60 mg) | 0.01-4.2 g (e.g., 1.04 g) |
| sodium stearyl fumarate | 0.01-3.25 mg (e.g., 0.65 mg) | 0.01-1.3 g (e.g., 0.26 g) |
| Capsule weight | 95.0-173 (e.g., 130 mg) | — |
| Batch weight | — | 45.57-58.44 g (e.g., 52.0 g) |

Chart A: Flow diagram for the manufacture of capsules containing Compound 1, maleate salt, by dry blend process.

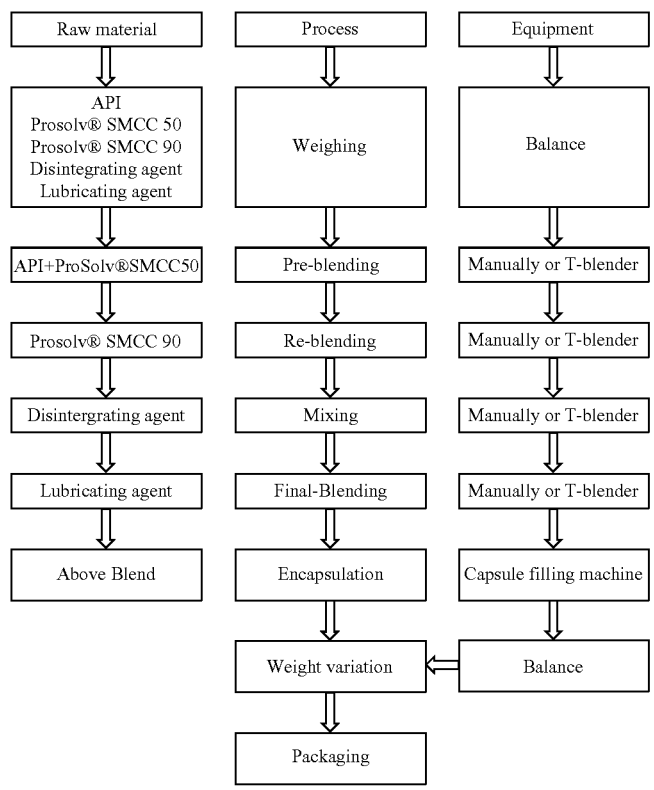

Preparation of Composition Rx1. Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (13.12 g; D (v, 0.9)≤19 μm) and adsorbing agent Prosolv® SMCC 50 (8.84 g) were mixed in a pre-blending process and the resulting mixture was mixed with Prosolv® SMCC 90 (28.74 g) by a re-blending process to obtain Composition A1. Composition A1, Vivasol® croscarmellose sodium (1.04 g), and sodium stearyl fumarate (0.26 g) were mixed and subjected to final blending to form a final powder, which was then filled into hollow gelatin capsules to prepare Composition Rx1. Characterization data for the final powder are shown in Table A2, and results of dissolution and stability studies for Composition Rx1 are reported in Table A3.

TABLE A2

| Final Powder | Characteristics |
| --- | --- |
| Bulk Density | 0.30 g/mL |
| Tapped Density | 0.50 g/mL |
| Carr's index | 34 |
| Angle of repose | 34.6° |

TABLE A3

| Rx1 | Characteristics |
| --- | --- |
| Dissolution (Medium; Method) | 99% (Medium, 0.1 N HCl; Basket method, 100 rpm) |
| Heat (60° C.-10 days) | Dimer Formation 0.01% |
| Humidity (75% RH-10 days) | Dimer Formation 0.01% |
| Light (4500 λ ± 500 λ-10 days) | Dimer Formation 0.01% |

Formulation Example B. Manufacture of Capsules by Roller Compaction Process (Rx2)

Capsules containing Compound 1, maleate salt, were prepared by a roller compaction process. The final composition of the capsules is shown in Table B1. In some embodiments, each of the adsorbing agents is variable by up to ±10% w/w of the adsorbing agent, the disintegrating agent is variable by up to ±6% w/w of the disintegrating agent, and the lubricant is variable by up to ±2% w/w of the lubricant.

Table B2 includes additional ranges for the composition of the capsules. In some embodiments of the capsule, the percentage w/w of the compound of Formula (I), or a pharmaceutically acceptable salt thereof (e.g., Compound 1, or a pharmaceutically acceptable salt thereof) is variable by up to ±20% w/w of the entire weight of the capsule. In some embodiments, each of the components of the capsule is variable by up to ±10% w/w of the entire weight of the capsule. In some embodiments, each of the adsorbing agents is variable by up to ±10% w/w of the entire weight of the capsule, the disintegrating agent is variable by up to ±6% w/w of the entire weight of the capsule, and the lubricant is variable by up to ±2% w/w of the entire weight of the capsule.

The flow diagram for the process is shown in Chart B and the process is described in detail below.

TABLE B1

Composition of roller compaction capsules (Rx2)

| Ingredient | Rx2 Quantity (per capsule) | Quantity (1000 capsules) |
|---|---|---|
| Pre-blending (roller compaction) | | |
| API/API Maleate (e.g., Compound 1/Compound 1 maleate) | 20-30 mg/26.24-39.36 mg (e.g., 25.00 mg/32.80 mg) | 26.24-39.36 g (e.g., 32.80 g) |
| Prosolv ® SMCC 50 | 19.71-24.09 mg (e.g., 21.90 mg) | 19.71-24.09 g (e.g., 21.90 g) |
| Re-blending | | |
| Prosolv ® SMCC90 | 80.37-98.23 mg (e.g., 89.30 mg) | 80.37-98.23 g (e.g., 89.30 g) |
| Capsule Preparation | | |
| Vivasol ® sodium croscarmellose | 2.82-3.18 mg (e.g., 3.00 mg) | 2.82-3.18 g (e.g., 3.00 g) |
| sodium stearyl fumarate | 2.94-3.06 mg (e.g., 3.00 mg) | 2.94-3.06 g (e.g., 3.00 g) |
| Capsule weight | 132.08-167.92 mg (e.g., 150 mg) | — |
| Batch weight | — | 132.08-167.92 g (e.g., 150.00 g) |

TABLE B2

Composition of roller compaction capsules (Rx2)

| Ingredient | Rx2 Quantity (per capsule) | Quantity (1000 capsules) |
|---|---|---|
| Pre-blending (roller compaction) | | |
| API/API Maleate (e.g., Compound 1/Compound 1 maleate) | 20-30 mg/26.24-39.36 mg (e.g., 25.00 mg/32.80 mg) | 26.24-39.36 g (e.g., 32.80 g) |
| Prosolv ® SMCC 50 | 6.9-36.9 mg (e.g., 21.90 mg) | 6.9-36.9 g (e.g., 21.90 g) |
| Re-blending | | |
| Prosolv ® SMCC90 | 74.3-104.3 mg (e.g., 89.30 mg) | 74.3-104.3 g (e.g., 89.30 g) |
| Capsule Preparation | | |
| Vivasol ® sodium croscarmellose | 0.01-12.0 mg (e.g., 3.00 mg) | 0.01-12.0 g (e.g., 3.00 g) |
| sodium stearyl fumarate | 0.01-6.0 mg (e.g., 3.00 mg) | 0.01-6.0 g (e.g., 3.00 g) |
| Capsule weight | 107.5-198.5 mg (e.g., 150 mg) | — |
| Batch weight | — | 107.5-198.5 g (e.g., 150.00 g) |

Chart B: Flow diagram for the manufacture of capsules containing Compound 1, maleate salt, b roller corn action process.

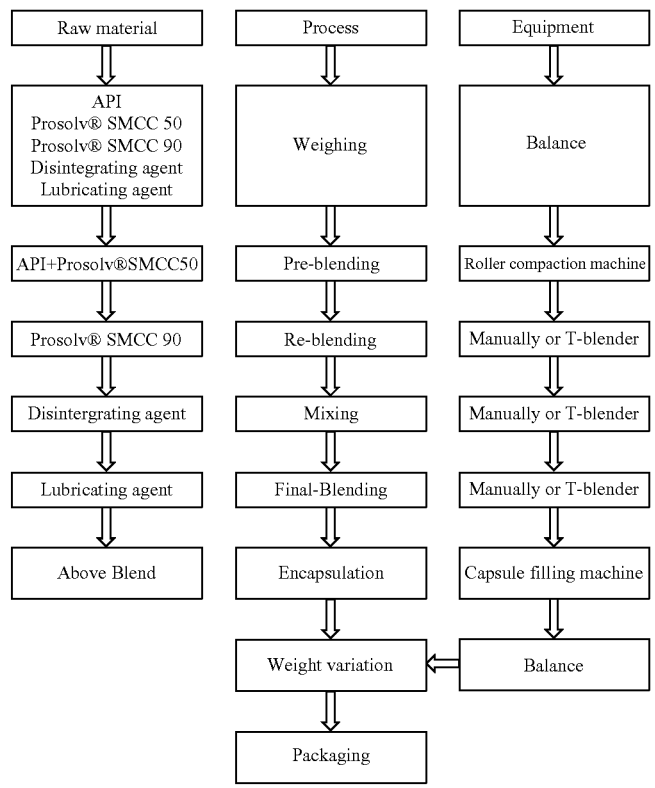

Preparation of Composition Rx2. Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (32.80 g; D (v, 0.9)≤37 sm) and adsorbing agent Prosolv® SMCC 50 (21.90 g) were mixed in a pre-blending/roller compaction process and the resulting mixture was mixed with Prosolv® SMCC 90 (89.30 g) by a re-blending process to obtain Composition B1. Composition B1, Vivasol® croscarmellose sodium (3.00 g), and sodium stearyl fumarate (3.00 g) were mixed and subjected to final blending to form a final powder, which was then filled into hollow gelatin capsules to prepare Composition Rx2. Characterization of the final powder is shown in Table B2, and the results of dissolution and stability studies of Composition Rx2 are reported in Table B3.

TABLE B2

| Final Powder | Characteristics |
|---|---|
| Bulk Density | 0.41 g/mL |
| Tapped Density | 0.58 g/mL |
| Carr's index | 29.3 |
| Angle of repose | 43.6° |

TABLE B3

| Rx2 | Characteristics |
|---|---|
| Dissolution (Medium; Method) | 96% (Medium, 0.1 N HCl; Basket method, 100 rpm) |
| Heat (60° C.-10 days) | Dimer Formation 0.21% |
| Humidity (75% RH-10 days) | Dimer Formation 0.05% |
| Light (4500 λ ± 500 λ-10 days) | Dimer Formation 0.06% |

Formulation Example C. Manufacture of Tablets by Direct Compression (Rx3)

Tablets containing Compound 1, maleate salt, were prepared by direct compression. The final composition of the tablets is shown in Table C1. In some embodiments, each of the adsorbing agents is variable by up to ±10% w/w of the adsorbing agent, the disintegrating agent is variable by up to ±6% w/w of the disintegrating agent, and the lubricant is variable by up to ±2% w/w of the lubricant.

Table C2 includes additional ranges for the composition of the tablets. In some embodiments of the tablet, the percentage w/w of the compound of Formula (I), or a pharmaceutically acceptable salt thereof (e.g., Compound 1, or a pharmaceutically acceptable salt thereof) is variable by up to ±20% w/w of the entire weight of the tablet. In some embodiments, each of the components of the tablet is variable by up to ±10% w/w of the entire weight of the tablet. In some embodiments, each of the adsorbing agents is variable by up to ±10% w/w of the entire weight of the tablet, the disintegrating agent is variable by up to ±6% w/w of the entire weight of the tablet, and the lubricant is variable by up to ±2% w/w of the entire weight of the tablet.

The flow diagram for the process is shown in Chart C and the process is described in detail below.

TABLE C1

Composition of direct compression tablets (Rx3)

| Ingredient | Rx3 Quantity (per tablet) | Rx3 Quantity (1000 tablets) |
|---|---|---|
| Pre-blending | | |
| API/API Maleate (e.g., Compound 1/Compound 1 maleate) | 20-30 mg/26.24-39.36 mg (e.g., 25.00 mg/32.80 mg) | 26.24-39.36 g (e.g., 32.80 g) |
| Prosolv® SMCC 50 | 19.71-24.09 mg (e.g., 21.90 mg) | 19.71-24.09 g (e.g., 21.90 g) |
| Re-blending | | |
| Prosolv® SMCC 90 | 80.37-98.23 mg (e.g., 89.30 mg) | 80.37-98.23 g (e.g., 89.30 g) |
| Tablet formation | | |
| Vivasol® sodium croscarmellose | 2.82-3.18 mg (e.g., 3.00 mg) | 2.82-3.18 g (e.g., 3.00 g) |
| sodium stearyl fumarate | 2.94-3.06 mg (e.g., 3.00 mg) | 2.94-3.06 g (e.g., 3.00 g) |
| Tablet weight | 132.08-167.92 mg (e.g., 150 mg) | — |
| Batch weight | — | 132.08-167.92 g (e.g., 150g) |

TABLE C2

Composition of direct compression tablets (Rx3)

| Ingredient | Rx3 Quantity (per tablet) | Rx3 Quantity (1000 tablets) |
|---|---|---|
| Pre-blending | | |
| API/API Maleate (e.g., Compound 1/Compound 1 maleate | 20-30 mg/26.24-39.36 mg (e.g., 25.00 mg/32.80 mg) | 26.24-39.36 g (e.g., 32.80 g) |
| Prosolv® SMCC 50 | 6.9-36.9 mg (e.g., 21.90 mg) | 6.9-36.9 g (e.g., 21.90 g) |
| Re-blending | | |
| Prosolv® SMCC 90 | 74.3-104.3 mg (e.g., 89.30 mg) | 74.3-104.3 g (e.g., 89.30 g) |
| Tablet formation | | |
| Vivasol® sodium croscarmellose | 0.01-12.0 mg (e.g., 3.00 mg) | 0.01-12.0 g (e.g., 3.00 g) |
| sodium stearyl fumarate | 0.01-6.0 mg (e.g., 3.00 mg) | 0.01-6.0 g (e.g., 3.00 g) |
| Tablet weight | 107.5-198.5 mg (e.g., 150 mg) | — |
| Batch weight | — | 107.5-198.5 g (e.g., 150g) |

Chart C: Flow diagram for the manufacture of tablets containing Compound 1, maleate salt, by a direct compression process.

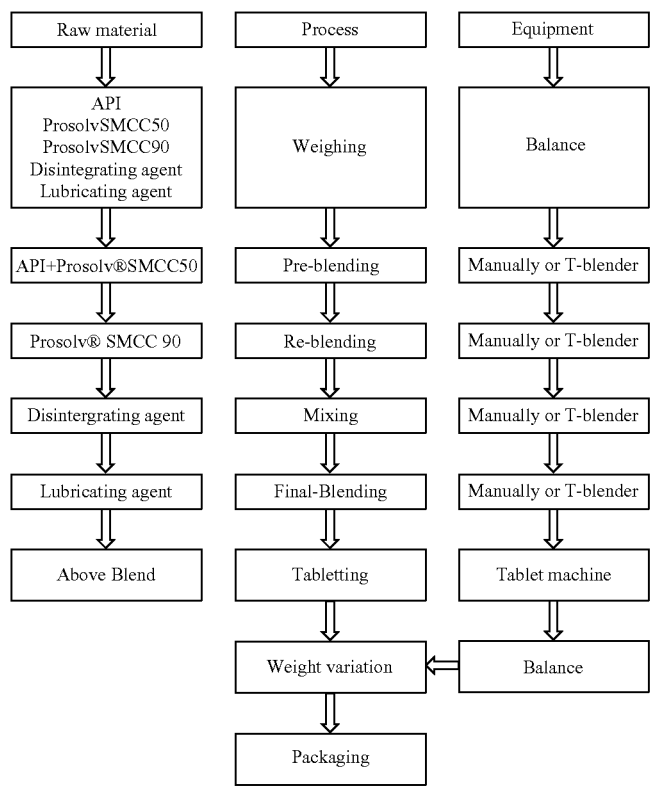

Preparation of Composition Rx3. Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (21.90 g; D (v, 0.9)≤150 µm) and adsorbing agent Prosolv® SMCC 50 (21.90 g) were mixed in a pre-blending process and the resulting mixture was mixed with Prosolv® SMCC 90 (89.30 g) by a re-blending process to obtain Composition C1. Composition C1, Vivasol® croscarmellose sodium (3.00 g), and sodium stearyl fumarate (3.00 g) were mixed and subjected to a final blending to form a final powder, which was then directly pressed into tablets of Composition Rx3. Characterization, of the final powder is shown in Table C2, and results of dissolution and stability studies of Composition Rx3 are reported in Table C3.

TABLE C2

| Final Powder | Characteristics |
|---|---|
| Bulk Density | 0.30 g/mL |
| Tapped Density | 0.50 g/mL |
| Carr's index | 34 |
| Angle of repose | 35.6° |

TABLE C3

| Composition Rx3 | Characteristics |
|---|---|
| Dissolution (Medium; Method) | 100% (Medium, 0.1 N HCl; Basket method, 100 rpm) |
| Heat (60° C.-10 days) | Dimer Formation 0.10% |
| Humidity (75% RH-10 days) | Dimer Formation 0.01% |
| Light (4500 λ ± 500 λ-10 days) | Dimer Formation 0.01% |

Formulation Example D. Manufacture of Tablets by Roller Compaction Process (Rx4)

Tablets containing Compound 1, maleate salt, were prepared by a roller compaction process. The final composition of the tablets is shown in Table D1. In some embodiments, each of the adsorbing agents is variable by up to ±10% w/w of the adsorbing agent, the disintegrating agent is variable by up to ±6% w/w of the disintegrating agent, and the lubricant is variable by up to ±2% w/w of the lubricant.

Table D2 includes additional ranges for the composition of the tablets. In some embodiments of the tablet, the percentage w/w of the compound of Formula (I), or a pharmaceutically acceptable salt thereof (e.g., Compound 1, or a pharmaceutically acceptable salt thereof) is variable by up to ±20% w/w of the entire weight of the tablet. In some embodiments, each of the components of the tablet is variable by up to ±10% w/w of the entire weight of the tablet. In some embodiments, each of the adsorbing agents is variable by up to ±10% w/w of the entire weight of the tablet, the disintegrating agent is variable by up to ±6% w/w of the entire weight of the tablet, and the lubricant is variable by up to ±2% w/w of the entire weight of the tablet.

The flow diagram for the process is shown in Chart D and the process is described in detail below.

TABLE D1

Composition of roller compaction tablets (Rx4)

| Ingredient | Rx4 Quantity (per Tablet) | Quantity (444 Tablets) |
|---|---|---|
| Pre-blending (roller compaction) | | |
| API/API Maleate (e.g., Compound 1/Compound 1 maleate) | 20-30 mg/26.24-39.36 mg (e.g., 25.00 mg/32.80 mg) | 11.66-17.50 g (e.g., 14.58 g) |
| Prosolv ® SMCC 50 | 19.71-24.09 mg (e.g., 21.90 mg) | 8.77-10.71 g (e.g., 9.74 g) |
| sodium stearyl fumarate | 1.47-1.53 mg (e.g., 1.50 mg) | 0.657-0.683 g (e.g., 0.67 g) |
| Re-blending | | |
| Prosolv ® SMCC 90 | 80.37-98.23 mg (e.g., 89.30 mg) | 36.18-44.22 g (e.g., 40.2 g) |
| Tablet preparation | | |
| Vivasol ® croscarmellose sodium | 2.82-3.18 mg (e.g., 3.00 mg) | 1.316-1.484 g (e.g., 1.4 g) |
| sodium stearyl fumarate | 1.47-1.53 mg (e.g., 1.50 mg) | 0.686-0.714 g (e.g., 0.7 g) |
| Table weight | 132.08-167.92 mg (e.g., 150 mg) | — |
| Batch weight | — | 59.27-75.31 g (e.g., 66.70 g) |

TABLE D2

Composition of roller compaction tablets (Rx4)

| Ingredient | Rx4 Quantity (per Tablet) | Quantity (444 Tablets) |
|---|---|---|
| Pre-blending (roller compaction) | | |
| API/API Maleate (e.g., Compound 1/Compound 1 maleate) | 20-30 mg/26.24-39.36 mg (e.g., 25.00 mg/32.80 mg) | 11.66-17.50 g (e.g., 14.58 g) |
| Prosolv ® SMCC 50 | 6.9-36.9 mg (e.g., 21.90 mg) | 3.1-16.4 g (e.g., 9.74 g) |
| sodium stearyl fumarate | 0.01-3.0 mg (e.g., 1.50 mg) | 0.01-1.3 g (e.g., 0.67 g) |
| Re-blending | | |
| Prosolv ® SMCC 90 | 74.3-104.3 mg (e.g., 89.30 mg) | 33.5-46.9 g (e.g., 40.2 g) |
| Tablet preparation | | |
| Vivasol ® croscarmellose sodium | 0.01-12.0 mg (e.g., 3.00 mg) | 0.01-5.4 g (e.g., 1.4 g) |
| sodium stearyl fumarate | 0.01-3.0 mg (e.g., 1.50 mg) | 0.01-1.3 g (e.g., 0.7 g) |
| Tablet weight | 107.5-198.5 mg (e.g., 150 mg) | — |
| Batch weight | — | 48.3-88.8 g (e.g., 66.70 g) |

Figure D: Flow diagram for the manufacture of tablets containing Compound 1, maleate salt, by a roller compaction process.

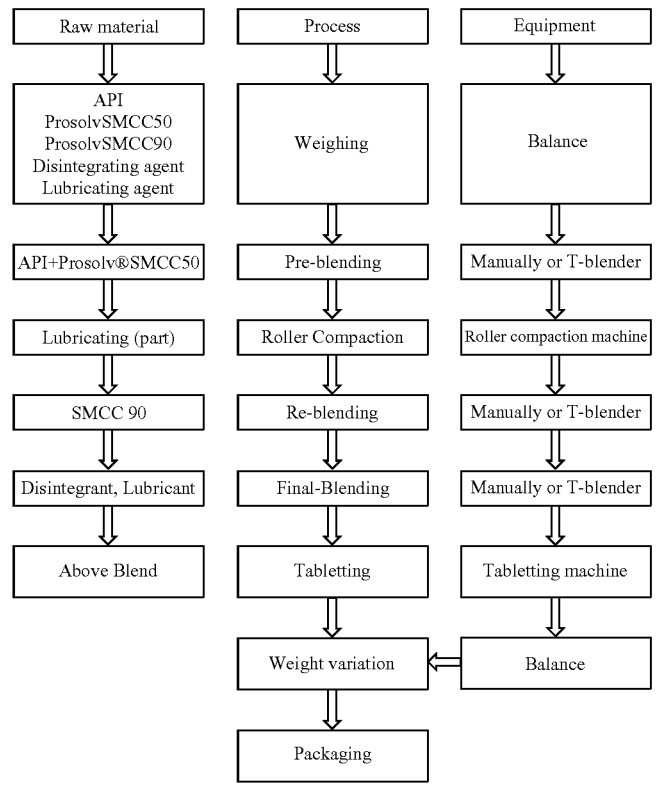

Preparation of Composition Rx4. Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (14.58 g; D (v, 0.9)≤85 μm) and adsorbing agent Prosolv® SMCC 50 (9.74 g) were mixed in a pre-blending/roller compaction process and the resulting mixture was mixed with Prosolv® SMCC 90 (40.2 g) by a re-blending process to obtain Composition D1. Composition D1, Vivasol® croscarmellose sodium (1.4 g), and sodium stearyl fumarate (0.7 g) were mixed and then subjected to a final blending process to form a final powder, which was used to manufacture tablets (Composition Rx4). Characterization of the final powder is shown in Table D2, and results of dissolution and stability studies of Composition Rx4 are reported in Table D3.

TABLE D2

| Final Powder | Characteristics |
| --- | --- |
| Bulk Density | 0.38 g/mL |
| Tapped Density | 0.56 g/mL |
| Carr's index | 32.1 |
| Angle of repose | 42.2° |

TABLE D3

| Rx4 | Characteristics |
| --- | --- |
| Dissolution (Medium; Method) | 97% (Medium, 0.1 N HCl; Basket method, 100 rpm) |
| Heat (60° C.-10 days) | Dimer Formation 0.20% |
| Humidity (75% RH-10 days) | Dimer Formation 0.05% |
| Light (4500 λ ± 500 λ-10 days) | Dimer Formation 0.06% |

The pharmaceutical compositions Rx1-Rx4 may be prepared using 25 mg, 50 mg, 100 mg, 150 mg, or 200 mg free base equivalent of the compound of Formula I or Compound 1, and the amounts of the remaining ingredients are adjusted accordingly so they are in the same ratios as in Rx1-Rx4. In other embodiments, the ingredients are the same but the ratios are adjusted as necessary to maintain low dimer formation.

Formulation Example E: Stability Testing

Compositions Rx1-Rx4 were studied in a long-term stability test at 60% (t 5%) relative humidity at 25±2° C. for 18 months. Stability testing showed that solid oral formulations manufactured using the methods described herein exhibit limited dimer formation (Table E).

TABLE E

| Composition | Dimer Detected after 18 months |
| --- | --- |
| Rx1 | 0.02% |
| Rx2 | 0.25% |
| Rx3 | 0.09% |
| Rx4 | 0.24% |

The invention claimed is:
1. A pharmaceutical composition comprising:
(1) (Compound 1):

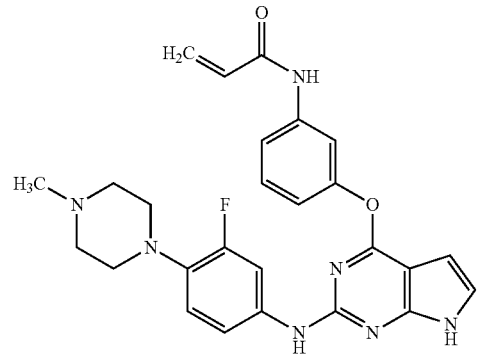

(Compound 1)

or a pharmaceutically acceptable salt thereof:
(2) at least two different types of adsorbing agents;
  wherein the pharmaceutical composition comprises from about 15% (w/w) to about 20% (w/w) of a first adsorbing agent;
  wherein the pharmaceutical composition comprises from about 45% (w/w) to about 65% (w/w) of a second adsorbing agent; and
  wherein at least one of the adsorbing agents eliminates or reduces the formation of a dimer of (Compound 1), or a pharmaceutically acceptable salt thereof:
(3) a disintegrating agent;
  wherein the pharmaceutical composition comprises from about 1.5% (w/w) to about 2.5% (w/w) of the disintegrating agent; and
(4) a lubricant;
  wherein the pharmaceutical composition comprises from about 0.1% (w/w) to about 1.0% (w/w) of the lubricant.

2. The pharmaceutical composition of claim 1, wherein the pharmaceutically acceptable salt is a maleate salt.

3. The pharmaceutical composition of claim 2, wherein the maleate salt is an amorphous form, polymorph Form I, polymorph Form II, or polymorph Form III.

4. The pharmaceutical composition of claim 2, wherein the maleate salt is polymorph Form VI.

5. The pharmaceutical composition of claim 1, wherein the pharmaceutical composition comprises from about 15% (w/w) to about 17% (w/w) of a first adsorbing agent and from about 55% (w/w) to about 60% (w/w) of a different second adsorbing agent.

6. The pharmaceutical composition of claim 5, wherein the pharmaceutical composition comprises from about 2% (w/w) of a disintegrating agent and from about 0.5% (w/w) to about 1.0% (w/w) of a lubricant.

7. The pharmaceutical composition of claim 1, wherein the pharmaceutical composition comprises a first adsorbing agent and a different second adsorbing agent independently selected from the group consisting of acacia, alginic acid, carboxymethylcellulose, croscarmellose, croscarmellose sodium, dicalcium phosphate, fructose, gelatin, gelatin hydrolysate, hydroxypropylcellulose, lactose, maltose, mannitol, microcrystalline cellulose, plasdone, polyethylene glycol, povidone, sodium starch glycolate, sorbitol, and sucrose.

8. The pharmaceutical composition of claim 7, wherein the microcrystalline cellulose comprises silicified microcrystalline cellulose.

9. The pharmaceutical composition of claim 1, wherein the pharmaceutical composition comprises a first adsorbing agent comprising a silicified microcrystalline cellulose and a second adsorbing agent comprising a different kind of silicified microcrystalline cellulose.

10. The pharmaceutical composition of claim 1, wherein the pharmaceutical composition comprises a disintegrating agent selected from the group consisting of cross-linked sodium carboxymethylcellulose and croscarmellose sodium.

11. The pharmaceutical composition of claim 1, wherein the pharmaceutical composition comprises a sodium stearyl fumarate lubricant.

12. The pharmaceutical composition of claim 1, wherein the pharmaceutical composition is formulated to contain a single dose or multiple doses.

13. The pharmaceutical composition of claim 1, wherein the pharmaceutical composition is formulated as an oral dosage form.

14. The pharmaceutical composition of claim 13, wherein the oral dosage form is a solid oral dosage form.

15. The pharmaceutical composition of claim 1, wherein the pharmaceutical composition further comprises one or more additional pharmaceutically acceptable additives.

16. A process for preparing a pharmaceutical composition of claim 1, wherein the process comprises the following steps:

1) combining (Compound 1):

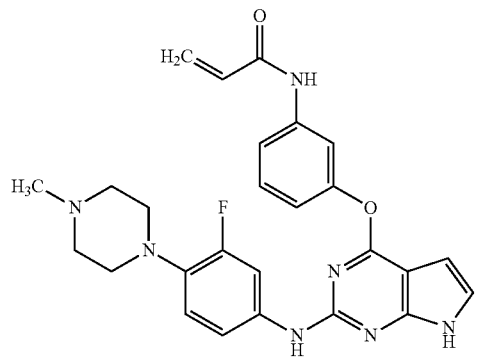

(Compound 1)

or a pharmaceutically acceptable salt thereof,
with at least two different types of adsorbing agents as defined in claim 1, to form a first mixture;
2) filling the first mixture formed in step 1) above with a disintegrating agent, as defined in claim 1, and a lubricant, as defined in claim 1, to form a second mixture; and
3) formulating the second mixture formed in step 2) above into a dosage form of the pharmaceutical composition of claim 1.

* * * * *

UNITED STATES PATENT AND TRADEMARK OFFICE
CERTIFICATE OF CORRECTION

| | |
|---|---|
| PATENT NO. | : 11,498,922 B2 |
| APPLICATION NO. | : 16/500384 |
| DATED | : November 15, 2022 |
| INVENTOR(S) | : Long Mao et al. |

It is certified that error appears in the above-identified patent and that said Letters Patent is hereby corrected as shown below:

In the Claims

In Claim 4 at Column 104, Line 47, "claim 2" should read --claim 1--.

In Claim 4 at Column 104, Line 48, "the maleate salt is polymorph Form VI" should read --the pharmaceutically acceptable salt is malate salt polymorph Form VI--.

Signed and Sealed this
Seventeenth Day of January, 2023

*Katherine Kelly Vidal*

Katherine Kelly Vidal
*Director of the United States Patent and Trademark Office*